US009688977B2

(12) United States Patent
Blake et al.

(10) Patent No.: US 9,688,977 B2
(45) Date of Patent: Jun. 27, 2017

(54) ENGINEERED PHOSPHOGLUCOSE ISOMERASE PROTEINS WITH A PROTEASE CLEAVAGE SITE

(71) Applicant: GreenLight Biosciences, Inc., Medford, MA (US)

(72) Inventors: William Jeremy Blake, Winchester, MA (US); Drew S. Cunningham, Cambridge, MA (US)

(73) Assignee: GreenLight Biosciences, Inc., Medford, MA (US)

( * ) Notice: Subject to any disclaimer, the term of this patent is extended or adjusted under 35 U.S.C. 154(b) by 220 days.

(21) Appl. No.: 14/451,708

(22) Filed: Aug. 5, 2014

(65) Prior Publication Data

US 2015/0037868 A1 Feb. 5, 2015

Related U.S. Application Data

(60) Provisional application No. 61/987,518, filed on May 2, 2014, provisional application No. 61/862,363, filed on Aug. 5, 2013.

(51) Int. Cl.
*C12N 9/92* (2006.01)
*C12N 9/10* (2006.01)

(52) U.S. Cl.
CPC ............ *C12N 9/92* (2013.01); *C12N 9/1022* (2013.01); *C12N 9/1029* (2013.01); *C12Y 202/01001* (2013.01); *C12Y 203/01008* (2013.01); *C12Y 503/01009* (2013.01)

(58) Field of Classification Search
None
See application file for complete search history.

(56) References Cited

U.S. PATENT DOCUMENTS

| | | |
|---|---|---|
| 3,223,592 A | 12/1965 | Sakaguchi et al. |
| 3,684,652 A | 8/1972 | Nakayama et al. |
| 3,950,357 A | 4/1976 | Kahan et al. |
| RE28,886 E | 6/1976 | Nakayama et al. |
| 4,006,060 A | 2/1977 | Kahan et al. |
| 4,194,047 A | 3/1980 | Christensen et al. |
| 4,248,966 A | 2/1981 | Demain et al. |
| 4,266,034 A | 5/1981 | Patel |
| 4,270,537 A | 6/1981 | Romaine |
| 4,292,436 A | 9/1981 | Liu et al. |
| 4,329,481 A | 5/1982 | Liu et al. |
| 4,374,772 A | 2/1983 | Hazen et al. |
| 4,438,201 A | 3/1984 | Kubo et al. |
| 4,458,066 A | 7/1984 | Caruthers et al. |
| 4,460,689 A | 7/1984 | Foor et al. |
| 4,596,556 A | 6/1986 | Morrow et al. |
| 4,790,824 A | 12/1988 | Morrow et al. |
| 4,886,499 A | 12/1989 | Cirelli et al. |
| 4,940,460 A | 7/1990 | Casey et al. |
| 4,941,880 A | 7/1990 | Burns |
| 4,946,783 A | 8/1990 | Beckwith et al. |
| 4,950,603 A | 8/1990 | Ingolia et al. |
| 5,001,055 A | 3/1991 | Imahori et al. |
| 5,015,235 A | 5/1991 | Crossman |
| 5,064,413 A | 11/1991 | McKinnon et al. |
| 5,070,020 A | 12/1991 | Ingolia et al. |
| 5,141,496 A | 8/1992 | Dalto et al. |
| 5,190,521 A | 3/1993 | Hubbard et al. |
| 5,312,335 A | 5/1994 | McKinnon et al. |
| 5,319,122 A | 6/1994 | Friedman |
| 5,328,483 A | 7/1994 | Jacoby |
| 5,334,144 A | 8/1994 | Alchas et al. |
| 5,339,163 A | 8/1994 | Homma et al. |
| 5,383,851 A | 1/1995 | McKinnon et al. |
| 5,417,662 A | 5/1995 | Hjertman et al. |
| 5,436,131 A | 7/1995 | Condra et al. |
| 5,466,220 A | 11/1995 | Brenneman |
| 5,480,381 A | 1/1996 | Weston |
| 5,503,627 A | 4/1996 | McKinnon et al. |
| 5,520,639 A | 5/1996 | Peterson et al. |
| 5,527,288 A | 6/1996 | Gross et al. |
| 5,569,189 A | 10/1996 | Parsons |
| 5,593,856 A | 1/1997 | Choi et al. |
| 5,599,302 A | 2/1997 | Lilley et al. |
| 5,649,912 A | 7/1997 | Peterson |

(Continued)

FOREIGN PATENT DOCUMENTS

| | | |
|---|---|---|
| CN | 1329506 C | 8/2007 |
| EP | 0 377 295 A1 | 7/1990 |

(Continued)

OTHER PUBLICATIONS

Ehrmann et al, TnTIN and TnTAP: Mini-transposons for site-specific proteolysis in vivo. Proc. Natl. Acad. Sci. USA vol. 94, pp. 13111-13115, Nov. 1997.*
Blattner et al, Analysis of the Escherichia coli genome. IV. DNA sequence of the region from 89.2 to 92.8 minutes. p. 5408-5417 Nucleic Acids Research, 1993, vol. 21, No. 23.*
GenBank AAC43119 from Blattner et al, 1993. Alignment with Seq ID No. 17.*
Eser et al, Target-Directed Proteolysis In Vivo. Methods in Enzymology, vol. 421, 2007 p. 68-83.*
Zhao et al, A Novel High-Throughput Screening Method for Microbial Transglutaminases with High Specificity toward Gln141 of Human Growth Hormone. Journal of Biomolecular Screening 15(2); 2010 p. 206-212.*
Invitation to Pay Additional Fees for PCT/US2012/054195, mailed Jan. 30, 2013.
International Search Report and Written Opinion for PCT/US2012/054195, mailed Apr. 12, 2013.
International Preliminary Report on Patentability for PCT/US2012/054195, mailed Mar. 20, 2014.

(Continued)

*Primary Examiner* — Sheridan Swope
(74) *Attorney, Agent, or Firm* — Wolf, Greenfield & Sacks, P.C.

(57) ABSTRACT

Various aspects and embodiments herein relate to recombinant proteins with at least one protease recognition sequence that can be inactivated by a cognate protease and methods of preparing such proteins. In some embodiments, recombinant phosphoglucose isomerase (Pgi) proteins are provided. In other embodiments, recombinant phosphotransacetylase (Pta) proteins are provided. In yet other embodiments, recombinant transketolase A (TktA) proteins are provided.

4 Claims, 8 Drawing Sheets

(56) References Cited

U.S. PATENT DOCUMENTS

| | | |
|---|---|---|
| 5,665,566 A | 9/1997 | Lavallie |
| 5,672,497 A | 9/1997 | Cox et al. |
| 5,704,911 A | 1/1998 | Parsons |
| 5,871,922 A | 2/1999 | Salmond et al. |
| 5,893,397 A | 4/1999 | Peterson et al. |
| 5,993,412 A | 11/1999 | Deily et al. |
| 6,159,693 A | 12/2000 | Shultz et al. |
| 6,168,931 B1 | 1/2001 | Swartz et al. |
| 6,387,667 B1 | 5/2002 | Maruyama et al. |
| 6,440,688 B1 | 8/2002 | Bruce et al. |
| 6,472,169 B1 | 10/2002 | Frost et al. |
| 6,531,299 B1 | 3/2003 | Khosla et al. |
| 6,746,859 B1 | 6/2004 | LaVallie |
| 6,921,659 B2 | 7/2005 | Joly |
| 6,994,986 B2 | 2/2006 | Swartz et al. |
| 7,041,479 B2 | 5/2006 | Swartz et al. |
| 7,223,390 B2 | 5/2007 | Brown |
| 7,226,767 B2 | 6/2007 | Maruyama et al. |
| 7,312,049 B2 | 12/2007 | Calhoun et al. |
| 7,338,789 B2 | 3/2008 | Swartz et al. |
| 7,341,852 B2 | 3/2008 | Voloshin et al. |
| 7,351,563 B2 | 4/2008 | Swartz et al. |
| 8,859,247 B2 | 10/2014 | Koltermann et al. |
| 8,916,358 B2 | 12/2014 | Swartz |
| 8,956,833 B2 | 2/2015 | Swartz |
| 9,469,861 B2 | 10/2016 | Blake et al. |
| 2002/0058303 A1 | 5/2002 | Swartz et al. |
| 2002/0127633 A1 | 9/2002 | Dilley et al. |
| 2002/0160459 A1 | 10/2002 | Berry et al. |
| 2003/0022178 A1 | 1/2003 | Schneewind et al. |
| 2003/0040086 A1 | 2/2003 | Dodge et al. |
| 2003/0113778 A1 | 6/2003 | Schulte et al. |
| 2004/0002103 A1 | 1/2004 | Short |
| 2004/0038250 A1 | 2/2004 | Nunez et al. |
| 2004/0091976 A1 | 5/2004 | Deng et al. |
| 2004/0209321 A1 | 10/2004 | Swartz et al. |
| 2005/0054044 A1 | 3/2005 | Swartz et al. |
| 2005/0239174 A1 | 10/2005 | Bao et al. |
| 2006/0234358 A1 | 10/2006 | Anderlei et al. |
| 2006/0281148 A1 | 12/2006 | Swartz et al. |
| 2007/0111283 A1 | 5/2007 | Cannon et al. |
| 2007/0154983 A1 | 7/2007 | Calhoun et al. |
| 2007/0161092 A1 | 7/2007 | Townsend et al. |
| 2007/0202198 A1 | 8/2007 | Purcell |
| 2008/0021205 A1 | 1/2008 | Blau et al. |
| 2008/0131925 A1 | 6/2008 | Berk et al. |
| 2009/0053779 A1 | 2/2009 | Lee et al. |
| 2009/0124012 A1 | 5/2009 | Nikolsky et al. |
| 2009/0155867 A1 | 6/2009 | Soucaille |
| 2009/0275096 A1 | 11/2009 | Burgard et al. |
| 2009/0275097 A1 | 11/2009 | Sun et al. |
| 2009/0312539 A1 | 12/2009 | Gnanaprakasam et al. |
| 2009/0325245 A1 | 12/2009 | Soucaille et al. |
| 2010/0120105 A1 | 5/2010 | Anthony et al. |
| 2010/0143997 A1 | 6/2010 | Buelter et al. |
| 2010/0291653 A1 | 11/2010 | Ness et al. |
| 2011/0008867 A1 | 1/2011 | Zarur et al. |
| 2011/0099670 A1 | 4/2011 | Koops et al. |
| 2011/0124069 A1 | 5/2011 | Mampel et al. |
| 2011/0262946 A1 | 10/2011 | Roy et al. |
| 2011/0269198 A1 | 11/2011 | Klein-Marcuschamer |
| 2011/0275116 A1 | 11/2011 | Swartz |
| 2011/0312052 A1 | 12/2011 | Koltermann et al. |
| 2012/0052547 A1 | 3/2012 | Swartz |
| 2012/0070870 A1 | 3/2012 | Way et al. |
| 2013/0065878 A1 | 3/2013 | Blake et al. |
| 2014/0193869 A1 | 7/2014 | Blake et al. |
| 2015/0064751 A1 | 3/2015 | Swartz |
| 2015/0191753 A1 | 7/2015 | Swartz |
| 2016/0115558 A1 | 4/2016 | Swartz |

FOREIGN PATENT DOCUMENTS

| | | |
|---|---|---|
| EP | 0 444 775 A1 | 9/1991 |
| EP | 0 553 821 A1 | 8/1993 |
| EP | 1 433 856 A1 | 6/2004 |
| EP | 1 502 956 A1 | 2/2005 |
| EP | 1 939 210 A1 | 7/2008 |
| EP | 2 204 453 A1 | 7/2010 |
| GB | 2 018 822 A | 10/1979 |
| JP | S61-260895 A | 11/1986 |
| JP | S63-7788 A | 1/1988 |
| JP | H01-228473 A | 9/1989 |
| JP | H07-298893 A | 11/1995 |
| JP | H08-502176 A | 3/1996 |
| JP | H08-196284 A | 8/1996 |
| JP | 2002-535008 A | 10/2002 |
| JP | 2007-534338 A | 11/2007 |
| JP | 2009-531050 A | 9/2009 |
| WO | WO 97/13537 A1 | 4/1997 |
| WO | WO 97/37705 A1 | 10/1997 |
| WO | WO 98/07690 A1 | 2/1998 |
| WO | WO 99/34850 A1 | 7/1999 |
| WO | WO 00/03581 A1 | 1/2000 |
| WO | WO 00/39288 A1 | 7/2000 |
| WO | WO 00/44923 A1 | 8/2000 |
| WO | WO 00/55353 A1 | 9/2000 |
| WO | WO 03/038117 A2 | 5/2003 |
| WO | WO 2005/030949 A1 | 4/2005 |
| WO | WO 2005/098048 A1 | 10/2005 |
| WO | WO 2006/001382 A1 | 1/2006 |
| WO | WO 2006/090385 A2 | 8/2006 |
| WO | WO 2007/053655 A2 | 5/2007 |
| WO | WO 2007/110619 A1 | 10/2007 |
| WO | WO 2007/137144 A2 | 11/2007 |
| WO | WO 2008/002661 A2 | 1/2008 |
| WO | WO 2008/002663 A2 | 1/2008 |
| WO | WO 2008/002673 A2 | 1/2008 |
| WO | WO 2008/066583 A2 | 6/2008 |
| WO | WO 2008/088884 A2 | 7/2008 |
| WO | WO 2008/094546 A2 | 8/2008 |
| WO | WO 2010/046713 A2 | 4/2010 |
| WO | WO 2010/074760 A1 | 7/2010 |
| WO | WO 2010/077806 A1 | 7/2010 |
| WO | WO 2011/017560 A1 | 2/2011 |
| WO | WO 2011/072287 A2 | 6/2011 |
| WO | WO 2011/140516 A2 | 11/2011 |
| WO | WO 2012/030980 A1 | 3/2012 |
| WO | WO 2012/135902 A1 | 10/2012 |
| WO | WO 2014/197655 A1 | 12/2014 |

OTHER PUBLICATIONS

Invitation to Pay Additional Fees for PCT/US2011/035639, mailed Sep. 12, 2011.
International Search Report and Written Opinion for PCT/US2011/035639, mailed Nov. 18, 2011.
International Preliminary Report on Patentability for PCT/US2011/035639, mailed Nov. 22, 2012.
International Search Report and Written Opinion for PCT/US2011/049997, mailed Dec. 13, 2011.
International Preliminary Report on Patentability for PCT/US2011/049997, mailed Mar. 14, 2013.
Extended European Search Report for EP 09836804.6, mailed Jun. 4, 2012.
International Search Report and Written Opinion for PCT/US2009/067841, mailed Mar. 22, 2010.
International Preliminary Report on Patentability for PCT/US2009/067841, mailed Jun. 30, 2011.
International Search Report and Written Opinion for PCT/US2009/006704, mailed Mar. 3, 2010.
International Preliminary Report on Patentabilityfor PCT/US2009/006704, mailed Jul. 7, 2011.
Invitation to Pay Additional Fees for PCT/US2013/077238, mailed Mar. 18, 2014.
International Search Report and Written Opinion for PCT/US2013/077238, mailed May 19, 2014.
Invitation to Pay Additional Fees for PCT/US2014/049805, mailed Nov. 14, 2014.
International Search Report for PCT/US2014/049805, mailed Feb. 16, 2015.

(56) References Cited

OTHER PUBLICATIONS

International Search Report and Written Opinion for PCT/US2014/041009, mailed Sep. 10, 2014.
[No Author Listed] Biapenem. Drugs Fut. 1994;19(7):631-637.
[No Author Listed] Biolistic® Particle Delivery System Bibliography. Bio-Rad Technical Bulletin #1687. Bio-Rad Laboratories. 12 pages.
Adams et al., Hindered dialkylamino nucleoside phosphite reagents in the synthesis of two DNA 51-mers. J Am Chem Soc. 1983;105(3):661-3.
Alber et al., Malonyl-coenzyme a reductase in the modified 3-hydroxypropionate cycle for autotrophic carbon fixation in archaeal Metallosphaera and *Sulfolobus* spp. J Bacteriol. Dec. 2006;188(24):8551-9. Epub Oct. 13, 2006.
Allain, Cell-free ethanol production: the future of fuel ethanol? J Chem Technol Biotechnol. 2007;82:117-20.
Alper et al., Tuning genetic control through promoter engineering. Proc Natl Acad Sci U S A. Sep. 6, 2005;102(36):12678-83. Epub Aug. 25, 2005.
Alves-Pereira et al., CDP-alcohol hydrolase, a very efficient activity of the 5'-nucleotidase/udp-sugar hydrolase encoded by the usha gene of yersinia intermedia and *Escherichia coli*. J Bacteriol. Sep. 15, 2008;190(18):6153-61. Published ahead of print Jul. 18, 2008, doi:10.1128/JB.00658-08.
Anthony et al., Optimization of the mevalonate-based isoprenoid biosynthetic pathway in *Escherichia coli* for production of the anti-malarial drug precursor amorpha-4,11-diene. Metab Eng. Jan. 2009;11(1):13-9. Epub Aug. 12, 2008.
Atsumi et al., Metabolic engineering of *Escherichia coli* for 1-butanol production. Metab Eng. Nov. 2008;10(6):305-11. Epub Sep. 14, 2007.
Atsumi et al., Non-fermentative pathways for synthesis of branched-chain higher alcohols as biofuels. Nature. Jan. 3, 2008;451(7174):86-9.
Baba et al., Construction of *Escherichia coli* K-12 in-frame, single-gene knockout mutants: the Keio collection. Mol Syst Biol. 2006;2:2006.0008. Epub Feb. 21, 2006.
Bateson et al., Olivanic acid analogues. Part 6. Biomimetic synthesis of (±)-PS-5, (±)-6-Epi-PS-5, and (±)-benzyl MM22381. J Chem Soc Perkin Trans 1. 1990;1793-1801.
Baum et al., beta-Galactosidase containing a human immunodeficiency virus protease cleavage site is cleaved and inactivated by human immunodeficiency virus protease. Proc Natl Acad Sci U S A. Dec. 1990;87(24):10023-7.
Beaucage et al., Deoxynucleoside phosphoramidites—A new class of key intermediates for deoxypolynucleotide synthesis. Tetra Lett. 1981;22(20):1859-62.
Belousov et al., Sequence-specific targeting and covalent modification of human genomic DNA. Nucleic Acids Res. Sep. 1, 1997;25(17):3440-4.
Benton et al., Screening lambdagt recombinant clones by hybridization to single plaques in situ. Science. Apr. 8, 1977;196(4286):180-2.
Berge et al., Pharmaceutical salts. J Pharmaceut Sci. Jan. 1977;66(1):1-19.
Blommers et al., Effects of the introduction of L-nucleotides into DNA. Solution structure of the heterochiral duplex d(G-C-G-(L)T-G-C-G).d(C-G-C-A-C-G-C) studied by NMR spectroscopy. Biochemistry. Jun. 28, 1994;33(25):7886-96.
Bodner et al., Definition of the common and divergent steps in carbapenem β-lactam antibiotic biosynthesis. Chembiochem. Sep. 19, 2011;12(14):2159-65. doi: 10.1002/cbic.201100366. Epub Aug. 24, 2011.
Bodner et al., Non-heme iron oxygenases generate natural structural diversity in carbapenem antibiotics. J Am Chem Soc. Jan. 13, 2010;132(1):12-3.
Boiteux et al., Design of glycolysis. Philos Trans R Soc Lond B Biol Sci. Jun. 26, 1981;293(1063):5-22.
Bongaerts et al., Metabolic engineering for microbial production of aromatic amino acids and derived compounds. Metab Eng. Oct. 2001;3(4):289-300.
Boyer et al., Cell-free synthesis and maturation of [FeFe] hydrogenases. Biotechnol Bioeng. Jan. 1, 2008;99(1):59-67.
Bradley, Star role for bacteria in controlling flu pandemic? Nat Rev Drug Discov. Dec. 2005;4(12):945-6.
Brown et al., Chemical synthesis and cloning of a tyrosine tRNA gene. Methods Enzymol. 1979;68:109-51.
Buist et al., Different subcellular locations of secretome components of Gram-positive bacteria. Microbiology. Oct. 2006;152(Pt 10):2867-74.
Bujara et al., Exploiting cell-free systems: Implementation and debugging of a system of biotransformations. Biotechnol Bioeng. Jun. 15, 2010;106(3):376-89. doi: 10.1002/bit.22666.
Bujara et al., Optimization of a blueprint for in vitro glycolysis by metabolic real-time analysis. Nat Chem Biol. May 2011;7(5):271-7. doi: 10.1038/nchembio.541. Epub Mar. 20, 2011.
Calhoun et al., An economical method for cell-free protein synthesis using glucose and nucleoside monophosphates. Biotechnol Prog. Jul.-Aug. 2005;21(4):1146-53.
Calhoun et al., Energizing cell-free protein synthesis with glucose metabolism. Biotechnol Bioeng. Jun. 5, 2005;90(5):606-13.
Calhoun et al., Energy systems for ATP regeneration in cell-free protein synthesis reactions. Methods in Molecular Biology. In vitro transcription and translation protocols. 2007;375(2):3-17.
Calhoun et al., Total amino acid stabilization during cell-free protein synthesis reactions. J Biotechnol. May 17, 2006;123(2):193-203. Epub Jan. 26, 2006.
Campbell et al., The CTP:phosphocholine cytidylyltransferase encoded by the licC gene of *Streptococcus pneumoniae*: cloning, expression, purification, and characterization. Biochim Biophys Acta. Dec. 30, 2001;1534(2-3):85-95.
Chandran et al., Phosphoenolpyruvate availability and the biosynthesis of shikimic acid. Biotechnol Prog. May-Jun. 2003;19(3):808-14.
Chang et al., YPA: an integrated repository of promoter features in *Saccharomyces cerevisiae*. Nucleic Acids Res. Jan. 2011;39(Database issue):D647-52. Epub Nov. 2, 2010.
Chen et al., A modified osmotic shock for periplasmic release of a recombinant creatinase from *Escherichia coli*. Biochem Eng J. 2004;19:211-5.
Chen et al., Crystal structures of penicillin-binding protein 6 from *Escherichia coli*. J Am Chem Soc. Oct. 14, 2009;131(40):14345-54.
Chen et al., High-level accumulation of a recombinant antibody fragment in the periplasm of *Escherichia coli* requires a triple-mutant (degP prc spr) host strain. Biotechnol Bioeng. Mar. 5, 2004;85(5):463-74.
Chiu et al., Site-directed, Ligase-Independent Mutagenesis (SLIM): a single-tube methodology approaching 100% efficiency in 4 h. Nucleic Acids Res. Dec. 7, 2004;32(21):e174.
Chong et al., Single-col. purification of free recombinant proteins using a self-cleavable affinity tag derived from a protein splicing element. Gene. Jun. 19, 1997;192(2):271-81.
Choubey et al., Molecular characterization and localization of Plasmodium falciparum choline kinase. Biochim Biophys Acta. Jul. 2006;1760(7):1027-38.
Collins-Racie et al., Production of recombinant bovine enterokinase catalytic subunit in *Escherichia coli* using the novel secretory fusion partner DsbA. Biotechnology (N Y). Sep. 1995;13(9):982-7.
Coulthurst et al., Regulation and biosynthesis of carbapenem antibiotics in bacteria. Nat Rev Microbiol. Apr. 2005;3(4):295-306. Erratum included.
Dahiyat et al., De novo protein design: fully automated sequence selection. Science. Oct. 3, 1997;278(5335):82-7.
Dahl et al., Isolation and characterization of Chinese hamster ovary cells defective in the intracellular metabolism of low density lipoprotein-derived cholesterol. J Biol Chem. Mar. 5, 1992;267(7):4889-96.
Danese et al., Targeting and assembly of periplasmic and outer-membrane proteins in *Escherichia coli*. Annu Rev Genet. 1998;32:59-94.

(56) References Cited

OTHER PUBLICATIONS

Dani et al., Isolation and characterization of a thylakoid membrane module showing partial light and dark reactions. Biochim Biophys Acta. May 15, 2005;1669(1):43-52.

Daniell et al., Transformation of the cyanobacterium Anacystis nidulans 6301 with the *Escherichia coli* plasmid pBR322. Proc Natl Acad Sci U S A. Apr. 1986;83(8):2546-50.

Datsenko et al., One-step inactivation of chromosomal genes in *Escherichia coli* K-12 using PCR products. Proc Natl Acad Sci U S A. Jun. 6, 2000;97(12):6640-5.

De Boer et al., Protein targeting towards the thylakoid lumen of chloroplasts: proper localization of fusion proteins is only observed in vivo. Embo J. Oct. 1991;10(10):2765-72.

De Mey et al., Construction and model-based analysis of a promoter library for *E. coli*: an indispensable tool for metabolic engineering. BMC Biotechnol. Jun. 18, 2007;7:34.

De Vries et al., Cloning, expression, and sequence analysis of the Bacillus methanolicus C1 methanol dehydrogenase gene. J Bacteriol. Aug. 1992;174(16):5346-53.

Dietrich et al., a novel semi-biosynthetic route for artemisinin production using engineered substrate-promiscuous P450(BM3). Acs Chem Biol. Apr. 17, 2009;4(4):261-7.

Ding et al., Functional analysis of the essential bifunctional tobacco enzyme 3-dehydroquinate dehydratase/shikimate dehydrogenase in transgenic tobacco plants. J Exp Bot. 2007;58(8):2053-67. Epub Apr. 26, 2007.

Dingwall et al., The nucleoplasmin nuclear location sequence is larger and more complex than that of SV-40 large T antigen. J Cell Biol. Sep. 1988;107(3):841-9.

Draper et al., Ti plasmid homologous sequences present in tissues from agrobacterium plasmid-transformed petunia protoplasts. Plant Cell Physiol. 1982;23(3):451-8.

Egan et al., Transketolase kinetics. The slow reconstitution of the holoenzyme is due to rate-limiting dimerization of the subunits. J Biol Chem. May 25, 1981;256(10):4877-83.

Elander, Industrial production of beta-lactam antibiotics. Appl Microbiol Biotechnol. Jun. 2003;61(5-6):385-92. Epub Apr. 3, 2003.

Erb et al., Carboxylation mechanism and stereochemistry of crotonyl-CoA carboxylase/reductase, a carboxylating enoyl-thioester reductase. Proc Natl Acad Sci U S A. Jun. 2, 2009;106(22):8871-6. Epub May 20, 2009.

Erb et al., Synthesis of C5-dicarboxylic acids from C2-units involving crotonyl-CoA carboxylase/reductase: The ethylmalonyl-CoA pathway. Proc Nat Acad Sci. Jun. 4, 2007;104(25):10631-6.

Evans et al., The asymmetric synthesis of β-lactam antibiotics—IV. A formal synthesis of thienamycin. Tetra Lett. 1986;27(41):4961-4.

Fischer et al., Metabolic flux profiling of *Escherichia coli* mutants in central carbon metabolism using GC-MS. Eur J Biochem. Mar. 2003;270(5):880-91.

Flores et al., Pathway engineering for the production of aromatic compounds in *Escherichia coli*. Nat Biotechnol. May 1996;14(5):620-3.

Flores et al., Analysis of carbon metabolism in *Escherichia coli* strains with an inactive phosphotransferase system by (13)C labeling and NMR spectroscopy. Metab Eng. Apr. 2002;4(2):124-37.

Flores et al., Growth-rate recovery of *Escherichia coli* cultures carrying a multicopy plasmid, by engineering of the pentose-phosphate pathway. Biotechnol Bioeng. Aug. 20, 2004;87(4):485-94.

Fox et al., Methane monooxygenase from Methylosinus trichosporium OB3b. Purification and properties of a three-component system with high specific activity from a type II methanotroph. J Biol Chem. Jun. 15, 1989;264(17):10023-33.

Fradejas et al., The control of shikimic acid synthesis by tyrosine and phenylalanine. Biochim Biophys Res Commun. Jul. 26, 1961;5:320-3.

Freeman et al., Four enzymes define the incorporation of coenzyme A in thienamycin biosynthesis. Proc Natl Acad Sci U S A. Aug. 12, 2008;105(32):11128-33. Epub Aug. 4, 2008. Supplemental material included.

Freeman et al., A comparison of methods for plasmid delivery into plant protoplasts. Plant Cell Physiol. 1984;25(8):1353-65.

Frenkel et al., 7,12-dimethylbenz[a]anthracene induces oxidative DNA modification in vivo. Free Radic Biol Med. Sep. 1995;19(3):373-80.

Friesen et al., Purification and Kinetic Characterization of CTP-:Phosphocholine Cytidylyltransferase from *Saccharomyces cerevisiae*. Protein Expression and Purification. Feb. 2001;21(1):141-8.

Fromm et al., Stable transformation of maize after gene transfer by electroporation. Nature. Feb. 27-Mar. 5, 1986;319(6056):791-3.

Fujio et al., Construction of a plasmid carrying both CTP synthetase and a fused gene formed from cholinephosphate cytidylyltransferase and choline kinase genes and its application to industrial CDP-choline production: enzymatic production of CDP-choline from orotic acid (Part II). Biosci Biotechnol Biochem. Jun. 1997;61(6):960-4.

Gaspar et al., High yields of 2,3-butanediol and mannitol in Lactococcus lactis through engineering of $NAD^+$ cofactor recycling. Appl Environ Microbiol. Oct. 2011;77(19):6826-35. Epub Aug. 12, 2011. Supplemental material included.

Genbank Submission; NIH/NCBI, Accession No. AAB59985; Ling et al.; Nov. 24, 1994.

Genbank Submission; NIH/NCBI, Accession No. AAC73225; Blattner et al.; Sep. 1, 2011.

Genbank Submission; NIH/NCBI, Accession No. AAC73226; Blattner et al.; Sep. 1, 2011.

Genbank Submission; NIH/NCBI, Accession No. AAC73296; Blattner et al.; Sep. 1, 2011.

Genbank Submission; NIH/NCBI, Accession No. AAC73346; Blattner et al.; Sep. 1, 2011.

Genbank Submission; NIH/NCBI, Accession No. AAC73347; Blattner et al.; Sep. 1, 2011.

Genbank Submission; NIH/NCBI, Accession No. AAC73842; Blattner et al.; Sep. 1, 2011.

Genbank Submission; NIH/NCBI, Accession No. AAC73957; Blattner et al.; Sep. 1, 2011.

Genbank Submission; NIH/NCBI, Accession No. AAC74746; Blattner et al.; Sep. 1, 2011.

Genbank Submission; NIH/NCBI, Accession No. AAC74849; Blattner et al.; Sep. 1, 2011.

Genbank Submission; NIH/NCBI, Accession No. AAC74924; Blattner et al.; Sep. 1, 2011.

Genbank Submission; NIH/NCBI, Accession No. AAC75447; Blattner et al.; Sep. 1, 2011.

Genbank Submission; NIH/NCBI, Accession No. AAC75821; Blattner et al.; Sep. 1, 2011.

Genbank Submission; NIH/NCBI, Accession No. AAC75962; Blattner et al.; Sep. 1, 2011.

Genbank Submission; NIH/NCBI, Accession No. AAC75963; Blattner et al.; Sep. 1, 2011.

Genbank Submission; NIH/NCBI, Accession No. AAC76849; Blattner et al.; Sep. 1, 2011.

Genbank Submission; NIH/NCBI, Accession No. AAC76898; Blattner et al.; Sep. 1, 2011.

Genbank Submission; NIH/NCBI, Accession No. AAC76901; Blattner et al.; Sep. 1, 2011.

Genbank Submission; NIH/NCBI, Accession No. AAC76995; Blattner et al.; Sep. 1, 2011.

Genbank Submission; NIH/NCBI, Accession No. AAD38229; McGowan et al.; Jul. 14, 1999.

Genbank Submission; NIH/NCBI, Accession No. AAD38230; McGowan et al.; Jul. 14, 1999.

Genbank Submission; NIH/NCBI, Accession No. AAD38231; McGowan et al.; Jul. 14, 1999.

Genbank Submission; NIH/NCBI, Accession No. ABA79923; Copeland et al.; Nov. 21, 2011.

Genbank Submission; NIH/NCBI, Accession No. ACJ71669; Erb et al.; Dec. 10, 2008.

(56) References Cited

OTHER PUBLICATIONS

Genbank Submission; NIH/NCBI, Accession No. AEW99093; Ou et al.; Dec. 29, 2011.
Genbank Submission; NIH/NCBI, Accession No. AEW99097; Ou et al.; Dec. 29, 2011.
Genbank Submission; NIH/NCBI, Accession No. AEW99098; Ou et al.; Dec. 29, 2011.
Genbank Submission; NIH/NCBI, Accession No. BAA22406; Mori et al.; Sep. 20, 1997.
Genbank Submission; NIH/NCBI, Accession No. BAB67276; Kawarabayasi et al.; Aug. 17, 2011.
Genbank Submission; NIH/NCBI, Accession No. CAD18973; Nunez et al.; Apr. 15, 2005.
Genbank Submission; NIH/NCBI, Accession No. CAD18975; Nunez et al.; Apr. 15, 2005.
Genbank Submission; NIH/NCBI, Accession No. CAD18981; Nunez et al.; Apr. 15, 2005.
Genbank Submission; NIH/NCBI, Accession No. CAD18985; Nunez et al.; Apr. 15, 2005.
Genbank Submission; NIH/NCBI, Accession No. CAD18990; Nunez et al.; Apr. 15, 2005.
Ger et al., A single Ser-180 mutation desensitizes feedback inhibition of the phenylalanine-sensitive3-deoxy-D-arabino-heptulosonate 7-phosphate (DAHP) synthetase in *Escherichia coli*. J Biochem. Nov. 1994;116(5):986-90.
Gibellini et al., Biochemical characterization of the initial steps of the Kennedy pathway in Trypanosoma brucei: the ethanolamine and choline kinases. Biochem J. 2008;415:135-44. Supplemental material included.
Goerke et al., Cell-free metabolic engineering promotes high-level production of bioactive Gaussia princeps luciferase.Metab Eng. May-Jul. 2008;10(3-4):187-200. doi: 10.1016/j.ymben.2008.04. 001. Epub May 2, 2008.
Goerke et al., Development of cell-free protein synthesis platforms for disulfide bonded proteins. Biotechnol Bioeng. Feb. 1, 2008;99(2):351-67. Epub Jul. 11, 2007.
Gordon-Kamm et al., Transformation of Maize Cells and Regeneration of Fertile Transgenic Plants. Plant Cell. Jul. 1990;2(7):603-618.
Gosset et al., A direct comparison of approaches for increasing carbon flow to aromatic biosynthesis in *Escherichia coli*. J Ind Microbiol. Jul. 1996;17(1):47-52.
Grabowski, Enantiopure drug synthesis: from methyldopa to imipenem to efavirenz. Chirality. 2005;17 Suppl:S249-59.
Grieco et al., β-Lactam antibiotics: a formal stereocontrolled total synthesis of (.+-.)-thienamycin. J Am Chem Soc. 1984;106(21):6414-7.
Grunstein et al., Colony hybridization: a method for the isolation of cloned DNAs that contain a specific gene. Proc Natl Acad Sci U S A. Oct. 1975;72(10):3961-5.
Hamed et al., Carboxymethylproline synthase catalysed syntheses of functionalized N-heterocycles. Chem Commun (Camb). Mar. 7, 2010;46(9):1413-5. Epub Jan. 12, 2010.
Hamed et al., Crotonase catalysis enables flexible production of functionalized prolines and carbapenams. J Am Chem Soc. Jan. 11, 2012;134(1):471-9. doi: 10.1021/ja208318d. Epub Dec. 14, 2011.
Hamed et al., Evidence that thienamycin biosynthesis proceeds via C-5 epimerization: I catalyzes the formation of (2S,5S)-trans-carboxymethylproline. Chembiochem. Jan. 26, 2009;10(2):246-50.
Hamed et al., The enzymes of β-lactam biosynthesis. Nat Prod Rep. Jan. 2013;30(1):21-107. doi: 10.1039/c2np20065a.
Han et al., Paraffin oil as a "methane vector" for rapid and high cell density cultivation of Methylosinus trichosporium OB3b. Appl Microbiol Biotechnol. Jun. 2009;83(4):669-77. doi: 10.1007/s00253-009-1866-2. Epub Feb. 12, 2009.
Hawley et al., Compilation and analysis of *Escherichia coli* promoter DNA sequences. Nucleic Acids Res. Apr. 25, 1983;11(8):2237-55.
Herrmann, The shikimate pathway as an entry to aromatic secondary metabolism. Plant Physiol. Jan. 1995;107(1):7-12.
Hikita et al., Effects of total hydrophobicity and length of the hydrophobic domain of a signal peptide on in vitro translocation efficiency. J Biol Chem. 1992;267:4882-8.
Hikita et al., The requirement of a positive charge at the amino terminus can be compensated for by a longer central hydrophobic stretch in the functioning of signal peptides. J Biol Chem. 1992;267:12375-9.
Hodgson et al., π-Allyltricarbonyliron lactone complexes in synthesis: application to the synthesis of the β-lactam antibiotic (+)-thienamycin. J Chem Soc Chem Comm 1984;8:494-6.
Inouye, The discovery of mRNA interferases: implication in bacterial physiology and application to biotechnology. J Cell Physiol. Dec. 2006;209(3):670-6.
Ishii et al., DBTBS: a database of Bacillus subtilis promoters and transcription factors. Nucleic Acids Res. Jan. 1, 2001;29(1):278-80.
Jacobi et al., Formal Total Syntheses of the β-Lactam Antibiotics Thienamycin and PS-5. J Org Chem. 1996;61(7):2413-27.
Jang et al., Sugar sensing in higher plants. Plant Cell. Nov. 1994;6(11):1665-79.
Jermutus et al., Recent advances in producing and selecting functional proteins by using cell-free translation. Curr Opin Biotechnol. Oct. 1998;9(5):534-48.
Jewett et al., an integrated cell-free metabolic platform for protein production and synthetic biology. Mol Syst Biol. 2008;4:220. Epub Oct. 14, 2008.
Jewett et al., Mimicking the *Escherichia coli* cytoplasmic environment activates long-lived and efficient cell-free protein synthesis. Biotechnol Bioeng. Apr. 5, 2004;86(1):19-26.
Kahan et al., Thienamycin, a new beta-lactam antibiotic. I. Discovery, taxonomy, isolation and physical properties. J Antibiot (Tokyo). Jan. 1979;32(1):1-12.
Kahan et al., Thienamycin: development of imipenen-cilastatin. J Antimicrob Chemother. Dec. 1983;12 Suppl D:1-35.
Kalderon et al., A short amino acid sequence able to specify nuclear location. Cell. Dec. 1984;39(3 Pt 2):499-509.
Kametani et al., Studies on the syntheses of heterocyclic compounds. 800. A formal total synthesis of (.+-.)-thienamycin and a (.+-.)-decysteaminylthienamycin derivative. J Am Chem Soc. 1980;102(6):2060-5.
Kapust et al., Tobacco etch virus protease: mechanism of autolysis and rational design of stable mutants with wild-type catalytic proficiency. Protein Eng. Dec. 2001;14(12):993-1000.
Kern et al., Engineering primary metabolic pathways of industrial micro-organisms. J Biotechnol. Mar. 30, 2007;129(1):6-29. Epub Dec. 2, 2006.
Kikuchi et al., Mutational analysis of the feedback sites of phenylalanine-sensitive 3-deoxy-D-arabino-heptulosonate-7-phosphate synthase of *Escherichia coli*. Appl Environ Microbiol. Feb. 1997;63(2):761-2.
Kim et al., Expression, purification, and characterization of choline kinase, product of the cki gene from *Saccharomyces cerevisiae*. J Bio Chem. 1998;273(12):6844-6852.
Kim et al., Metabolic flux analysis for calcium dependent antibiotic (CDA) production in Streptomyces coelicolor. Metab Eng. Oct. 2004;6(4):313-25.
Kim et al., Prolonged cell-free protein synthesis using dual energy sources: Combined use of creatine phosphate and glucose for the efficient supply of ATP and retarded accumulation of phosphate. Biotechnol Bioeng. Aug. 15, 2007;97(6):1510-5.
Kimmel, Identification and characterization of specific clones: strategy for confirming the validity of presumptive clones. Methods Enzymol. 1987;152:507-11.
Kindle, High-frequency nuclear transformation of Chlamydomonas reinhardtii. Proc Natl Acad Sci U S A. Feb. 1990;87(3):1228-32.
Knapp et al., Cell-free production of active *E. coli* thioredoxin reductase and glutathione reductase. FEBS Lett. Feb. 13, 2004;559(1-3):66-70.
Knop et al., Hydroaromatic equilibration during biosynthesis of shikimic acid. J Am Chem Soc. Oct. 24, 2001;123(42):10173-82.
Ko et al., Targeting of proteins to the thylakoid lumen by the bipartite transit peptide of the 33 kd oxygen-evolving protein. EMBO J. Nov. 1989;8(11):3187-94.

(56) References Cited

OTHER PUBLICATIONS

Krämer et al., Metabolic engineering for microbial production of shikimic acid. Metab Eng. Oct. 2003;5(4):277-83.
Krell et al., Crystallization and preliminary X-ray crystallographic analysis of shikimate kinase from Erwinia chrysanthemi. Acta Crystallogr D Biol Crystallogr. Sep. 1, 1997;53(Pt 5):612-4.
Krutsakorn et al., In vitro production of n-butanol from glucose. Metab Eng. Nov. 2013;20:84-91. doi: 10.1016/j.ymben.2013.09.006. Epub Sep. 19, 2013.
Kumagai et al., Current status of oral carbapenem development. Curr Med Chem—Anti-Infective Agents. Jan. 2002;1(1):1-14.
Kunkel, Rapid and efficient site-specific mutagenesis without phenotypic selection. Proc Natl Acad Sci U S A. Jan. 1985;82(2):488-92.
Lee et al., Fermentative production of thymidine by a metabolically engineered *Escherichia coli* strain. Appl Environ Microbiol. Apr. 2009;75(8):2423-32. Epub Feb. 27, 2009.
Lee et al., Systems metabolic engineering of *Escherichia coli* for L-threonine production. Mol Syst Biol. 2007;3:149. Epub Dec. 4, 2007.
Lee, High cell-density culture of *Escherichia coli*. Trends Biotechnol. Mar. 1996;14(3):98-105.
Liu et al., Streamlining *Escherichia coli* S30 extract preparation for economical cell-free protein synthesis. Biotechnol Prog. Mar.-Apr. 2005;21(2):460-5.
Ludwig et al., Mutations affecting export and activity of cytolysin A from *Escherichia coli*. J Bacteriol. Aug. 2010;192(15):4001-11. Epub May 28, 2010.
Luli et al., Comparison of growth, acetate production, and acetate inhibition of *Escherichia coli* strains in batch and fed-batch fermentations. Appl Environ Microbiol. Apr. 1990;56(4):1004-11.
Mackle et al., Role of signal peptides in targeting of proteins in cyanobacteria. J Bacteriol. Apr. 1994;176(7): 1857-64.
Mandel et al., Modular synthesis of pantetheine and phosphopantetheine. Org Lett. Dec. 23, 2004;6(26):4801-3.
Martin et al., Engineering a mevalonate pathway in *Escherichia coli* for production of terpenoids. Nat Biotechnol. Jul. 2003;21(7):796-802. Epub Jun. 1, 2003.
Mergulhão et al., Analysis of factors affecting the periplasmic production of recombinant proteins in *Escherichia coli*. J Microbiol Biotechnol. Aug. 2007;17(8):1236-41.
Mergulhão et al., Recombinant protein secretion in *Escherichia coli*. Biotechnol Adv. May 2005;23(3):177-202. Epub Jan. 8, 2005.
Meyerhof, New investigations in the kinetics of cell free alcoholic fermentation. Antonie Van Leeuwenhoek. Jan.-Apr. 1947;12(1-4):140-4.
Meynial-Salles et al., New tool for metabolic pathway engineering in *Escherichia coli*: one-step method to modulate expression of chromosomal genes. Appl Environ Microbiol. Apr. 2005;71(4):2140-4.
Michel-Reydellet et al., Amino acid stabilization for cell-free protein synthesis by modification of the *Escherichia coli* genome. Metab Eng. Jul. 2004;6(3):197-203.
Muchmore et al., Crystal structure of glutamine phosphoribosylpyrophosphate amidotransferase from *Escherichia coli*.Protein Sci. Jan. 1998;7(1):39-51.
Muktiono et al., Isolation and purification assay of ex vivo photosystem II D1 protein toward integrated biointeraction analysis. Anal Bioanal Chem. Feb. 2008;390(4):1195-202. Epub Jan. 3, 2008.
Murphy, Use of bacteriophage lambda recombination functions to promote gene replacement in *Escherichia coli*. J Bacteriol. Apr. 1998;180(8):2063-71.
Myers et al., Determination of imipenem and cilastatin in serum by high-pressure liquid chromatography. Antimicrob Agents Chemother. Jul. 1984;26(1):78-81.
Narang et al., Improved phosphotriester method for the synthesis of gene fragments. Methods Enzymol. 1979;68:90-8.
Neidhardt et al., Culture medium for enterobacteria. J Bacteriol. Sep. 1974;119(3):736-47.

Ninh et al., Assembly and multiple gene expression of thermophilic enzymes in *Escherichia coli* for in vitro metabolic engineering. Biotechnol Bioeng. Jul. 26, 2014. doi: 10.1002/bit.25338.
Niu et al., Benzene-free synthesis of adipic acid. Biotechnol Prog. Mar.-Apr. 2002;18(2):201-11.
Nunez et al., The Biosynthetic Gene Cluster for the β-Lactam Carbapenem Thienamycin in Streptomyces cattleya. Chem Biol. Apr. 2003;10(4):301-11.
Ono et al., Photosynthetic electron transport and phosphorylation reactions in thylakoid membranes from the blue-green alga Anacystis nidulans. Biochim Biophys Acta. Jun. 8, 1978;502(3):477-85.
Pace et al., Photosynthetic regeneration of ATP using bacterial chromatophores. Biotechnol Bioeng. Oct. 1976;18(10):1413-23.
Park et al., Metal-catalyzed oxidation of phenylalanine-sensitive 3-deoxy-D-arabino heptulosonate-7-phosphate synthase from *Escherichia coli*: inactivation and destabilization by oxidation of active-site cysteines. J Bacteriol. Mar. 1999;181(5):1636-42.
Patnaik et al., Engineering of Escherichia coli central metabolism for aromatic metabolite production with near theoretical yield. Appl Environ Microbiol. Nov. 1994;60(11):3903-8.
Paul et al., Photophosphorylation in bacterial chromatophores entrapped in alginate gel: Improvement of the physical and biochemical properties of gel beads with barium as gel-inducing agent. Enzyme Microb Technol. 1980;2(4):281-87.
Peralta-Yahya et al., Microbial engineering for the production of advanced biofuels. Nature. Aug. 16, 2012;488(7411):320-8. doi: 10.1038/nature11478.
Pitera et al., Balancing a heterologous mevalonate pathway for improved isoprenoid production in *Escherichia coli*. Metab Eng. Mar. 2007;9(2):193-207. Epub Nov. 6, 2006.
Qi et al., A one-step PCR-based method for rapid and efficient site-directed fragment deletion, insertion, and substitution mutagenesis. J Virolog Meth. Apr. 2008;149(1):85-90.
Ray et al., Mutational analysis of the catalytic and feedback sites of the tryptophan-sensitive 3-deoxy-D-arabino-heptulosonate-7-phosphate synthase of *Escherichia coli*. J Bacteriol. Dec. 1988;170(12):5500-6.
Reider et al., Total synthesis of thienamycin: a new approach from aspartic acid. Tetra Lett. 1982;23(22):2293-6.
Reyes et al., Genomic library screens for genes involved in n-butanol tolerance in *Escherichia coli*. PloS One. Mar. 8, 2011;6(3):e17678.
Rodríguez et al., Identification of transcriptional activators for thienamycin and cephamycin C biosynthetic genes within the thienamycin gene cluster from Streptomyces cattleya. Mol Microbiol. Aug. 2008;69(3):633-45.
Rodríguez et al., Transcriptional organization of ThnI-regulated thienamycin biosynthetic genes in Streptomyces cattleya. J Antibiot (Tokyo). Mar. 2010;63(3):135-8. Epub Jan. 22, 2010.
Romanowski et al., Crystal structure of the *Escherichia coli* shikimate kinase I (AroK) that confers sensitivity to mecillinam. Proteins. Jun. 1, 2002;47(4):558-62.
Sagui et al., Enzymatic synthesis of ω-carboxy-β-hydroxy-(l)-α-amino acids. Tetrahedron. May 26, 2008;64(22):5079-84.
Salis et al., Automated design of synthetic ribosome binding sites to control protein expression. Nat Biotechnol. Oct. 2009;27(10):946-50. Epub Oct. 4, 2009. Supplemental material included.
Salzmann et al., A stereocontrolled synthesis of (+)-thienamycin. J Am Chem Soc. 1980;102(19):6161-3.
Salzmann et al., A stereocontrolled, enantiomerically specific total synthesis of thienamycin. Philos Trans R Soc Lond B Biol Sci. May 16, 1980;289(1036):191-5.
Sarath et al., Use of GFP as a reporter for the analysis of sequence-specific proteases. Curr Protoc Protein Sci. Feb. 2001;Chapter 21 Unit 9 Suppl. 26: 21.9.1-.10.
Sato et al., Poly[(R)-3-hydroxybutyrate] formation in *Escherichia coli* from glucose through an enoyl-CoA hydratase-mediated pathway. J Biosci Bioeng. Jan. 2007;103(1):38-44.
Sauer et al., The soluble and membrane-bound transhydrogenases UdhA and PntAB have divergent functions in NADPH metabolism of *Escherichia coli*. J Biol Chem. Feb. 20, 2004;279(8):6613-9. Epub Dec. 3, 2003.

(56) References Cited

OTHER PUBLICATIONS

Schlehuber et al., Prediction and identification of a permissive epitope insertion site in the vesicular stomatitis virus glycoprotein. J Virol. May 2004;78(10):5079-87.
Schnell, Protein targeting to the thylakoid membrane. Annu Rev Plant Physiol Plant Mol Biol. Jun. 1998;49:97-126.
Scopes, Glycolysis in cell-free systems. New beer in an old bottle: Eduard Buchner and the growth of biochemical knowledge. Ed A. Cornish-Bowden. 1997;151-8.
Sheen, Metabolic repression of transcription in higher plants. Plant Cell. Oct. 1990;2(10):1027-38.
Shi et al., Molecular properties, functions, and potential applications of NAD kinases. Acta Biochim Biophys Sin (Shanghai). May 2009;41(5):352-61.
Shine et al., Determinant of cistron specificity in bacterial ribosomes. Nature. Mar. 6, 1975;254(5495):34-8.
Simmons et al., Translational level is a critical factor for the secretion of heterologous proteins in *Escherichia coli*. Nat Biotechnol. May 1996;14(5):629-34.
Sleeman et al., Carboxymethylproline synthase (CarB), an unusual carbon-carbon bond-forming enzyme of the crotonase superfamily involved in carbapenem biosynthesis. J Biol Chem. Feb. 20, 2004;279(8):6730-6. Epub Nov. 18, 2003.
Soares et al., Periplasmic expression of human growth hormone via plasmid vectors containing the lambdaPL promoter: use of HPLC for product quantification. Protein Eng. Dec. 2003;16(12):1131-8.
Sorci et al., Nicotinamide mononucleotide synthetase is the key enzyme for an alternative route of NAD biosynthesis in Francisella tularensis.Proc Natl Acad Sci U S A. Mar. 3, 2009;106(9):3083-8. Epub Feb. 9, 2009. Supplemental material included.
Srinivasan et al., The Enzymatic Synthesis of Shikimic Acid From D-Erythrose-4-Phosphate and Phosphoenolpyruvate1,2,3. J. Am. Chem. Soc. 1955;77(18):4943-4944.
Stadtman et al., Metal-catalyzed oxidation of proteins. Physiological consequences. J Biol Chem. Feb. 5, 1991;266(4):2005-8.
Stapon et al., Synthesis of (3S,5R)-carbapenam-3-carboxylic acid and its role in carbapenem biosynthesis and the stereoinversion problem. J Am Chem Soc. Dec. 24, 2003;125(51):15746-7.
Stephanopoulos et al., Exploiting biological complexity for strain improvement through systems biology. Nat Biotechnol. Oct. 2004;22(10):1261-7.
Suzuki et al., Single protein production (SPP) system in *Escherichia coli*. Nat Protoc. 2007;2(7):1802-10.
Suzuki et al., Single protein production in living cells facilitated by an mRNA interferase. Mol Cell. Apr. 15, 2005;18(2):253-61.
Swartz et al., Advances in *Escherichia coli* production of therapeutic proteins. Curr Opin Biotechnol. Apr. 2001;12(2):195-201.
Swartz, Developing cell-free biology for industrial applications. J Ind Microbiol Biotechnol. Jul. 2006;33(7):476-85. Epub May 9, 2006. Review.
Swartz, Transforming biochemical engineering with cell-free biology. AIChE J. 2012;58(1):5-13.
Sybesma et al., Increased production of folate by metabolic engineering of Lactococcus lactis. Appl Environ Microbiol. Jun. 2003;69(6):3069-76.
Tjalsma et al., Proteomics of protein secretion by Bacillus subtilis: separating the "secrets" of the secretome. Microbiol Mol Biol Rev. Jun. 2004;68(2):207-33.
Tracewell et al., Directed enzyme evolution: climbing fitness peaks one amino acid at a time. Curr Opin Chem Biol. Feb. 2009;13(1):3-9. Epub Feb. 25, 2009.
Tyo et al., Analysis of polyhydroxybutyrate flux limitations by systematic genetic and metabolic perturbations. Metab Eng. May 2010;12(3):187-95. Epub Oct. 30, 2009.
UniProtKB/Swiss-Prot; Accession No. P28269; Yonaha et al.; Jul. 11, 2012.
Van Bloois et al., Export of functional Streptomyces coelicolor alditol oxidase to the periplasm or cell surface of *Escherichia coli* and its application in whole-cell biocatalysis. Appl Microbiol Biotechnol. Jun. 2009;83(4):679-87. Epub Feb. 18, 2009.
Van Hees et al., Determination of low molecular weight organic acids in soil solution by HPLC. Talanta. Jan. 5, 1999;48(1):173-9.
Voloshin et al., Efficient and scalable method for scaling up cell free protein synthesis in batch mode. Biotechnol Bioeng. Aug. 20, 2005;91(4):516-21.
Wahl et al., Molecular hybridization of immobilized nucleic acids: theoretical concepts and practical considerations. Methods Enzymol. 1987;152:399-407.
Wang et al., Programming cells by multiplex genome engineering and accelerated evolution. Nature. Aug. 13, 2009;460(7257):894-8. Epub Jul. 26, 2009.
Ward et al., Genomic insights into methanotrophy: the complete genome sequence of Methylococcus capsulatus (Bath). Plos Biology. 2004;2(10):1616-28.
Weaver et al., Cloning of an aroF allele encoding a tyrosine-insensitive 3-deoxy-D-arabino-heptulosonate 7-phosphate synthase. J Bacteriol. Nov. 1990;172(11):6581-4.
Welch et al., Studies on cell-free metabolism: Ethanol production by a yeast glycolytic system reconstituted from purified enzymes. J Biotechnol. 1985;2:257-73.
Wiechert et al., A universal framework for 13C metabolic flux analysis. Metab Eng. Jul. 2001;3(3):265-83.
Wiechert, 13C metabolic flux analysis. Metab Eng. Jul. 2001;3(3):195-206.
Wilen et al., Tetrahedron report No. 38: Strategies in optical resolutions. Tetrahedron. 1977;33:2725-2736.
Williamson et al., Biosynthesis of the beta-lactam antibiotic, thienamycin, by Streptomyces cattleya. J Biol Chem. Apr. 25, 1985;260(8):4637-47.
Wilson et al., the shikimic acid pathway and polyketide biosynthesis. J Indust Microbiol Biotechnol. 1998;20:299-303.
Withers et al., Identification of isopentenol biosynthetic genes from Bacillus subtilis by a screening method based on isoprenoid precursor toxicity. Appl Environ Microbiol. Oct. 2007;73(19):6277-83. Epub Aug. 10, 2007.
Woodrow et al., A sequential expression system for high-throughput functional genomic analysis. Proteomics. Nov. 2007;7(21):3870-9.
Woodrow et al., Rapid expression of functional genomic libraries. J Proteome Res. Dec. 2006;5(12):3288-300.
Wylie et al., A single point mutation in ctp synthetase of chlamydia trachomatis confers resistance to cyclopentenyl cytosine. J Biol Chem. 1996;271:15393-400.
Yamaguchi et al., MqsR, a crucial regulator for quorum sensing and biofilm formation, is a GCU-specific mRNA interferase in *Escherichia coli*. J Biol Chem. Oct. 16, 2009;284(42):28746-53. Epub Aug. 18, 2009.
Yamaguchi et al., mRNA interferases, sequence-specific endoribonucleases from the toxin-antitoxin systems. Prog Mol Biol Transl Sci. 2009;85:467-500.
Yang et al., Export of methyl parathion hydrolase to the periplasm by the twin-arginine translocation pathway in *Escherichia coli*. J Agric Food Chem. Oct. 14, 2009;57(19):8901-5.
Yang et al., Rapid expression of vaccine proteins for B-cell lymphoma in a cell-free system. Biotechnol Bioeng. Mar. 5, 2005;89(5):503-11.
Ye et al., Synthetic metabolic engineering—a novel, simple technology for designing a chimeric metabolic pathway. Microb Cell Fact. Sep. 6, 2012;11:120. doi: 10.1186/1475-2859-11-120.
Yeo et al., Plasmodium falciparum CTP:phosphocholine cytidylyltransferase expressed in *Escherichia coli*: purification, characterization and lipid regulation. Biochem J. 1997;324:903-10.
Yu et al., Production of high-quality particulate methane monooxygenase in high yields from Methylococcus capsulatus (bath) with a hollow-fiber membrane bioreactor. J Bacteriol. Oct. 2003;185(20):5915-24.
Zamboni et al., 13C-based metabolic flux analysis. Nat Protoc. 2009;4(6):878-92. Epub May 21, 2009.
Zawada et al., Effects of growth rate on cell extract performance in cell-free protein synthesis. Biotechnol Bioeng. Jul. 5, 2006;94(4):618-24.
Zawada et al., Maintaining rapid growth in moderate-density *Escherichia coli* fermentations. Biotechnol Bioeng. Feb. 20, 2005;89(4):407-15.

(56) References Cited

OTHER PUBLICATIONS

Zhang et al., Characterization of ChpBK, an mRNA interferase from *Escherichia coli*. J Biol Chem. Jul. 15, 2005;280(28):26080-8. Epub May 18, 2005.
Zhang et al., Characterization of YafO, an *Escherichia coli* toxin. J Biol Chem. Sep. 18, 2009;284(38):25522-31. Epub Jul. 17, 2009.
Zhang et al., Efficient regeneration of transgenic plants from rice protoplasts and correctly regulated expression of the foreign gene in the plants. Theor Appl Genet. 1988;76(6):835-40.
Zhang et al., Insights into the mRNA cleavage mechanism by MazF, an mRNA interferase. J Biol Chem. Feb. 4, 2005;280(5):3143-50. Epub Nov. 10, 2004.
Extended European Search Report for EP09835395.6, mailed Mar. 16, 2016.
International Preliminary Report on Patentability for PCT/US2013/077238, mailed Jul. 2, 2015.
International Preliminary Report on Patentability for PCT/US2014/049805, mailed Feb. 18, 2016.
International Preliminary Report on Patentability for PCT/US2014/041009, mailed Dec. 17, 2015.
[No Author Listed] Crude Lysate. Wikipedia entry for Crude Lysate, http://en.wikipedia.org/wiki/Crude_lysate downloaded on Mar. 3, 2015. Page Last Modified on Nov. 3, 2013. 1 page.
Brady et al.,Transfer of Pantoea citrea, Pantoea punctata and Pantoea terrea to the genus *Tatumella* emend. as *Tatumella citrea* comb. nov., *Tatumella punctata* comb. nov. and *Tatumella terrea* comb. nov. and description of *Tatumella morbirosei* sp. nov. Int J Syst Evol Microbiol. Mar. 2010;60(Pt 3):484-94. doi: 10.1099/ijs.0.012070-0. Epub Aug. 4, 2009.
Chisti et al., Disruption of microbial cells for intracellular products. Enzyme Micro Technol 1986;8(4):194-204. doi 10.1016/0141-0229(86)90087-6.
Daube et al., Cell-free co-synthesis of protein nanoassemblies: tubes, rings, and doughnuts. Nano Lett. Mar. 2007;7(3):638-41. Epub Feb. 2, 2007.
Eser et al.,Target-directed proteolysis in vivo. Methods Enzymol. 2007;421:68-83.
Fujio et al., Production of ATP from Adenine by *Brevibacterium ammoniagenes*, J Ferment Technol. 1983;61(3):261-267.
Horak et al., Two distinct proteolytic systems responsible for glucose-induced degradation of fructose-1,6-bisphosphatase and the Gal2p transporter in the yeast *Saccharomyces cerevisiae* share the same protein components of the glucose signaling pathway. J Biol Chem. Mar. 8, 2002;277(10):8248-54. Epub Dec. 28, 2001.
Hryniewicz et al., Sulfate and thiosulfate transport in *Escherichia coli* K-12: identification of a gene encoding a novel protein involved in thiosulfate binding. J Bacteriol. Jun. 1990;172(6):3358-66.
Jenny et al., A critical review of the methods for cleavage of fusion proteins with thrombin and factor Xa. Protein Expr Purif. Sep. 2003;31(1):1-11.
Kang et al., Enhanced biodegradation of toxic organophosphate compounds using recombinant *Escherichia coli* with sec pathway-driven periplasmic secretion of organophosphorus hydrolase. Biotechnol Prog. Mar.-Apr. 2006;22(2):406-10.
Kawarasaki et al., Prolonged cell-free protein synthesis in a batch system using wheat germ extract.Biosci Biotechnol Biochem. Oct. 1994;58(10):1911-3.
Kim et al., Regeneration of adenosine triphosphate from glycolytic intermediates for cell-free protein synthesis.Biotechnol Bioeng. Aug. 20, 2001;74(4):309-16.
Klemme, Photoproduction of hydrogen by purple bacteria:A critical evaluation of the rate limiting enzymatic steps. J Bioscience 1993;48 482-87.
Li et al., Rational strain improvement for enhanced clavulanic acid production by genetic engineering of the glycolytic pathway in *Streptomyces clavuligerus*. Metab Eng. May 2006;8(3):240-52. Epub Mar. 10, 2006.

Liu et al., Combined biosynthetic pathway for de novo production of UDP-galactose: catalysis with multiple enzymes immobilized on agarose beads. Chembiochem. Apr. 2, 2002;3(4):348-55.
Mayes, Metabolism of Glycogen. In: Harper's Biochemistry—a LANGE medical book. 1990. Twenty-second edition. Murray et al., Eds. Chapter 20: 171-178.
Noireaux et al., Principles of cell-free genetic circuit assembly. Proc Natl Acad Sci U S A. Oct. 28, 2003;100(22):12672-7. Epub Oct. 14, 2003.
Schierle et al., the DsbA signal sequence directs efficient, cotranslational export of passenger proteins to the *Escherichia coli* periplasm via the signal recognition particle pathway. J Bacteriol. Oct. 2003;185(19):5706-13.
Schultheisz et al., Pathway engineered enzymatic de novo purine nucleotide synthesis. ACS Chem Biol. Aug. 15, 2008;3(8):499-511. doi: 10.1021/cb800066p.
Scopes, Studies with a reconstituted muscle glycolytic system. The anaerobic glycolytic response to simulated tetanic contraction. Biochem J. Jan. 1974;138(1):119-23.
Spirin, High-throughput cell-free systems for synthesis of functionally active proteins.Trends Biotechnol. Oct. 2004;22(10):538-45. With Supplementary data.
Sroga et al., Periplasmic expression as a basis for whole cell kinetic screening of unnatural enzyme reactivities. Methods Enzymol. 2004;388:145-56.
Stapon et al., Carbapenem biosynthesis: confirmation of stereochemical assignments and the role of CarC in the ring stereoinversion process from L-proline. J Am Chem Soc. Jul. 16, 2003;125(28):8486-93.
Swartz, Universal cell-free protein synthesis. Nat Biotechnol. Aug. 2009;27(8):731-2. doi: 10.1038/nbt0809-731.
Thöny-Meyer et al., Translocation to the periplasm and signal sequence cleavage of preapocytochrome c depend on sec and lep, but not on the ccm gene products. Eur J Biochem. Jun. 15, 1997;246(3):794-9.
Wuu et al., High yield cell-free production of integral membrane proteins without refolding or detergents. Biochim Biophys Acta. May 2008;1778(5):1237-50. doi: 10.1016/j.bbamem.2008.01.023. Epub Feb. 11, 2008.
Invitation to Pay Additional Fees for PCT/US2016/023173, mailed Jul. 8, 2016.
International Search Report and Written Opinion for PCT/US2016/023173, mailed Sep. 16, 2016.
International Search Report and Written Opinion for PCT/US2016/024937, mailed Sep. 9, 2016.
Goody, A simple and rapid method for the synthesis of nucleoside 5'-monophosphates enriched with 17O or 18O on the phosphate group. Anal Biochem. Jan. 15, 1982;119(2):322-4.
Jonnalagadda et al., Flux regulation in glycogen-induced oscillatory glycolysis in cell-free extracts of *Saccharomyces carlsbergensis*. Biosystems. 1982;15(1):49-58.
Pines et al., Expression and secretion of proteins in *E. coli*. Mol Biotechnol. Aug. 1999;12(1):25-34.
Spickler et al., Action of RNase II and polynucleotide phosphorylase against RNAs containing stem-loops of defined structure. J Bacteriol. May 2000;182(9):2422-7.
Stazic et al., Antisense RNA protects mRNA from RNase E degradation by RNA-RNA duplex formation during phage infection. Nucleic Acids Res. Jun. 2011;39(11):4890-9. doi: 10.1093/nar/gkr037. Epub Feb. 15, 2011.
Vander Heiden et al., Understanding the Warburg effect: the metabolic requirements of cell proliferation. Science. May 22, 2009;324(5930):1029-33. doi: 10.1126/science.1160809.
Zago et al., Cloning and characterization of polyphosphate kinase and exopolyphosphatase genes from Pseudomonas aeruginosa 8830. Appl Environ Microbiol. May 1999;65(5):2065-71.

\* cited by examiner

FIGURE 1A

HRV Protease Recognition Sequence

Amino Acids: L E V L F Q G P (SEQ ID NO:38)
Nucleotides: CTG GAA GTG CTG TTT CAG GGT CCG (SEQ ID NO:69)

Pgi Amino Acid Sequence: M K N I N P T Q T A A ... (SEQ ID NO:70)
pgi Nucleotide Sequence: ATG AAA AAC ATC AAT CCA ACG CAG ACC GCT GCC (SEQ ID NO:71)

SEQ ID Nos.:

Pgi-HRV-I001 Amino Acid Sequence: M L E V L F Q G P K N I N P T Q T A A ... 72
pgi-hrv-I001 Nucleotide Sequence: ATG CTG GAA GTG CTG TTT CAG GGT CCG AAA AAC ATC AAT CCA ACG CAG ACC GCT GCC ... 73

Pgi-HRV-I002 Amino Acid Sequence: M K L E V L F Q G P K I N P T Q T A A ... 74
pgi-hrv-I002 Nucleotide Sequence: ATG AAA CTG GAA GTG CTG TTT CAG GGT CCG AAC ATC AAT CCA ACG CAG ACC GCT GCC ... 75

Pgi-HRV-I003 Amino Acid Sequence: M K N L E V L F Q G P I N P T Q T A A ... 76
pgi-hrv-I003 Nucleotide Sequence: ATG AAA AAC CTG GAA GTG CTG TTT CAG GGT CCG ATC AAT CCA ACG CAG ACC GCT GCC ... 77

FIGURE 1B

HRV Protease Recognition Sequence

Amino Acids: L E V L F Q G P (SEQ ID NO:38)
Nucleotides: CTG GAA GTG CTG TTT CAG GGT CCG (SEQ ID NO:69)

Pgi Amino Acid Sequence: M K N I N P T Q T A A ... (SEQ ID NO:70)
pgi Nucleotide Sequence: ATG AAA AAC ATC AAT CCA ACG CAG ACC GCT GCC (SEQ ID NO:71)

SEQ ID Nos.:

Pgi-HRV-R001 Amino Acid Sequence: M L E V L F Q G P A A ... 78
pgi-hrv-R001 Nucleotide Sequence: ATG CTG GAA GTG CTG TTT CAG GGT CCG GCT GCC ... 79

Pgi-HRV-R002 Amino Acid Sequence: M K L E V L F Q G P A ... 80
pgi-hrv-R002 Nucleotide Sequence: ATG AAA CTG GAA GTG CTG TTT CAG GGT CCG GCC ... 81

Pgi-HRV-R003 Amino Acid Sequence: M K N L E V L F Q G P ... 82
pgi-hrv-R003 Nucleotide Sequence: ATG AAA AAC CTG GAA GTG CTG TTT CAG GGT CCG ... 83

US 9,688,977 B2

ENGINEERED PHOSPHOGLUCOSE ISOMERASE PROTEINS WITH A PROTEASE CLEAVAGE SITE

RELATED APPLICATIONS

This application claims priority under 35 U.S.C. §119(e) to U.S. provisional patent applications, U.S. Ser. No. 61/862,363, filed Aug. 5, 2013, and U.S. Ser. No. 61/987,518, filed May 2, 2014, each of which is incorporated herein by reference.

BACKGROUND OF INVENTION

Metabolic engineering permits production of compounds through manipulation of biochemical reactions (e.g., biosynthetic pathways) in a cell. Nonetheless, production of certain compounds may conflict with essential cellular goals. For example, diversion of nutrients and energy for the production of a compound may result in a shortage of those substrates and cofactors for production of biomass. The engineered organism may either evolve away from producing the compound of interest or grow sub-optimally. To address this issue, cell-free systems have been developed for the in vitro production of compounds through coordinated expression of proteins in a biosynthetic pathway. One caveat to both in vivo and in vitro bioproduction systems is that many key proteins that divert flux from a biosynthetic pathway are also important or even essential for cell growth. Deletion or inactivation of these proteins is often difficult or impossible because doing so results in reduced cell growth or viability. One way to inactivate proteins is through protease-mediated inactivation. Protease-mediated inactivation of a target protein can be achieved through the incorporation of a protease recognition site in the primary amino acid sequence of the target protein. The protease recognition site can be incorporated into the primary sequence such that the resulting protein is active in the absence of a protease that cleaves the recognition site and inactive in the presence of the protease. Such engineered or recombinant target proteins are particularly useful for the cell-free synthesis of compounds of interest.

SUMMARY OF INVENTION

Provided herein are recombinant enzymes that can be inactivated selectively during in vitro cell-free production of a compound. Selective inactivation of recombinant enzymes is achieved by introducing, between two codons (e.g., two adjacent codons) in a gene that codes for the recombinant enzyme, at least one nucleotide sequence that codes for a protease recognition sequence. Prior to in vitro cell-free production of a compound, the cognate protease (i.e., a protease that specifically recognizes and cleaves the protease recognition sequence in the recombinant protein) is introduced to, or activated in, the cell-free system such that it can cleave the recombinant enzyme, thereby inactivating it. Also provided herein are methods of producing and screening for recombinant enzymes that can be inactivated selectively and that retain an activity level comparable to that of the wild-type enzymes.

In some aspects of the invention, provided herein are recombinant phosphoglucose isomerase (Pgi) proteins with at least one (or one) protease recognition sequence located between two amino acids (e.g., two adjacent amino acids) of the native protein. In other aspects, nucleic acids encoding the recombinant phosphoglucose isomerase proteins are provided.

In some embodiments, the Pgi protein comprises the sequence of SEQ ID NO:17. In certain embodiments, the Pgi protein may comprise a sequence that is 90%, 95%, 98%, or 99% homologous to SEQ ID NO:25. In some embodiments, the nucleic acid encoding the Pgi protein comprises the sequence of SEQ ID NO:1 In certain embodiments, the nucleic acid encoding the Pgi protein may comprise a sequence that is 90%, 95%, 98%, or 99% homologous to SEQ ID NO:9.

In some aspects of the invention, provided herein are recombinant phosphotransacetylase (Pta) proteins with at least one (or one) protease recognition sequence located between two amino acids (e.g., two adjacent amino acids) of the native protein. In other aspects, nucleic acids encoding the recombinant phosphotransacetylase proteins are provided.

In some embodiments, the Pta protein comprises the sequence of SEQ ID NO:48. In certain embodiments, the Pta protein may comprise a sequence that is 90%, 95%, 98%, or 99% homologous to SEQ ID NO:48. In some embodiments, the nucleic acid encoding the Pta protein comprises the sequence of SEQ ID NO:47. In certain embodiments, the nucleic acid encoding the Pta protein may comprise a sequence that is 90%, 95%, 98%, or 99% homologous to SEQ ID NO:47.

In some aspects of the invention, provided herein are recombinant transketolase A (TktA) proteins with at least one (or one) protease recognition sequence located between two amino acids (e.g., two adjacent amino acids) of the native protein. In other aspects, nucleic acids encoding the recombinant transketolase A proteins are provided.

In some embodiments, the TktA protein comprises the sequence of SEQ ID NO:63. In certain embodiments, the TktA protein may comprise a sequence that is 90%, 95%, 98%, or 99% homologous to SEQ ID NO:63. In some embodiments, the nucleic acid encoding the TktA protein comprises the sequence of SEQ ID NO:57. In certain embodiments, the nucleic acid encoding the TktA protein may comprise a sequence that is 90%, 95%, 98%, or 99% homologous to SEQ ID NO:57.

In some embodiments, at least one protease recognition sequence is a protease recognition sequence recognized by a protease selected from the group consisting of alanine carboxypeptidase, *Armillaria mellea* astacin, bacterial leucyl aminopeptidase, cancer procoagulant, cathepsin B, clostripain, cytosol alanyl aminopeptidase, elastase, endoproteinase Arg-C, enterokinase, gastricsin, gelatinase, Gly-X carboxypeptidase, glycyl endopeptidase, human rhinovirus 3C protease, hypodermin C, Iga-specific serine endopeptidase, leucyl aminopeptidase, leucyl endopeptidase, lysC, lysosomal pro-X carboxypeptidase, lysyl aminopeptidase, methionyl aminopeptidase, myxobacter, nardilysin, pancreatic endopeptidase E, picornain 2A, picornain 3C, proendopeptidase, prolyl aminopeptidase, proprotein convertase I, proprotein convertase II, russellysin, saccharopepsin, semenogelase, T-plasminogen activator, thrombin, tissue kallikrein, tobacco etch virus (TEV), togavirin, tryptophanyl aminopeptidase, U-plasminogen activator, V8, venombin A, venombin AB, and Xaa-pro aminopeptidase.

In some embodiments, at least one protease recognition sequence is a protease recognition sequence recognized by human rhinovirus 3C protease. In some embodiments, the amino acid sequence of the protease recognition sequence recognized by human rhinovirus 3C protease comprises the sequence of SEQ ID NO:38. In some embodiments, the nucleic acid sequence of the protease recognition sequence recognized by human rhinovirus 3C protease comprises the sequence of SEQ ID NO:37.

In some embodiments, at least one protease recognition sequence of the Pgi protein is located after amino acid 410, 526, 527, 528, 529, 530, 531 or 532 of the sequence of SEQ ID NO:17. In some embodiments, at least one protease recognition sequence of the Pgi protein is located after amino acid 526 of the sequence of SEQ ID NO:17. In some embodiments, at least one protease recognition sequence of the nucleic acid encoding the Pgi protein is located after codons 410, 526, 527, 528, 529, 530, 531 or 532 of the sequence of SEQ ID NO: 1. In some embodiments, the protease recognition sequence of the nucleic acid encoding the Pgi protein is located after codon 526 of the sequence of SEQ ID NO: 1.

In some embodiments, at least one protease recognition sequence of the Pta protein is located after amino acid 381, 382, 387, or 409 of the sequence of SEQ ID NO:48. In some embodiments, at least one protease recognition sequence of the Pta protein is located after amino acid 381 of the sequence of SEQ ID NO:48. In some embodiments, at least one protease recognition sequence of the nucleic acid encoding the Pta protein is located after codons 381, 382, 387, or 409 of the sequence of SEQ ID NO:47. In some embodiments, the protease recognition sequence of the nucleic acid encoding the Pta protein is located after codon 381 of the sequence of SEQ ID NO:47.

In some embodiments, at least one protease recognition sequence of the TktA protein is located after amino acid 635, 636, 637, 638, or 640 of the sequence of SEQ ID NO:63. In some embodiments, at least one protease recognition sequence of the TktA protein is located after amino acid 637 of the sequence of SEQ ID NO:63. In some embodiments, at least one protease recognition sequence of the nucleic acid encoding the TktA protein is located after codons 635, 636, 637, 638, or 640 of the sequence of SEQ ID NO:57. In some embodiments, the protease recognition sequence of the nucleic acid encoding the TktA protein is located after codon 637 of the sequence of SEQ ID NO:57.

In some embodiments, at least one protease recognition sequence of the Pgi protein may be located in a C terminal region of the protein. In some embodiments, at least one protease recognition sequence of the Pta protein may be located in a central region or a C terminal region of the protein. In some embodiments, at least one protease recognition sequence of the TktA protein may be located in a central region or a C terminal region of the protein. In some embodiments, at least one protease recognition sequence of the Pgi protein may be located in a solvent-exposed loop region of the protein. In some embodiments, at least one protease recognition sequence of the Pta protein may be located in a solvent-exposed loop region of the protein. In some embodiments, at least one protease recognition sequence of the TktA protein may be located in a solvent-exposed loop region of the protein.

Some aspects of the invention provide vectors comprising a nucleic acid encoding a recombinant Pgi protein. Some aspects of the invention provide vectors comprising a nucleic acid encoding a recombinant Pta protein. Some aspects of the invention provide vectors comprising a nucleic acid encoding a recombinant TktA protein. In some embodiments, a vector may be a cloning vector or an expression vector. In some embodiments, a vector may be a plasmid, a fosmid, a phagemid, a virus genome or an artificial chromosome. In certain embodiments, a vector is a plasmid.

Other aspects of the invention provide cells that comprise any one of the proteins, nucleic acids, or vectors described herein. In some embodiments, the cell is a bacterial cell, a fungal cell, a mammalian cell or a plant cell. In some embodiments, the cell is a bacterial cell. In some embodiments, the bacterial cell is an *Escherichia coli* cell.

Further aspects of the invention provide cells that express recombinant proteins with a protease cleave site as described herein. In certain embodiments, the recombinant protein is a recombinant Pgi protein. In certain other embodiments, the recombinant protein is a recombinant Pta protein. In certain other embodiments, the recombinant protein is a recombinant TktA protein. In some embodiments, the cell is a bacterial cell, a fungal cell, a mammalian cell, or a plant cell. In certain embodiments, the cell is a bacterial cell such as, for example, an *Escherichia coli* cell.

Also provided are lysates of any of the cells described herein.

In various aspects of the invention, provided herein are recombinant proteins with at least one protease recognition sequence located between two amino acids (e.g., two adjacent amino acids) of the native protein in a solvent-exposed loop region of the protein, wherein at least one protease recognition sequence is cleaved by a cognate protease with single recognition sequence specificity, and wherein the recombinant protein activity in the presence of the cognate protease is reduced by at least 30%, at least 40%, at least 50%, at least 75%, at least 90%, at least 99%, or at least 99.9% (or is about 70%, about 60%, about 50%, about 25%, about 10%, about 1%, or about 0.1%) of the recombinant protein activity in the absence of the cognate protease. In some embodiments, the activity of the recombinant protein in the absence of the cognate protease is sufficient to permit wild-type growth of the cell. In some embodiments, the activity of the recombinant protein in the presence of the cognate protease is reduced by at least 50% in comparison to a wild-type control protein, and wherein the activity of the recombinant protein in the absence of the cognate protease is at least 80% in comparison to a wild-type control protein. In some embodiments, the recombinant protein, in the absence of the cognate protease, maintains a cellular growth rate of at least 75% of a wild-type cellular growth rate (e.g., growth rate of a cell without the recombinant protein).

Methods of engineering recombinant proteins (e.g., recombinant Pgi proteins and/or recombinant Pta proteins and/or recombinant TktA proteins) with a protease recognition sequence are also provided. The methods may comprise the steps of: (a) transforming cells with a plurality of nucleic acid variants, wherein each nucleic acid variant contains a nucleotide sequence that encodes a recombinant protein with at least one protease recognition sequence located between two amino acids (e.g., two adjacent amino acids) of the native protein, and a nucleic acid with an inducible promoter sequence operably linked to a nucleotide sequence encoding a cognate protease; (b) culturing the cells under non-inducing conditions on media that prohibits cell growth of inactive recombinant proteins and collecting cells with a growth rate comparable to wild-type control cells; and (c) culturing the cells under conditions that induce expression of the cognate protease and collecting cells that do not grow or that have a reduced growth rate in comparison to wild-type control cells. In some embodiments, the cells are transformed with the nucleic acid with an inducible promoter sequence operably linked to a nucleotide sequence encoding a cognate protease after step (b) and before step (c). In some embodiments, the methods further comprise sequencing the nucleic acid variants of the cells collected in step (c) to identify the location of at least one protease recognition sequence.

In some embodiments, the wild-type protein (e.g., Pgi protein and/or Pta protein and/or TktA protein) is required for cell growth and the genome of the cell lacks a chromosomal copy of the wild-type gene encoding the wild-type protein.

In some aspects, provided herein are methods of engineering a plurality of nucleic acid variants encoding recombinant proteins. The methods may comprise inserting at least one sequence that encodes at least one protease recognition sequence after each codon of a nucleic acid encoding a target protein to produce a plurality of nucleic acid variants encoding recombinant proteins, wherein each recombinant protein has a protease recognition sequence at a unique location in its primary amino acid sequence. In some embodiments, the methods further comprise (a) transforming cells with the plurality of nucleic acid variants, and a nucleic acid with an inducible promoter sequence operably linked to a nucleotide sequence encoding a cognate protease; (b) culturing the cells under non-inducing conditions on media that prohibits cell growth of inactive recombinant proteins and collecting cells with a normal growth rate; and (c) culturing the cells under conditions that induce expression of the cognate protease and collecting cells that do not grow or that have a reduced growth rate. In some embodiments, the cells are transformed with the nucleic acid with an inducible promoter sequence operably linked to a nucleotide sequence encoding a cognate protease after step (b) and before step (c). In some embodiments, the methods further comprise sequencing the nucleic acid variants of the cells collected in step (c) to identify the location of the protease recognition sequence.

In other aspects of the invention, provided herein are heterogeneous pluralities of nucleic acid variants, wherein each nucleic acid variant encodes a recombinant protein that is modified to include at least one protease recognition sequence located between two amino acids (e.g., two adjacent amino acids) of the native sequence. In some embodiments, a single protease recognition sequence is located between two amino acids of the native protein.

Also provided herein are heterogeneous cell populations, wherein each cell of the population comprises a nucleic acid variant, and wherein each nucleic acid variant encodes a recombinant protein that is modified to include at least one protease recognition sequence located between two amino acids (e.g., two adjacent amino acids) of the native sequence; and a nucleic acid encoding a cognate protease operably linked to an inducible promoter. In some embodiments, a single protease recognition sequence is located between two amino acids of the native protein.

BRIEF DESCRIPTION OF DRAWINGS

The accompanying drawings are not intended to be drawn to scale. For purposes of clarity, not every component may be labeled in every drawing.

FIG. 1A shows a schematic of one exemplary method for preparing a recombinant protein with a protease recognition sequence by inserting the protease recognition sequence between two amino acids of the recombinant protein.

FIG. 1B shows a schematic of another exemplary method for preparing a recombinant protein with a protease recognition sequence by replacing native amino acids of the recombinant protein with a protease recognition sequence.

BRIEF DESCRIPTION OF SEQUENCE LISTING

Figures 2, 3:
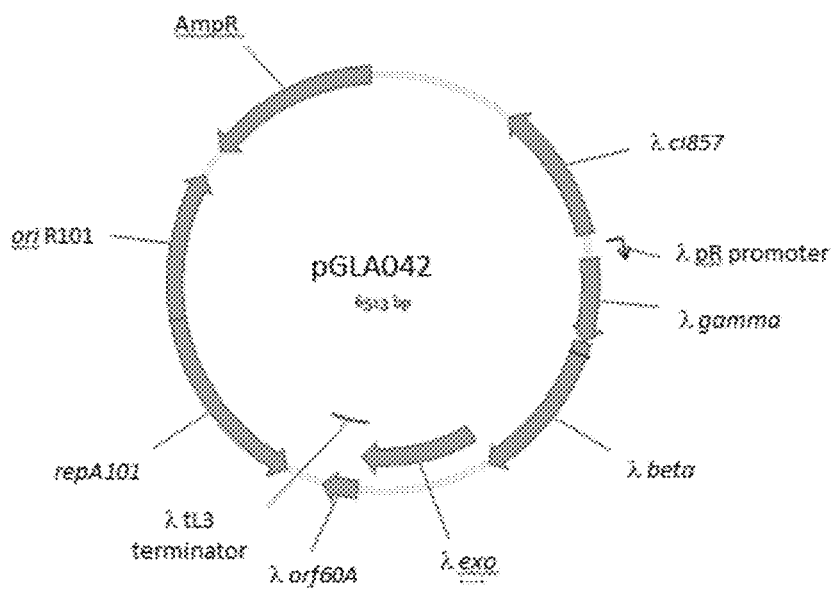
FIG. 2 shows a schematic of a modification to one of the methods of the invention, where a partial protease recognition sequence is inserted between two amino acids of the wild-type protein or codons such that the full recognition sequence is reconstituted in the final product.
FIG. 3 is a diagram of plasmid pGLA042.

SEQ ID NO:1 is a nucleotide sequence of a wild-type pgi gene.

SEQ ID NO:2 is a nucleotide sequence of a pgi gene variant with a human rhinovirus (HRV) 3C recognition sequence inserted after codon 108.

SEQ ID NO:3 is a nucleotide sequence of a pgi gene variant with an HRV 3C recognition sequence inserted after codon 109.

SEQ ID NO:4 is a nucleotide sequence of a pgi gene variant with an HRV 3C recognition sequence inserted after codon 110.

SEQ ID NO:5 is a nucleotide sequence of a pgi gene variant with an HRV 3C recognition sequence inserted after codon 138.

SEQ ID NO:6 is a nucleotide sequence of a pgi gene variant with an HRV 3C recognition sequence inserted after codon 410.

SEQ ID NO:7 is a nucleotide sequence of a pgi gene variant with an HRV 3C recognition sequence inserted after codon 524.

SEQ ID NO:8 is a nucleotide sequence of a pgi gene variant with an HRV 3C recognition sequence inserted after codon 525.

SEQ ID NO:9 is a nucleotide sequence of a pgi gene variant with an HRV 3C recognition sequence inserted after codon 526.

SEQ ID NO:10 is a nucleotide sequence of a pgi gene variant with an HRV 3C recognition sequence inserted after codon 527.

SEQ ID NO:11 is a nucleotide sequence of a pgi gene variant with an HRV 3C recognition sequence inserted after codon 528.

SEQ ID NO:12 is a nucleotide sequence of a pgi gene variant with an HRV 3C recognition sequence inserted after codon 529.

SEQ ID NO:13 is a nucleotide sequence of a pgi gene variant with an HRV 3C recognition sequence inserted after codon 530.

SEQ ID NO:14 is a nucleotide sequence of a pgi gene variant with an HRV 3C recognition sequence inserted after codon 531.

SEQ ID NO:15 is a nucleotide sequence of a pgi gene variant with an HRV 3C recognition sequence inserted after codon 532.

SEQ ID NO:16 is a nucleotide sequence of a pgi gene variant with an HRV 3C recognition sequence inserted after codon 545.

SEQ ID NO:17 is an amino acid sequence of a wild-type Pgi protein.

SEQ ID NO:18 is an amino acid sequence of a Pgi protein encoded by SEQ ID NO:2.

SEQ ID NO:19 is an amino acid sequence of a Pgi protein encoded by SEQ ID NO:3.

SEQ ID NO:20 is an amino acid sequence of a Pgi protein encoded by SEQ ID NO:4.

SEQ ID NO:21 is an amino acid sequence of a Pgi protein encoded by SEQ ID NO:5.

SEQ ID NO:22 is an amino acid sequence of a Pgi protein encoded by SEQ ID NO:6.

SEQ ID NO:23 is an amino acid sequence of a Pgi protein encoded by SEQ ID NO:7.

SEQ ID NO:24 is an amino acid sequence of a Pgi protein encoded by SEQ ID NO:8.

SEQ ID NO:25 is an amino acid sequence of a Pgi protein encoded by SEQ ID NO:9.

SEQ ID NO:26 is an amino acid sequence of a Pgi protein encoded by SEQ ID NO:10.

SEQ ID NO:27 is an amino acid sequence of a Pgi protein encoded by SEQ ID NO:11.

SEQ ID NO:28 is an amino acid sequence of a Pgi protein encoded by SEQ ID NO:12.

SEQ ID NO:29 is an amino acid sequence of a Pgi protein encoded by SEQ ID NO:13.

SEQ ID NO:30 is an amino acid sequence of a Pgi protein encoded by SEQ ID NO:14.

SEQ ID NO:31 is an amino acid sequence of a Pgi protein encoded by SEQ ID NO:15.

SEQ ID NO:32 is an amino acid sequence of a Pgi protein encoded by SEQ ID NO:16.

SEQ ID NO:33 is a nucleotide sequence of a codon-optimized HRV 3C protease.

SEQ ID NO:34 is an amino acid sequence of a codon-optimized HRV 3C protease.

SEQ ID NO:35 is a nucleotide sequence of a codon-optimized HRV 3C protease with an OmpA leader sequence.

SEQ ID NO:36 is an amino acid sequence of a codon-optimized HRV 3C protease with an OmpA leader sequence.

SEQ ID NO:37 is a nucleotide sequence of a HRV 3C protease recognition sequence.

SEQ ID NO:38 is an amino acid sequence of a HRV 3C protease recognition sequence.

SEQ ID NO:39 is an amino acid sequence of a partial HRV 3C protease recognition sequence.

SEQ ID NO:40 is an amino acid sequence of a partial HRV 3C protease recognition sequence.

SEQ ID NO:41 is an amino acid sequence of a partial HRV 3C protease recognition sequence.

SEQ ID NO:42 is an amino acid sequence of a partial HRV 3C protease recognition sequence.

SEQ ID NO:43 is an amino acid sequence of a partial HRV 3C protease recognition sequence.

SEQ ID NO:44 is an amino acid sequence of a partial HRV 3C protease recognition sequence.

SEQ ID NO:45 is an amino acid sequence of a partial HRV 3C protease recognition sequence.

SEQ ID NO:46 is an amino acid sequence of an N-terminal OmpA leader sequence.

SEQ ID NO:47 is a nucleotide sequence of a wild-type pta gene.

SEQ ID NO:48 is an amino acid sequence of a wild-type Pta protein.

SEQ ID NO:49 is a nucleotide sequence of a pta gene variant with an HRV 3C recognition sequence inserted after codon 381.

SEQ ID NO:50 is an amino acid sequence of a Pta protein encoded by SEQ ID NO:49.

SEQ ID NO:51 is a nucleotide sequence of a pta gene variant with an HRV 3C recognition sequence inserted after codon 382.

SEQ ID NO:52 is an amino acid sequence of a Pta protein encoded by SEQ ID NO:51.

SEQ ID NO:53 is a nucleotide sequence of a pta gene variant with an HRV 3C recognition sequence inserted after codon 387.

SEQ ID NO:54 is an amino acid sequence of a Pta protein encoded by SEQ ID NO:53.

SEQ ID NO:55 is a nucleotide sequence of a pta gene variant with an HRV 3C recognition sequence inserted after codon 409.

SEQ ID NO:56 is an amino acid sequence of a Pta protein encoded by SEQ ID NO:55.

SEQ ID NO:57 is a nucleotide sequence of a wild-type tktA gene.

SEQ ID NO:58 is a nucleotide sequence of a tktA gene variant with an HRV 3C recognition sequence inserted after codon 635.

SEQ ID NO:59 is a nucleotide sequence of a tktA gene variant with an HRV 3C recognition sequence inserted after codon 636.

SEQ ID NO:60 is a nucleotide sequence of a tktA gene variant with an HRV 3C recognition sequence inserted after codon 637.

SEQ ID NO:61 is a nucleotide sequence of a tktA gene variant with an HRV 3C recognition sequence inserted after codon 638.

SEQ ID NO:62 is a nucleotide sequence of a tktA gene variant with an HRV 3C recognition sequence inserted after codon 640.

SEQ ID NO:63 is an amino acid sequence of a wild-type TktA protein.

SEQ ID NO:64 is an amino acid sequence of a TktA protein encoded by SEQ ID NO:58.

SEQ ID NO:65 is an amino acid sequence of a TktA protein encoded by SEQ ID NO:59.

SEQ ID NO:66 is an amino acid sequence of a TktA protein encoded by SEQ ID NO:60.

SEQ ID NO:67 is an amino acid sequence of a TktA protein encoded by SEQ ID NO:61.

SEQ ID NO:68 is an amino acid sequence of a TktA protein encoded by SEQ ID NO:62.

SEQ ID NO:69 is a nucleotide sequence of a HRV protease recognition sequence.

SEQ ID NO:70 is an amino acid sequence of a Pgi protein encoded by SEQ ID NO:71.

SEQ ID NO:71 is a nucleotide sequence of a Pgi protein.

SEQ ID NO:72 is an amino acid sequence of a Pgi-HRV-I001 protein encoded by SEQ ID NO:73.

SEQ ID NO:73 is a nucleotide sequence of a pgi-hrv-I001 gene variant with an HRV protease recognition sequence inserted after the first illustrated codon in FIG. 1A.

SEQ ID NO:74 is an amino acid sequence of a Pgi-HRV-I002 protein encoded by SEQ ID NO:75.

SEQ ID NO:75 is a nucleotide sequence of a pgi-hrv-I002 gene variant with an HRV protease recognition sequence inserted after the second illustrated codon in FIG. 1A.

SEQ ID NO:76 is an amino acid sequence of a Pgi-HRV-I003 protein encoded by SEQ ID NO:77.

SEQ ID NO:77 is a nucleotide sequence of a pgi-hrv-I003 gene variant with an HRV protease recognition sequence inserted after the third illustrated codon in FIG. 1A.

SEQ ID NO:78 is an amino acid sequence of a Pgi-HRV-R001 protein encoded by SEQ ID NO:79.

SEQ ID NO:79 is a nucleotide sequence of a pgi-hrv-R001 gene variant with an HRV protease recognition sequence substitution after the first illustrated codon in FIG. 2A.

SEQ ID NO:80 is an amino acid sequence of a Pgi-HRV-R002 protein encoded by SEQ ID NO:81.

SEQ ID NO:81 is a nucleotide sequence of a pgi-hrv-R002 gene variant with an HRV protease recognition sequence substitution after the second illustrated codon in FIG. 2A.

SEQ ID NO:82 is an amino acid sequence of a Pgi-HRV-R003 protein encoded by SEQ ID NO:83.

SEQ ID NO:83 is a nucleotide sequence of a pgi-hrv-R003 gene variant with an HRV protease recognition sequence substitution after the third illustrated codon in FIG. 2A.

SEQ ID NO:84 is an amino acid sequence of a Pgi-HRV-I005 protein encoded by SEQ ID NO:85.

SEQ ID NO:85 is a nucleotide sequence of a pgi-hrv-I005 gene variant with an HRV protease recognition sequence insertion before a proline.

SEQ ID NO:86 is an amino acid sequence of a Pgi-HRV-I015 protein encoded by SEQ ID NO:87.

SEQ ID NO:87 is a nucleotide sequence of a pgi-prv-I015 gene variant with an HRV protease recognition sequence insertion after a leucine.

DETAILED DESCRIPTION OF CERTAIN EMBODIMENTS OF THE INVENTION

Many key proteins in biosynthetic pathways are important for cell growth. Deletion or inactivation of these proteins is often difficult or impossible because doing so results in reduced cell growth or viability, rendering the cells unsatisfactory for producing a compound of interest. The invention addresses this problem of cell growth inhibition by providing recombinant proteins (e.g., enzymes) that are active during cell growth and inactive during in vitro cell-free production of a compound of interest. The recombinant proteins engineered by the methods provided herein have a protease recognition sequence selectively located in their primary amino acid sequence such that, despite the presence of the recognition sequence, the activity of the recombinant protein is sufficient to enable wild-type growth of the cell. The recombinant proteins can be selectively inactivated by the introduction, expression, and/or activation of a cognate protease, which cleaves the recombinant target protein specifically at the protease recognition sequence, thereby rendering the recombinant target protein inactive (or with reduced activity). Thus, the recombinant proteins of the invention are useful for engineering and/or altering biosynthetic pathways to produce a compound of interest.

The recombinant proteins and methods provided herein are useful for engineering and altering metabolic pathways in a cell and a cell-free system. For example, protease targeting of the recombinant Pgi enzymes of the invention permits control of carbon flux between glycolysis and the pentose phosphate pathway in cell-free reactions without altering the function of this key enzyme during cell growth. Thus, the invention provides a way to control metabolic flux through the manipulation of key pathway enzymes, including manipulation to maintain or alter the cellular activity of key pathway enzymes or competitive enzymes.

To produce recombinant proteins with a protease recognition sequence that have an activity level that enables wild-type growth of the cell, a library of nucleic acid variants may be generated, wherein each nucleic acid variant encodes a recombinant protein with at least one protease recognition sequence located between two amino acids (e.g., two adjacent amino acids) of the wild-type primary sequence of the protein. From this library of variants, recombinant proteins are produced and screened for protein activity in the absence of protease and protein inactivity in the presence of protease. A population of cells is first transformed with the library of nucleic acid variants. To select for active expressed recombinant proteins, the cells are grown on media that prohibits growth of inactive recombinant proteins. Cells that do not display growth defects are presumed to contain an active recombinant protein, despite introduction of the protease recognition sequence, and are selected for further characterization. To select for cells that contain a recombinant protein that can be inactivated, a nucleic acid with an inducible promoter sequence operably linked to a nucleotide sequence encoding a cognate protease may be introduced into the cells. The nucleic acid encoding the inducible cognate protease may be introduced either before or after selection of active recombinant protein. The cells presumably containing active recombinant protein are then grown under conditions that induce expression of a cognate protease. Cells that do not grow, or that grow poorly (e.g., display growth defects), are presumed to contain the desired inactive recombinant protein and are selected for further characterization and/or use. The nucleic acid variants of the selected cells may be amplified and sequenced to identify the location of the protease recognition sequence.

Proteins and Metabolic Pathways

A "protein" or "wild-type protein," as used herein, refers to a molecule composed of amino acids joined together by peptide bonds in a linear chain. A "native" amino acid, as used herein, refers to an amino acid in the primary amino acid sequence of a wild-type protein (i.e., not a modified or mutated amino acid). A "target protein," as used herein, refers to a wild-type protein of interest (i.e., not a recombinant protein) or a protein to be engineered with a protease recognition sequence as described herein. A "recombinant protein," as used herein, refers to a protein derived from recombinant nucleic acid, which is formed artificially by combining nucleic acid from different sources. In some embodiments, recombinant proteins of the invention differ from each other in that the location of the single protease recognition sequence is unique to each recombinant protein. For example, one recombinant protein may have a protease recognition sequence located after the first amino acid of the primary amino acid sequence, another recombinant protein may have a protease recognition sequence located after the second amino acid of the primary amino acid sequence, yet another recombinant protein may have a protease recognition sequence located after the third amino acid of the primary amino acid sequence, and so on. Thus, a plurality of recombinant proteins is typically a heterogeneous plurality.

The recombinant proteins of the invention may be used to engineer metabolic pathways, or a sequence of biochemical reactions catalyzed by enzymes. Examples of metabolic pathways that may be engineered in accordance with the invention include, without limitation, those involved in carbohydrate metabolism, lipid metabolism, amino acid metabolism, and energy metabolism. In some embodiments, the metabolic pathway is glycolysis. In some embodiments, the metabolic pathway is acetate overflow metabolism. In some embodiments, the metabolic pathway is the pentose phosphate pathway.

Phosphoglucose isomerase (Pgi)

In some embodiments, the target protein is a phosphoglucose isomerase (Pgi) enzyme, for example, a Pgi enzyme from *Escherichia coli* (*E. coli*). This enzyme catalyzes the inter-conversion of glucose-6-phosphate and fructose-6-phosphate and is the first committed step in glycolysis. Inactivation of Pgi inhibits cell growth; however, Pgi activity results in the diversion of glucose to the glycolysis pathway, which in turn results in a shortage of glucose for cell-free production of compounds of interest that are derived from ribose. A nucleic acid containing the pgi gene that encodes Pgi enzyme may be modified by any of the methods provided herein or known in the art to generate a variant comprising a protease recognition sequence. In some embodiments, the protease recognition sequence used is a human rhinovirus (HRV) 3C protease recognition sequence (e.g., SEQ ID NO:37, SEQ ID NO:38), though the invention is not so limited. In some embodiments, the HRV 3C recognition sequence is inserted in-frame after each codon of the pgi gene. In some embodiments, the HRV 3C recognition sequence is inserted after each codon of the pgi gene, excluding the first and/or last codon. In some embodiments, the HRV 3C recognition sequence is inserted after amino acids 2-5, 9, 24-25, 33-36, 58-59, 85-96, 105-111, 113-115, 137-141, 143-144, 146, 173-176, 196, 250-251, 254, 366-370, 398-399, 410-414, 447-451, 477, 526-532 or 545. In some embodiments, the HRV 3C recognition sequence is inserted after at least one, or each, codon of the solvent-exposed loop regions of the Pgi protein.

In some embodiments, the recombinant Pgi proteins of the invention contain an HRV 3C recognition sequence located after amino acid 108, 109, 110, 138, 410, 524, 525, 526, 527, 528, 529, 530, 531, 532 or 545. In some embodiments, the Pgi variants of the invention comprise an amino acid sequence selected from SEQ ID NO:18-32.

In some embodiments, the nucleic acid pgi variants (e.g., genes) of the invention contain an HRV 3C recognition sequence located after codon 108, 109, 110, 138, 410, 524, 525, 526, 527, 528, 529, 530, 531, 532 or 545. In some embodiments, the pgi variants of the invention comprise a nucleotide sequence selected from SEQ ID NO:2-16.

In some embodiments, the HRV 3C recognition sequence is inserted between non-adjacent codons of the pgi gene. In some embodiments, the HRV 3C recognition sequence replaces native codons of the pgi gene. For example, in some embodiments, the eight codons of HRV 3C recognition sequence (i.e., CTG GAA GTG CTG TTT CAG GGT CCG; SEQ ID NO:37) may replace eight contiguous codons of the pgi gene.

Phosphotransacetylase (Pta)

In some embodiments, the target protein is a phosphotransacetylase (Pta) enzyme, for example, a Pta enzyme from *Escherichia coli* (*E. coli*). This enzyme catalyzes the reversible interconversion of acetyl-CoA and acetyl phosphate. A nucleic acid containing the pta gene that encodes Pta enzyme may be modified by any of the methods provided herein or known in the art to generate a variant comprising a protease recognition sequence. In some embodiments, the protease recognition sequence used is a human rhinovirus (HRV) 3C protease recognition sequence (e.g., SEQ ID NO:37, SEQ ID NO:38), though the invention is not so limited. In some embodiments, the HRV 3C recognition sequence is inserted in-frame after each codon of the pta gene. In some embodiments, the HRV 3C recognition sequence is inserted after each codon of the pta gene, excluding the first and/or last codon. In some embodiments, the HRV 3C recognition sequence is inserted after at least one, or each, codon of the solvent-exposed loop regions of the Pta protein.

In some embodiments, the recombinant Pta proteins of the invention contain an HRV 3C recognition sequence located after amino acid 381, 382, 387, or 409. In some embodiments, the Pta variants of the invention comprise an amino acid sequence selected from SEQ ID NO:50, SEQ ID NO:52, SEQ ID NO:54, and SEQ ID NO:56.

In some embodiments, the nucleic acid pta variants (e.g., genes) of the invention contain an HRV 3C recognition sequence located after codon 381, 382, 387, or 409. In some embodiments, the pta variants of the invention comprise a nucleotide sequence selected from SEQ ID NO:49, SEQ ID NO:51, SEQ ID NO:53, and SEQ ID NO:55.

In some embodiments, the HRV 3C recognition sequence is inserted between non-adjacent codons of the pta gene. In some embodiments, the HRV 3C recognition sequence replaces native codons of the pta gene. For example, in some embodiments, the eight codons of HRV 3C recognition sequence (i.e., CTG GAA GTG CTG TTT CAG GGT CCG; SEQ ID NO:37) may replace eight contiguous codons of the pta gene.

Transketolase A (TktA)

In some embodiments, the target protein is a transketolase A (TktA) enzyme, for example, a TktA enzyme from *Escherichia coli* (*E. coli*). TktA, together with transketolase B (TktB) catalyze two reversible ketol transfer reactions in the pentose phosphate pathway. A nucleic acid containing the tktA gene that encodes TktA enzyme may be modified by any of the methods provided herein or known in the art to generate a variant comprising a protease recognition sequence. In some embodiments, the protease recognition sequence used is a human rhinovirus (HRV) 3C protease recognition sequence (e.g., SEQ ID NO:37, SEQ ID NO:38), though the invention is not so limited. In some embodiments, the HRV 3C recognition sequence is inserted in-frame after each codon of the tktA gene. In some embodiments, the HRV 3C recognition sequence is inserted after each codon of the tktA gene, excluding the first and/or last codon. In some embodiments, the HRV 3C recognition sequence is inserted after at least one, or each, codon of the solvent-exposed loop regions of the TktA protein.

In some embodiments, the recombinant TktA proteins of the invention contain an HRV 3C recognition sequence located after amino acid 635, 636, 637, 638, or 640. In some embodiments, the TktA variants of the invention comprise an amino acid sequence selected from SEQ ID NO:64, SEQ ID NO:65, SEQ ID NO:66, SEQ ID NO: 67 and SEQ ID NO:68.

In some embodiments, the nucleic acid tktA variants (e.g., genes) of the invention contain an HRV 3C recognition sequence located after codon 635, 636, 637, 638, or 640. In some embodiments, the tktA variants of the invention comprise a nucleotide sequence selected from SEQ ID NO:58, SEQ ID NO:59, SEQ ID NO:60, SEQ ID NO:61 and SEQ ID NO:62.

In some embodiments, the HRV 3C recognition sequence is inserted between non-adjacent codons of the tktA gene. In some embodiments, the HRV 3C recognition sequence replaces native codons of the tktA gene. For example, in some embodiments, the eight codons of HRV 3C recognition sequence (i.e., CTG GAA GTG CTG TTT CAG GGT CCG; SEQ ID NO:37) may replace eight contiguous codons of the tktA gene.

Proteases and Cognate Recognition Sequences

The proteins of the invention may be inactivated by any one of a variety of proteases that cleave at specific recognition sequences. As used herein, "protease recognition sequence," in the context of a protein, refers to an amino acid sequence that is recognized and cleaved by a cognate protease. In the context of a nucleic acid that encodes a protein, a "protease recognition sequence" refers to a sequence that encodes the amino acid sequence recognized and cleaved by a cognate protease. As used herein, "cognate protease" refers to a protease that cleaves and thereby inactivates a recombinant target protein (e.g., enzyme). Cognate proteases that may be used herein include those with single, specific recognition sequence, meaning the proteases cleave within or adjacent to a specific sequence of one or more amino acids. For example, human rhinovirus 3C protease is highly specific for the recognition sequence Leu-Glu-Val-Leu-Phe-Gln-Gly-Pro (SEQ ID NO:38). The protease recognizes this sequence and cleaves after the glutamine residue. The human rhinovirus 3C protease does not typically recognize and cleave other recognition sequences although all proteases are somewhat promiscuous and may recognize and cleave other sites but at a much reduced rate. In some embodiments, the proteins of the invention are prepared with an engineered human rhinovirus 3C protease recognition sequence.

Other examples of proteases that may be used in accordance with the invention include, without limitation, alanine carboxypeptidase, *Armillaria mellea* astacin, bacterial leucyl aminopeptidase, cancer procoagulant, cathepsin B, clostripain, cytosol alanyl aminopeptidase, elastase, endoproteinase Arg-C, enterokinase, gastricsin, gelatinase, Gly-X carboxypeptidase, glycyl endopeptidase, human rhinovirus 3C protease, hypodermin C, Iga-specific serine endopeptidase, leucyl aminopeptidase, leucyl endopeptidase, lysC, lysosomal pro-X carboxypeptidase, lysyl aminopeptidase, methionyl aminopeptidase, myxobacter, nardilysin, pancreatic endopeptidase E, picornain 2A, picornain 3C, proendopeptidase, prolyl aminopeptidase, proprotein convertase I, proprotein convertase II, russellysin, saccharopepsin, semenogelase, T-plasminogen activator, thrombin, tissue kallikrein, tobacco etch virus (TEV), togavirin, tryptophanyl aminopeptidase, U-plasminogen activator, V8, venombin A, venombin AB and Xaa-pro aminopeptidase (see Rawlings, S. D., et al., *Handbook of Proteolytic Enzymes*, Academic Press, 2013, *Science*, Elsevier Ltd., 4094 pages, incorporated herein by reference for its teachings relating to the structural chemistry and biological aspects of the proteases described therein). Other proteases may be used in accordance with the invention.

Nucleic Acids

The invention encompasses nucleic acids encoding the recombinant proteins (e.g., recombinant Pgi proteins and/or recombinant Pta proteins and/or recombinant TktA proteins) described herein. A "nucleic acid," as used herein, refers to at least two nucleotides (e.g., adenine, thymine, cytosine, guanine, uracil) covalently linked together. A nucleic acid of the invention will generally contain phosphodiester bonds. A nucleic acid may be single-stranded (ss) or double-stranded (ds), DNA or RNA. In some embodiments, the nucleic acid is in the form of cDNA. In some embodiments, the nucleic acid is in the form of genomic DNA. A "codon," as used herein, refers to a set of three adjacent nucleotides that encode an amino acid. The codons of the invention are defined and numbered by the initial nucleotide from which translation starts.

In some embodiments, linear double-stranded nucleic acid (e.g., DNA) variants are prepared in accordance with the invention. In some instances, the linear double-stranded nucleic acid variants comprise a variant gene sequence encoding a recombinant protein with a protease recognition sequence as well as at least 30 nucleotide base pairs (bp) of additional sequence upstream of the start codon and at least 30 nucleotide base pairs of additional sequence downstream of the stop codon of the gene, wherein each additional sequence is homologous to the wild-type gene locus of the genome of the cell into which the nucleic acid will be transformed. As used herein, "wild-type gene" refers to the wild-type gene encoding the wild-type protein that corresponds to the recombinant protein with at least one (or one) protease recognition site. For example, if the target protein is Pgi and the cell being transformed is *E. coli*, the nucleic acid will contain a gene variant encoding Pgi with at least one protease recognition sequence, at least 30 bp of additional sequence upstream of the start codon of the gene variant and homologous to the pgi locus of the *E. coli* genome, and at least 30 bp of additional sequence downstream of the start codon of the gene variant and homologous to the pgi locus of the *E. coli* genome. The additional sequence, in some instances, facilitates recombination of the gene variant with the chromosomal wild-type copy of the gene.

The invention encompasses vectors comprising a nucleic acid variant provided herein. A "vector," as used herein, may be any of a number of nucleic acids into which a desired sequence or sequences may be inserted by restriction and ligation for transport between different genetic environments or for expression in a cell. Vectors are typically composed of DNA although RNA vectors are also available. Examples of vectors in accordance with the invention include, without limitation, plasmids, fosmids, phagemids, virus genomes, and artificial chromosomes. In some embodiments, a nucleic acid variant of the invention is provided in a recombinant cloning vector. In some embodiments, a nucleic acid variant of the invention is expressed in a recombinant expression vector.

A cloning vector of the invention is able to replicate autonomously or integrated in the genome of a cell. A cloning vector has an endonuclease restriction sequence at which the vector may be cut in a determinable fashion and into which a desired DNA sequence may be ligated such that the new recombinant vector retains its ability to replicate in a cell. In the case of plasmids, replication of the desired sequence may occur many times as the plasmid increases in copy number within a cell such as a bacterium or just a single time per cell before the cell reproduces by mitosis. In the case of phage, replication may occur actively during a lytic phase or passively during a lysogenic phase.

An expression vector of the invention is one into which a desired DNA coding sequence may be inserted by restriction and ligation such that it is operably linked to regulatory sequences and may be expressed as an RNA transcript.

As used herein, a coding sequence and regulatory sequences (e.g., promoter sequences) are said to be "operably" linked when they are covalently linked in such a way as to place the expression or transcription of the coding sequence under the influence or control of the regulatory sequences (e.g., such that the regulatory sequence "drives" transcriptional initiation and/or expression of the coding sequence). If the coding sequences are to be translated into a functional protein, two DNA sequences are considered operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a coding sequence if the promoter region can effect transcription of that DNA sequence such that the resulting transcript can be translated into the desired protein or polypeptide.

Vectors of the invention may further comprise a marker sequence for use in the identification of cells that have or have not been transformed or transfected with the vector. Markers include, for example, genes encoding proteins that increase or decrease either resistance or sensitivity to antibiotics (e.g., ampicillin resistance genes, kanamycin resistance genes, neomycin resistance genes, tetracycline resistance genes and chloramphenicol resistance genes) or other compounds, genes encoding enzymes with activities detectable by standard assays known in the art (e.g., β-galactosidase, luciferase or alkaline phosphatase), and genes that visibly affect the phenotype of transformed or transfected cells, hosts, colonies or plaques (e.g., green fluorescent protein). In some embodiments, the vectors used herein are capable of autonomous replication and expression of the structural gene products present in the DNA segments to which they are operably linked.

When a nucleic acid that encodes any of the proteins of the invention is expressed in a cell, a variety of transcription control sequences may be used to direct its expression. For example, a nucleic acid of the invention may contain a promoter, an enhancer, and/or a terminator. Alternatively, the vector into which the nucleic acid is inserted may contain such regulatory sequences.

A "promoter," as used herein, refers to a control region of a nucleic acid sequence at which initiation and rate of transcription of the remainder of a nucleic acid sequence are controlled. A promoter may also contain subregions at which regulatory proteins and molecules may bind, such as RNA polymerase and other transcription factors. Promoters may be constitutive, inducible, activatable, repressible, tissue-specific or any combination thereof. A promoter drives expression or drives transcription of the nucleic acid sequence that it regulates. A promoter may be one naturally associated with a gene or sequence, as may be obtained by isolating the 5'-non-coding sequences located upstream of the coding segment and/or exon of a given gene or sequence. Such a promoter can be referred to as "endogenous."

In some embodiments, a coding nucleic acid segment may be positioned under the control of a recombinant or heterologous promoter, which refers to a promoter that is not normally associated with the encoded nucleic acid sequence in its natural environment. A recombinant or heterologous enhancer refers to an enhancer not normally associated with a nucleic acid sequence in its natural environment. Such promoters or enhancers may include promoters or enhancers of other genes; promoters or enhancers isolated from any other prokaryotic, viral or eukaryotic cell; and synthetic promoters or enhancers that are not "naturally occurring" such as, for example, those that contain different elements of different transcriptional regulatory regions and/or mutations that alter expression through methods of genetic engineering that are known in the art. In addition to producing nucleic acid sequences of promoters and enhancers synthetically, sequences may be produced using recombinant cloning and/or nucleic acid amplification technology, including polymerase chain reaction (PCR). Furthermore, control sequences that direct transcription and/or expression of sequences within non-nuclear organelles such as mitochondria, chloroplasts and the like, may be used in accordance with the invention.

An "inducible promoter," as used herein, is one that is characterized by initiating or enhancing transcriptional activity when in the presence of, influenced by or contacted by an inducer or inducing agent. An "inducer" or "inducing agent" may be endogenous or a normally exogenous compound or protein that is administered in such a way as to be active in inducing transcriptional activity from the inducible promoter.

Inducible promoters for use in accordance with the invention include any inducible promoter described herein or known to one of ordinary skill in the art. Examples of inducible promoters include, without limitation, chemically/biochemically-regulated and physically-regulated promoters such as isopropyl β-D-1-thiogalactopyranoside (IPTG)-regulated promoters, alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

Inducible promoters for use in accordance with the invention may function in both prokaryotic and eukaryotic host organisms. In some embodiments, mammalian inducible promoters are used. Examples of mammalian inducible promoters for use herein include, without limitation, promoter type PAct:PAIR, PART, PBIT, PCR5, PCTA, PETR, PNIC, PPIP, PROP, PSPA/PSCA, PTET, PTtgR, promoter type PRep:PCuO, PETR ON8, PNIC, PPIR ON, PSCA ON8, PTetO, PUREX8, promoter type PHyb:tetO7-ETR8-PhCMVmin, tetO7-PIR3-ETR8-PhCMVmin, and scbR8-PIR3-PhCMVmin. In some embodiments, inducible promoters from other organisms, as well as synthetic promoters designed to function in a prokaryotic or eukaryotic host may be used. Examples of non-mammalian inducible promoters for use herein include, without limitation, Lentivirus promoters (e.g., EFa, CMV, Human SynapsinI (hSynI), CaMKIIα, hGFAP and TPH-2) and Adeno-Associated Virus promoters (e.g., CaMKIIα (AAV5), hSynI (AAV2), hThy1 (AAV5), fSST (AAV1), hGFAP (AAV5, AAV8), MBP (AAV8), SST (AAV2)). One important functional characteristic of the inducible promoters of the present invention is their inducibility by exposure to an externally applied inducer.

An inducible promoter for use in accordance with the invention may be induced by (or repressed by) one or more physiological condition(s), such as changes in pH, temperature, radiation, osmotic pressure, saline gradients, cell surface binding, and the concentration of one or more extrinsic or intrinsic inducing agent(s). The extrinsic inducer or inducing agent may comprise, without limitation, amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones, or combinations thereof. Other inducible promoters may be used in accordance with the invention.

In some embodiments of the invention, a promoter may or may not be used in conjunction with an "enhancer," which refers to a cis-acting regulatory sequence involved in the transcriptional activation of a nucleic acid sequence downstream of the promoter. An enhancer may be one naturally associated with a nucleic acid sequence, located either downstream or upstream of that sequence. The enhancer may be located at any functional location before or after the promoter and/or the encoded nucleic acid.

A "terminator" or "terminator sequence," as used herein, is a nucleic acid sequence that causes transcription to stop. A terminator may be unidirectional or bidirectional. It is comprised of a DNA sequence involved in specific termination of an RNA transcript by an RNA polymerase. A terminator sequence prevents transcriptional activation of downstream nucleic acid sequences by upstream promoters. Thus, in certain embodiments, a terminator that ends the production of an RNA transcript is contemplated.

The most commonly used type of terminator is a forward terminator. When placed downstream of a nucleic acid sequence that is usually transcribed, a forward transcriptional terminator will cause transcription to abort. In some embodiments, bidirectional transcriptional terminators may be used, which usually cause transcription to terminate on both the forward and reverse strand. In some embodiments, reverse transcriptional terminators may be used, which usually terminate transcription on the reverse strand only.

In prokaryotic systems, terminators usually fall into two categories (1) rho-independent terminators and (2) rho-dependent terminators. Rho-independent terminators are generally composed of palindromic sequence that forms a stem loop rich in G-C base pairs followed by several T bases. Terminators for use in accordance with the invention include any terminator of transcription described herein or known to one of ordinary skill in the art. Examples of terminators include, without limitation, the termination sequences of genes such as, for example, the bovine growth hormone terminator, and viral termination sequences such as, for example, the SV40 terminator, spy, yejM, secG-leuU, thrLABC, rrnB T1, hisLGDCBHAFI, metZWV, rrnC, xapR, aspA, and arcA terminator. In some embodiments, the termination signal may be a sequence that cannot be transcribed or translated, such as those resulting from a sequence truncation. Other terminators may be used in accordance with the invention.

In some embodiments, the nucleic acids are codon-optimized for improved expression of the recombinant proteins of the invention. Codon optimization, also referred to as biased codon usage, refers to differences in the frequency of occurrence of synonymous codons in coding DNA.

Cells

The invention encompasses any type of cell, including a prokaryotic and a eukaryotic cell, that recombinantly expresses the proteins provided herein. In some embodiments, the cell is a bacterial cell. In some embodiments, the bacterial cell is a cell of a bacterium from the genus *Escherichia*. In some embodiments, the bacterial cell is an *Escherichia coli* (*E. coli*) cell. In some embodiments, the cell is a fungal cell, such as, for example, a yeast cell (e.g., a *Saccharomyces cerevisiae* cell). In some embodiments, the cell is a mammalian cell or a plant cell. It should be appreciated that some cells for use in accordance with the invention do not contain the wild-type chromosomal copy of a gene encoding the wild-type protein (e.g., the wild-type protein corresponding to the recombinant protein with a protease recognition sequence).

The cells provided herein, in some embodiments, are prokaryotic cells that may be transformed with any of the nucleic acids of the invention. Transformation and transfection are processes by which exogenous genetic material is introduced into a prokaryotic cell and into a eukaryotic cell, respectively. Transformation can be achieved by electroporation or by chemical means. The cells to be transformed are typically in a state of competence. Thus, in some embodiments, the cells provided herein are electrocompetent or chemically competent cells. A variety of electrocompetent and chemically competent cells are known in the art and may be used in accordance with the invention.

In some embodiments, the cells are *Escherichia coli* (*E. coli*) cells such as, for example, JW3985-1 *E. coli* cells (*Coli* Genetic Shock Center; CHSC #10867; *Mol. Sys. Biol.* 2:2006-08, 2006, incorporated by reference herein). Other commercially available and non-commercially available cell lines may be used in accordance with the invention.

The cells of the invention may comprise selectable markers. Selectable markers include, without limitation, genes encoding proteins that increase or decrease either resistance or sensitivity to antibiotics (e.g., ampicillin resistance genes, kanamycin resistance genes, neomycin resistance genes, tetracyclin resistance genes and chloramphenicol resistance genes) or other compounds, genes encoding enzymes with activities detectable by standard assays known in the art (e.g., β-galactosidase, luciferase or alkaline phosphatase), and genes that visibly affect the phenotype of transformed or transfected cells, hosts, colonies, or plaques (e.g., green fluorescent protein). Other selectable markers may be used in accordance with the invention.

Library Construction

The methods of the invention may be used to construct a library of the nucleic acid variants provided herein. Library design may utilize two nucleotide sequences—one that codes for the primary amino acid sequence of the target protein, and one that codes for the protease recognition sequence of the protease that will be used for inactivation of the recombinant protein of the invention. The protease recognition sequence may be "walked" along the former sequence in one of two methods (FIGS. 1A and 1B).

In one method, the protease recognition sequence may be inserted after multiple codons of the nucleotide sequence that encodes the target protein, thereby producing a plurality of nucleic acid variants, wherein each nucleic acid variant contains the protease recognition sequence located at a unique position between two native codons (FIG. 1A). In another method, the protease recognition sequence may replace an equivalent number of nucleotides in the sequence that encodes the target protein, thereby producing a plurality of nucleic acid variants, wherein each nucleic acid variant contains the protease recognition sequence in place of an equivalent stretch of native nucleotides (FIG. 1B).

In some embodiments, the protease recognition sequence may be inserted after every codon of the nucleic acid sequence that encodes the target protein, thereby producing a plurality of nucleic acid variants, wherein each nucleic acid variant contains the protease recognition sequence located at a unique position between two native codons (e.g., two adjacent native codons). In some embodiments, the protease recognition sequence may be inserted after every codon of the nucleic acid sequence excluding the first and/or last codon. Alternatively, in some embodiments, the protease recognition sequence may be inserted after every other codon, after every third codon, after every fourth codon, after every fifth codon, after every tenth codon or after every twentieth codon. In some embodiments, the protease recognition sequence may be inserted randomly. In some embodiments, the protease recognition sequence may be inserted in a particular region of the nucleic acid, such as, for example, the N terminal region or the C terminal region. In some embodiments, the protease recognition sequence may replace contiguous codons of the nucleic acid sequence that encodes the target protein. The "N terminal region" of a protein, as used herein, may refer to the stretch of 100, 90, 80, 70, 60, 50, 40, 30, 20 or 10 amino acids located adjacent to the 5' terminal amino acid. The "C terminal region" of a protein, as used herein, may refer to the stretch of 100, 90, 80, 70, 60, 50, 40, 30, 20 or 10 amino acids located adjacent to the 3' terminal amino acid. In each embodiment, it is to be understood that each nucleic acid variant contains at least one (or one) protease recognition sequence.

In some embodiments, wherein the structure of a target protein is known or can be predicted, the protease recognition sequence may be inserted in regions corresponding to solvent-exposed loop regions of the protein. It has been discovered that, in some instances, these solvent-exposed loop regions are tolerant to insertion of a protease recognition sequence that is readily cleavable. Thus, in some embodiments, provided herein are methods of constructing a library of nucleic acids containing a protease recognition sequence in regions corresponding to solvent-exposed loop regions of the protein. Such methods save time and the cost of preparing proteins with a protease recognition sequence. In some embodiments, it may be advantageous to use polymerase chain reaction (PCR)-based library construction strategies that prohibit synthesis of the wild-type nucleic acid sequences.

It is to be understood that, in some embodiments, it may be advantageous to incorporate as much of the protease recognition sequence as is necessary to produce a full-length recognition sequence. For example, if the protease recognition sequence begins with a leucine and the sequence is being inserted after a leucine, only a partial recognition sequence may be inserted such that the leucine is not repeated (FIG. 2). Likewise, if the last amino acid in the protease recognition sequence is a proline, and the protease recognition sequence is being inserted before a proline, only a partial recognition sequence may be inserted such that the proline is not doubled. Thus, a protein or nucleic acid with a protease recognition sequence located between two native amino acids or codons (e.g., two adjacent native amino acids or codons), respectively, encompasses proteins and nucleic acids with partial protease recognition sequences inserted between two native amino acids or codons such that the full recognition sequence is reconstituted in the final product.

Strain Construction

The nucleic acid variants of the invention may be transformed into recombinant cells (e.g., bacterial cells) to screen for optimal (e.g., active and inactivatable) recombinant proteins. It is to be understood that the cells used for screening are not necessarily the cells used to express an optimal recombinant protein for the purpose of engineering, for example, a metabolic pathway of interest.

In some embodiments, the genome of the cells may be modified to (a) delete or mutate the chromosomal wild-type (or endogenous) copy of a gene encoding the target protein and/or (b) include a means of inducing cytoplasmic cognate protease expression. The latter may be accomplished by adding a gene encoding the cognate protease with an inducible promoter to the cell genome, or by providing a gene encoding the cognate protease with an inducible promoter on a vector, such as, for example, a plasmid. Alternatively, in some embodiments, the cells may altogether lack the cognate protease, which can then be added at a later screening/selection step. In some embodiments, the cognate protease is added in purified form.

In some embodiments, the recombinant cell is modified to lack a functional chromosomal copy of the wild-type gene (i.e., the wild-type gene encoding the wild-type protein that corresponds to the recombinant protein with the protease recognition site) and is transformed with a plasmid containing nucleic acid variants of the invention. Without being bound by theory, deletion of the chromosomal wild-type copy of the gene from the cell permits complementation and aids in minimizing background when the nucleic acid is inserted through low efficiency recombination methods (e.g., when cell growth due to the presence of a compensatory wild-type gene represents a false positive). In some embodiments, inclusion of a selectable marker (e.g., an antibiotic resistance marker) in the cells, for example, in an episomal vector containing a nucleic acid variant, may reduce the rate of false positives.

In some embodiments, the cells may be modified to delete wild-type genes encoding proteins with functions similar to those of the target protein. For example, in some embodiments, chromosomal copies of genes encoding isozymes of a target enzyme (i.e., enzymes that provide similar function) are deleted from the cells in order to minimize background in the screening/selection step(s).

In some embodiments, the recombinant cells are modified to contain an inducible recombinase system such as, for example, at least one nucleic acid containing the lambda phage (λ) recombinase system genes gamma (γ), beta (β), and exo. Thus, in some embodiments, recombineering (or recombination-mediated genetic engineering) methods are used to modify the recombinant cells of the invention. Such homologous recombination systems may be used to introduce or delete chromosomal copies of wild-type genes from the cell genome. Other recombineering methods are also contemplated and may be used herein. The invention also contemplates the use of restriction enzymes and ligases to combine nucleic acid sequences in a specified order (Strachan, T., et al., Human Molecular Genetics, Chapter 4, Garland Science, New York, 1999).

Selection for Protein Activity

The recombinant cells expressing the nucleic acid variants of the invention may be grown in selective media in the absence of a functional protease to permit recovery of recombinant proteins encoded by the nucleic acid variants. For example, in some embodiments, the activity of the target protein may be required for cell growth. If insertion of a cognate protease recognition sequence adversely affects the activity of the recombinant protein, then presumably, the cells will display growth defects such as, for example, a reduced growth rate. Accordingly, at this screening/selection step, only those cells with a normal growth rate (or without growth defects) are selected for further characterization. A "normal growth rate," as used herein, refers to a growth rate that is comparable to control wild-type cells. In some embodiments, a cell is considered to have a "normal growth rate" if its growth rate is within about 15% of the growth rate of a wild-type control cell (e.g., cell without a nucleic acid variant/recombinant protein of the invention). For example, a cell may be considered to have a normal growth rate if its growth rate is within 50%, 40%, 30%, 25%, 20%, 15%, 14%, 13%, 12%, 11%, 10%, 9%, 8%, 7%, 6%, 5%, 4%, 3%, 2% or 1% of the growth rate of a wild-type control cell. A cell with a "growth defect," as used herein, may refer to a cell that fails to grow or that has a reduced growth rate of greater than 10%, greater than 15%, greater than 20%, or greater than 25% in comparison to the growth rate of a wild-type control cell.

The selective growth media used in accordance with the invention, in some embodiments, may depend on particular characteristics of the recombinant proteins, such as the specific function of the active recombinant protein. For example, when recombinant Pgi protein is grown on minimal medium where the only available carbon source is glucose, cells containing an active recombinant Pgi variant grow well, whereas cells containing an inactive recombinant Pgi variant grow poorly. In some embodiments, the selective media used may depend on the substrate of the recombinant Pgi variant. In some embodiments, a "rescue" approach is used to produce selective growth conditions, where the activity of the recombinant protein, which is required for cell growth, is deleted from the genome of the cell (e.g., gene(s) encoding the wild-type protein(s) is/are deleted or mutated), and then nucleic acid pgi variants are introduced into the cell. Those nucleic acid variants that are active should rescue cell growth (e.g., cells grows), and those that are inactive should not rescue cell growth (e.g., cells do not grow).

Selection for Protein Inactivation

Cells that do not display growth defects are then grown under selective conditions that induce cognate protease expression. This step permits recovery of cells that display growth defects.

The cells that display growth defects presumably carry recombinant proteins that are inactivated in the presence of a functional cognate protease (and are active in the absence of a functional cognate protease). These growth defective cells are then recovered, and the nucleic acid variants contained therein are sequenced for further characterization.

Further characterization may involve the expression of selected nucleic acid variants in cells that lack functional cognate protease. Growth of these cells may then be characterized and lysates produced and collected. The lysates may then be tested in vitro for loss of recombinant protein activity. Such testing may utilize protein activity assays upon incubation with or without exogenous, purified cognate protease. Various protein activity assays are known in the art, any of which may be used in accordance with the invention. The protein activity assay selected will depend on the type of protein. In some embodiments, the recombinant protein that inactivates the most completely and rapidly when exposed to protease may be selected for further use in, for example, engineering metabolic pathways of interest.

Cognate protease induction conditions will depend on the type of inducible promoter system chosen to drive the expression of the cognate protease and are known in the art. For example, isopropyl β-D-1-thiogalactopyranoside (IPTG) may be added to an in vitro cell-free system to activate an IPTG-responsive promoter operably linked to the cognate protease.

These and other aspects are illustrated by the following non-limiting examples.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

EXAMPLES

Example 1—Phosphoglucose Isomerase Enzymes of *Escherichia coli*

The phosphoglucose isomerase (Pgi) enzyme of *Escherichia coli* (*E. coli*) catalyzes the inter-conversion of glucose-6-phosphate and fructose-6-phosphate and is the first committed step in glycolysis. Protease targeting of this enzyme, without altering the function/activity of this key enzyme during cell growth, enables control of carbon flux between glycolysis and the pentose phosphate pathway in cell-free reactions.

Pgi Variant Library Construction

A 562-member linear double-stranded DNA library was designed and constructed by polymerase chain reaction (PCR), where the native *E. coli* pgi gene sequence (SEQ ID NO:1) was modified to include a nucleotide sequence (SEQ ID NO:37) encoding the eight amino acid protease recognition sequence (SEQ ID NO:38) of the human rhinovirus 3C (HRV) protease (FIGS. 1A and 1B). 547 members of the library contained mutant pgi genes with nucleotides encoding the protease recognition sequence inserted after each of the 549 codons in the wild-type pgi gene (excluding the first and last codons). Additional library members were created by replacing wild-type pgi gene sequence with a nucleotide sequence encoding the eight amino acids of the protease recognition sequence. These members contained replacements in the wild-type gene at 15 different locations starting with codon numbers 244, 245, 357, 358, 359, 360, 361, 362, 363, 364, 365, 366, 367, 461, 462 (where the codon numbers correspond to the first codon of the replacement sequence). In addition to the gene's coding sequence, each library member also contained 50 bp homology arms (e.g., 50 bp additional sequence upstream of the gene's start codon and 50 bp downstream of the gene's stop codon that are homologous to the wild-type pgi locus of the *E. coli* genome). If the LEVLFQGP (SEQ ID NO:38) sequence was to be inserted after amino acids L, LE or LEV, only EVLFQGP (SEQ ID NO:39), VLFQGP (SEQ ID NO:40) or LFQGP (SEQ ID NO:41) were inserted, respectively. Similarly, if the sequence was to be inserted before amino acids P, GP or QGP, only LEVLFQG (SEQ ID NO:42), LEVLFQ (SEQ ID NO:43) or LEVLF (SEQ ID NO:44) were inserted, respectively. In addition, if the insertion (or replacement) was between amino acids LP, for example, only EVLFQG (SEQ ID NO:45) was inserted (or replaced).

Strain Design

Figure 4:
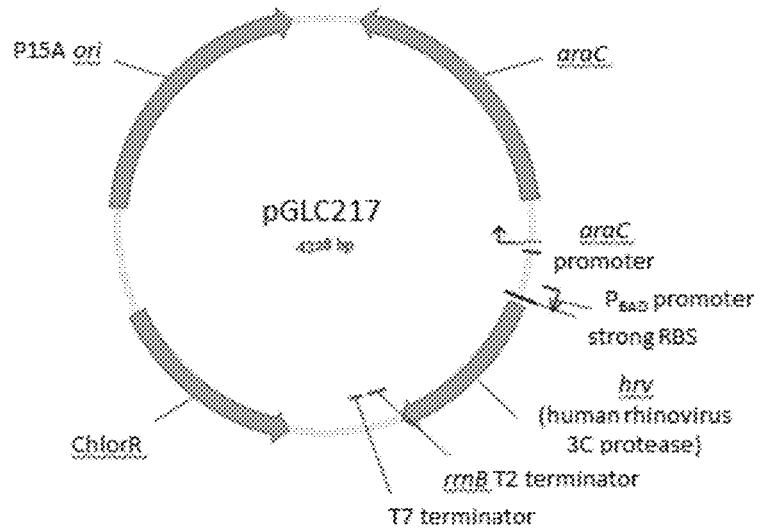
FIG. 4 is a diagram of plasmid pGLC217.

E. coli JW3985-1 (Coli Genetic Stock Center; CGSC #10867) from the Keio collection (Mol. Syst. Biol. 2006; 2:2006-08) was selected as the strain for the Pgi library screen. This strain contains a kanamycin-resistance marker (KanR) in place of the pgi gene. To prepare the strain for use in the screen, several modifications were made. First, KanR was removed using pCP20, which was obtained from E. coli BT340 (CGSC #7629), by employing the method described by Datsenko & Wanner (Proc Natl Acad Sci USA. 2000 Jun. 6; 97(12):6640-45, incorporated by reference herein). The resulting pgi locus of the strain contained the first three bases and the last 21 bases of the pgi gene, with a short scar sequence in between. Two plasmids (pGLA042 and pGLC217; FIGS. 3 and 4) were co-transformed into this strain to create the final strain that was used in the Pgi screen (GL12-085) through the pooled high-throughput selection approach (described below). pGLA042 was created from pKD46 (obtained from E. coli BW25113; GCSC #7739) by replacing pKD46's arabinose-inducible expression system with the temperature-inducible λ c1857-pR expression system. This change enables the temperature-inducible expression of the phage λ recombinase system genes γ, β, and exo from pGLA042. pGLC217 is a low-copy plasmid that provides for arabinose-inducible expression of the HRV 3C protease (codon-optimized for expression in E. coli; SEQ ID NO:34), the translation of which is facilitate by a strong ribosome binding site. A strain lacking pGLC217 was also produced (GL12-052) for use in the individual selection and assay approach (see below).

Individual Selection and Assay Approach

The chromosomal locus of pgi in GL12-052 was recombined with a 76-member subset of the linear, double-stranded DNA library described above. This subset contained the protease recognition sequence in solvent-accessible loop regions of Pgi, as predicted by its crystal structure (Protein Data Bank ID: 3NBU). Resulting Pgi library members carried protease recognition sequence insertions after the following positions in the wild-type Pgi primary amino acid sequence: 2-5, 9, 24-25, 33-36, 58-59, 85-96, 105-111, 113-115, 137-141, 143-144, 146, 173-176, 196, 250-251, 254, 366-370, 398-399, 410-414, 447-451, 477, 526-532.

GL12-052 was grown at 30° C. in low-salt-LB (lysogeny broth) (0.5×NaCl) to an optical density (OD) of 0.5. The culture was transferred to a 42° C. water bath and shaken for 15 minutes to induce the recombinase system from pGLA042. Induced cells were made electrocompetent following standard methods and transformed with the library of nuclei acid variants. Each library member (or nucleic acid variant) was transformed individually (25 µL cells and 250 ng library member), or in three-member subsets, and recovered in 1 mL low-salt-LB for greater than 1 h at 30° C. Recovered transformations were plated on M9-agar medium supplemented with 1% glucose (M9G). Plates were incubated at 30° C. for 1.5-2 days. The resulting colonies represented library members who contained active Pgi molecules despite the inclusion of the protease recognition sequence. The Pgi region of these library members' genomes were PCR-amplified and sequenced. Sequence-verified strains were then grown in small-scale shake flask cultures with M9G medium at 37° C. in order to determine their growth rates, thereby providing an in vivo method for assessing the impact of protease recognition sequence insertion on Pgi activity. Those strains with growth rates within 15% of the wild-type growth rate were advanced for a second round of screening to determine susceptibility to protease inactivation; 41 of the original 76-member subset were advanced.

To assess protease susceptibility, clarified lysates were created and assayed in vitro for Pgi activity in the presence or absence of exogenous HRV 3C protease. M9G cultures were grown to an OD of 2, pelleted (8000×g, 8 min., 4° C.), washed (10 mL 1×PBS, 4° C.), resuspended (12 mL 100 mM Tris-HCl, pH 7.5, 4° C.), lysed (AVESTIN® Emulsiflex C3 homogenizer at 15,000 psi), and clarified (22,000×g, 15 min, 4° C.). Clarified lysates (100 µL) were treated with ±10 units of exogenous HRV 3C protease (ACCELAGEN™ H0101S) for 4 hours at 37° C. and assayed for Pgi activity. Pgi activity was assayed by coupling to glucose-6-phosphate dehydrogenase (G6PDH) and following a reduction of nicotinamide adenine dinucleotide phosphate (NADP$^+$) at an absorbance of 340 nm for five minutes at 37° C. Reactions contained 100 mM Tris-HCl (pH 7.5), 8 mM MgSO$_4$, 5 mM fructose-6-phosphate, 1 mM NADP$^+$, 0.25 mg/mL bovine serum albumin, 2.5 units of purified G6PDH from Leuconostoc mesenteroides (MEGAZYME® E-GPDH5), and 30 volume-percent lysate/protease samples.

Figure 5:
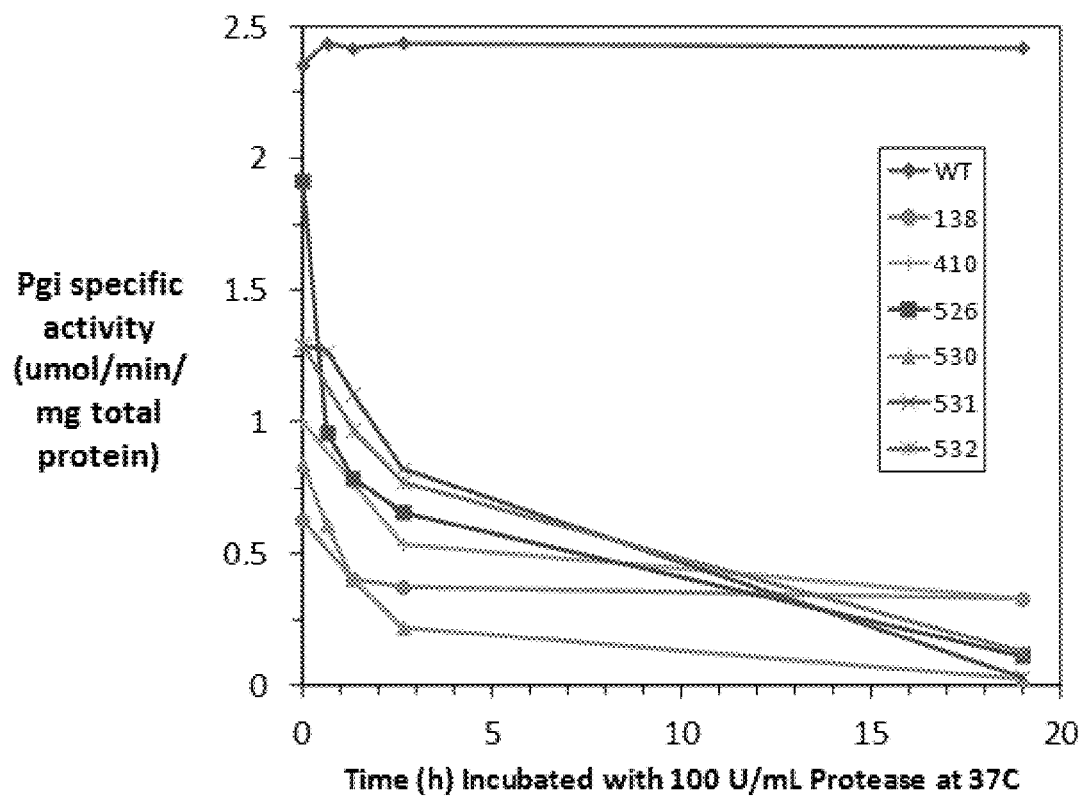
FIG. 5 shows a graph of phosphoglucose isomerase (Pgi) protein activity in cell lysates as a function of time. The graph shows enzymatic activity for wild-type (WT) Pgi as well as enzymatic activity for Pgi enzymes encoded by one of six unique pgi gene sequences, each containing the HRV 3C recognition sequence inserted after the following codons: 138, 410, 526, 530, 531, and 532.

Ultimately, 12 unique pgi gene sequences were selected, which contained the HRV 3C recognition sequence inserted after the following codons: 108, 109, 110, 138, 410, 526, 527, 528, 529, 530, 531, and 532. These 12 members of the original 76-member subset showed growth rates in M9G medium within 15% of wild-type and were significantly inactivated upon exposure to exogenous protease (Table 1). FIG. 5 shows a longer time-course treatment with protease for a subset of the library. Based on data obtained from the experiments described above, the optimal Pgi variant contained the HRV 3C recognition sequence after amino acid 526 (aka, Pgi-HRV-I526 from gene pgi-HRV-1526).

TABLE 1

Comparison of cell growth rates and Pgi activity.

| Protease Recognition Sequence Inserted after Amino Acid # | $\mu(h^{-1})$ | $\mu/_{wild\text{-}type}$ | Pgi Activity (µmol/min/mg total protein) | | Activity/Activity$^{wild\ type}$ | |
|---|---|---|---|---|---|---|
| | | | −protease | +protease | −protease | +protease |
| Δpgi | 0.15 | 0.22 | 0 | 0 | | |
| wild-type | 0.68 | 1 | 2.31 | 2.37 | 1 | 1 |
| 108 | 0.60 | 0.88 | 2.16 | 2.03 | 0.94 | 0.86 |
| 109 | 0.71 | 1.04 | 2.54 | 1.86 | 1.10 | 0.78 |
| 110 | 0.70 | 1.03 | 2.13 | 1.99 | 0.92 | 0.84 |
| 138 | 0.58 | 0.86 | 0.62 | 0.37 | 0.27 | 0.16 |
| 410 | 0.59 | 0.87 | 1.16 | 0.96 | 0.50 | 0.41 |

TABLE 1-continued

Comparison of cell growth rates and Pgi activity.

| Protease Recognition Sequence Inserted after Amino Acid # | $\mu(h^{-1})$ | $\mu/_{wild\text{-}type}$ | Pgi Activity (μmol/min/mg total protein) | | Activity/Activity$^{wild\ type}$ | |
|---|---|---|---|---|---|---|
| | | | −protease | +protease | −protease | +protease |
| 526 | 0.66 | 0.97 | 1.92 | 0.44 | 0.83 | 0.19 |
| 527 | 0.70 | 1.03 | 1.93 | 1.42 | 0.84 | 0.60 |
| 528 | 0.65 | 0.96 | 1.04 | 0.63 | 0.45 | 0.26 |
| 529 | 0.66 | 0.97 | 1.48 | 1.19 | 0.64 | 0.50 |
| 530 | 0.68 | 1.00 | 0.77 | 0.29 | 0.33 | 0.12 |
| 531 | 0.62 | 0.91 | 1.29 | 0.67 | 0.56 | 0.28 |
| 532 | 0.69 | 1.01 | 1.15 | 0.52 | 0.50 | 0.22 |

Note:
Small Δpgi control activity assay value (0.089) subtracted from all reported Pgi activities Pooled High-Throughput Selection Approach The chromosomal locus of pgi in GL12-085 was recombined with the 562-member pooled library (at equimolar concentrations), using the methods described above. The resulting cell library was plated onto M9-agar medium lacking arabinose and supplemented with 34 μg/mL of chloramphenicol and 1% glucose (M9CG). Cells were plated to obtain 5× coverage of the library, which amounted to 11 plates with approximately 250 cells/plate, thereby permitting easier replica-plating in the next step of the method. These pooled-library plates were incubated at 37° C. for 1.5-2 days. Colonies representing library members that provide active Pgi were subsequently replica-plated onto both M9GC media as well as M9-agar medium supplemented with 34 μg/mL chloramphenicol, 1% glucose and 2% arabinose (M9CGA). Replica plates were incubated at 37° C. for 1.5-2 days. All colonies that were present on M9CG plates but not present on M9CGA plates were recovered for further analysis.

The Pgi region of these colonies' genomes were PCR-amplified and sequenced. Seven unique pgi gene sequences were identified, which contained the HRV 3C recognition sequence inserted after the following codons: 524, 525, 526, 528, 529, 531 and 545. Members 526, 528, 529, and 531 were also identified from the 76-member-subset using the individual screening assay, described above.

Protein Crystal Structure

Figure 6:
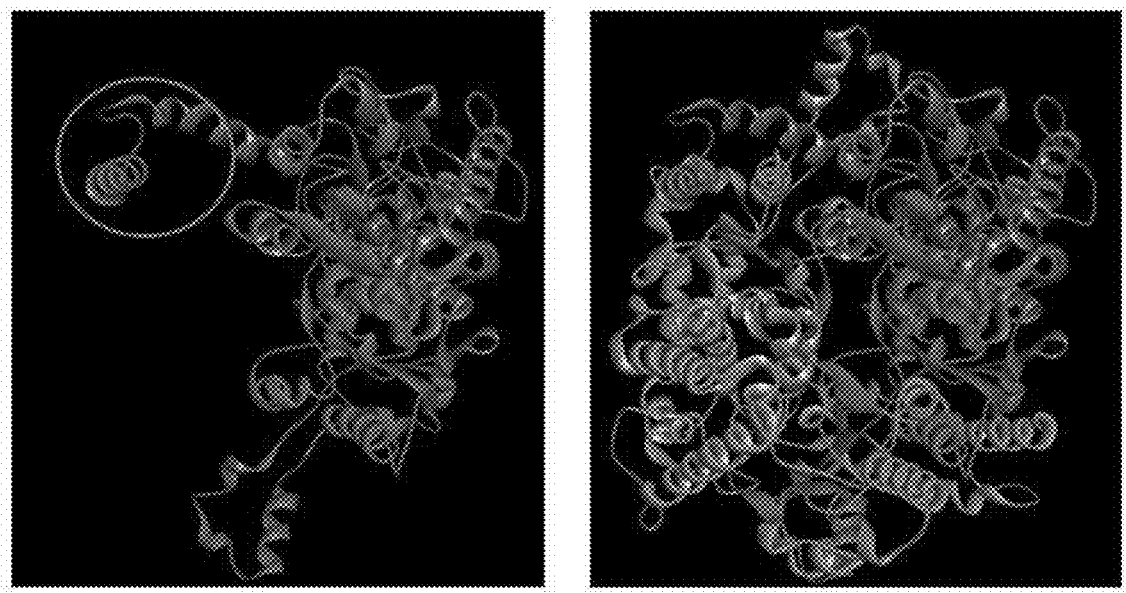
FIG. 6 shows a crystal structure of Pgi indicating a location of protease site insertion.

Nearly all 15 Pgi variants obtained from the individual and pooled screens map onto solvent-exposed loop regions of the published crystal structure for Pgi (Protein Data Bank ID: 3NBU). Further, variants 526-532 correspond to a loop region that precedes the C-terminal helix of Pgi, and variants 524-525 correspond to the C-terminal end of another helix, which possesses catalytic activity (FIG. 6). Protease-mediated cleavage of a recognition sequence inserted in the 524-532 region would thus cleave off the C-terminal helix and may result in the malformation of the preceding catalytic helix. Removal of the C-terminal helix is likely detrimental because Pgi is a dimer, and this helix helps to "latch" the dimer together.

Demonstration of Effective Protease-Mediated Inactivation of Targeted Pgi

Figure 7:
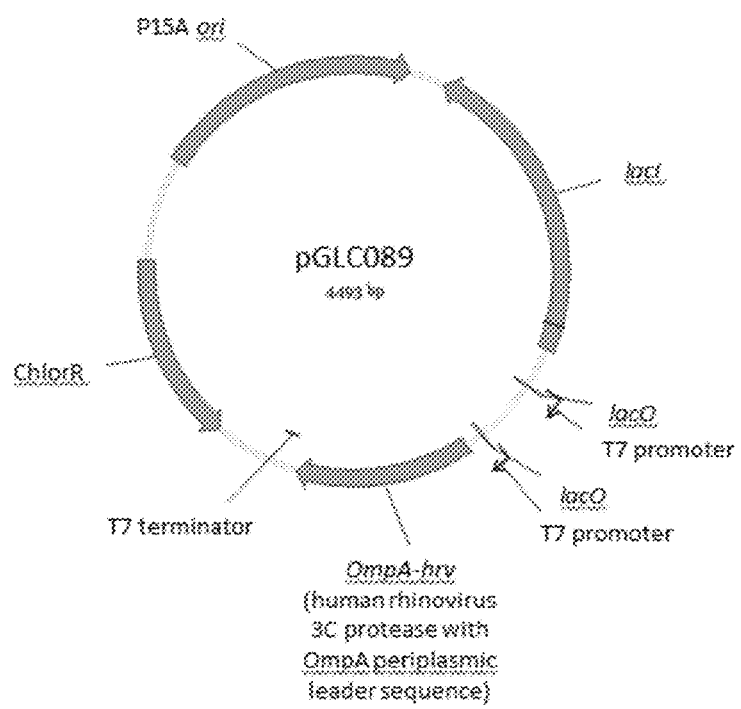
FIG. 7 is a diagram of plasmid pGLC089.
Figure 8:
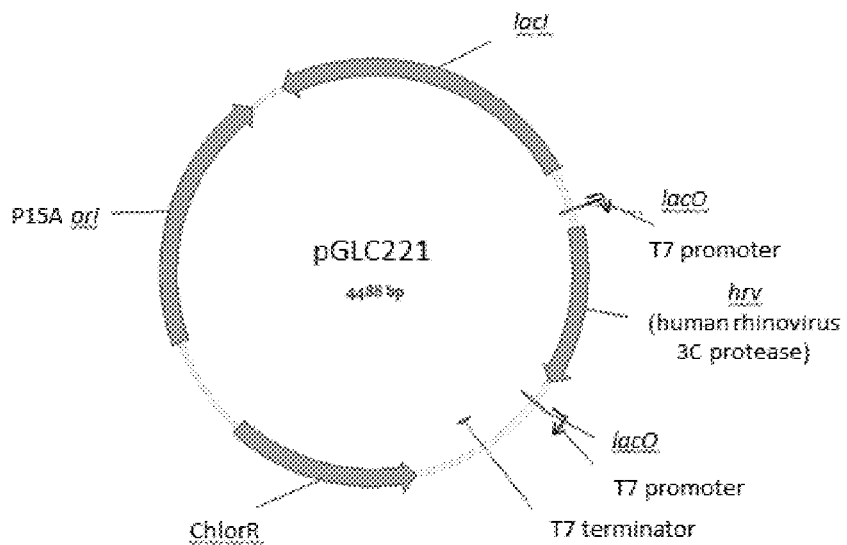
FIG. 8 is a diagram of plasmid pGLC221.
Figure 9:
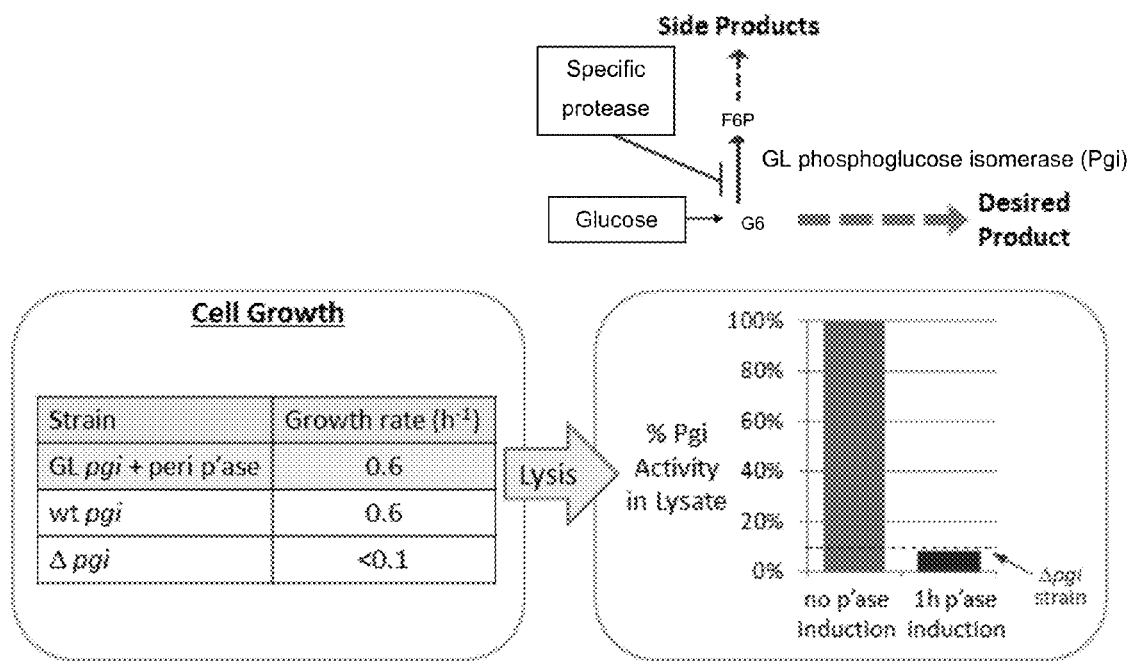
FIG. 9 is a table summarizing strain and growth rate data (left) and a graph of Pgi (GL pgi+peri p'ase) activity with and without protease induction (right). "GL pgi+peri p'ase" refers to cells containing a Pgi enzyme encoded by a pgi gene modified to include a periplasmic targeting sequence and a HRV 3C protease recognition site. "wt pgi" refers to cells containing a wild-type Pgi enzyme. "Δ pgi" refers to cells having a deleted wild-type pgi gene.

The pgi gene of E. coli BL21(DE3) was replaced with pgi-HRV-1526 (SEQ ID NO:9). This strain (GL12-116) was transformed individually with three plasmids: pACYCDuet-1, pGLC089 (FIG. 7), and pGLC221 (FIG. 8). pACYC-Duet-1 is a low-copy empty vector control plasmid, whereas pGLC089 & pGLC221 are capable of expressing HRV 3C protease (codon-optimized for expression in E. coli) from a T7 promoter when induced with isopropyl β-D-1 thiogalactopyranoside (IPTG). The protease gene of pGLC089 contains additional sequence such that the resulting HRV 3C protease possesses an N-terminal OmpA leader (MKKTAI-AIAVALAGFATVAQA) (SEQ ID NO:46) that sequesters the protease in the periplasm, whereas the protease gene of pGLC221 lacks such a leader and expresses in the cytoplasm. These strains were grown in a defined glucose medium at 37° C. to mid-log phase and induced with 0.8 mM IPTG for 2 hours. Clarified lysates were created and subsequently assayed for Pgi activity (as described above) (FIG. 9). Table 2 shows the growth rate of each strain prior to induction and the Pgi activity measured in the clarified lysate. When HRV 3C protease is expressed cytoplasmically, the growth rate falls by 40% as compared to the strain lacking protease, presumably due to leaky expression of the protease prior to IPTG-induced over-expression.

TABLE 2

Comparison

| OmpA Leader Sequence for Periplasmic Sequestration | Pre-Induction $\mu$ (h$^{-1}$) | Pgi Activity (μmol/min/mg total protein) |
|---|---|---|
| no protease | 0.62 | 1.3 |
| No | 0.38 | −0.01 |
| Yes | 0.55 | 0.01 |

Example 2—Phosphotransacetylase Enzymes of *Escherichia coli*

The phosphotransacetylase (Pta) enzyme (also referred to as phosphate acetyltransferase) of *Escherichia coli* (*E. coli*) catalyzes the first committed reaction of acetate overflow metabolism:

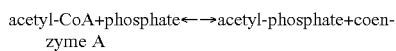

acetyl-CoA+phosphate↔acetyl-phosphate+coenzyme A

Acetate overflow occurs in rapidly growing glucose-fed aerobic cultures of *E. coli*. Accumulation of acetate excreted into production media limits growth rate, growth density, and recombinant protein production, which is a typical problem in industrial fermentation. Strains deleted for Pta activity routinely grow 15-20% slower than their wild-type counterparts, and while they diminish acetate excretion, they do not solve the overflow problem, as strains instead excrete lactate and pyruvate with similar deleterious effects. Protease targeting of Pta in cell-free production processes prevents acetate accumulation and shifts carbon flux into the tricarboxylic acid cycle, while allowing strains to grow at faster maximum growth rates than their pta-deleted counterparts.

Pta Variant Library Construction

A 200-member linear double-stranded DNA library was designed and constructed by polymerase chain reaction (PCR), where the native *E. coli* pta gene sequence (SEQ ID NO: 47) was modified to include a nucleotide sequence (SEQ ID NO:37) encoding the eight amino acid protease recognition sequence (SEQ ID NO:38) of the human rhinovirus 3C (HRV) protease. The nucleotide sequence encoding the protease recognition motif was inserted after the following codons in the wild-type pta gene: 350, 380-388, 401-405, 409-415, 426-431, 434-438, 446-465, 475-483, 490-495, 502-508, 511-518, 526-538, 544-549, 552-563, 577-586, 589-603, 615-620, 626-627, 629-632, 639-650, 653-660, 669-674, 681-687, 689-698, 709-713. In addition to the gene's coding sequence, each library member also contained 50 base pair (bp) homology arms (e.g., 50 bp additional sequence upstream of the gene's start codon and 50 bp downstream of the gene's stop codon that are homologous to the wild-type pta locus of the *E. coli* genome). If the LEVLFQGP (SEQ ID NO:38) sequence was to be inserted after amino acids L, LE or LEV, only EVLFQGP (SEQ ID NO:39), VLFQGP (SEQ ID NO:40) or LFQGP (SEQ ID NO:41) were inserted, respectively. Similarly, if the sequence was to be inserted before amino acids P, GP or QGP, only LEVLFQG (SEQ ID NO:42), LEVLFQ (SEQ ID NO:43) or LEVLF (SEQ ID NO:44) were inserted, respectively. In addition, if the insertion was between amino acids LP, for example, only EVLFQG (SEQ ID NO:45) was inserted.

Strain Design

For the Pta library screen, a modified version of *E. coli* JW2294-1 (*Coli* Genetic Stock Center; CGSC #9844) from the Keio collection (*Mol. Syst. Biol.* 2006; 2:2006-08) was created. To prepare the strain for use in the screen, the genome of JW2294-1 was modified in two ways, using methods described previously in Example 1 for phosphoglucose isomerase. First, the KanR marker, located in place of the pta gene, was removed, leaving a pta locus that contained the first three bases and the last 21 bases of the pta gene, with a short scar sequence in between. Second, the gene encoding the acetyl-CoA synthetase (i.e., acs) was replaced with KanR, thereby creating a strain that lacks the ability to grow on acetate as a sole carbon source and restores resistance to kanamycin. The recombinase plasmid described previously (pGLA042; FIG. 3) was transformed into this strain to create the final screen strain (GL13-052), which was used in an individual selection and assay approach.

Individual Selection and Assay Approach

The chromosomal locus of pta in GL13-052 was recombined individually with the 200-member linear, double-stranded DNA library described above, which places the HRV protease recognition sequence in predicted solvent-accessible loop regions of the C-terminal catalytic domain of Pta. As the crystal structure of the *E. coli* Pta has not yet been determined, the aforementioned loop regions were predicted by performing an amino acid sequence alignment of the C-terminal catalytic domain of the *E. coli* Pta to that of heterologous enzymes with published crystal structures (i.e., Protein Data Bank IDs: 1R5J & 2AF3).

A 2 liter (L) culture of GL13-052 was grown to an optical density at 600 nm of 0.5 at 30° C. in low-salt LB (5 g/L yeast extract, 10 g/L tryptone, 5 g/L NaCl) containing 10 μg/mL kanamycin and 50 μg/mL carbenicillin. The culture was transferred to a 42° C. water bath and shaken for 30 minutes to induce the recombinase system from pGLA042. Induced cells were made electrocompetent following standard methods, and 50 μL aliquots were flash frozen in liquid nitrogen and subsequently stored at −80° C. prior to recombination with library members.

Each library member DNA was transformed individually (25 μL cells and 50 ng library member DNA) and recovered in 1 mL low-salt LB for greater than 3 hours at 30° C. Recovered transformations were plated on M9-agar medium supplemented with 1% acetate and 10 μg/mL kanamycin, and plates were incubated at 37° C. for 2-3 days. Recombination events that yielded colonies were representative of library members that contained active Pta enzymes despite the inclusion of the protease recognition sequence motif. The Pta region of these library members' genomes were PCR-amplified and sequenced. Sequence-verified strains were then made competent and transformed with pGLC217 to enable the arabinose-inducible expression of HRV protease. Strains were also transformed with a control plasmid (pGLC219), which is identical to pGLC217 except that the gene encoding the HRV protease was replaced with a gene encoding the tobacco etch virus (TEV) protease. This protease will not cleave Pta variants.

To assess protease susceptibility in vivo, growth rates and acetate excretion were measured for strains containing viable Pta variants bearing either pGLC217 or pGLC219 that were grown at 37° C. in M9-minimal medium containing 0.5% glucose, 10 μg/mL kanamycin, and 34 μg/mL chloramphenicol. These cultures were grown±2% arabinose to overexpress the protease. Thus, the growth rate of each viable Pta variant was examined under four conditions: (1) TEV protease expression not induced, (2) arabinose-induced TEV protease expression, (3) HRV protease expression not induced, and (4) arabinose-induced HRV protease expression. Conditions (3) and (4) enable HRV protease-mediated Pta deactivation to be assessed via growth rate, while conditions (1) and (2) provide a control for the metabolic burden brought about by plasmid maintenance and arabinose-induced protein expression. As a positive control, a strain with wild-type pta was included in the study, whereas a strain deleted for pta served as the negative control.

Figure 10A:
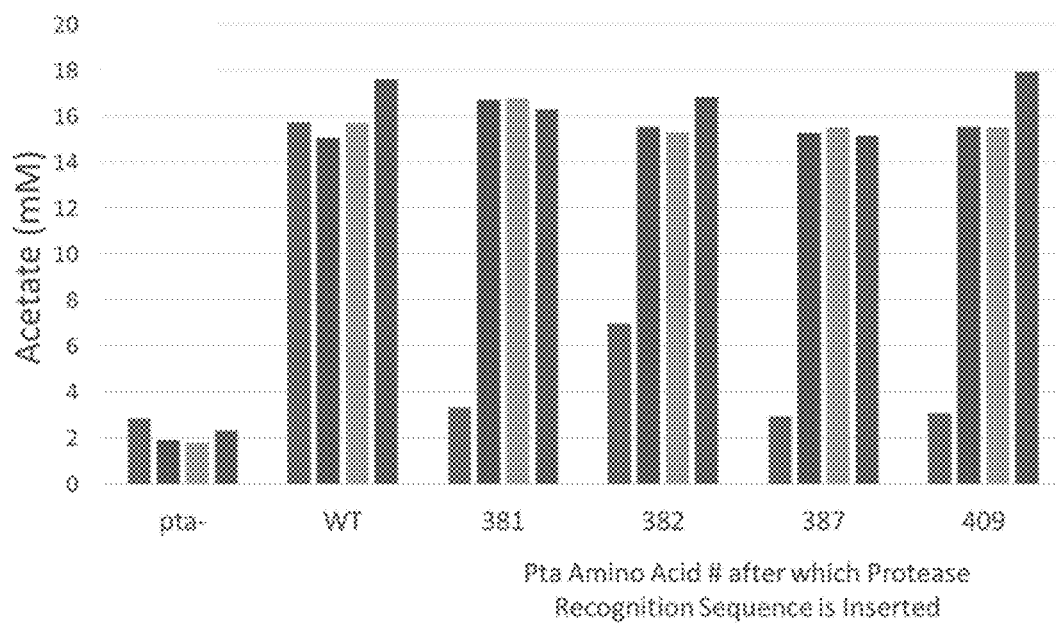
FIG. 10A shows a graph of acetate excretion in Pta variants with and without protease induction.
Figure 10B:
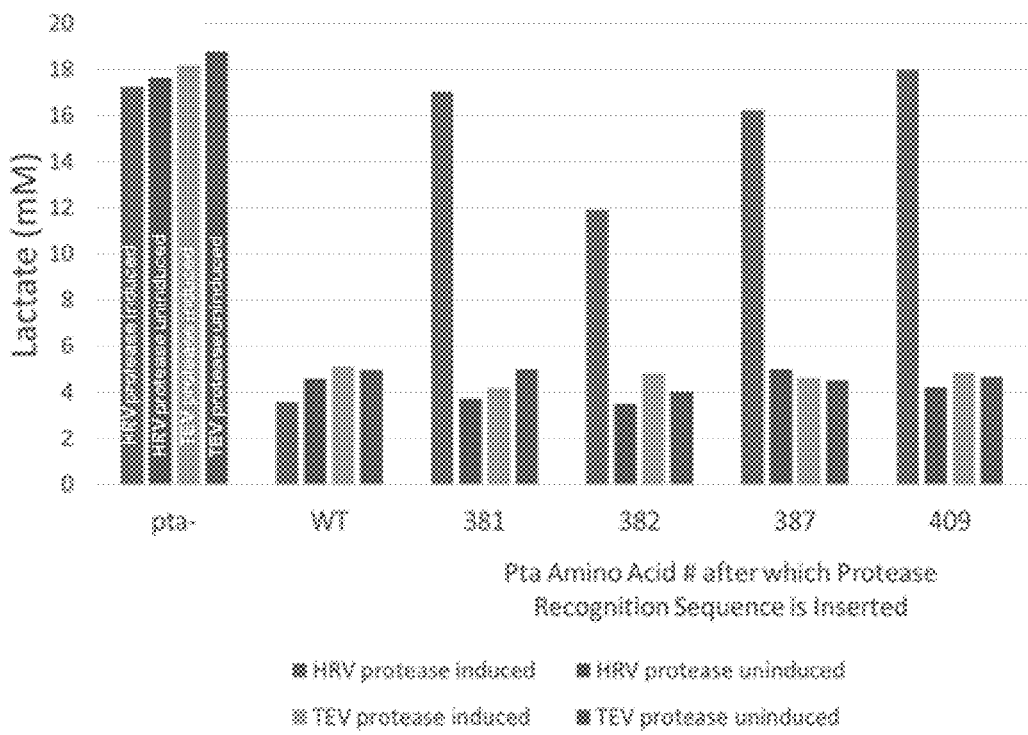
FIG. 10B shows a graph of lactate excretion in Pta variants with and without protease induction.

Based on growth and acetate excretion phenotypes in comparison to the control strains, four unique Pta variants were ultimately selected from the 200-member library. These variants contained the HRV protease cleavage motif inserted after amino acid 381, 382, 387, and 409 (SEQ ID NO: 50, 52, 54, 56, encoded respectively by SEQ ID NO: 49, 51, 53, 55). FIG. 10A shows the acetate excretion data, and FIG. 10B shows the lactate excretion data for the selected variants in comparison to the wild-type Pta and pta-controls. The wild-type Pta control exhibits a phenotype of high acetate and low lactate, whereas the pta-control exhibits the opposite phenotype. Thus, if a particular Pta variant is susceptible to HRV protease-mediated deactivation, it should show high acetate and low lactate in the absence of HRV protease induction, while showing the opposite when the HRV protease is induced. In the TEV protease controls, acetate should be high and lactate should be low regardless of induction, as the TEV protease recognition sequence is not present in the Pta variants. Clearly, variants 381, 382, 387, and 409 meet these criteria.

Figure 11:
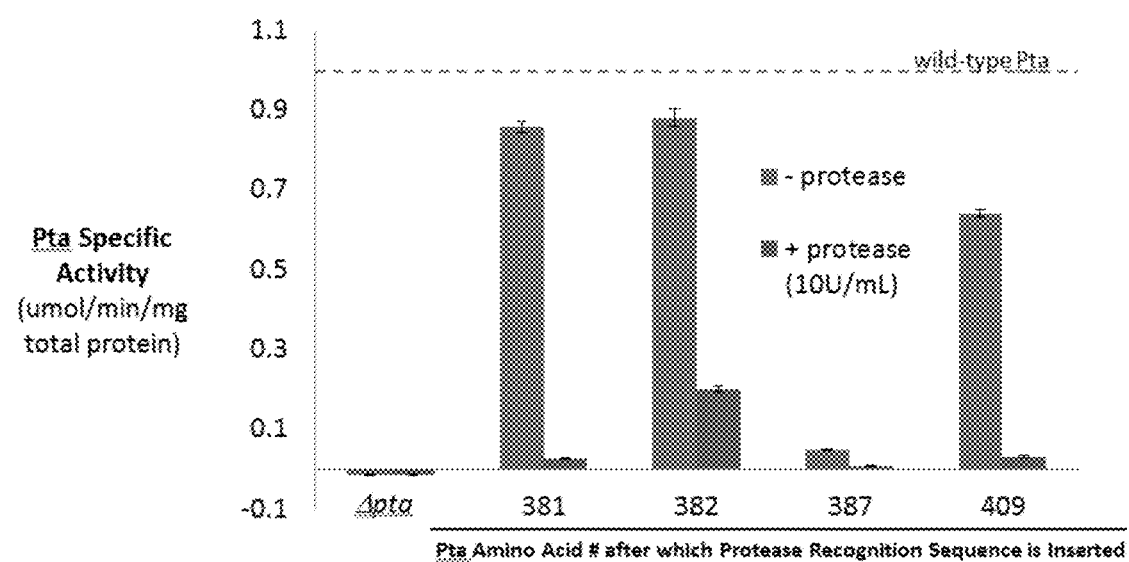
FIG. 11 shows a graph of phosphotransacetylase (Pta) protein activity in cell lysates with and without protease induction.

To further demonstrate that these Pta variants were susceptible to HRV protease, in vitro activity assays were performed. FIG. 11 shows the activity of each Pta variant in the presence or absence of exogenously supplied HRV protease after incubation for 30 minutes at 37° C. In all cases, Pta activity was dramatically reduced upon incubation with HRV protease. Variant 381 (SEQ ID NO: 50) exhibited the best balance between having both near-wild-type activity and being particularly susceptible to protease-mediated deactivation.

Example 3—Transketolase Enzymes of *Escherichia coli*

Figure 12:
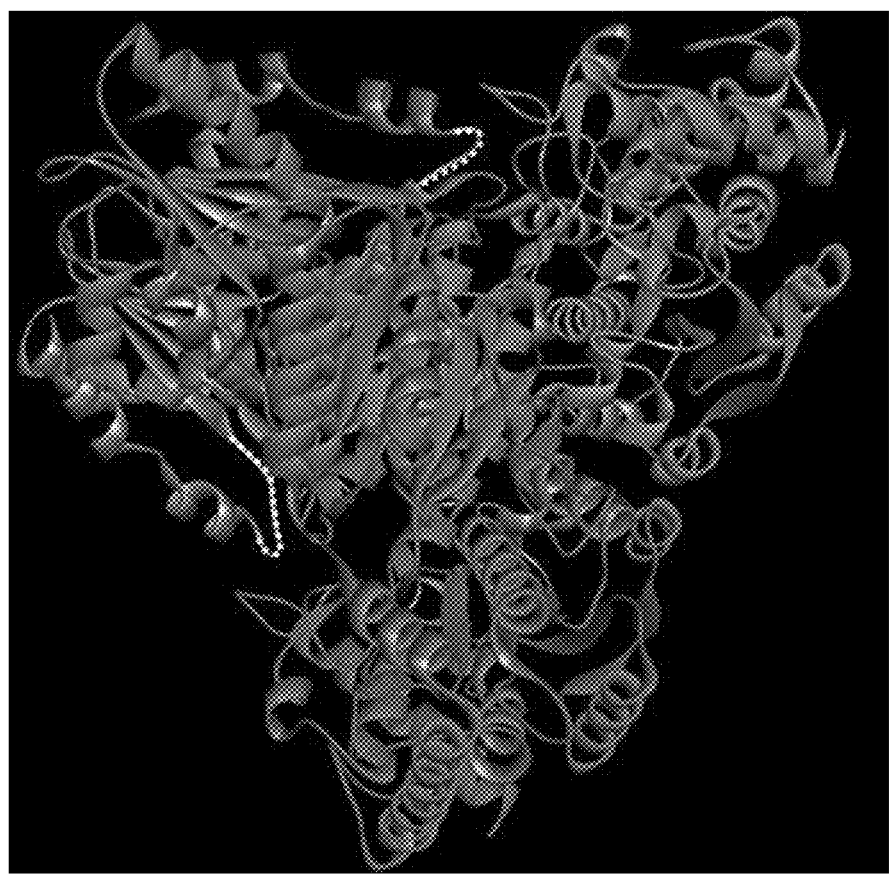
FIG. 12 shows a crystal structure of a transketolase A (TktA) protein dimer. The loops highlighted by a white dotted line (top-center and left-center) illustrate the location where the human rhinovirus (HRV) protease recognition sequence motif was inserted to enable protease-mediated deactivation of the TktA protein.

The major and minor transketolase isozymes (TktA and TktB, respectively) of *Escherichia coli* (*E. coli*) catalyze two reversible ketol transfer reactions in the pentose phosphate pathway:

fructose-6-phosphate+glyceraldehyde-3-phosphate⇌erythrose-4-phosphate+xylulose-5-phosphate ribose-5-phosphate+xylulose-5-phosphate⇌sedoheptulose-7-phosphate+glyceraldehyde-3-phosphate Transketolase activity ensures an adequate supply of erythrose-4-phosphate, a key central carbon metabolite necessary for the production of the three aromatic amino acids as well as several vitamins. Strains lacking transketolase activity require supplementation with erythrose-4-phosphate-derived compounds, such as aromatic amino acids and vitamins. Even with such supplementation, which can be costly, growth to high cell densities in fermentations is challenging. Transketolase also connects the pentose phosphate pathway to glycolysis, siphoning pentose phosphates away from excessive nucleotide production when the flux of glucose is high. Protease targeting of transketolase, without significantly altering its critical function during cell growth, benefits the production of pentose-derived molecules in cell-free reactions, as high pentose phosphate pathway flux is prevented from siphoning away to glycolysis. The crystal structure of transketolase is shown in FIG. 12.

Transketolase A Variant Library Construction

A 200-member linear double-stranded DNA library was designed and constructed by polymerase chain reaction (PCR), where the native *E. coli* transketolase A (tktA) gene sequence (SEQ ID NO:57) was modified to include a nucleotide sequence (SEQ ID NO:37) encoding the eight amino acid protease recognition sequence (SEQ ID NO:38) of the HRV protease. The nucleotide sequence encoding the protease recognition motif was inserted after the following codons in the wild-type tktA gene: 22-24, 43-55, 78-83, 88-110, 138-148, 172-175, 185-192, 196-200, 208-210, 218-220, 233-238, 245-257, 261-287, 294-296, 331-336, 350-354, 371-372, 388-403, 484-487, 508-511, 523-529, 544-551, 573-577, 591-593, 601-607, 624-627, 633-640, 648-651. In addition to the gene's coding sequence, each library member also contained 50 base pair (bp) homology arms (e.g., 50 bp of additional sequence upstream of the gene's start codon and 50 bp of additional sequence downstream of the gene's stop codon, each 50 bp sequence homologous to the wild-type tktA locus of the *E. coli* genome). For insertion of LEVLFQGP (SEQ ID NO:38) sequence after amino acids L, LE or LEV, only EVLFQGP (SEQ ID NO:39), VLFQGP (SEQ ID NO:40) or LFQGP (SEQ ID NO:41) were inserted, respectively. Similarly, for insertion of LEVLFQGP (SEQ ID NO:38) before amino acids P, GP or QGP, only LEVLFQG (SEQ ID NO:42), LEVLFQ (SEQ ID NO:43) or LEVLF (SEQ ID NO:44) were inserted, respectively. In addition, for insertion of LEVLFQGP (SEQ ID NO:38) between amino acids LP, for example, only EVLFQG (SEQ ID NO:45) was inserted.

Strain Design

For the TktA library screen, a modified version of *E. coli* JW5478-1 (*Coli* Genetic Stock Center; CGSC #11606) from the Keio collection (*Mol. Syst. Biol.* 2006; 2:2006-08) was created. To prepare the strain for use in the screen, the genome of JW5478-1 was modified in two ways using methods described in Example 1. First, the KanR marker, located in place of the tktA gene, was removed, leaving a tktA locus that contained the first 3 bases and the last 21 bases of the tktA gene, with a short scar sequence in between. Second, the gene encoding the minor transketolase (tktB) was replaced with KanR, thereby creating a strain that lacks any transketolase activity and restores resistance to kanamycin. The recombinase plasmid, pGLA042, (FIG. 3) was transformed into this strain to create the final screen strain, GL13-050, which was used in an individual selection and assay approach.

Individual Selection and Assay Approach

The chromosomal locus of tktA in GL13-050 was recombined individually with the 200-member linear, double-stranded DNA library described above, which places the HRV protease recognition sequence in solvent-accessible loop regions of TktA, as predicted by its crystal structure (Protein Data Bank ID: 1QGD) (see FIG. 11).

A 2 liter (L) culture of GL13-050 was grown to an optical density at 600 nm of 0.5 at 30° C. in a modified Vogel Bonner E (mVBE) medium (1×VBE minimal salts, 0.4% glucose, 2% casamino acids, 1 mM tryptophan, 0.25 mM 2,3-dihydroxybenzoate, 30 μM p-aminobenzoate, 30 uM p-hydroxybenzoate, 5 μM pyridoxine-HCl, 10 μg/mL kanamycin). The culture was transferred to a 42° C. water bath and shaken for 30 minutes to induce the recombinase system from pGLA042. Induced cells were made electrocompetent following standard methods, and 50 μL aliquots were flash frozen in liquid nitrogen and subsequently stored at −80° C. prior to recombination with library members.

Each library member DNA was transformed individually (25 μL cells and 50 ng library member DNA) and recovered in 1 mL low-salt-LB for greater than 3 hours at 30° C. Recovered transformants were plated on M9-agar medium supplemented with 1% glucose and 10 μg/mL kanamycin, and plates were incubated at 37° C. for 2-3 days. Transformations/recombinations that yielded colonies were representative of library members that contained active TktA molecules despite the inclusion of the protease recognition sequence motif. The TktA region of the genomes of these library members were PCR-amplified and sequenced. Sequence-verified strains were then made competent and transformed with pGLC217 to enable the arabinose-inducible expression of HRV protease. Strains were also transformed with a control plasmid, pGLC219, which is nearly identical to pGLC217, with the difference that the gene encoding the HRV protease was replaced with a gene encoding the tobacco etch virus (TEV) protease. This protease will not cleave TktA variants.

To assess protease susceptibility in vivo, growth rates were measured for strains containing viable TktA variants bearing either pGLC217 or pGLC219 that were grown at 37° C. in M9-minimal medium containing 0.5% glucose, 10 μg/mL kanamycin, and 34 μg/mL chloramphenicol. These cultures were grown±2% arabinose to overexpress the protease. Thus, the growth rate of each viable TktA variant was examined under four conditions: (1) TEV protease expression not induced, (2) arabinose-induced TEV protease expression, (3) HRV protease expression not induced, and (4) arabinose-induced HRV protease expression. Conditions (3) and (4) enabled HRV protease-mediated TktA deactivation to be assessed via growth rate, while conditions (1) and (2) provided a control for the metabolic burden brought about by plasmid maintenance and arabinose-induced protein expression.

Five unique TktA variants were selected from the 200-member library. The selected variants contained the HRV protease cleavage motif inserted after amino acid 635, 636, 637, 638, and 640 (SEQ ID NO:64-SEQ ID NO:68, encoded respectively by SEQ ID NO:58-SEQ ID NO:62). As shown in Table 3, the selected variants were able to support growth in minimal glucose medium when HRV protease expression was not induced but were significantly impaired for growth when HRV protease was induced. As the TEV protease controls show, the growth impairment brought about via protease induction was not simply the result of the burdensome nature of protein over-expression. Thus, these TktA variants were susceptible to HRV protease-mediated deactivation in vivo.

TABLE 3

Growth rates of protease-targetable TktA variants in minimal glucose medium

| Protease Recognition Sequence Inserted | TEV protease | | HRV protease | |
| --- | --- | --- | --- | --- |
| after Amino Acid # | −inducer | +inducer | −inducer | +inducer |
| wild-type | 0.55 | 0.53 | 0.60 | 0.57 |
| 635 | 0.52 | 0.52 | 0.58 | 0.47 |
| 636 | 0.39 | 0.42 | 0.43 | 0.17 |
| 637 | 0.46 | 0.46 | 0.40 | 0.11 |
| 638 | 0.18 | 0.18 | 0.13 | 0.08 |
| 640 | 0.48 | 0.52 | 0.55 | 0.34 |

Protein Crystal Structure

According to the published crystal structure for TktA (Protein Data Bank ID: 1QGD), the five TktA variants obtained from the screen (Table 3) map to the loop that immediately precedes the C-terminal helix (FIG. 11). TktA is active as a dimer, and this loop occurs at a dimerization interface. Without being bound by theory, cleavage of this loop by HRV protease likely disrupts the ability of the TktA to dimerize. Indeed, dimerization of transketolase is rate-limiting in formation of the active enzyme (*J. Biol. Chem.* 1981; 256:4877-83).

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

All references, patents and patent applications disclosed herein are incorporated by reference with respect to the subject matter for which each is cited, which in some cases may encompass the entirety of the document.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

SEQUENCE LISTING

SEQ ID NO: 1

ATGAAAAACATCAATCCAACGCAGACCGCTGCCTGGCAGGCACTACAGAAACACTTCGATGA

AATGAAAGACGTTACGATCGCCGATCTTTTTGCTAAAGACGGCGATCGTTTTTCTAAGTTCT

CCGCAACCTTCGACGATCAGATGCTGGTGGATTACTCCAAAAACCGCATCACTGAAGAGACG

CTGGCGAAATTACAGGATCTGGCGAAAGAGTGCGATCTGGCGGGCGCGATTAAGTCGATGTT

CTCTGGCGAGAAGATCAACCGCACTGAAAACCGCGCCGTGCTGCACGTAGCGCTGCGTAACC

GTAGCAATACCCCGATTTTGGTTGATGGCAAAGACGTAATGCCGGAAGTCAACGCGGTGCTG

GAGAAGATGAAAACCTTCTCAGAAGCGATTATTTCCGGTGAGTGGAAAGGTTATACCGGCAA

AGCAATCACTGACGTAGTGAACATCGGGATCGGCGGTTCTGACCTCGGCCCATACATGGTGA

CCGAAGCTCTGCGTCCGTACAAAAACCACCTGAACATGCACTTTGTTTCTAACGTCGATGGG

ACTCACATCGCGGAAGTGCTGAAAAAAGTAAACCCGGAAACCACGCTGTTCTTGGTAGCATC

TAAAACCTTCACCACTCAGGAAACTATGACCAACGCCCATAGCGCGCGTGACTGGTTCCTGA

AAGCGGCAGGTGATGAAAAACACGTTGCAAAACACTTTGCGGCGCTTTCCACCAATGCCAAA

GCCGTTGGCGAGTTTGGTATTGATACTGCCAACATGTTCGAGTTCTGGGACTGGGTTGGCGG

CCGTTACTCTTTGTGGTCAGCGATTGGCCTGTCGATTGTTCTCTCCATCGGCTTTGATAACT

TCGTTGAACTGCTTTCCGGCGCACACGCGATGGACAAGCATTTCTCCACCACGCCTGCCGAG

AAAAACCTGCCTGTACTGCTGGCGCTGATTGGCATCTGGTACAACAATTTCTTTGGTGCGGA

AACTGAAGCGATTCTGCCGTATGACCAGTATATGCACCGTTTCGCGGCGTACTTCCAGCAGG

GCAATATGGAGTCCAACGGTAAGTATGTTGACCGTAACGGTAACGTTGTGGATTACCAGACT

GGCCCGATTATCTGGGGTGAACCAGGCACTAACGGTCAGCACGCGTTCTACCAGCTGATCCA

CCAGGGAACCAAAATGGTACCGTGCGATTTCATCGCTCCGGCTATCACCCATAACCCGCTCT

CTGATCATCACCAGAAACTGCTGTCTAACTTCTTCGCCCAGACCGAAGCGCTGGCGTTTGGT

AAATCCCGCGAAGTGGTTGAGCAGGAATATCGTGATCAGGGTAAAGATCCGGCAACGCTTGA

CTACGTGGTGCCGTTCAAAGTATTCGAAGGTAACCGCCCGACCAACTCCATCCTGCTGCGTG

AAATCACTCCGTTCAGCCTGGGTGCGTTGATTGCGCTGTATGAGCACAAAATCTTTACTCAG

GGCGTGATCCTGAACATCTTCACCTTCGACCAGTGGGGCGTGGAACTGGGTAAACAGCTGGC

GAACCGTATTCTGCCAGAGCTGAAAGATGATAAAGAAATCAGCAGCCACGATAGCTCGACCA

ATGGTCTGATTAACCGCTATAAAGCGTGGCGCGGTTAA

SEQUENCE LISTING

SEQ ID NO: 2
ATGAAAAACATCAATCCAACGCAGACCGCTGCCTGGCAGGCACTACAGAAACACTTCGATGA
AATGAAAGACGTTACGATCGCCGATCTTTTTGCTAAAGATGGTGATCGTTTTTCTAAGTTCT
CCGCAACCTTCGACGATCAGATGCTGGTGGATTACTCCAAAAACCGCATCACTGAAGAGACG
CTGGCGAAATTACAGGATCTGGCGAAAGAGTGCGATCTGGCGGGCGCGATTAAGTCGATGTT
CTCTGGCGAGAAGATCAACCGCACTGAAAACCGCGCCGTGCTGCACGTAGCGCTGCGTAACC
GTAGCAATACCCCGCTGGAAGTGCTGTTTCAGGGTCCGATTTTGGTTGATGGCAAAGACGTA
ATGCCGGAAGTCAACGCGGTGCTGGAGAAGATGAAAACCTTCTCAGAAGCGATTATTTCCGG
TGAGTGGAAAGGTTATACCGGCAAAGCAATCACTGACGTAGTGAACATCGGGATCGGCGGTT
CTGACCTCGGCCCATACATGGTGACCGAAGCTCTGCGTCCGTACAAAAACCACCTGAACATG
CACTTTGTTTCTAACGTCGATGGGACTCACATCGCGGAAGTGCTGAAAAAAGTAAACCCGGA
AACCACGCTGTTCTTGGTAGCATCTAAAACCTTCACCACTCAGGAAACTATGACCAACGCCC
ATAGCGCGCGTGACTGGTTCCTGAAAGCGGCAGGTGATGAGAAGCACGTTGCAAAACACTTT
GCGGCGCTTTCCACCAATGCCAAAGCCGTTGGCGAGTTTGGTATTGATACTGCCAACATGTT
CGAGTTCTGGGACTGGGTTGGCGGCCGTTACTCTTTGTGGTCAGCGATTGGCCTGTCGATTG
TTCTCTCCATCGGCTTTGATAACTTCGTTGAACTGCTTTCCGGCGCACACGCGATGGACAAG
CATTTCTCCACCACGCCTGCCGAGAAAAACCTGCCTGTACTGCTGGCGCTGATTGGCATCTG
GTACAACAATTTCTTTGGTGCGGAAACTGAAGCGATTCTGCCGTATGACCAGTATATGCACC
GTTTCGCGGCGTACTTCCAGCAGGGCAATATGGAGTCCAACGGTAAGTATGTTGACCGTAAC
GGTAACGTTGTGGATTACCAGACTGGCCCGATTATCTGGGGTGAACCAGGCACTAACGGTCA
GCACGCGTTCTACCAGCTGATCCACCAGGGAACCAAAATGGTACCGTGCGATTTCATCGCTC
CGGCTATCACCCATAACCCGCTCTCTGATCATCACCAGAAACTGCTGTCTAACTTCTTCGCC
CAGACCGAAGCGCTGGCGTTTGGTAAATCCCGCGAAGTGGTTGAGCAGGAATATCGTGATCA
GGGTAAAGATCCGGCAACGCTTGACTACGTGGTGCCGTTCAAAGTATTCGAAGGTAACCGCC
CGACCAACTCCATCCTGCTGCGTGAAATCACTCCGTTCAGCCTGGGTGCGTTGATTGCGCTG
TATGAGCACAAAATCTTTACTCAGGGCGTGATCCTGAACATCTTCACCTTCGACCAGTGGGG
CGTGGAACTGGGTAAACAGCTGGCGAACCGTATTCTGCCAGAGCTGAAAGATGATAAAGAAA
TCAGCAGCCACGATAGCTCGACCAATGGTCTGATTAACCGCTATAAAGCGTGGCGCGGTtaa SEQ ID NO: 3
ATGAAAAACATCAATCCAACGCAGACCGCTGCCTGGCAGGCACTACAGAAACACTTCGATGA
AATGAAAGACGTTACGATCGCCGATCTTTTTGCTAAAGATGGTGATCGTTTTTCTAAGTTCT
CCGCAACCTTCGACGATCAGATGCTGGTGGATTACTCCAAAAACCGCATCACTGAAGAGACG
CTGGCGAAATTACAGGATCTGGCGAAAGAGTGCGATCTGGCGGGCGCGATTAAGTCGATGTT
CTCTGGCGAGAAGATCAACCGCACTGAAAACCGCGCCGTGCTGCACGTAGCGCTGCGTAACC
GTAGCAATACCCCGATTCTGGAAGTGCTGTTTCAGGGTCCGTTGGTTGATGGCAAAGACGTA
ATGCCGGAAGTCAACGCGGTGCTGGAGAAGATGAAAACCTTCTCAGAAGCGATTATTTCCGG
TGAGTGGAAAGGTTATACCGGCAAAGCAATCACTGACGTAGTGAACATCGGGATCGGCGGTT
CTGACCTCGGCCCATACATGGTGACCGAAGCTCTGCGTCCGTACAAAAACCACCTGAACATG
CACTTTGTTTCTAACGTCGATGGGACTCACATCGCGGAAGTGCTGAAAAAAGTAAACCCGGA

SEQUENCE LISTING

```
AACCACGCTGTTCTTGGTAGCATCTAAAACCTTCACCACTCAGGAAACTATGACCAACGCCC
ATAGCGCGCGTGACTGGTTCCTGAAAGCGGCAGGTGATGAGAAGCACGTTGCAAAACACTTT
GCGGCGCTTTCCACCAATGCCAAAGCCGTTGGCGAGTTTGGTATTGATACTGCCAACATGTT
CGAGTTCTGGGACTGGGTTGGCGGCCGTTACTCTTTGTGGTCAGCGATTGGCCTGTCGATTG
TTCTCTCCATCGGCTTTGATAACTTCGTTGAACTGCTTTCCGGCGCACACGCGATGGACAAG
CATTTCTCCACCACGCCTGCCGAGAAAAACCTGCCTGTACTGCTGGCGCTGATTGGCATCTG
GTACAACAATTTCTTTGGTGCGGAAACTGAAGCGATTCTGCCGTATGACCAGTATATGCACC
GTTTCGCGGCGTACTTCCAGCAGGGCAATATGGAGTCCAACGGTAAGTATGTTGACCGTAAC
GGTAACGTTGTGGATTACCAGACTGGCCCGATTATCTGGGGTGAACCAGGCACTAACGGTCA
GCACGCGTTCTACCAGCTGATCCACCAGGGAACCAAAATGGTACCGTGCGATTTCATCGCTC
CGGCTATCACCCATAACCCGCTCTCTGATCATCACCAGAAACTGCTGTCTAACTTCTTCGCC
CAGACCGAAGCGCTGGCGTTTGGTAAATCCCGCGAAGTGGTTGAGCAGGAATATCGTGATCA
GGGTAAAGATCCGGCAACGCTTGACTACGTGGTGCCGTTCAAAGTATTCGAAGGTAACCGCC
CGACCAACTCCATCCTGCTGCGTGAAATCACTCCGTTCAGCCTGGGTGCGTTGATTGCGCTG
TATGAGCACAAAATCTTTACTCAGGGCGTGATCCTGAACATCTTCACCTTCGACCAGTGGGG
CGTGGAACTGGGTAAACAGCTGGCGAACCGTATTCTGCCAGAGCTGAAAGATGATAAAGAAA
TCAGCAGCCACGATAGCTCGACCAATGGTCTGATTAACCGCTATAAAGCGTGGCGCGGTtaa
                                                      SEQ ID NO: 4
ATGAAAAACATCAATCCAACGCAGACCGCTGCCTGGCAGGCACTACAGAAACACTTCGATGA
AATGAAAGACGTTACGATCGCCGATCTTTTTGCTAAAGATGGTGATCGTTTTTCTAAGTTCT
CCGCAACCTTCGACGATCAGATGCTGGTGGATTACTCCAAAAACCGCATCACTGAAGAGACG
CTGGCGAAATTACAGGATCTGGCGAAAGAGTGCGATCTGGCGGGCGCGATTAAGTCGATGTT
CTCTGGCGAGAAGATCAACCGCACTGAAAACCGCGCCGTGCTGCACGTAGCGCTGCGTAACC
GTAGCAATACCCCGATTTTGGAAGTGCTGTTTCAGGGTCCGGTTGATGGCAAAGACGTAATG
CCGGAAGTCAACGCGGTGCTGGAGAAGATGAAAACCTTCTCAGAAGCGATTATTTCCGGTGA
GTGGAAAGGTTATACCGGCAAAGCAATCACTGACGTAGTGAACATCGGGATCGGCGGTTCTG
ACCTCGGCCCATACATGGTGACCGAAGCTCTGCGTCCGTACAAAAACCACCTGAACATGCAC
TTTGTTTCTAACGTCGATGGGACTCACATCGCGGAAGTGCTGAAAAAAGTAAACCCGGAAAC
CACGCTGTTCTTGGTAGCATCTAAAACCTTCACCACTCAGGAAACTATGACCAACGCCCATA
GCGCGCGTGACTGGTTCCTGAAAGCGGCAGGTGATGAGAAGCACGTTGCAAAACACTTTGCG
GCGCTTTCCACCAATGCCAAAGCCGTTGGCGAGTTTGGTATTGATACTGCCAACATGTTCGA
GTTCTGGGACTGGGTTGGCGGCCGTTACTCTTTGTGGTCAGCGATTGGCCTGTCGATTGTTC
TCTCCATCGGCTTTGATAACTTCGTTGAACTGCTTTCCGGCGCACACGCGATGGACAAGCAT
TTCTCCACCACGCCTGCCGAGAAAAACCTGCCTGTACTGCTGGCGCTGATTGGCATCTGGTA
CAACAATTTCTTTGGTGCGGAAACTGAAGCGATTCTGCCGTATGACCAGTATATGCACCGTT
TCGCGGCGTACTTCCAGCAGGGCAATATGGAGTCCAACGGTAAGTATGTTGACCGTAACGGT
AACGTTGTGGATTACCAGACTGGCCCGATTATCTGGGGTGAACCAGGCACTAACGGTCAGCA
CGCGTTCTACCAGCTGATCCACCAGGGAACCAAAATGGTACCGTGCGATTTCATCGCTCCGG
CTATCACCCATAACCCGCTCTCTGATCATCACCAGAAACTGCTGTCTAACTTCTTCGCCCAG
```

ACCGAAGCGCTGGCGTTTGGTAAATCCCGCGAAGTGGTTGAGCAGGAATATCGTGATCAGGG
TAAAGATCCGGCAACGCTTGACTACGTGGTGCCGTTCAAAGTATTCGAAGGTAACCGCCCGA
CCAACTCCATCCTGCTGCGTGAAATCACTCCGTTCAGCCTGGGTGCGTTGATTGCGCTGTAT
GAGCACAAAATCTTTACTCAGGGCGTGATCCTGAACATCTTCACCTTCGACCAGTGGGGCGT
GGAACTGGGTAAACAGCTGGCGAACCGTATTCTGCCAGAGCTGAAAGATGATAAAGAAATCA
GCAGCCACGATAGCTCGACCAATGGTCTGATTAACCGCTATAAAGCGTGGCGCGGTtaa

SEQ ID NO: 5

ATGAAAAACATCAATCCAACGCAGACCGCTGCCTGGCAGGCACTACAGAAACACTTCGATGA
AATGAAAGACGTTACGATCGCCGATCTTTTTGCTAAAGATGGTGATCGTTTTTCTAAGTTCT
CCGCAACCTTCGACGATCAGATGCTGGTGGATTACTCCAAAAACCGCATCACTGAAGAGACG
CTGGCGAAATTACAGGATCTGGCGAAAGAGTGCGATCTGGCGGGCGCGATTAAGTCGATGTT
CTCTGGCGAGAAGATCAACCGCACTGAAAACCGCGCCGTGCTGCACGTAGCGCTGCGTAACC
GTAGCAATACCCCGATTTTGGTTGATGGCAAAGACGTAATGCCGGAAGTCAACGCGGTGCTG
GAGAAGATGAAAACCTTCTCAGAAGCGATTATTTCCGGTGAGCTGGAAGTGCTGTTTCAGGG
TCCGTGGAAAGGTTATACCGGCAAAGCAATCACTGACGTAGTGAACATCGGGATCGGCGGTT
CTGACCTCGGCCCATACATGGTGACCGAAGCTCTGCGTCCGTACAAAAACCACCTGAACATG
CACTTTGTTTCTAACGTCGATGGGACTCACATCGCGGAAGTGCTGAAAAAAGTAAACCCGGA
AACCACGCTGTTCTTGGTAGCATCTAAAACCTTCACCACTCAGGAAACTATGACCAACGCCC
ATAGCGCGCGTGACTGGTTCCTGAAAGCGGCAGGTGATGAGAAGCACGTTGCAAAACACTTT
GCGGCGCTTTCCACCAATGCCAAAGCCGTTGGCGAGTTTGGTATTGATACTGCCAACATGTT
CGAGTTCTGGGACTGGGTTGGCGGCCGTTACTCTTTGTGGTCAGCGATTGGCCTGTCGATTG
TTCTCTCCATCGGCTTTGATAACTTCGTTGAACTGCTTTCCGGCGCACACGCGATGGACAAG
CATTTCTCCACCACGCCTGCCGAGAAAAACCTGCCTGTACTGCTGGCGCTGATTGGCATCTG
GTACAACAATTTCTTTGGTGCGGAAACTGAAGCGATTCTGCCGTATGACCAGTATATGCACC
GTTTCGCGGCGTACTTCCAGCAGGGCAATATGGAGTCCAACGGTAAGTATGTTGACCGTAAC
GGTAACGTTGTGGATTACCAGACTGGCCCGATTATCTGGGGTGAACCAGGCACTAACGGTCA
GCACGCGTTCTACCAGCTGATCCACCAGGGAACCAAAATGGTACCGTGCGATTTCATCGCTC
CGGCTATCACCCATAACCCGCTCTCTGATCATCACCAGAAACTGCTGTCTAACTTCTTCGCC
CAGACCGAAGCGCTGGCGTTTGGTAAATCCCGCGAAGTGGTTGAGCAGGAATATCGTGATCA
GGGTAAAGATCCGGCAACGCTTGACTACGTGGTGCCGTTCAAAGTATTCGAAGGTAACCGCC
CGACCAACTCCATCCTGCTGCGTGAAATCACTCCGTTCAGCCTGGGTGCGTTGATTGCGCTG
TATGAGCACAAAATCTTTACTCAGGGCGTGATCCTGAACATCTTCACCTTCGACCAGTGGGG
CGTGGAACTGGGTAAACAGCTGGCGAACCGTATTCTGCCAGAGCTGAAAGATGATAAAGAAA
TCAGCAGCCACGATAGCTCGACCAATGGTCTGATTAACCGCTATAAAGCGTGGCGCGGTtaa

SEQ ID NO: 6

ATGAAAAACATCAATCCAACGCAGACCGCTGCCTGGCAGGCACTACAGAAACACTTCGATGA
AATGAAAGACGTTACGATCGCCGATCTTTTTGCTAAAGATGGTGATCGTTTTTCTAAGTTCT
CCGCAACCTTCGACGATCAGATGCTGGTGGATTACTCCAAAAACCGCATCACTGAAGAGACG
CTGGCGAAATTACAGGATCTGGCGAAAGAGTGCGATCTGGCGGGCGCGATTAAGTCGATGTT

```
CTCTGGCGAGAAGATCAACCGCACTGAAAACCGCGCCGTGCTGCACGTAGCGCTGCGTAACC

GTAGCAATACCCCGATTTTGGTTGATGGCAAAGACGTAATGCCGGAAGTCAACGCGGTGCTG

GAGAAGATGAAAACCTTCTCAGAAGCGATTATTTCCGGTGAGTGGAAAGGTTATACCGGCAA

AGCAATCACTGACGTAGTGAACATCGGGATCGGCGGTTCTGACCTCGGCCCATACATGGTGA

CCGAAGCTCTGCGTCCGTACAAAAACCACCTGAACATGCACTTTGTTTCTAACGTCGATGGG

ACTCACATCGCGGAAGTGCTGAAAAAAGTAAACCCGGAAACCACGCTGTTCTTGGTAGCATC

TAAAACCTTCACCACTCAGGAAACTATGACCAACGCCCATAGCGCGCGTGACTGGTTCCTGA

AAGCGGCAGGTGATGAGAAGCACGTTGCAAAACACTTTGCGGCGCTTTCCACCAATGCCAAA

GCCGTTGGCGAGTTTGGTATTGATACTGCCAACATGTTCGAGTTCTGGGACTGGGTTGGCGG

CCGTTACTCTTTGTGGTCAGCGATTGGCCTGTCGATTGTTCTCTCCATCGGCTTTGATAACT

TCGTTGAACTGCTTTCCGGCGCACACGCGATGGACAAGCATTTCTCCACCACGCCTGCCGAG

AAAAACCTGCCTGTACTGCTGGCGCTGATTGGCATCTGGTACAACAATTTCTTTGGTGCGGA

AACTGAAGCGATTCTGCCGTATGACCAGTATATGCACCGTTTCGCGGCGTACTTCCAGCAGG

GCAATATGGAGTCCAACGGTAAGTATGTTGACCGTAACGGTAACGTTGTGGATTACCAGACT

GGCCCGATTATCTGGGGTGAACCAGGCACTAACGGTCAGCACGCGTTCTACCAGCTGATCCA

CCAGGGAACCAAAATGGTACCGTGCGATTTCATCGCTCCGGCTATCACCCATCTGGAAGTGC

TGTTTCAGGGTCCGAACCCGCTCTCTGATCATCACCAGAAACTGCTGTCTAACTTCTTCGCC

CAGACCGAAGCGCTGGCGTTTGGTAAATCCCGCGAAGTGGTTGAGCAGGAATATCGTGATCA

GGGTAAAGATCCGGCAACGCTTGACTACGTGGTGCCGTTCAAAGTATTCGAAGGTAACCGCC

CGACCAACTCCATCCTGCTGCGTGAAATCACTCCGTTCAGCCTGGGTGCGTTGATTGCGCTG

TATGAGCACAAAATCTTTACTCAGGGCGTGATCCTGAACATCTTCACCTTCGACCAGTGGGG

CGTGGAACTGGGTAAACAGCTGGCGAACCGTATTCTGCCAGAGCTGAAAGATGATAAAGAAA

TCAGCAGCCACGATAGCTCGACCAATGGTCTGATTAACCGCTATAAAGCGTGGCGCGGTtaa
                                                                SEQ ID NO: 7
ATGAAAAACATCAATCCAACGCAGACCGCTGCCTGGCAGGCACTACAGAAACACTTCGATGA

AATGAAAGACGTTACGATCGCCGATCTTTTTGCTAAAGATGGTGATCGTTTTTCTAAGTTCT

CCGCAACCTTCGACGATCAGATGCTGGTGGATTACTCCAAAAACCGCATCACTGAAGAGACG

CTGGCGAAATTACAGGATCTGGCGAAAGAGTGCGATCTGGCGGGCGCGATTAAGTCGATGTT

CTCTGGCGAGAAGATCAACCGCACTGAAAACCGCGCCGTGCTGCACGTAGCGCTGCGTAACC

GTAGCAATACCCCGATTTTGGTTGATGGCAAAGACGTAATGCCGGAAGTCAACGCGGTGCTG

GAGAAGATGAAAACCTTCTCAGAAGCGATTATTTCCGGTGAGTGGAAAGGTTATACCGGCAA

AGCAATCACTGACGTAGTGAACATCGGGATCGGCGGTTCTGACCTCGGCCCATACATGGTGA

CCGAAGCTCTGCGTCCGTACAAAAACCACCTGAACATGCACTTTGTTTCTAACGTCGATGGG

ACTCACATCGCGGAAGTGCTGAAAAAAGTAAACCCGGAAACCACGCTGTTCTTGGTAGCATC

TAAAACCTTCACCACTCAGGAAACTATGACCAACGCCCATAGCGCGCGTGACTGGTTCCTGA

AAGCGGCAGGTGATGAGAAGCACGTTGCAAAACACTTTGCGGCGCTTTCCACCAATGCCAAA

GCCGTTGGCGAGTTTGGTATTGATACTGCCAACATGTTCGAGTTCTGGGACTGGGTTGGCGG

CCGTTACTCTTTGTGGTCAGCGATTGGCCTGTCGATTGTTCTCTCCATCGGCTTTGATAACT

TCGTTGAACTGCTTTCCGGCGCACACGCGATGGACAAGCATTTCTCCACCACGCCTGCCGAG
```

-continued

SEQUENCE LISTING

AAAAACCTGCCTGTACTGCTGGCGCTGATTGGCATCTGGTACAACAATTTCTTTGGTGCGGA

AACTGAAGCGATTCTGCCGTATGACCAGTATATGCACCGTTTCGCGGCGTACTTCCAGCAGG

GCAATATGGAGTCCAACGGTAAGTATGTTGACCGTAACGGTAACGTTGTGGATTACCAGACT

GGCCCGATTATCTGGGGTGAACCAGGCACTAACGGTCAGCACGCGTTCTACCAGCTGATCCA

CCAGGGAACCAAAATGGTACCGTGCGATTTCATCGCTCCGGCTATCACCCATAACCCGCTCT

CTGATCATCACCAGAAACTGCTGTCTAACTTCTTCGCCCAGACCGAAGCGCTGGCGTTTGGT

AAATCCCGCGAAGTGGTTGAGCAGGAATATCGTGATCAGGGTAAAGATCCGGCAACGCTTGA

CTACGTGGTGCCGTTCAAAGTATTCGAAGGTAACCGCCCGACCAACTCCATCCTGCTGCGTG

AAATCACTCCGTTCAGCCTGGGTGCGTTGATTGCGCTGTATGAGCACAAAATCTTTACTCAG

GGCGTGATCCTGAACATCTTCACCTTCGACCAGTGGGGCGTGGAACTGGGTAAACAGCTGGC

GAACCGTATTCTGCCAGAGCTGGAAGTGCTGTTTCAGGGTCCGAAAGATGATAAAGAAATCA

GCAGCCACGATAGCTCGACCAATGGTCTGATTAACCGCTATAAAGCGTGGCGCGGTtaa

SEQ ID NO: 8

ATGAAAAACATCAATCCAACGCAGACCGCTGCCTGGCAGGCACTACAGAAACACTTCGATGA

AATGAAAGACGTTACGATCGCCGATCTTTTTGCTAAAGATGGTGATCGTTTTTCTAAGTTCT

CCGCAACCTTCGACGATCAGATGCTGGTGGATTACTCCAAAAACCGCATCACTGAAGAGACG

CTGGCGAAATTACAGGATCTGGCGAAAGAGTGCGATCTGGCGGGCGCGATTAAGTCGATGTT

CTCTGGCGAGAAGATCAACCGCACTGAAAACCGCGCCGTGCTGCACGTAGCGCTGCGTAACC

GTAGCAATACCCCGATTTTGGTTGATGGCAAAGACGTAATGCCGGAAGTCAACGCGGTGCTG

GAGAAGATGAAAACCTTCTCAGAAGCGATTATTTCCGGTGAGTGGAAAGGTTATACCGGCAA

AGCAATCACTGACGTAGTGAACATCGGGATCGGCGGTTCTGACCTCGGCCCATACATGGTGA

CCGAAGCTCTGCGTCCGTACAAAAACCACCTGAACATGCACTTTGTTTCTAACGTCGATGGG

ACTCACATCGCGGAAGTGCTGAAAAAAGTAAACCCGGAAACCACGCTGTTCTTGGTAGCATC

TAAAACCTTCACCACTCAGGAAACTATGACCAACGCCCATAGCGCGCGTGACTGGTTCCTGA

AAGCGGCAGGTGATGAGAAGCACGTTGCAAAACACTTTGCGGCGCTTTCCACCAATGCCAAA

GCCGTTGGCGAGTTTGGTATTGATACTGCCAACATGTTCGAGTTCTGGGACTGGGTTGGCGG

CCGTTACTCTTTGTGGTCAGCGATTGGCCTGTCGATTGTTCTCTCCATCGGCTTTGATAACT

TCGTTGAACTGCTTTCCGGCGCACACGCGATGGACAAGCATTTCTCCACCACGCCTGCCGAG

AAAAACCTGCCTGTACTGCTGGCGCTGATTGGCATCTGGTACAACAATTTCTTTGGTGCGGA

AACTGAAGCGATTCTGCCGTATGACCAGTATATGCACCGTTTCGCGGCGTACTTCCAGCAGG

GCAATATGGAGTCCAACGGTAAGTATGTTGACCGTAACGGTAACGTTGTGGATTACCAGACT

GGCCCGATTATCTGGGGTGAACCAGGCACTAACGGTCAGCACGCGTTCTACCAGCTGATCCA

CCAGGGAACCAAAATGGTACCGTGCGATTTCATCGCTCCGGCTATCACCCATAACCCGCTCT

CTGATCATCACCAGAAACTGCTGTCTAACTTCTTCGCCCAGACCGAAGCGCTGGCGTTTGGT

AAATCCCGCGAAGTGGTTGAGCAGGAATATCGTGATCAGGGTAAAGATCCGGCAACGCTTGA

CTACGTGGTGCCGTTCAAAGTATTCGAAGGTAACCGCCCGACCAACTCCATCCTGCTGCGTG

AAATCACTCCGTTCAGCCTGGGTGCGTTGATTGCGCTGTATGAGCACAAAATCTTTACTCAG

GGCGTGATCCTGAACATCTTCACCTTCGACCAGTGGGGCGTGGAACTGGGTAAACAGCTGGC

GAACCGTATTCTGCCAGAGCTGAAACTGGAAGTGCTGTTTCAGGGTCCGGATGATAAAGAAA

TCAGCAGCCACGATAGCTCGACCAATGGTCTGATTAACCGCTATAAAGCGTGGCGCGGTtaa

SEQUENCE LISTING

SEQ ID NO: 9
ATGAAAAACATCAATCCAACGCAGACCGCTGCCTGGCAGGCACTACAGAAACACTTCGATGA
AATGAAAGACGTTACGATCGCCGATCTTTTTGCTAAAGATGGTGATCGTTTTTCTAAGTTCT
CCGCAACCTTCGACGATCAGATGCTGGTGGATTACTCCAAAAACCGCATCACTGAAGAGACG
CTGGCGAAATTACAGGATCTGGCGAAAGAGTGCGATCTGGCGGGCGCGATTAAGTCGATGTT
CTCTGGCGAGAAGATCAACCGCACTGAAAACCGCGCCGTGCTGCACGTAGCGCTGCGTAACC
GTAGCAATACCCCGATTTTGGTTGATGGCAAAGACGTAATGCCGGAAGTCAACGCGGTGCTG
GAGAAGATGAAAACCTTCTCAGAAGCGATTATTTCCGGTGAGTGGAAAGGTTATACCGGCAA
AGCAATCACTGACGTAGTGAACATCGGGATCGGCGGTTCTGACCTCGGCCCATACATGGTGA
CCGAAGCTCTGCGTCCGTACAAAAACCACCTGAACATGCACTTTGTTTCTAACGTCGATGGG
ACTCACATCGCGGAAGTGCTGAAAAAAGTAAACCCGGAAACCACGCTGTTCTTGGTAGCATC
TAAAACCTTCACCACTCAGGAAACTATGACCAACGCCCATAGCGCGCGTGACTGGTTCCTGA
AAGCGGCAGGTGATGAGAAGCACGTTGCAAAACACTTTGCGGCGCTTTCCACCAATGCCAAA
GCCGTTGGCGAGTTTGGTATTGATACTGCCAACATGTTCGAGTTCTGGGACTGGGTTGGCGG
CCGTTACTCTTTGTGGTCAGCGATTGGCCTGTCGATTGTTCTCTCCATCGGCTTTGATAACT
TCGTTGAACTGCTTTCCGGCGCACACGCGATGGACAAGCATTTCTCCACCACGCCTGCCGAG
AAAAACCTGCCTGTACTGCTGGCGCTGATTGGCATCTGGTACAACAATTTCTTTGGTGCGGA
AACTGAAGCGATTCTGCCGTATGACCAGTATATGCACCGTTTCGCGGCGTACTTCCAGCAGG
GCAATATGGAGTCCAACGGTAAGTATGTTGACCGTAACGGTAACGTTGTGGATTACCAGACT
GGCCCGATTATCTGGGGTGAACCAGGCACTAACGGTCAGCACGCGTTCTACCAGCTGATCCA
CCAGGGAACCAAATGGTACCGTGCGATTTCATCGCTCCGGCTATCACCCATAACCCGCTCT
CTGATCATCACCAGAAACTGCTGTCTAACTTCTTCGCCCAGACCGAAGCGCTGGCGTTTGGT
AAATCCCGCGAAGTGGTTGAGCAGGAATATCGTGATCAGGGTAAAGATCCGGCAACGCTTGA
CTACGTGGTGCCGTTCAAAGTATTCGAAGGTAACCGCCCGACCAACTCCATCCTGCTGCGTG
AAATCACTCCGTTCAGCCTGGGTGCGTTGATTGCGCTGTATGAGCACAAAATCTTTACTCAG
GGCGTGATCCTGAACATCTTCACCTTCGACCAGTGGGGCGTGGAACTGGGTAAACAGCTGGC
GAACCGTATTCTGCCAGAGCTGAAAGATCTGGAAGTGCTGTTTCAGGGTCCGGATAAAGAAA
TCAGCAGCCACGATAGCTCGACCAATGGTCTGATTAACCGCTATAAAGCGTGGCGCGGTtaa SEQ ID NO: 10
ATGAAAAACATCAATCCAACGCAGACCGCTGCCTGGCAGGCACTACAGAAACACTTCGATGA
AATGAAAGACGTTACGATCGCCGATCTTTTTGCTAAAGATGGTGATCGTTTTTCTAAGTTCT
CCGCAACCTTCGACGATCAGATGCTGGTGGATTACTCCAAAAACCGCATCACTGAAGAGACG
CTGGCGAAATTACAGGATCTGGCGAAAGAGTGCGATCTGGCGGGCGCGATTAAGTCGATGTT
CTCTGGCGAGAAGATCAACCGCACTGAAAACCGCGCCGTGCTGCACGTAGCGCTGCGTAACC
GTAGCAATACCCCGATTTTGGTTGATGGCAAAGACGTAATGCCGGAAGTCAACGCGGTGCTG
GAGAAGATGAAAACCTTCTCAGAAGCGATTATTTCCGGTGAGTGGAAAGGTTATACCGGCAA
AGCAATCACTGACGTAGTGAACATCGGGATCGGCGGTTCTGACCTCGGCCCATACATGGTGA
CCGAAGCTCTGCGTCCGTACAAAAACCACCTGAACATGCACTTTGTTTCTAACGTCGATGGG
ACTCACATCGCGGAAGTGCTGAAAAAAGTAAACCCGGAAACCACGCTGTTCTTGGTAGCATC

```
TAAAACCTTCACCACTCAGGAAACTATGACCAACGCCCATAGCGCGCGTGACTGGTTCCTGA
AAGCGGCAGGTGATGAGAAGCACGTTGCAAAACACTTTGCGGCGCTTTCCACCAATGCCAAA
GCCGTTGGCGAGTTTGGTATTGATACTGCCAACATGTTCGAGTTCTGGGACTGGTTGGCGG
CCGTTACTCTTTGTGGTCAGCGATTGGCCTGTCGATTGTTCTCTCCATCGGCTTTGATAACT
TCGTTGAACTGCTTTCCGGCGCACACGCGATGGACAAGCATTTCTCCACCACGCCTGCCGAG
AAAAACCTGCCTGTACTGCTGGCGCTGATTGGCATCTGGTACAACAATTTCTTTGGTGCGGA
AACTGAAGCGATTCTGCCGTATGACCAGTATATGCACCGTTTCGCGGCGTACTTCCAGCAGG
GCAATATGGAGTCCAACGGTAAGTATGTTGACCGTAACGGTAACGTTGTGGATTACCAGACT
GGCCCGATTATCTGGGGTGAACCAGGCACTAACGGTCAGCACGCGTTCTACCAGCTGATCCA
CCAGGGAACCAAATGGTACCGTGCGATTTCATCGCTCCGGCTATCACCCATAACCCGCTCT
CTGATCATCACCAGAAACTGCTGTCTAACTTCTTCGCCCAGACCGAAGCGCTGGCGTTTGGT
AAATCCCGCGAAGTGGTTGAGCAGGAATATCGTGATCAGGGTAAAGATCCGGCAACGCTTGA
CTACGTGGTGCCGTTCAAAGTATTCGAAGGTAACCGCCCGACCAACTCCATCCTGCTGCGTG
AAATCACTCCGTTCAGCCTGGGTGCGTTGATTGCGCTGTATGAGCACAAAATCTTTACTCAG
GGCGTGATCCTGAACATCTTCACCTTCGACCAGTGGGGCGTGGAACTGGGTAAACAGCTGGC
GAACCGTATTCTGCCAGAGCTGAAAGATGATCTGGAAGTGCTGTTTCAGGGTCCGAAAGAAA
TCAGCAGCCACGATAGCTCGACCAATGGTCTGATTAACCGCTATAAAGCGTGGCGCGGTtaa
                                                SEQ ID NO: 11
ATGAAAAACATCAATCCAACGCAGACCGCTGCCTGGCAGGCACTACAGAAACACTTCGATGA
AATGAAAGACGTTACGATCGCCGATCTTTTTGCTAAAGATGGTGATCGTTTTTCTAAGTTCT
CCGCAACCTTCGACGATCAGATGCTGGTGGATTACTCCAAAAACCGCATCACTGAAGAGACG
CTGGCGAAATTACAGGATCTGGCGAAAGAGTGCGATCTGGCGGGCGCGATTAAGTCGATGTT
CTCTGGCGAGAAGATCAACCGCACTGAAAACCGCGCCGTGCTGCACGTAGCGCTGCGTAACC
GTAGCAATACCCCGATTTTGGTTGATGGCAAAGACGTAATGCCGGAAGTCAACGCGGTGCTG
GAGAAGATGAAAACCTTCTCAGAAGCGATTATTTCCGGTGAGTGGAAAGGTTATACCGGCAA
AGCAATCACTGACGTAGTGAACATCGGGATCGGCGGTTCTGACCTCGGCCCATACATGGTGA
CCGAAGCTCTGCGTCCGTACAAAAACCACCTGAACATGCACTTTGTTTCTAACGTCGATGGG
ACTCACATCGCGGAAGTGCTGAAAAAAGTAAACCCGGAAACCACGCTGTTCTTGGTAGCATC
TAAAACCTTCACCACTCAGGAAACTATGACCAACGCCCATAGCGCGCGTGACTGGTTCCTGA
AAGCGGCAGGTGATGAGAAGCACGTTGCAAAACACTTTGCGGCGCTTTCCACCAATGCCAAA
GCCGTTGGCGAGTTTGGTATTGATACTGCCAACATGTTCGAGTTCTGGGACTGGTTGGCGG
CCGTTACTCTTTGTGGTCAGCGATTGGCCTGTCGATTGTTCTCTCCATCGGCTTTGATAACT
TCGTTGAACTGCTTTCCGGCGCACACGCGATGGACAAGCATTTCTCCACCACGCCTGCCGAG
AAAAACCTGCCTGTACTGCTGGCGCTGATTGGCATCTGGTACAACAATTTCTTTGGTGCGGA
AACTGAAGCGATTCTGCCGTATGACCAGTATATGCACCGTTTCGCGGCGTACTTCCAGCAGG
GCAATATGGAGTCCAACGGTAAGTATGTTGACCGTAACGGTAACGTTGTGGATTACCAGACT
GGCCCGATTATCTGGGGTGAACCAGGCACTAACGGTCAGCACGCGTTCTACCAGCTGATCCA
CCAGGGAACCAAATGGTACCGTGCGATTTCATCGCTCCGGCTATCACCCATAACCCGCTCT
CTGATCATCACCAGAAACTGCTGTCTAACTTCTTCGCCCAGACCGAAGCGCTGGCGTTTGGT
```

AAATCCCGCGAAGTGGTTGAGCAGGAATATCGTGATCAGGGTAAAGATCCGGCAACGCTTGA

CTACGTGGTGCCGTTCAAAGTATTCGAAGGTAACCGCCCGACCAACTCCATCCTGCTGCGTG

AAATCACTCCGTTCAGCCTGGGTGCGTTGATTGCGCTGTATGAGCACAAAATCTTTACTCAG

GGCGTGATCCTGAACATCTTCACCTTCGACCAGTGGGGCGTGGAACTGGGTAAACAGCTGGC

GAACCGTATTCTGCCAGAGCTGAAAGATGATAAACTGGAAGTGCTGTTTCAGGGTCCGGAAA

TCAGCAGCCACGATAGCTCGACCAATGGTCTGATTAACCGCTATAAAGCGTGGCGCGGTtaa

SEQ ID NO: 12
ATGAAAAACATCAATCCAACGCAGACCGCTGCCTGGCAGGCACTACAGAAACACTTCGATGA

AATGAAAGACGTTACGATCGCCGATCTTTTTGCTAAAGATGGTGATCGTTTTTCTAAGTTCT

CCGCAACCTTCGACGATCAGATGCTGGTGGATTACTCCAAAAACCGCATCACTGAAGAGACG

CTGGCGAAATTACAGGATCTGGCGAAAGAGTGCGATCTGGCGGGCGCGATTAAGTCGATGTT

CTCTGGCGAGAAGATCAACCGCACTGAAAACCGCGCCGTGCTGCACGTAGCGCTGCGTAACC

GTAGCAATACCCCGATTTTGGTTGATGGCAAAGACGTAATGCCGGAAGTCAACGCGGTGCTG

GAGAAGATGAAAACCTTCTCAGAAGCGATTATTTCCGGTGAGTGGAAAGGTTATACCGGCAA

AGCAATCACTGACGTAGTGAACATCGGGATCGGCGGTTCTGACCTCGGCCCATACATGGTGA

CCGAAGCTCTGCGTCCGTACAAAAACCACCTGAACATGCACTTTGTTTCTAACGTCGATGGG

ACTCACATCGCGGAAGTGCTGAAAAAAGTAAACCCGGAAACCACGCTGTTCTTGGTAGCATC

TAAAACCTTCACCACTCAGGAAACTATGACCAACGCCCATAGCGCGCGTGACTGGTTCCTGA

AAGCGGCAGGTGATGAGAAGCACGTTGCAAAACACTTTGCGGCGCTTTCCACCAATGCCAAA

GCCGTTGGCGAGTTTGGTATTGATACTGCCAACATGTTCGAGTTCTGGGACTGGGTTGGCGG

CCGTTACTCTTTGTGGTCAGCGATTGGCCTGTCGATTGTTCTCTCCATCGGCTTTGATAACT

TCGTTGAACTGCTTTCCGGCGCACACGCGATGGACAAGCATTTCTCCACCACGCCTGCCGAG

AAAAACCTGCCTGTACTGCTGGCGCTGATTGGCATCTGGTACAACAATTTCTTTGGTGCGGA

AACTGAAGCGATTCTGCCGTATGACCAGTATATGCACCGTTTCGCGGCGTACTTCCAGCAGG

GCAATATGGAGTCCAACGGTAAGTATGTTGACCGTAACGGTAACGTTGTGGATTACCAGACT

GGCCCGATTATCTGGGGTGAACCAGGCACTAACGGTCAGCACGCGTTCTACCAGCTGATCCA

CCAGGGAACCAAAATGGTACCGTGCGATTTCATCGCTCCGGCTATCACCCATAACCCGCTCT

CTGATCATCACCAGAAACTGCTGTCTAACTTCTTCGCCCAGACCGAAGCGCTGGCGTTTGGT

AAATCCCGCGAAGTGGTTGAGCAGGAATATCGTGATCAGGGTAAAGATCCGGCAACGCTTGA

CTACGTGGTGCCGTTCAAAGTATTCGAAGGTAACCGCCCGACCAACTCCATCCTGCTGCGTG

AAATCACTCCGTTCAGCCTGGGTGCGTTGATTGCGCTGTATGAGCACAAAATCTTTACTCAG

GGCGTGATCCTGAACATCTTCACCTTCGACCAGTGGGGCGTGGAACTGGGTAAACAGCTGGC

GAACCGTATTCTGCCAGAGCTGAAAGATGATAAAGAACTGGAAGTGCTGTTTCAGGGTCCGA

TCAGCAGCCACGATAGCTCGACCAATGGTCTGATTAACCGCTATAAAGCGTGGCGCGGTtaa

SEQ ID NO: 13
ATGAAAAACATCAATCCAACGCAGACCGCTGCCTGGCAGGCACTACAGAAACACTTCGATGA

AATGAAAGACGTTACGATCGCCGATCTTTTTGCTAAAGATGGTGATCGTTTTTCTAAGTTCT

CCGCAACCTTCGACGATCAGATGCTGGTGGATTACTCCAAAAACCGCATCACTGAAGAGACG

CTGGCGAAATTACAGGATCTGGCGAAAGAGTGCGATCTGGCGGGCGCGATTAAGTCGATGTT

SEQUENCE LISTING

```
CTCTGGCGAGAAGATCAACCGCACTGAAAACCGCGCCGTGCTGCACGTAGCGCTGCGTAACC

GTAGCAATACCCCGATTTTGGTTGATGGCAAAGACGTAATGCCGGAAGTCAACGCGGTGCTG

GAGAAGATGAAAACCTTCTCAGAAGCGATTATTTCCGGTGAGTGGAAAGGTTATACCGGCAA

AGCAATCACTGACGTAGTGAACATCGGGATCGGCGGTTCTGACCTCGGCCCATACATGGTGA

CCGAAGCTCTGCGTCCGTACAAAAACCACCTGAACATGCACTTTGTTTCTAACGTCGATGGG

ACTCACATCGCGGAAGTGCTGAAAAAAGTAAACCCGGAAACCACGCTGTTCTTGGTAGCATC

TAAAACCTTCACCACTCAGGAAACTATGACCAACGCCCATAGCGCGCGTGACTGGTTCCTGA

AAGCGGCAGGTGATGAGAAGCACGTTGCAAAACACTTTGCGGCGCTTTCCACCAATGCCAAA

GCCGTTGGCGAGTTTGGTATTGATACTGCCAACATGTTCGAGTTCTGGGACTGGGTTGGCGG

CCGTTACTCTTTGTGGTCAGCGATTGGCCTGTCGATTGTTCTCTCCATCGGCTTTGATAACT

TCGTTGAACTGCTTTCCGGCGCACACGCGATGGACAAGCATTTCTCCACCACGCCTGCCGAG

AAAAACCTGCCTGTACTGCTGGCGCTGATTGGCATCTGGTACAACAATTTCTTTGGTGCGGA

AACTGAAGCGATTCTGCCGTATGACCAGTATATGCACCGTTTCGCGGCGTACTTCCAGCAGG

GCAATATGGAGTCCAACGGTAAGTATGTTGACCGTAACGGTAACGTTGTGGATTACCAGACT

GGCCCGATTATCTGGGGTGAACCAGGCACTAACGGTCAGCACGCGTTCTACCAGCTGATCCA

CCAGGGAACCAAAATGGTACCGTGCGATTTCATCGCTCCGGCTATCACCCATAACCCGCTCT

CTGATCATCACCAGAAACTGCTGTCTAACTTCTTCGCCCAGACCGAAGCGCTGGCGTTTGGT

AAATCCCGCGAAGTGGTTGAGCAGGAATATCGTGATCAGGGTAAAGATCCGGCAACGCTTGA

CTACGTGGTGCCGTTCAAAGTATTCGAAGGTAACCGCCCGACCAACTCCATCCTGCTGCGTG

AAATCACTCCGTTCAGCCTGGGTGCGTTGATTGCGCTGTATGAGCACAAAATCTTTACTCAG

GGCGTGATCCTGAACATCTTCACCTTCGACCAGTGGGGCGTGGAACTGGGTAAACAGCTGGC

GAACCGTATTCTGCCAGAGCTGAAAGATGATAAAGAAATCCTGGAAGTGCTGTTTCAGGGTC

CGAGCAGCCACGATAGCTCGACCAATGGTCTGATTAACCGCTATAAAGCGTGGCGCGGTtaa
                                                                SEQ ID NO: 14
ATGAAAAACATCAATCCAACGCAGACCGCTGCCTGGCAGGCACTACAGAAACACTTCGATGA

AATGAAAGACGTTACGATCGCCGATCTTTTTGCTAAAGATGGTGATCGTTTTTCTAAGTTCT

CCGCAACCTTCGACGATCAGATGCTGGTGGATTACTCCAAAAACCGCATCACTGAAGAGACG

CTGGCGAAATTACAGGATCTGGCGAAAGAGTGCGATCTGGCGGGCGCGATTAAGTCGATGTT

CTCTGGCGAGAAGATCAACCGCACTGAAAACCGCGCCGTGCTGCACGTAGCGCTGCGTAACC

GTAGCAATACCCCGATTTTGGTTGATGGCAAAGACGTAATGCCGGAAGTCAACGCGGTGCTG

GAGAAGATGAAAACCTTCTCAGAAGCGATTATTTCCGGTGAGTGGAAAGGTTATACCGGCAA

AGCAATCACTGACGTAGTGAACATCGGGATCGGCGGTTCTGACCTCGGCCCATACATGGTGA

CCGAAGCTCTGCGTCCGTACAAAAACCACCTGAACATGCACTTTGTTTCTAACGTCGATGGG

ACTCACATCGCGGAAGTGCTGAAAAAAGTAAACCCGGAAACCACGCTGTTCTTGGTAGCATC

TAAAACCTTCACCACTCAGGAAACTATGACCAACGCCCATAGCGCGCGTGACTGGTTCCTGA

AAGCGGCAGGTGATGAGAAGCACGTTGCAAAACACTTTGCGGCGCTTTCCACCAATGCCAAA

GCCGTTGGCGAGTTTGGTATTGATACTGCCAACATGTTCGAGTTCTGGGACTGGGTTGGCGG

CCGTTACTCTTTGTGGTCAGCGATTGGCCTGTCGATTGTTCTCTCCATCGGCTTTGATAACT

TCGTTGAACTGCTTTCCGGCGCACACGCGATGGACAAGCATTTCTCCACCACGCCTGCCGAG
```

SEQUENCE LISTING

```
AAAAACCTGCCTGTACTGCTGGCGCTGATTGGCATCTGGTACAACAATTTCTTTGGTGCGGA
AACTGAAGCGATTCTGCCGTATGACCAGTATATGCACCGTTTCGCGGCGTACTTCCAGCAGG
GCAATATGGAGTCCAACGGTAAGTATGTTGACCGTAACGGTAACGTTGTGGATTACCAGACT
GGCCCGATTATCTGGGGTGAACCAGGCACTAACGGTCAGCACGCGTTCTACCAGCTGATCCA
CCAGGGAACCAAAATGGTACCGTGCGATTTCATCGCTCCGGCTATCACCCATAACCCGCTCT
CTGATCATCACCAGAAACTGCTGTCTAACTTCTTCGCCCAGACCGAAGCGCTGGCGTTTGGT
AAATCCCGCGAAGTGGTTGAGCAGGAATATCGTGATCAGGGTAAAGATCCGGCAACGCTTGA
CTACGTGGTGCCGTTCAAAGTATTCGAAGGTAACCGCCCGACCAACTCCATCCTGCTGCGTG
AAATCACTCCGTTCAGCCTGGGTGCGTTGATTGCGCTGTATGAGCACAAAATCTTTACTCAG
GGCGTGATCCTGAACATCTTCACCTTCGACCAGTGGGGCGTGGAACTGGGTAAACAGCTGGC
GAACCGTATTCTGCCAGAGCTGAAAGATGATAAAGAAATCAGCCTGGAAGTGCTGTTTCAGG
GTCCGAGCCACGATAGCTCGACCAATGGTCTGATTAACCGCTATAAAGCGTGGCGCGGTtaa
                                                   SEQ ID NO: 15
ATGAAAAACATCAATCCAACGCAGACCGCTGCCTGGCAGGCACTACAGAAACACTTCGATGA
AATGAAAGACGTTACGATCGCCGATCTTTTTGCTAAAGATGGTGATCGTTTTTCTAAGTTCT
CCGCAACCTTCGACGATCAGATGCTGGTGGATTACTCCAAAAACCGCATCACTGAAGAGACG
CTGGCGAAATTACAGGATCTGGCGAAAGAGTGCGATCTGGCGGGCGCGATTAAGTCGATGTT
CTCTGGCGAGAAGATCAACCGCACTGAAAACCGCGCCGTGCTGCACGTAGCGCTGCGTAACC
GTAGCAATACCCCGATTTTGGTTGATGGCAAAGACGTAATGCCGGAAGTCAACGCGGTGCTG
GAGAAGATGAAAACCTTCTCAGAAGCGATTATTTCCGGTGAGTGGAAAGGTTATACCGGCAA
AGCAATCACTGACGTAGTGAACATCGGGATCGGCGGTTCTGACCTCGGCCCATACATGGTGA
CCGAAGCTCTGCGTCCGTACAAAAACCACCTGAACATGCACTTTGTTTCTAACGTCGATGGG
ACTCACATCGCGGAAGTGCTGAAAAAAGTAAACCCGGAAACCACGCTGTTCTTGGTAGCATC
TAAAACCTTCACCACTCAGGAAACTATGACCAACGCCCATAGCGCGCGTGACTGGTTCCTGA
AAGCGGCAGGTGATGAGAAGCACGTTGCAAAACACTTTGCGGCGCTTTCCACCAATGCCAAA
GCCGTTGGCGAGTTTGGTATTGATACTGCCAACATGTTCGAGTTCTGGGACTGGGTTGGCGG
CCGTTACTCTTTGTGGTCAGCGATTGGCCTGTCGATTGTTCTCTCCATCGGCTTTGATAACT
TCGTTGAACTGCTTTCCGGCGCACACGCGATGGACAAGCATTTCTCCACCACGCCTGCCGAG
AAAAACCTGCCTGTACTGCTGGCGCTGATTGGCATCTGGTACAACAATTTCTTTGGTGCGGA
AACTGAAGCGATTCTGCCGTATGACCAGTATATGCACCGTTTCGCGGCGTACTTCCAGCAGG
GCAATATGGAGTCCAACGGTAAGTATGTTGACCGTAACGGTAACGTTGTGGATTACCAGACT
GGCCCGATTATCTGGGGTGAACCAGGCACTAACGGTCAGCACGCGTTCTACCAGCTGATCCA
CCAGGGAACCAAAATGGTACCGTGCGATTTCATCGCTCCGGCTATCACCCATAACCCGCTCT
CTGATCATCACCAGAAACTGCTGTCTAACTTCTTCGCCCAGACCGAAGCGCTGGCGTTTGGT
AAATCCCGCGAAGTGGTTGAGCAGGAATATCGTGATCAGGGTAAAGATCCGGCAACGCTTGA
CTACGTGGTGCCGTTCAAAGTATTCGAAGGTAACCGCCCGACCAACTCCATCCTGCTGCGTG
AAATCACTCCGTTCAGCCTGGGTGCGTTGATTGCGCTGTATGAGCACAAAATCTTTACTCAG
GGCGTGATCCTGAACATCTTCACCTTCGACCAGTGGGGCGTGGAACTGGGTAAACAGCTGGC
GAACCGTATTCTGCCAGAGCTGAAAGATGATAAAGAAATCAGCAGCCTGGAAGTGCTGTTTC
AGGGTCCGCACGATAGCTCGACCAATGGTCTGATTAACCGCTATAAAGCGTGGCGCGGTtaa
```

SEQUENCE LISTING

SEQ ID NO: 16
ATGAAAAACATCAATCCAACGCAGACCGCTGCCTGGCAGGCACTACAGAAACACTTCGATGA
AATGAAAGACGTTACGATCGCCGATCTTTTTGCTAAAGATGGTGATCGTTTTTCTAAGTTCT
CCGCAACCTTCGACGATCAGATGCTGGTGGATTACTCCAAAAACCGCATCACTGAAGAGACG
CTGGCGAAATTACAGGATCTGGCGAAAGAGTGCGATCTGGCGGGCGCGATTAAGTCGATGTT
CTCTGGCGAGAAGATCAACCGCACTGAAAACCGCGCCGTGCTGCACGTAGCGCTGCGTAACC
GTAGCAATACCCCGATTTTGGTTGATGGCAAAGACGTAATGCCGGAAGTCAACGCGGTGCTG
GAGAAGATGAAAACCTTCTCAGAAGCGATTATTTCCGGTGAGTGGAAAGGTTATACCGGCAA
AGCAATCACTGACGTAGTGAACATCGGGATCGGCGGTTCTGACCTCGGCCCATACATGGTGA
CCGAAGCTCTGCGTCCGTACAAAAACCACCTGAACATGCACTTTGTTTCTAACGTCGATGGG
ACTCACATCGCGGAAGTGCTGAAAAAAGTAAACCCGGAAACCACGCTGTTCTTGGTAGCATC
TAAAACCTTCACCACTCAGGAAACTATGACCAACGCCCATAGCGCGCGTGACTGGTTCCTGA
AAGCGGCAGGTGATGAGAAGCACGTTGCAAAACACTTTGCGGCGCTTTCCACCAATGCCAAA
GCCGTTGGCGAGTTTGGTATTGATACTGCCAACATGTTCGAGTTCTGGGACTGGGTTGGCGG
CCGTTACTCTTTGTGGTCAGCGATTGGCCTGTCGATTGTTCTCTCCATCGGCTTTGATAACT
TCGTTGAACTGCTTTCCGGCGCACACGCGATGGACAAGCATTTCTCCACCACGCCTGCCGAG
AAAAACCTGCCTGTACTGCTGGCGCTGATTGGCATCTGGTACAACAATTTCTTTGGTGCGGA
AACTGAAGCGATTCTGCCGTATGACCAGTATATGCACCGTTTCGCGGCGTACTTCCAGCAGG
GCAATATGGAGTCCAACGGTAAGTATGTTGACCGTAACGGTAACGTTGTGGATTACCAGACT
GGCCCGATTATCTGGGGTGAACCAGGCACTAACGGTCAGCACGCGTTCTACCAGCTGATCCA
CCAGGGAACCAAAATGGTACCGTGCGATTTCATCGCTCCGGCTATCACCCATAACCCGCTCT
CTGATCATCACCAGAAACTGCTGTCTAACTTCTTCGCCCAGACCGAAGCGCTGGCGTTTGGT
AAATCCCGCGAAGTGGTTGAGCAGGAATATCGTGATCAGGGTAAAGATCCGGCAACGCTTGA
CTACGTGGTGCCGTTCAAAGTATTCGAAGGTAACCGCCCGACCAACTCCATCCTGCTGCGTG
AAATCACTCCGTTCAGCCTGGGTGCGTTGATTGCGCTGTATGAGCACAAAATCTTTACTCAG
GGCGTGATCCTGAACATCTTCACCTTCGACCAGTGGGGCGTGGAACTGGGTAAACAGCTGGC
GAACCGTATTCTGCCAGAGCTGAAAGATGATAAAGAAATCAGCAGCCACGATAGCTCGACCA
ATGGTCTGATTAACCGCTATAAACTGGAAGTGCTGTTTCAGGGTCCGGCGTGGCGCGGTtaa SEQ ID NO: 17
MKNINPTQTAAWQALQKHFDEMKDVTIADLFAKDGDRFSKFSATFDDQMLVDYSKNRITEET
LAKLQDLAKECDLAGAIKSMFSGEKINRTENRAVLHVALRNRSNTPILVDGKDVMPEVNAVL
EKMKTFSEAIISGEWKGYTGKAITDVVNIGIGGSDLGPYMVTEALRPYKNHLNMHFVSNVDG
THIAEVLKKVNPETTLFLVASKTFTTQETMTNAHSARDWFLKAAGDEKHVAKHFAALSTNAK
AVGEFGIDTANMFEFWDWVGGRYSLWSAIGLSIVLSIGFDNFVELLSGAHAMDKHFSTTPAE
KNLPVLLALIGIWYNNFFGAETEAILPYDQYMHRFAAYFQQGNMESNGKYVDRNGNVVDYQT
GPIIWGEPGTNGQHAFYQLIHQGTKMVPCDFIAPAITHNPLSDHHQKLLSNFFAQTEALAFG
KSREVVEQEYRDQGKDPATLDYVVPFKVFEGNRPINSILLREITPFSLGALIALYEHKIFTQ
GVILNIFTFDQWGVELGKQLANRILPELKDDKEISSHDSSTNGLINRYKAWRG

SEQUENCE LISTING

```
                                                        SEQ ID NO: 18
MKNINPTQTAAWQALQKHFDEMKDVTIADLFAKDGDRFSKFSATFDDQMLVDYSKNRITEET

LAKLQDLAKECDLAGAIKSMFSGEKINRTENRAVLHVALRNRSNTPLEVLFQGPILVDGKDV

MPEVNAVLEKMKTFSEAIISGEWKGYTGKAITDVVNIGIGGSDLGPYMVTEALRPYKNHLNM

HEVSNVDGTHIAEVLKKVNPETTLFLVASKTFTTQETMTNAHSARDWFLKAAGDEKHVAKHE

AALSTNAKAVGEFGIDTANMFEFWDWVGGRYSLWSAIGLSIVLSIGFDNFVELLSGAHAMDK

HFSTTPAEKNLPVLLALIGIWYNNFFGAETEAILPYDQYMHRFAAYFQQGNMESNGKYVDRN

GNVVDYQTGPIIWGEPGTNGQHAFYQLIHQGTKMVPCDFIAPAITHNPLSDHHQKLLSNFFA

QTEALAFGKSREVVEQEYRDQGKDPATLDYVVPFKVFEGNRPTNSILLREITPFSLGALIAL

YEHKIFTQGVILNIFTFDQWGVELGKQLANRILPELKDDKEISSHDSSTNGLINRYKAWRG

SEQ ID NO: 19
MKNINPTQTAAWQALQKHFDEMKDVTIADLFAKDGDRFSKFSATFDDQMLVDYSKNRITEET

LAKLQDLAKECDLAGAIKSMFSGEKINRTENRAVLHVALRNRSNTPILEVLFQGPLVDGKDV

MPEVNAVLEKMKTFSEAIISGEWKGYTGKAITDVVNIGIGGSDLGPYMVTEALRPYKNHLNM

HFVSNVDGTHIAEVLKKVNPETTLFLVASKTFTTQETMTNAHSARDWFLKAAGDEKHVAKHF

AALSTNAKAVGEFGIDTANMFEFWDWVGGRYSLWSAIGLSIVLSIGFDNFVELLSGAHAMDK

HFSTTPAEKNLPVLLALIGIWYNNFFGAETEAILPYDQYMHRFAAYFQQGNMESNGKYVDRN

GNVVDYQTGPIIWGEPGTNGQHAFYQLIHQGTKMVPCDFIAPAITHNPLSDHHQKLLSNFFA

QTEALAFGKSREVVEQEYRDQGKDPATLDYVVPFKVFEGNRPTNSILLREITPFSLGALIAL

YEHKIFTQGVILNIFTFDQWGVELGKQLANRILPELKDDKEISSHDSSTNGLINRYKAWRG

SEQ ID NO: 20
MKNINPTQTAAWQALQKHFDEMKDVTIADLFAKDGDRFSKFSATFDDQMLVDYSKNRITEET

LAKLQDLAKECDLAGAIKSMFSGEKINRTENRAVLHVALRNRSNTPILEVLFQGPVDGKDVM

PEVNAVLEKMKTFSEAIISGEWKGYTGKAITDVVNIGIGGSDLGPYMVTEALRPYKNHLNMH

FVSNVDGTHIAEVLKKVNPETTLFLVASKTFTTQETMTNAHSARDWFLKAAGDEKHVAKHFA

ALSTNAKAVGEFGIDTANMFEFWDWVGGRYSLWSAIGLSIVLSIGFDNFVELLSGAHAMDKH

FSTTPAEKNLPVLLALIGIWYNNFFGAETEAILPYDQYMHRFAAYFQQGNMESNGKYVDRNG

NVVDYQTGPIIWGEPGTNGQHAFYQLIHQGTKMVPCDFIAPAITHNPLSDHHQKLLSNFFAQ

TEALAFGKSREVVEQEYRDQGKDPATLDYVVPFKVFEGNRPTNSILLREITPFSLGALIALY

EHKIFTQGVILNIFTFDQWGVELGKQLANRILPELKDDKEISSHDSSTNGLINRYKAWRG

SEQ ID NO: 21
MKNINPTQTAAWQALQKHFDEMKDVTIADLFAKDGDRFSKFSATFDDQMLVDYSKNRITEET

LAKLQDLAKECDLAGAIKSMFSGEKINRTENRAVLHVALRNRSNTPILVDGKDVMPEVNAVL

EKMKTFSEAIISGELEVLFQGPWKGYTGKAITDVVNIGIGGSDLGPYMVTEALRPYKNHLNM

HFVSNVDGTHIAEVLKKVNPETTLFLVASKTFTTQETMTNAHSARDWFLKAAGDEKHVAKHF

AALSTNAKAVGEFGIDTANMFEFWDWVGGRYSLWSAIGLSIVLSIGFDNFVELLSGAHAMDK

HFSTTPAEKNLPVLLALIGIWYNNFFGAETEAILPYDQYMHRFAAYFQQGNMESNGKYVDRN

GNVVDYQTGPIIWGEPGTNGQHAFYQLIHQGTKMVPCDFIAPAITHNPLSDHHQKLLSNFFA

QTEALAFGKSREVVEQEYRDQGKDPATLDYVVPFKVFEGNRPTNSILLREITPFSLGALIAL

YEHKIFTQGVILNIFTFDQWGVELGKQLANRILPELKDDKEISSHDSSTNGLINRYKAWRG
```

SEQUENCE LISTING

SEQ ID NO: 22
MKNINPTQTAAWQALQKHFDEMKDVTIADLFAKDGDRFSKFSATFDDQMLVDYSKNRITEET
LAKLQDLAKECDLAGAIKSMFSGEKINRTENRAVLHVALRNRSNTPILVDGKDVMPEVNAVL
EKMKTFSEAIISGEWKGYTGKAITDVVNIGIGGSDLGPYMVTEALRPYKNHLNMHFVSNVDG
THIAEVLKKVNPETTLFLVASKTFTTQETMTNAHSARDWFLKAAGDEKHVAKHFAALSTNAK
AVGEFGIDTANMFEFWDWVGGRYSLWSAIGLSIVLSIGFDNFVELLSGAHAMDKHFSTTPAE
KNLPVLLALIGIWYNNFFGAETEAILPYDQYMHRFAAYFQQGNMESNGKYVDRNGNVVDYQT
GPIIWGEPGTNGQHAFYQLIHQGTKMVPCDFIAPAITHLEVLFQGPNPLSDHHQKLLSNFFA
QTEALAFGKSREVVEQEYRDQGKDPATLDYVVPFKVFEGNRPTNSILLREITPFSLGALIAL
YEHKIFTQGVILNIFTFDQWGVELGKQLANRILPELKDDKEISSHDSSTNGLINRYKAWRG

SEQ ID NO: 23
MKNINPTQTAAWQALQKHFDEMKDVTIADLFAKDGDRFSKFSATFDDQMLVDYSKNRITEET
LAKLQDLAKECDLAGAIKSMFSGEKINRTENRAVLHVALRNRSNTPILVDGKDVMPEVNAVL
EKMKTFSEAIISGEWKGYTGKAITDVVNIGIGGSDLGPYMVTEALRPYKNHLNMHFVSNVDG
THIAEVLKKVNPETTLFLVASKTFTTQETMTNAHSARDWFLKAAGDEKHVAKHFAALSTNAK
AVGEFGIDTANMFEFWDWVGGRYSLWSAIGLSIVLSIGFDNFVELLSGAHAMDKHFSTTPAE
KNLPVLLALIGIWYNNFFGAETEAILPYDQYMHRFAAYFQQGNMESNGKYVDRNGNVVDYQT
GPIIWGEPGTNGQHAFYQLIHQGTKMVPCDFIAPAITHNPLSDHHQKLLSNFFAQTEALAFG
KSREVVEQEYRDQGKDPATLDYVVPFKVFEGNRPTNSILLREITPFSLGALIALYEHKIFTQ
GVILNIFTFDQWGVELGKQLANRILPELEVLFQGPKDDKEISSHDSSTNGLINRYKAWRG

SEQ ID NO: 24
MKNINPTQTAAWQALQKHFDEMKDVTIADLFAKDGDRFSKFSATFDDQMLVDYSKNRITEET
LAKLQDLAKECDLAGAIKSMFSGEKINRTENRAVLHVALRNRSNTPILVDGKDVMPEVNAVL
EKMKTFSEAIISGEWKGYTGKAITDVVNIGIGGSDLGPYMVTEALRPYKNHLNMHFVSNVDG
THIAEVLKKVNPETTLFLVASKTFTTQETMTNAHSARDWFLKAAGDEKHVAKHFAALSTNAK
AVGEFGIDTANMFEFWDWVGGRYSLWSAIGLSIVLSIGFDNFVELLSGAHAMDKHFSTTPAE
KNLPVLLALIGIWYNNFFGAETEAILPYDQYMHRFAAYFQQGNMESNGKYVDRNGNVVDYQT
GPIIWGEPGTNGQHAFYQLIHQGTKMVPCDFIAPAITHNPLSDHHQKLLSNFFAQTEALAFG
KSREVVEQEYRDQGKDPATLDYVVPFKVFEGNRPTNSILLREITPFSLGALIALYEHKIFTQ
GVILNIFTFDQWGVELGKQLANRILPELKLEVLFQGPDDKEISSHDSSTNGLINRYKAWRG

SEQ ID NO: 25
MKNINPTQTAAWQALQKHFDEMKDVTIADLFAKDGDRFSKFSATFDDQMLVDYSKNRITEET
LAKLQDLAKECDLAGAIKSMFSGEKINRTENRAVLHVALRNRSNTPILVDGKDVMPEVNAVL
EKMKTFSEAIISGEWKGYTGKAITDVVNIGIGGSDLGPYMVTEALRPYKNHLNMHFVSNVDG
THIAEVLKKVNPETTLFLVASKTFTTQETMTNAHSARDWFLKAAGDEKHVAKHFAALSTNAK
AVGEFGIDTANMFEFWDWVGGRYSLWSAIGLSIVLSIGFDNFVELLSGAHAMDKHFSTTPAE
KNLPVLLALIGIWYNNFFGAETEAILPYDQYMHRFAAYFQQGNMESNGKYVDRNGNVVDYQT
GPIIWGEPGTNGQHAFYQLIHQGTKMVPCDFIAPAITHNPLSDHHQKLLSNFFAQTEALAFG
KSREVVEQEYRDQGKDPATLDYVVPFKVFEGNRPTNSILLREITPFSLGALIALYEHKIFTQ
GVILNIFTFDQWGVELGKQLANRILPELKDLEVLFQGPDKEISSHDSSTNGLINRYKAWRG

-continued

SEQUENCE LISTING

SEQ ID NO: 26
MKNINPTQTAAWQALQKHFDEMKDVTIADLFAKDGDRFSKFSATFDDQMLVDYSKNRITEET
LAKLQDLAKECDLAGAIKSMFSGEKINRTENRAVLHVALRNRSNTPILVDGKDVMPEVNAVL
EKMKTFSEAIISGEWKGYTGKAITDVVNIGIGGSDLGPYMVTEALRPYKNHLNMHFVSNVDG
THIAEVLKKVNPETTLFLVASKTFTTQETMTNAHSARDWFLKAAGDEKHVAKHFAALSTNAK
AVGEFGIDTANMFEFWDWVGGRYSLWSAIGLSIVLSIGFDNFVELLSGAHAMDKHFSTTPAE
KNLPVLLALIGIWYNNFFGAETEAILPYDQYMHRFAAYFQQGNMESNGKYVDRNGNVVDYQT
GPIIWGEPGTNGQHAFYQLIHQGTKMVPCDFIAPAITHNPLSDHHQKLLSNFFAQTEALAFG
KSREVVEQEYRDQGKDPATLDYVVPFKVFEGNRPTNSILLREITPFSLGALIALYEHKIFTQ
GVILNIFTFDQWGVELGKQLANRILPELKDDLEVLFQGPKEISSHDSSTNGLINRYKAWRG

SEQ ID NO: 27
MKNINPTQTAAWQALQKHFDEMKDVTIADLFAKDGDRFSKFSATFDDQMLVDYSKNRITEET
LAKLQDLAKECDLAGAIKSMFSGEKINRTENRAVLHVALRNRSNTPILVDGKDVMPEVNAVL
EKMKTFSEAIISGEWKGYTGKAITDVVNIGIGGSDLGPYMVTEALRPYKNHLNMHFVSNVDG
THIAEVLKKVNPETTLFLVASKTFTTQETMTNAHSARDWFLKAAGDEKHVAKHFAALSTNAK
AVGEFGIDTANMFEFWDWVGGRYSLWSAIGLSIVLSIGFDNFVELLSGAHAMDKHFSTTPAE
KNLPVLLALIGIWYNNFFGAETEAILPYDQYMHRFAAYFQQGNMESNGKYVDRNGNVVDYQT
GPIIWGEPGTNGQHAFYQLIHQGTKMVPCDFIAPAITHNPLSDHHQKLLSNFFAQTEALAFG
KSREVVEQEYRDQGKDPATLDYVVPFKVFEGNRPTNSILLREITPFSLGALIALYEHKIFTQ
GVILNIFTFDQWGVELGKQLANRILPELKDDKLEVLFQGPEISSHDSSTNGLINRYKAWRG

SEQ ID NO: 28
MKNINPTQTAAWQALQKHFDEMKDVTIADLFAKDGDRFSKFSATFDDQMLVDYSKNRITEET
LAKLQDLAKECDLAGAIKSMFSGEKINRTENRAVLHVALRNRSNTPILVDGKDVMPEVNAVL
EKMKTFSEAIISGEWKGYTGKAITDVVNIGIGGSDLGPYMVTEALRPYKNHLNMHFVSNVDG
THIAEVLKKVNPETTLFLVASKTFTTQETMTNAHSARDWFLKAAGDEKHVAKHFAALSTNAK
AVGEFGIDTANMFEFWDWVGGRYSLWSAIGLSIVLSIGFDNFVELLSGAHAMDKHFSTTPAE
KNLPVLLALIGIWYNNFFGAETEAILPYDQYMHRFAAYFQQGNMESNGKYVDRNGNVVDYQT
GPIIWGEPGTNGQHAFYQLIHQGTKMVPCDFIAPAITHNPLSDHHQKLLSNFFAQTEALAFG
KSREVVEQEYRDQGKDPATLDYVVPFKVFEGNRPTNSILLREITPFSLGALIALYEHKIFTQ
GVILNIFTFDQWGVELGKQLANRILPELKDDKELEVLFQGPISSHDSSTNGLINRYKAWRG

SEQ ID NO: 29
MKNINPTQTAAWQALQKHFDEMKDVTIADLFAKDGDRFSKFSATFDDQMLVDYSKNRITEET
LAKLQDLAKECDLAGAIKSMFSGEKINRTENRAVLHVALRNRSNTPILVDGKDVMPEVNAVL
EKMKTFSEAIISGEWKGYTGKAITDVVNIGIGGSDLGPYMVTEALRPYKNHLNMHFVSNVDG
THIAEVLKKVNPETTLFLVASKTFTTQETMTNAHSARDWFLKAAGDEKHVAKHFAALSTNAK
AVGEFGIDTANMFEFWDWVGGRYSLWSAIGLSIVLSIGFDNFVELLSGAHAMDKHFSTTPAE
KNLPVLLALIGIWYNNFFGAETEAILPYDQYMHRFAAYFQQGNMESNGKYVDRNGNVVDYQT
GPIIWGEPGTNGQHAFYQLIHQGTKMVPCDFIAPAITHNPLSDHHQKLLSNFFAQTEALAFG
KSREVVEQEYRDQGKDPATLDYVVPFKVFEGNRPTNSILLREITPFSLGALIALYEHKIFTQ
GVILNIFTFDQWGVELGKQLANRILPELKDDKEILEVLFQGPSSHDSSTNGLINRYKAWRG

-continued

SEQUENCE LISTING

SEQ ID NO: 30
MKNINPTQTAAWQALQKHFDEMKDVTIADLFAKDGDRFSKFSATFDDQMLVDYSKNRITEET
LAKLQDLAKECDLAGAIKSMFSGEKINRTENRAVLHVALRNRSNTPILVDGKDVMPEVNAVL
EKMKTFSEAIISGEWKGYTGKAITDVVNIGIGGSDLGPYMVTEALRPYKNHLNMHFVSNVDG
THIAEVLKKVNPETTLFLVASKTFTTQETMTNAHSARDWFLKAAGDEKHVAKHFAALSTNAK
AVGEFGIDTANMFEFWDWVGGRYSLWSAIGLSIVLSIGFDNFVELLSGAHAMDKHFSTTPAE
KNLPVLLALIGIWYNNFFGAETEAILPYDQYMHRFAAYFQQGNMESNGKYVDRNGNVVDYQT
GPIIWGEPGTNGQHAFYQLIHQGTKMVPCDFIAPAITHNPLSDHHQKLLSNFFAQTEALAFG
KSREVVEQEYRDQGKDPATLDYVVPFKVFEGNRPTNSILLREITPFSLGALIALYEHKIFTQ
GVILNIFTFDQWGVELGKQLANRILPELKDDKEISLEVLFQGPSHDSSTNGLINRYKAWRG

SEQ ID NO: 31
MKNINPTQTAAWQALQKHFDEMKDVTIADLFAKDGDRFSKFSATFDDQMLVDYSKNRITEET
LAKLQDLAKECDLAGAIKSMFSGEKINRTENRAVLHVALRNRSNTPILVDGKDVMPEVNAVL
EKMKTFSEAIISGEWKGYTGKAITDVVNIGIGGSDLGPYMVTEALRPYKNHLNMHFVSNVDG
THIAEVLKKVNPETTLFLVASKTFTTQETMTNAHSARDWFLKAAGDEKHVAKHFAALSTNAK
AVGEFGIDTANMFEFWDWVGGRYSLWSAIGLSIVLSIGFDNFVELLSGAHAMDKHFSTTPAE
KNLPVLLALIGIWYNNFFGAETEAILPYDQYMHRFAAYFQQGNMESNGKYVDRNGNVVDYQT
GPIIWGEPGTNGQHAFYQLIHQGTKMVPCDFIAPAITHNPLSDHHQKLLSNFFAQTEALAFG
KSREVVEQEYRDQGKDPATLDYVVPFKVFEGNRPTNSILLREITPFSLGALIALYEHKIFTQ
GVILNIFTFDQWGVELGKQLANRILPELKDDKEISSLEVLFQGPHDSSTNGLINRYKAWRG

SEQ ID NO: 32
MKNINPTQTAAWQALQKHFDEMKDVTIADLFAKDGDRFSKFSATFDDQMLVDYSKNRITEET
LAKLQDLAKECDLAGAIKSMFSGEKINRTENRAVLHVALRNRSNTPILVDGKDVMPEVNAVL
EKMKTFSEAIISGEWKGYTGKAITDVVNIGIGGSDLGPYMVTEALRPYKNHLNMHFVSNVDG
THIAEVLKKVNPETTLFLVASKTFTTQETMTNAHSARDWFLKAAGDEKHVAKHFAALSTNAK
AVGEFGIDTANMFEFWDWVGGRYSLWSAIGLSIVLSIGFDNFVELLSGAHAMDKHFSTTPAE
KNLPVLLALIGIWYNNFFGAETEAILPYDQYMHRFAAYFQQGNMESNGKYVDRNGNVVDYQT
GPIIWGEPGTNGQHAFYQLIHQGTKMVPCDFIAPAITHNPLSDHHQKLLSNFFAQTEALAFG
KSREVVEQEYRDQGKDPATLDYVVPFKVFEGNRPTNSILLREITPFSLGALIALYEHKIFTQ
GVILNIFTFDQWGVELGKQLANRILPELKDDKEISSHDSSTNGLINRYKLEVLFQGPAWRG

SEQ ID NO: 33
ATGGGCCCAGAAGAAGAATTCGGCATGAGCCTGATCAAGCATAACTCTTGCGTCATTACCAC
GGAGAATGGTAAGTTCACGGGCTTGGGCGTTTATGACCGTTTCGTCGTGGTTCCGACCCACG
CTGACCCGGGTAAAGAAATCCAGGTTGACGGTATCACGACCAAAGTGATTGATAGCTATGAT
CTCTATAATAAGAACGGCATCAAGCTGGAAATCACGGTGCTGAAACTGGACCGTAATGAAAA
GTTTCGTGATATCCGTCGCTATATTCCGAATAACGAGGATGACTACCCAAATTGCAATCTGG
CGCTGCTGGCAAATCAGCCGGAACCGACGATCATCAACGTGGGTGACGTGGTGAGCTATGGC
AATATCCTGCTGAGCGGTAACCAGACCGCGCGTATGCTGAAGTATTCCTATCCGACGAAAAG
CGGCTATTGCGGCGGCGTGCTCTATAAGATTGGTCAAGTCCTGGGCATCCACGTCGGCGGTA
ATGGCCGCGATGGTTTCAGCGCGATGCTGCTGCGTAGCTATTTCACCGACGTCCAGTGATAA

SEQUENCE LISTING

SEQ ID NO: 34
MGPEEEFGMSLIKHNSCVITTENGKFTGLGVYDRFVVVPTHADPGKEIQVDGITTKVIDSYD
LYNKNGIKLEITVLKLDRNEKFRDIRRYIPNNEDDYPNCNLALLANQPEPTIINVGDVVSYG
NILLSGNQTARMLKYSYPTKSGYCGGVLYKIGQVLGIHVGGNRDGFSAMLLRSYFTDVQ

SEQ ID NO: 35
ATGAAAAAAACGGCAATTGCGATAGCGGTTGCGCTAGCTGGTTTTGCCACGGTGGCGCAGGC
TGGCCCAGAAGAAGAATTCGGCATGAGCCTGATCAAGCATAACTCTTGCGTCATTACCACGG
AGAATGGTAAGTTCACGGGCTTGGGCGTTTATGACCGTTTCGTCGTGGTTCCGACCCACGCT
GACCCGGGTAAAGAAATCCAGGTTGACGGTATCACGACCAAAGTGATTGATAGCTATGATCT
CTATAATAAGAACGGCATCAAGCTGGAAATCACGGTGCTGAAACTGGACCGTAATGAAAAGT
TTCGTGATATCCGTCGCTATATTCCGAATAACGAGGATGACTACCCAAATTGCAATCTGGCG
CTGCTGGCAAATCAGCCGGAACCGACGATCATCAACGTGGGTGACGTGGTGAGCTATGGCAA
TATCCTGCTGAGCGGTAACCAGACCGCGCGTATGCTGAAGTATTCCTATCCGACGAAAAGCG
GCTATTGCGGCGGCGTGCTCTATAAGATTGGTCAAGTCCTGGGCATCCACGTCGGCGGTAAT
GGCCGCGATGGTTTCAGCGCGATGCTGCTGCGTAGCTATTTCACCGACGTCCAGTGATAA

SEQ ID NO: 36
MKKTAIAIAVALAGFATVAQAGPEEEFGMSLIKHNSCVITTENGKFTGLGVYDREVVVPTHA
DPGKEIQVDGITTKVIDSYDLYNKNGIKLEITVLKLDRNEKFRDIRRYIPNNEDDYPNCNLA
LLANQPEPTIINVGDVVSYGNILLSGNQTARMLKYSYPTKSGYCGGVLYKIGQVLGIHVGGN
GRDGFSAMLLRSYFTDVQ

SEQ ID NO: 37
CTGGAAGTGCTGTTTCAGGGTCCG

SEQ ID NO: 38
LEVLFQGP

SEQ ID NO: 39
EVLFQGP

SEQ ID NO: 40
VLFQGP

SEQ ID NO: 41
LFQGP

SEQ ID NO: 42
LEVLFQG

SEQ ID NO: 43
LEVLFQ

SEQ ID NO: 44
LEVLF

SEQ ID NO: 45
EVLFQG

SEQ ID NO: 46
MKKTAIAIAVALAGFATVAQA

SEQ ID NO: 47
GTGTCCCGTATTATTATGCTGATCCCTACCGGAACCAGCGTCGGTCTGACCAGCGTCAGCCT
TGGCGTGATCCGTGCAATGGAACGCAAAGGCGTTCGTCTGAGCGTTTTCAAACCTATCGCTC
AGCCGCGTACCGGTGGCGATGCGCCCGATCAGACTACGACTATCGTGCGTGCGAACTCTTCC
ACCACGACGGCCGCTGAACCGCTGAAAATGAGCTACGTTGAAGGTCTGCTTTCCAGCAATCA

```
GAAAGATGTGCTGATGGAAGAGATCGTCGCAAACTACCACGCTAACACCAAAGACGCTGAAG
TCGTTCTGGTTGAAGGTCTGGTCCCGACACGTAAGCACCAGTTTGCCCAGTCTCTGAACTAC
GAAATCGCTAAAACGCTGAATGCGGAAATCGTCTTCGTTATGTCTCAGGGCACTGACACCCC
GGAACAGCTGAAAGAGCGTATCGAACTGACCCGCAACAGCTTCGGCGGTGCCAAAAACACCA
ACATCACCGGCGTTATCGTTAACAAACTGAACGCACCGGTTGATGAACAGGGTCGTACTCGC
CCCGGATCTGTCCGAGATTTTCGACGACTCTTCCAAAGCTAAAGTAAACAATGTTGATCCGGC
GAAGCTGCAAGAATCCAGCCCGCTGCCGGTTCTCGGCGCTGTGCCGTGGAGCTTTGACCTGA
TCGCGACTCGTGCGATCGATATGGCTCGCCACCTGAATGCGACCATCATCAACGAAGGCGAC
ATCAATACTCGCCGCGTTAAATCCGTCACTTTCTGCGCACGCAGCATTCCGCACATGCTGGA
GCACTTCCGTGCCGGTTCTCTGCTGGTGACTTCCGCAGACCGTCCTGACGTGCTGGTGGCCG
CTTGCCTGGCAGCCATGAACGGCGTAGAAATCGGTGCCCTGCTGCTGACTGGCGGTTACGAA
ATGGACGCGCGCATTTCTAAACTGTGCGAACGTGCTTTCGCTACCGGCCTGCCGGTATTTAT
GGTGAACACCAACACCTGGCAGACCTCTCTGAGCCTGCAGAGCTTCAACCTGGAAGTTCCGG
TTGACGATCACGAACGTATCGAGAAAGTTCAGGAATACGTTGCTAACTACATCAACGCTGAC
TGGATCGAATCTCTGACTGCCACTTCTGAGCGCAGCCGTCGTCTGTCTCCGCCTGCGTTCCG
TTATCAGCTGACTGAACTTGCGCGCAAAGCGGGCAAACGTATCGTACTGCCGGAAGGTGACG
AACCGCGTACCGTTAAAGCAGCCGCTATCTGTGCTGAACGTGGTATCGCAACTTGCGTACTG
CTGGGTAATCCGGCAGAGATCAACCGTGTTGCAGCGTCTCAGGGTGTAGAACTGGGTGCAGG
GATTGAAATCGTTGATCCAGAAGTGGTTCGCGAAAGCTATGTTGGTCGTCTGGTCGAACTGC
GTAAGAACAAAGGCATGACCGAAACCGTTGCCCGCGAACAGCTGGAAGACAACGTGGTGCTC
GGTACGCTGATGCTGGAACAGGATGAAGTTGATGGTCTGGTTTCCGGTGCTGTTCACACTAC
CGCAAACACCATCCGTCCGCCGCTGCAGCTGATCAAAACTGCACCGGGCAGCTCCCTGGTAT
CTTCCGTGTTCTTCATGCTGCTGCCGGAACAGGTTTACGTTTACGGTGACTGTGCGATCAAC
CCGGATCCGACCGCTGAACAGCTGGCAGAAATCGCGATTCAGTCCGCTGATTCCGCTGCGGC
CTTCGGTATCGAACCGCGCGTTGCTATGCTCTCCTACTCCACCGGTACTTCTGGTGCAGGTA
GCGACGTAGAAAAAGTTCGCGAAGCAACTCGTCTGGCGCAGGAAAAACGTCCTGACCTGATG
ATCGACGGTCCGCTGCAGTACGACGCTGCGGTAATGGCTGACGTTGCGAAATCCAAAGCGCC
GAACTCTCCGGTTGCAGGTCGCGCTACCGTGTTCATCTTCCCGGATCTGAACACCGGTAACA
CCACCTACAAAGCGGTACAGCGTTCTGCCGACCTGATCTCCATCGGGCCGATGCTGCAGGGT
ATGCGCAAGCCGGTTAACGACCTGTCCCGTGGCGCACTGGTTGACGATATCGTCTACACCAT
CGCGCTGACTGCGATTCAGTCTGCACAGCAGCAGTAA
```

SEQ ID NO: 48
VSRIIMLIPTGTSVGLTSVSLGVIRAMERKGVRLSVFKPIAQPRTGGDAPDQTTTIVRANSS
ITTAAEPLKMSYVEGLLSSNQKDVLMEEIVANYHANTKDAEVVLVEGLVPIRKHQFAQSLNY
EIAKTLNAEIVFVMSQGTDTPEQLKERIELTRNSFGGAKNTNITGVIVNKLNAPVDEQGRTR
PDLSEIFDDSSKAKVNNVDPAKLQESSPLPVLGAVPWSFDLIATRAIDMARHLNATIINEGD
INTRRVKSVTFCARSIPHMLEHFRAGSLLVTSADRPDVLVAACLAAMNGVEIGALLLTGGYE
MDARISKLCERAFATGLPVFMVNTNTWQTSLSLQSFNLEVPVDDHERIEKVQEYVANYINAD
WIESLTATSERSRRLSPPAFRYQLTELARKAGKRIVLPEGDEPRTVKAAAICAERGIATCVL

-continued

SEQUENCE LISTING

LGNPAEINRVAASQGVELGAGIEIVDPEVVRESYVGRLVELRKNKGMTETVAREQLEDNVVL

GTLMLEQDEVDGLVSGAVHTTANTIRPPLQLIKTAPGSSLVSSVFFMLLPEQVYVYGDCAIN

PDPTAEQLAEIAIQSADSAAAFGIEPRVAMLSYSTGTSGAGSDVEKVREATRLAQEKRPDLM

IDGPLQYDAAVMADVAKSKAPNSPVAGRATVFIFPDLNTGNTTYKAVQRSADLISIGPMLQG

MRKPVNDLSRGALVDDIVYTIALTAIQSAQQQ

SEQ ID NO: 49
GTGTCCCGTATTATTATGCTGATCCCTACCGGAACCAGCGTCGGTCTGACCAGCGTCAGCCT

TGGCGTGATCCGTGCAATGGAACGCAAAGGCGTTCGTCTGAGCGTTTTCAAACCTATCGCTC

AGCCGCGTACCGGTGGCGATGCGCCCGATCAGACTACGACTATCGTGCGTGCGAACTCTTCC

ACCACGACGGCCGCTGAACCGCTGAAAATGAGCTACGTTGAAGGTCTGCTTTCCAGCAATCA

GAAAGATGTGCTGATGGAAGAGATCGTCGCAAACTACCACGCTAACACCAAAGACGCTGAAG

TCGTTCTGGTTGAAGGTCTGGTCCCGACACGTAAGCACCAGTTTGCCCAGTCTCTGAACTAC

GAAATCGCTAAAACGCTGAATGCGGAAATCGTCTTCGTTATGTCTCAGGGCACTGACACCCC

GGAACAGCTGAAAGAGCGTATCGAACTGACCCGCAACAGCTTCGGCGGTGCCAAAAACACCA

ACATCACCGGCGTTATCGTTAACAAACTGAACGCACCGGTTGATGAACAGGGTCGTACTCGC

CCCGGATCTGTCCGAGATTTTCGACGACTCTTCCAAAGCTAAAGTAAACAATGTTGATCCGGC

GAAGCTGCAAGAATCCAGCCCGCTGCCGGTTCTCGGCGCTGTGCCGTGGAGCTTTGACCTGA

TCGCGACTCGTGCGATCGATATGGCTCGCCACCTGAATGCGACCATCATCAACGAAGGCGAC

ATCAATACTCGCCGCGTTAAATCCGTCACTTTCTGCGCACGCAGCATTCCGCACATGCTGGA

GCACTTCCGTGCCGGTTCTCTGCTGGTGACTTCCGCAGACCGTCCTGACGTGCTGGTGGCCG

CTTGCCTGGCAGCCATGAACGGCGTAGAAATCGGTGCCCTGCTGCTGACTGGCGGTTACGAA

ATGGACGCGCGCATTTCTAAACTGTGCGAACGTGCTTTCGCTACCGGCCTGCCGGTATTTAT

GGTGAACACCAACACCTGGCAGACCTCTCTGAGCCTGCAGAGCTTCAACCTGGAAGTTCCGG

TTGACGATCACGAACGTATCGAGAAAGTTCAGGAATACGTTGCTAACTACATCAACGCTGAC

TGGATCGAATCTCTGACTGCCACTTCTCTGGAAGTGCTGTTTCAGGGTCCGGAGCGCAGCCG

TCGTCTGTCTCCGCCTGCGTTCCGTTATCAGCTGACTGAACTTGCGCGCAAAGCGGGCAAAC

GTATCGTACTGCCGGAAGGTGACGAACCGCGTACCGTTAAAGCAGCCGCTATCTGTGCTGAA

CGTGGTATCGCAACTTGCGTACTGCTGGGTAATCCGGCAGAGATCAACCGTGTTGCAGCGTC

TCAGGGTGTAGAACTGGGTGCAGGGATTGAAATCGTTGATCCAGAAGTGGTTCGCGAAAGCT

ATGTTGGTCGTCTGGTCGAACTGCGTAAGAACAAAGGCATGACCGAAACCGTTGCCCGCGAA

CAGCTGGAAGACAACGTGGTGCTCGGTACGCTGATGCTGGAACAGGATGAAGTTGATGGTCT

GGTTTCCGGTGCTGTTCACACTACCGCAAACACCATCCGTCCGCCGCTGCAGCTGATCAAAA

CTGCACCGGGCAGCTCCCTGGTATCTTCCGTGTTCTTCATGCTGCTGCCGGAACAGGTTTAC

GTTTACGGTGACTGTGCGATCAACCCGGATCCGACCGCTGAACAGCTGGCAGAAATCGCGAT

TCAGTCCGCTGATTCCGCTGCGGCCTTCGGTATCGAACCGCGCGTTGCTATGCTCTCCTACT

CCACCGGTACTTCTGGTGCAGGTAGCGACGTAGAAAAAGTTCGCGAAGCAACTCGTCTGGCG

CAGGAAAAACGTCCTGACCTGATGATCGACGGTCCGCTGCAGTACGACGCTGCGGTAATGGC

TGACGTTGCGAAATCCAAAGCGCCGAACTCTCCGGTTGCAGGTCGCGCTACCGTGTTCATCT

TCCCGGATCTGAACACCGGTAACACCACCTACAAAGCGGTACAGCGTTCTGCCGACCTGATC

SEQUENCE LISTING

TCCATCGGGCCGATGCTGCAGGGTATGCGCAAGCCGGTTAACGACCTGTCCCGTGGCGCACT

GGTTGACGATATCGTCTACACCATCGCGCTGACTGCGATTCAGTCTGCACAGCAGCAGTAA

SEQ ID NO: 50
VSRIIMLIPTGTSVGLTSVSLGVIRAMERKGVRLSVFKPIAQPRTGGDAPDQTTTIVRANSS

TTTAAEPLKMSYVEGLLSSNQKDVLMEEIVANYHANTKDAEVVLVEGLVPTRKHQFAQSLNY

EIAKTLNAEIVEVMSQGTDTPEQLKERIELTRNSEGGAKNTNITGVIVNKLNAPVDEQGRTR

PDLSEIFDDSSKAKVNNVDPAKLQESSPLPVLGAVPWSFDLIATRAIDMARHLNATIINEGD

INTRRVKSVTFCARSIPHMLEHFRAGSLLVTSADRPDVLVAACLAAMNGVEIGALLLTGGYE

MDARISKLCERAFATGLPVFMVNINTWQTSLSLQSFNLEVPVDDHERIEKVQEYVANYINAD

WIESLTATSLEVLFQGPERSRRLSPPAFRYQLTELARKAGKRIVLPEGDEPRTVKAAAICAE

RGIATCVLLGNPAEINRVAASQGVELGAGIEIVDPEVVRESYVGRLVELRKNKGMTETVARE

QLEDNVVLGTLMLEQDEVDGLVSGAVHTTANTIRPPLQLIKTAPGSSLVSSVFFMLLPEQVY

VYGDCAINPDPTAEQLAEIAIQSADSAAAFGIEPRVAMLSYSTGTSGAGSDVEKVREATRLA

QEKRPDLMIDGPLQYDAAVMADVAKSKAPNSPVAGRATVFIFPDLNIGNITYKAVQRSADLI

SIGPMLQGMRKPVNDLSRGALVDDIVYTIALTAIQSAQQQ

SEQ ID NO: 51
GTGTCCCGTATTATTATGCTGATCCCTACCGGAACCAGCGTCGGTCTGACCAGCGTCAGCCT

TGGCGTGATCCGTGCAATGGAACGCAAAGGCGTTCGTCTGAGCGTTTTCAAACCTATCGCTC

AGCCGCGTACCGGTGGCGATGCGCCCGATCAGACTACGACTATCGTGCGTGCGAACTCTTCC

ACCACGACGGCCGCTGAACCGCTGAAAATGAGCTACGTTGAAGGTCTGCTTTCCAGCAATCA

GAAAGATGTGCTGATGGAAGAGATCGTCGCAAACTACCACGCTAACACCAAAGACGCTGAAG

TCGTTCTGGTTGAAGGTCTGGTCCCGACACGTAAGCACCAGTTTGCCCAGTCTCTGAACTAC

GAAATCGCTAAAACGCTGAATGCGGAAATCGTCTTCGTTATGTCTCAGGGCACTGACACCCC

GGAACAGCTGAAAGAGCGTATCGAACTGACCCGCAACAGCTTCGGCGGTGCCAAAAACACCA

ACATCACCGGCGTTATCGTTAACAAACTGAACGCACCGGTTGATGAACAGGGTCGTACTCGC

CCGGATCTGTCCGAGATTTTCGACGACTCTTCCAAAGCTAAAGTAAACAATGTTGATCCGGC

GAAGCTGCAAGAATCCAGCCCGCTGCCGGTTCTCGGCGCTGTGCCGTGGAGCTTTGACCTGA

TCGCGACTCGTGCGATCGATATGGCTCGCCACCTGAATGCGACCATCATCAACGAAGGCGAC

ATCAATACTCGCCGCGTTAAATCCGTCACTTTCTGCGCACGCAGCATTCCGCACATGCTGGA

GCACTTCCGTGCCGGTTCTCTGCTGGTGACTTCCGCAGACCGTCCTGACGTGCTGGTGGCCG

CTTGCCTGGCAGCCATGAACGGCGTAGAAATCGGTGCCCTGCTGCTGACTGGCGGTTACGAA

ATGGACGCGCGCATTTCTAAACTGTGCGAACGTGCTTTCGCTACCGGCCTGCCGGTATTTAT

GGTGAACACCAACACCTGGCAGACCTCTCTGAGCCTGCAGAGCTTCAACCTGGAAGTTCCGG

TTGACGATCACGAACGTATCGAGAAAGTTCAGGAATACGTTGCTAACTACATCAACGCTGAC

TGGATCGAATCTCTGACTGCCACTTCTGAGCTGGAAGTGCTGTTTCAGGGTCCGCGCAGCCG

TCGTCTGTCTCCGCCTGCGTTCCGTTATCAGCTGACTGAACTTGCGCGCAAAGCGGGCAAAC

GTATCGTACTGCCGGAAGGTGACGAACCGCGTACCGTTAAAGCAGCCGCTATCTGTGCTGAA

CGTGGTATCGCAACTTGCGTACTGCTGGGTAATCCGGCAGAGATCAACCGTGTTGCAGCGTC

TCAGGGTGTAGAACTGGGTGCAGGGATTGAAATCGTTGATCCAGAAGTGGTTCGCGAAAGCT

ATGTTGGTCGTCTGGTCGAACTGCGTAAGAACAAAGGCATGACCGAAACCGTTGCCCGCGAA

```
CAGCTGGAAGACAACGTGGTGCTCGGTACGCTGATGCTGGAACAGGATGAAGTTGATGGTCT

GGTTTCCGGTGCTGTTCACACTACCGCAAACACCATCCGTCCGCCGCTGCAGCTGATCAAAA

CTGCACCGGGCAGCTCCCTGGTATCTTCCGTGTTCTTCATGCTGCTGCCGGAACAGGTTTAC

GTTTACGGTGACTGTGCGATCAACCCGGATCCGACCGCTGAACAGCTGGCAGAAATCGCGAT

TCAGTCCGCTGATTCCGCTGCGGCCTTCGGTATCGAACCGCGCGTTGCTATGCTCTCCTACT

CCACCGGTACTTCTGGTGCAGGTAGCGACGTAGAAAAAGTTCGCGAAGCAACTCGTCTGGCG

CAGGAAAAACGTCCTGACCTGATGATCGACGGTCCGCTGCAGTACGACGCTGCGGTAATGGC

TGACGTTGCGAAATCCAAAGCGCCGAACTCTCCGGTTGCAGGTCGCGCTACCGTGTTCATCT

TCCCGGATCTGAACACCGGTAACACCACCTACAAAGCGGTACAGCGTTCTGCCGACCTGATC

TCCATCGGGCCGATGCTGCAGGGTATGCGCAAGCCGGTTAACGACCTGTCCCGTGGCGCACT

GGTTGACGATATCGTCTACACCATCGCGCTGACTGCGATTCAGTCTGCACAGCAGCAGTAA
```

SEQ ID NO: 52
```
VSRIIMLIPTGTSVGLTSVSLGVIRAMERKGVRLSVFKPIAQPRTGGDAPDQTTTIVRANSS

TTTAAEPLKMSYVEGLLSSNQKDVLMEEIVANYHANTKDAEVVLVEGLVPTRKHQFAQSLNY

EIAKTLNAEIVEVMSQGTDTPEQLKERIELTRNSEGGAKNTNITGVIVNKLNAPVDEQGRTR

PDLSEIFDDSSKAKVNNVDPAKLQESSPLPVLGAVPWSFDLIATRAIDMARHLNATIINEGD

INTRRVKSVTFCARSIPHMLEHFRAGSLLVTSADRPDVLVAACLAAMNGVEIGALLLTGGYE

MDARISKLCERAFATGLPVFMVNTNTWQTSLSLQSFNLEVPVDDHERIEKVQEYVANYINAD

WIESLTATSELEVLFQGPRSRRLSPPAFRYQLTELARKAGKRIVLPEGDEPRTVKAAAICAE

RGIATCVLLGNPAEINRVAASQGVELGAGIEIVDPEVVRESYVGRLVELRKNKGMTETVARE

QLEDNVVLGTLMLEQDEVDGLVSGAVHTTANTIRPPLQLIKTAPGSSLVSSVFFMLLPEQVY

VYGDCAINPDPTAEQLAEIAIQSADSAAAFGIEPRVAMLSYSTGTSGAGSDVEKVREATRLA

QEKRPDLMIDGPLQYDAAVMADVAKSKAPNSPVAGRATVFIFPDLNIGNITYKAVQRSADLI

SIGPMLQGMRKPVNDLSRGALVDDIVYTIALTAIQSAQQQ
```

SEQ ID NO: 53
```
GTGTCCCGTATTATTATGCTGATCCCTACCGGAACCAGCGTCGGTCTGACCAGCGTCAGCCT

TGGCGTGATCCGTGCAATGGAACGCAAAGGCGTTCGTCTGAGCGTTTTCAAACCTATCGCTC

AGCCGCGTACCGGTGGCGATGCGCCCGATCAGACTACGACTATCGTGCGTGCGAACTCTTCC

ACCACGACGGCCGCTGAACCGCTGAAAATGAGCTACGTTGAAGGTCTGCTTTCCAGCAATCA

GAAAGATGTGCTGATGGAAGAGATCGTCGCAAACTACCACGCTAACACCAAAGACGCTGAAG

TCGTTCTGGTTGAAGGTCTGGTCCCGACACGTAAGCACCAGTTTGCCCAGTCTCTGAACTAC

GAAATCGCTAAAACGCTGAATGCGGAAATCGTCTTCGTTATGTCTCAGGGCACTGACACCCC

GGAACAGCTGAAAGAGCGTATCGAACTGACCCGCAACAGCTTCGGCGGTGCCAAAAACACCA

ACATCACCGGCGTTATCGTTAACAAACTGAACGCACCGGTTGATGAACAGGGTCGTACTCGC

CCGGATCTGTCCGAGATTTTCGACGACTCTTCCAAAGCTAAAGTAAACAATGTTGATCCGGC

GAAGCTGCAAGAATCCAGCCCGCTGCCGGTTCTCGGCGCTGTGCCGTGGAGCTTTGACCTGA

TCGCGACTCGTGCGATCGATATGGCTCGCCACCTGAATGCGACCATCATCAACGAAGGCGAC

ATCAATACTCGCCGCGTTAAATCCGTCACTTTCTGCGCACGCAGCATTCCGCACATGCTGGA

GCACTTCCGTGCCGGTTCTCTGCTGGTGACTTCCGCAGACCGTCCTGACGTGCTGGTGGCCG
```

SEQUENCE LISTING

CTTGCCTGGCAGCCATGAACGGCGTAGAAATCGGTGCCCTGCTGCTGACTGGCGGTTACGAA

ATGGACGCGCGCATTTCTAAACTGTGCGAACGTGCTTTCGCTACCGGCCTGCCGGTATTTAT

GGTGAACACCAACACCTGGCAGACCTCTCTGAGCCTGCAGAGCTTCAACCTGGAAGTTCCGG

TTGACGATCACGAACGTATCGAGAAAGTTCAGGAATACGTTGCTAACTACATCAACGCTGAC

TGGATCGAATCTCTGACTGCCACTTCTGAGCGCAGCCGTCGTCTGGAAGTGCTGTTTCAGGG

TCCGTCTCCGCCTGCGTTCCGTTATCAGCTGACTGAACTTGCGCGCAAAGCGGGCAAACGTA

TCGTACTGCCGGAAGGTGACGAACCGCGTACCGTTAAAGCAGCCGCTATCTGTGCTGAACGT

GGTATCGCAACTTGCGTACTGCTGGGTAATCCGGCAGAGATCAACCGTGTTGCAGCGTCTCA

GGGTGTAGAACTGGGTGCAGGGATTGAAATCGTTGATCCAGAAGTGGTTCGCGAAAGCTATG

TTGGTCGTCTGGTCGAACTGCGTAAGAACAAAGGCATGACCGAAACCGTTGCCCGCGAACAG

CTGGAAGACAACGTGGTGCTCGGTACGCTGATGCTGGAACAGGATGAAGTTGATGGTCTGGT

TTCCGGTGCTGTTCACACTACCGCAAACACCATCCGTCCGCCGCTGCAGCTGATCAAAACTG

CACCGGGCAGCTCCCTGGTATCTTCCGTGTTCTTCATGCTGCTGCCGGAACAGGTTTACGTT

TACGGTGACTGTGCGATCAACCCGGATCCGACCGCTGAACAGCTGGCAGAAATCGCGATTCA

GTCCGCTGATTCCGCTGCGGCCTTCGGTATCGAACCGCGCGTTGCTATGCTCTCCTACTCCA

CCGGTACTTCTGGTGCAGGTAGCGACGTAGAAAAAGTTCGCGAAGCAACTCGTCTGGCGCAG

GAAAAACGTCCTGACCTGATGATCGACGGTCCGCTGCAGTACGACGCTGCGGTAATGGCTGA

CGTTGCGAAATCCAAAGCGCCGAACTCTCCGGTTGCAGGTCGCGCTACCGTGTTCATCTTCC

CGGATCTGAACACCGGTAACACCACCTACAAAGCGGTACAGCGTTCTGCCGACCTGATCTCC

ATCGGGCCGATGCTGCAGGGTATGCGCAAGCCGGTTAACGACCTGTCCCGTGGCGCACTGGT

TGACGATATCGTCTACACCATCGCGCTGACTGCGATTCAGTCTGCACAGCAGCAGTAA

SEQ ID NO: 54
VSRIIMLIPTGTSVGLTSVSLGVIRAMERKGVRLSVFKPIAQPRTGGDAPDQTTTIVRANSS

TTTAAEPLKMSYVEGLLSSNQKDVLMEEIVANYHANTKDAEVVLVEGLVPTRKHQFAQSLNY

EIAKTLNAEIVEVMSQGTDTPEQLKERIELTRNSEGGAKNTNITGVIVNKLNAPVDEQGRTR

PDLSEIFDDSSKAKVNNVDPAKLQESSPLPVLGAVPWSFDLIATRAIDMARHLNATIINEGD

INTRRVKSVTFCARSIPHMLEHFRAGSLLVTSADRPDVLVAACLAAMNGVEIGALLLTGGYE

MDARISKLCERAFATGLPVFMVNTNTWQTSLSLQSFNLEVPVDDHERIEKVQEYVANYINAD

WIESLTATSERSRRLEVLFQGPSPPAFRYQLTELARKAGKRIVLPEGDEPRTVKAAAICAER

GIATCVLLGNPAEINRVAASQGVELGAGIEIVDPEVVRESYVGRLVELRKNKGMTETVAREQ

LEDNVVLGTLMLEQDEVDGLVSGAVHTTANTIRPPLQLIKTAPGSSLVSSVFFMLLPEQVYV

YGDCAINPDPTAEQLAEIAIQSADSAAAFGIEPRVAMLSYSTGTSGAGSDVEKVREATRLAQ

EKRPDLMIDGPLQYDAAVMADVAKSKAPNSPVAGRATVFIFPDLNIGNTTYKAVQRSADLIS

IGPMLQGMRKPVNDLSRGALVDDIVYTIALTAIQSAQQQ

SEQ ID NO: 55
GTGTCCCGTATTATTATGCTGATCCCTACCGGAACCAGCGTCGGTCTGACCAGCGTCAGCCT

TGGCGTGATCCGTGCAATGGAACGCAAAGGCGTTCGTCTGAGCGTTTTCAAACCTATCGCTC

AGCCGCGTACCGGTGGCGATGCGCCCGATCAGACTACGACTATCGTGCGTGCGAACTCTTCC

ACCACGACGGCCGCTGAACCGCTGAAAATGAGCTACGTTGAAGGTCTGCTTTCCAGCAATCA

GAAAGATGTGCTGATGGAAGAGATCGTCGCAAACTACCACGCTAACACCAAAGACGCTGAAG

TCGTTCTGGTTGAAGGTCTGGTCCCGACACGTAAGCACCAGTTTGCCCAGTCTCTGAACTAC

GAAATCGCTAAAACGCTGAATGCGGAAATCGTCTTCGTTATGTCTCAGGGCACTGACACCCC

GGAACAGCTGAAAGAGCGTATCGAACTGACCCGCAACAGCTTCGGCGGTGCCAAAAACACCA

ACATCACCGGCGTTATCGTTAACAAACTGAACGCACCGGTTGATGAACAGGGTCGTACTCGC

CCGGATCTGTCCGAGATTTTCGACGACTCTTCCAAAGCTAAAGTAAACAATGTTGATCCGGC

GAAGCTGCAAGAATCCAGCCCGCTGCCGGTTCTCGGCGCTGTGCCGTGGAGCTTTGACCTGA

TCGCGACTCGTGCGATCGATATGGCTCGCCACCTGAATGCGACCATCATCAACGAAGGCGAC

ATCAATACTCGCCGCGTTAAATCCGTCACTTTCTGCGCACGCAGCATTCCGCACATGCTGGA

GCACTTCCGTGCCGGTTCTCTGCTGGTGACTTCCGCAGACCGTCCTGACGTGCTGGTGGCCG

CTTGCCTGGCAGCCATGAACGGCGTAGAAATCGGTGCCCTGCTGCTGACTGGCGGTTACGAA

ATGGACGCGCGCATTTCTAAACTGTGCGAACGTGCTTTCGCTACCGGCCTGCCGGTATTTAT

GGTGAACACCAACACCTGGCAGACCTCTCTGAGCCTGCAGAGCTTCAACCTGGAAGTTCCGG

TTGACGATCACGAACGTATCGAGAAAGTTCAGGAATACGTTGCTAACTACATCAACGCTGAC

TGGATCGAATCTCTGACTGCCACTTCTGAGCGCAGCCGTCGTCTGTCTCCGCCTGCGTTCCG

TTATCAGCTGACTGAACTTGCGCGCAAAGCGGGCAAACGTATCGTACTGGAAGTGCTGTTTC

AGGGTCCGGAAGGTGACGAACCGCGTACCGTTAAAGCAGCCGCTATCTGTGCTGAACGTGGT

ATCGCAACTTGCGTACTGCTGGGTAATCCGGCAGAGATCAACCGTGTTGCAGCGTCTCAGGG

TGTAGAACTGGGTGCAGGGATTGAAATCGTTGATCCAGAAGTGGTTCGCGAAAGCTATGTTG

GTCGTCTGGTCGAACTGCGTAAGAACAAAGGCATGACCGAAACCGTTGCCCGCGAACAGCTG

GAAGACAACGTGGTGCTCGGTACGCTGATGCTGGAACAGGATGAAGTTGATGGTCTGGTTTC

CGGTGCTGTTCACACTACCGCAAACACCATCCGTCCGCCGCTGCAGCTGATCAAAACTGCAC

CGGGCAGCTCCCTGGTATCTTCCGTGTTCTTCATGCTGCTGCCGGAACAGGTTTACGTTTAC

GGTGACTGTGCGATCAACCCGGATCCGACCGCTGAACAGCTGGCAGAAATCGCGATTCAGTC

CGCTGATTCCGCTGCGGCCTTCGGTATCGAACCGCGCGTTGCTATGCTCTCCTACTCCACCG

GTACTTCTGGTGCAGGTAGCGACGTAGAAAAAGTTCGCGAAGCAACTCGTCTGGCGCAGGAA

AAACGTCCTGACCTGATGATCGACGGTCCGCTGCAGTACGACGCTGCGGTAATGGCTGACGT

TGCGAAATCCAAAGCGCCGAACTCTCCGGTTGCAGGTCGCGCTACCGTGTTCATCTTCCCGG

ATCTGAACACCGGTAACACCACCTACAAAGCGGTACAGCGTTCTGCCGACCTGATCTCCATC

GGGCCGATGCTGCAGGGTATGCGCAAGCCGGTTAACGACCTGTCCCGTGGCGCACTGGTTGA

CGATATCGTCTACACCATCGCGCTGACTGCGATTCAGTCTGCACAGCAGCAGTAA

SEQ ID NO: 56
VSRIIMLIPTGTSVGLTSVSLGVIRAMERKGVRLSVFKPIAQPRTGGDAPDQTTTIVRANSS

TTTAAEPLKMSYVEGLLSSNQKDVLMEEIVANYHANTKDAEVVLVEGLVPTRKHQFAQSLNY

EIAKTLNAEIVEVMSQGTDTPEQLKERIELTRNSEGGAKNTNITGVIVNKLNAPVDEQGRTR

PDLSEIFDDSSKAKVNNVDPAKLQESSPLPVLGAVPWSFDLIATRAIDMARHLNATIINEGD

INTRRVKSVTFCARSIPHMLEHFRAGSLLVTSADRPDVLVAACLAAMNGVEIGALLLTGGYE

MDARISKLCERAFATGLPVFMVNTNTWQTSLSLQSFNLEVPVDDHERIEKVQEYVANYINAD

WIESLTATSERSRRLSPPAFRYQLTELARKAGKRIVLEVLFQGPEGDEPRTVKAAAICAERG

IATCVLLGNPAEINRVAASQGVELGAGIEIVDPEVVRESYVGRLVELRKNKGMTETVAREQL

EDNVVLGTLMLEQDEVDGLVSGAVHTTANTIRPPLQLIKTAPGSSLVSSVFFMLLPEQVYVY
GDCAINPDPTAEQLAEIAIQSADSAAAFGIEPRVAMLSYSTGTSGAGSDVEKVREATRLAQE
KRPDLMIDGPLQYDAAVMADVAKSKAPNSPVAGRATVFIFPDLNIGNITYKAVQRSADLISI
GPMLQGMRKPVNDLSRGALVDDIVYTIALTAIQSAQQQ

SEQ ID NO: 57

ATGTCCTCACGTAAAGAGCTTGCCAATGCTATTCGTGCGCTGAGCATGGACGCAGTACAGAA
AGCCAAATCCGGTCACCCGGGTGCCCCTATGGGTATGGCTGACATTGCCGAAGTCCTGTGGC
GTGATTTCCTGAAACACAACCCGCAGAATCCGTCCTGGGCTGACCGTGACCGCTTCGTGCTG
TCCAACGGCCACGGCTCCATGCTGATCTACAGCCTGCTGCACCTCACCGGTTACGATCTGCC
GATGGAAGAACTGAAAAACTTCCGTCAGCTGCACTCTAAAACTCCGGGTCACCCGGAAGTGG
GTTACACCGCTGGTGTGGAAACCACCACCGGTCCGCTGGGTCAGGGTATTGCCAACGCAGTC
GGTATGGCGATTGCAGAAAAAACGCTGGCGGCGCAGTTTAACCGTCCGGGCCACGACATTGT
CGACCACTACACCTACGCCTTCATGGGCGACGGCTGCATGATGGAAGGCATCTCCCACGAAG
TTTGCTCTCTGGCGGGTACGCTGAAGCTGGGTAAACTGATTGCATTCTACGATGACAACGGT
ATTTCTATCGATGGTCACGTTGAAGGCTGGTTCACCGACGACACCGCAATGCGTTTCGAAGC
TTACGGCTGGCACGTTATTCGCGACATCGACGGTCATGACGCGGCATCTATCAAACGCGCAG
TAGAAGAAGCGCGCGCAGTGACTGACAAACCTTCCCTGCTGATGTGCAAAACCATCATCGGT
TTCGGTTCCCCGAACAAAGCCGGTACCCACGACTCCCACGGTGCGCCGCTGGGCGACGCTGA
AATTGCCCTGACCCGCGAACAACTGGGCTGGAAATATGCGCCGTTCGAAATCCCGTCTGAAA
TCTATGCTCAGTGGGATGCGAAAGAAGCAGGCCAGGCGAAAGAATCCGCATGGAACGAGAAA
TTCGCTGCTTACGCGAAAGCTTATCCGCAGGAAGCCGCTGAATTTACCCGCCGTATGAAAGG
CGAAATGCCGTCTGACTTCGACGCTAAAGCGAAAGAGTTCATCGCTAAACTGCAGGCTAATC
CGGCGAAAATCGCCAGCCGTAAAGCGTCTCAGAATGCTATCGAAGCGTTCGGTCCGCTGTTG
CCGGAATTCCTCGGCGGTTCTGCTGACCTGGCGCCGTCTAACCTGACCCTGTGGTCTGGTTC
TAAAGCAATCAACGAAGATGCTGCGGGTAACTACATCCACTACGGTGTTCGCGAGTTCGGTA
TGACCGCGATTGCTAACGGTATCTCCCTGCACGGTGGCTTCCTGCCGTACACCTCCACCTTC
CTGATGTTCGTGGAATACGCACGTAACGCCGTACGTATGGCTGCGCTGATGAAACAGCGTCA
GGTGATGGTTTACACCCACGACTCCATCGGTCTGGGCGAAGACGGCCCGACTCACCAGCCGG
TTGAGCAGGTCGCTTCTCTGCGCGTAACCCCGAACATGTCTACATGGCGTCCGTGTGACCAG
GTTGAATCCGCGGTCGCGTGGAAATACGGTGTTGAGCGTCAGGACGGCCCGACCGCACTGAT
CCTCTCCCGTCAGAACCTGGCGCAGCAGGAACGAACTGAAGAGCAACTGGCAAACATCGCGC
GCGGTGGTTATGTGCTGAAAGACTGCGCCGGTCAGCCGGAACTGATTTTCATCGCTACCGGT
TCAGAAGTTGAACTGGCTGTTGCTGCCTACGAAAAACTGACTGCCGAAGGCGTGAAAGCGCG
CGTGGTGTCCATGCCGTCTACCGACGCATTTGACAAGCAGGATGCTGCTTACCGTGAATCCG
TACTGCCGAAAGCGGTTACTGCACGCGTTGCTGTAGAAGCGGGTATTGCTGACTACTGGTAC
AAGTATGTTGGCCTGAACGGTGCTATCGTCGGTATGACCACCTTCGGTAATCTGCTCCGGC
AGAGCTGCTGTTTGAAGAGTTCGGCTTCACTGTTGATAACGTTGTTGCGAAAGCAAAAGAAC
TGCTGTAA

-continued

SEQUENCE LISTING

SEQ ID NO: 58
ATGTCCTCACGTAAAGAGCTTGCCAATGCTATTCGTGCGCTGAGCATGGACGCAGTACAGAA

AGCCAAATCCGGTCACCCGGGTGCCCCTATGGGTATGGCTGACATTGCCGAAGTCCTGTGGC

GTGATTTCCTGAAACACAACCCGCAGAATCCGTCCTGGGCTGACCGTGACCGCTTCGTGCTG

TCCAACGGCCACGGCTCCATGCTGATCTACAGCCTGCTGCACCTCACCGGTTACGATCTGCC

GATGGAAGAACTGAAAAACTTCCGTCAGCTGCACTCTAAAACTCCGGGTCACCCGGAAGTGG

GTTACACCGCTGGTGTGGAAACCACCACCGGTCCGCTGGGTCAGGGTATTGCCAACGCAGTC

GGTATGGCGATTGCAGAAAAAACGCTGGCGGCGCAGTTTAACCGTCCGGGCCACGACATTGT

CGACCACTACACCTACGCCTTCATGGGCGACGGCTGCATGATGGAAGGCATCTCCCACGAAG

TTTGCTCTCTGGCGGGTACGCTGAAGCTGGGTAAACTGATTGCATTCTACGATGACAACGGT

ATTTCTATCGATGGTCACGTTGAAGGCTGGTTCACCGACGACACCGCAATGCGTTTCGAAGC

TTACGCTGGCACGTTATTCGCGACATCGACGGTCATGACGCGGCATCTATCAAACGCGCAG

TAGAAGAAGCGCGCGCAGTGACTGACAAACCTTCCCTGCTGATGTGCAAAACCATCATCGGT

TTCGGTTCCCCGAACAAAGCCGGTACCCACGACTCCCACGGTGCGCCGCTGGGCGACGCTGA

AATTGCCCTGACCCGCGAACAACTGGGCTGGAAATATGCGCCGTTCGAAATCCCGTCTGAAA

TCTATGCTCAGTGGGATGCGAAAGAAGCAGGCCAGGCGAAAGAATCCGCATGGAACGAGAAA

TTCGCTGCTTACGCGAAAGCTTATCCGCAGGAAGCCGCTGAATTTACCCGCCGTATGAAAGG

CGAAATGCCGTCTGACTTCGACGCTAAAGCGAAAGAGTTCATCGCTAAACTGCAGGCTAATC

CGGCGAAAATCGCCAGCCGTAAAGCGTCTCAGAATGCTATCGAAGCGTTCGGTCCGCTGTTG

CCCGGAATTCCTCGGCGGTTCTGCTGACCTGGCGCCGTCTAACCTGACCCTGTGGTCTGGTTC

TAAAGCAATCAACGAAGATGCTGCGGGTAACTACATCCACTACGGTGTTCGCGAGTTCGGTA

TGACCGCGATTGCTAACGGTATCTCCCTGCACGGTGGCTTCCTGCCGTACACCTCCACCTTC

CTGATGTTCGTGGAATACGCACGTAACGCCGTACGTATGGCTGCGCTGATGAAACAGCGTCA

GGTGATGGTTTACACCCACGACTCCATCGGTCTGGGCGAAGACGGCCCGACTCACCAGCCGG

TTGAGCAGGTCGCTTCTCTGCGCGTAACCCCGAACATGTCTACATGGCGTCCGTGTGACCAG

GTTGAATCCGCGGTCGCGTGGAAATACGGTGTTGAGCGTCAGGACGGCCCGACCGCACTGAT

CCTCTCCCGTCAGAACCTGGCGCAGCAGGAACGAACTGAAGAGCAACTGGCAAACATCGCGC

GCGGTGGTTATGTGCTGAAAGACTGCGCCGGTCAGCCGGAACTGATTTTCATCGCTACCGGT

TCAGAAGTTGAACTGGCTGTTGCTGCCTACGAAAAACTGACTGCCGAAGGCGTGAAAGCGCG

CGTGGTGTCCATGCCGTCTACCGACGCATTTGACAAGCAGGATGCTGCTTACCGTGAATCCG

TACTGCCGAAAGCGGTTACTGCACGCGTTGCTGTAGAAGCGGGTATTGCTGACTACTGGTAC

AAGTATGTTGGCCTGAACGGTGCTATCGTCGGTATGACCACCTTCCTGGAAGTGCTGTTTCA

GGGTCCGGGTGAATCTGCTCCGGCAGAGCTGCTGTTTGAAGAGTTCGGCTTCACTGTTGATA

ACGTTGTTGCGAAAGCAAAAGAACTGCTGTAA

SEQ ID NO: 59
ATGTCCTCACGTAAAGAGCTTGCCAATGCTATTCGTGCGCTGAGCATGGACGCAGTACAGAA

AGCCAAATCCGGTCACCCGGGTGCCCCTATGGGTATGGCTGACATTGCCGAAGTCCTGTGGC

GTGATTTCCTGAAACACAACCCGCAGAATCCGTCCTGGGCTGACCGTGACCGCTTCGTGCTG

TCCAACGGCCACGGCTCCATGCTGATCTACAGCCTGCTGCACCTCACCGGTTACGATCTGCC

```
GATGGAAGAACTGAAAAACTTCCGTCAGCTGCACTCTAAAACTCCGGGTCACCCGGAAGTGG

GTTACACCGCTGGTGTGGAAACCACCACCGGTCCGCTGGGTCAGGGTATTGCCAACGCAGTC

GGTATGGCGATTGCAGAAAAAACGCTGGCGGCGCAGTTTAACCGTCCGGGCCACGACATTGT

CGACCACTACACCTACGCCTTCATGGGCGACGGCTGCATGATGGAAGGCATCTCCCACGAAG

TTTGCTCTCTGGCGGGTACGCTGAAGCTGGGTAAACTGATTGCATTCTACGATGACAACGGT

ATTTCTATCGATGGTCACGTTGAAGGCTGGTTCACCGACGACACCGCAATGCGTTTCGAAGC

TTACGGCTGGCACGTTATTCGCGACATCGACGGTCATGACGCGGCATCTATCAAACGCGCAG

TAGAAGAAGCGCGCGCAGTGACTGACAAACCTTCCCTGCTGATGTGCAAAACCATCATCGGT

TTCGGTTCCCCGAACAAAGCCGGTACCCACGACTCCCACGGTGCGCCGCTGGGCGACGCTGA

AATTGCCCTGACCCGCGAACAACTGGGCTGGAAATATGCGCCGTTCGAAATCCCGTCTGAAA

TCTATGCTCAGTGGGATGCGAAAGAAGCAGGCCAGGCGAAAGAATCCGCATGGAACGAGAAA

TTCGCTGCTTACGCGAAAGCTTATCCGCAGGAAGCCGCTGAATTTACCCGCCGTATGAAAGG

CGAAATGCCGTCTGACTTCGACGCTAAAGCGAAAGAGTTCATCGCTAAACTGCAGGCTAATC

CGGCGAAAATCGCCAGCCGTAAAGCGTCTCAGAATGCTATCGAAGCGTTCGGTCCGCTGTTG

CCGGAATTCCTCGGCGGTTCTGCTGACCTGGCGCCGTCTAACCTGACCCTGTGGTCTGGTTC

TAAAGCAATCAACGAAGATGCTGCGGGTAACTACATCCACTACGGTGTTCGCGAGTTCGGTA

TGACCGCGATTGCTAACGGTATCTCCCTGCACGGTGGCTTCCTGCCGTACACCTCCACCTTC

CTGATGTTCGTGGAATACGCACGTAACGCCGTACGTATGGCTGCGCTGATGAAACAGCGTCA

GGTGATGGTTTACACCCACGACTCCATCGGTCTGGGCGAAGACGGCCCGACTCACCAGCCGG

TTGAGCAGGTCGCTTCTCTGCGCGTAACCCCGAACATGTCTACATGGCGTCCGTGTGACCAG

GTTGAATCCGCGGTCGCGTGGAAATACGGTGTTGAGCGTCAGGACGGCCCGACCGCACTGAT

CCTCTCCCGTCAGAACCTGGCGCAGCAGGAACGAACTGAAGAGCAACTGGCAAACATCGCGC

GCGGTGGTTATGTGCTGAAAGACTGCGCCGGTCAGCCGGAACTGATTTTCATCGCTACCGGT

TCAGAAGTTGAACTGGCTGTTGCTGCCTACGAAAAACTGACTGCCGAAGGCGTGAAAGCGCG

CGTGGTGTCCATGCCGTCTACCGACGCATTTGACAAGCAGGATGCTGCTTACCGTGAATCCG

TACTGCCGAAAGCGGTTACTGCACGCGTTGCTGTAGAAGCGGGTATTGCTGACTACTGGTAC

AAGTATGTTGGCCTGAACGGTGCTATCGTCGGTATGACCACCTTCGGTCTGGAAGTGCTGTT

TCAGGGTCCGGAATCTGCTCCGGCAGAGCTGCTGTTTGAAGAGTTCGGCTTCACTGTTGATA

ACGTTGTTGCGAAAGCAAAAGAACTGCTGTAA
                                                       SEQ ID NO: 60
ATGTCCTCACGTAAAGAGCTTGCCAATGCTATTCGTGCGCTGAGCATGGACGCAGTACAGAA

AGCCAAATCCGGTCACCCGGGTGCCCCTATGGGTATGGCTGACATTGCCGAAGTCCTGTGGC

GTGATTTCCTGAAACACAACCCGCAGAATCCGTCCTGGGCTGACCGTGACCGCTTCGTGCTG

TCCAACGGCCACGGCTCCATGCTGATCTACAGCCTGCTGCACCTCACCGGTTACGATCTGCC

GATGGAAGAACTGAAAAACTTCCGTCAGCTGCACTCTAAAACTCCGGGTCACCCGGAAGTGG

GTTACACCGCTGGTGTGGAAACCACCACCGGTCCGCTGGGTCAGGGTATTGCCAACGCAGTC

GGTATGGCGATTGCAGAAAAAACGCTGGCGGCGCAGTTTAACCGTCCGGGCCACGACATTGT

CGACCACTACACCTACGCCTTCATGGGCGACGGCTGCATGATGGAAGGCATCTCCCACGAAG

TTTGCTCTCTGGCGGGTACGCTGAAGCTGGGTAAACTGATTGCATTCTACGATGACAACGGT
```

SEQUENCE LISTING

ATTTCTATCGATGGTCACGTTGAAGGCTGGTTCACCGACGACACCGCAATGCGTTTCGAAGC

TTACGGCTGGCACGTTATTCGCGACATCGACGGTCATGACGCGGCATCTATCAAACGCGCAG

TAGAAGAAGCGCGCGCAGTGACTGACAAACCTTCCCTGCTGATGTGCAAAACCATCATCGGT

TTCGGTTCCCCGAACAAAGCCGGTACCCACGACTCCCACGGTGCGCCGCTGGGCGACGCTGA

AATTGCCCTGACCCGCGAACAACTGGGCTGGAAATATGCGCCGTTCGAAATCCCGTCTGAAA

TCTATGCTCAGTGGGATGCGAAAGAAGCAGGCCAGGCGAAAGAATCCGCATGGAACGAGAAA

TTCGCTGCTTACGCGAAAGCTTATCCGCAGGAAGCCGCTGAATTTACCCGCCGTATGAAAGG

CGAAATGCCGTCTGACTTCGACGCTAAAGCGAAAGAGTTCATCGCTAAACTGCAGGCTAATC

CGGCGAAAATCGCCAGCCGTAAAGCGTCTCAGAATGCTATCGAAGCGTTCGGTCCGCTGTTG

CCGGAATTCCTCGGCGGTTCTGCTGACCTGGCGCCGTCTAACCTGACCCGTGGTCTGGTTC

TAAAGCAATCAACGAAGATGCTGCGGGTAACTACATCCACTACGGTGTTCGCGAGTTCGGTA

TGACCGCGATTGCTAACGGTATCTCCCTGCACGGTGGCTTCCTGCCGTACACCTCCACCTTC

CTGATGTTCGTGGAATACGCACGTAACGCCGTACGTATGGCTGCGCTGATGAAACAGCGTCA

GGTGATGGTTTACACCCACGACTCCATCGGTCTGGGCGAAGACGGCCCGACTCACCAGCCGG

TTGAGCAGGTCGCTTCTCTGCGCGTAACCCCGAACATGTCTACATGGCGTCCGTGTGACCAG

GTTGAATCCGCGGTCGCGTGGAAATACGGTGTTGAGCGTCAGGACGGCCCGACCGCACTGAT

CCTCTCCCGTCAGAACCTGGCGCAGCAGGAACGAACTGAAGAGCAACTGGCAAACATCGCGC

GCGGTGGTTATGTGCTGAAAGACTGCGCCGGTCAGCCGGAACTGATTTTCATCGCTACCGGT

TCAGAAGTTGAACTGGCTGTTGCTGCCTACGAAAAACTGACTGCCGAAGGCGTGAAAGCGCG

CGTGGTGTCCATGCCGTCTACCGACGCATTTGACAAGCAGGATGCTGCTTACCGTGAATCCG

TACTGCCGAAAGCGGTTACTGCACGCGTTGCTGTAGAAGCGGGTATTGCTGACTACTGGTAC

AAGTATGTTGGCCTGAACGGTGCTATCGTCGGTATGACCACCTTCGGTGAACTGGAAGTGCT

GTTTCAGGGTCCGTCTGCTCCGGCAGAGCTGCTGTTTGAAGAGTTCGGCTTCACTGTTGATA

ACGTTGTTGCGAAAGCAAAAGAACTGCTGTAA

SEQ ID NO: 61
ATGTCCTCACGTAAAGAGCTTGCCAATGCTATTCGTGCGCTGAGCATGGACGCAGTACAGAA

AGCCAAATCCGGTCACCCGGGTGCCCCTATGGGTATGGCTGACATTGCCGAAGTCCTGTGGC

GTGATTTCCTGAAACACAACCCGCAGAATCCGTCCTGGGCTGACCGTGACCGCTTCGTGCTG

TCCAACGGCCACGGCTCCATGCTGATCTACAGCCTGCTGCACCTCACCGGTTACGATCTGCC

GATGGAAGAACTGAAAAACTTCCGTCAGCTGCACTCTAAAACTCCGGGTCACCCGGAAGTGG

GTTACACCGCTGGTGTGGAAACCACCACCGGTCCGCTGGGTCAGGGTATTGCCAACGCAGTC

GGTATGGCGATTGCAGAAAAAACGCTGGCGGCGCAGTTTAACCGTCCGGGCCACGACATTGT

CGACCACTACACCTACGCCTTCATGGGCGACGGCTGCATGATGGAAGGCATCTCCCACGAAG

TTTGCTCTCTGGCGGGTACGCTGAAGCTGGGTAAACTGATTGCATTCTACGATGACAACGGT

ATTTCTATCGATGGTCACGTTGAAGGCTGGTTCACCGACGACACCGCAATGCGTTTCGAAGC

TTACGGCTGGCACGTTATTCGCGACATCGACGGTCATGACGCGGCATCTATCAAACGCGCAG

TAGAAGAAGCGCGCGCAGTGACTGACAAACCTTCCCTGCTGATGTGCAAAACCATCATCGGT

TTCGGTTCCCCGAACAAAGCCGGTACCCACGACTCCCACGGTGCGCCGCTGGGCGACGCTGA

AATTGCCCTGACCCGCGAACAACTGGGCTGGAAATATGCGCCGTTCGAAATCCCGTCTGAAA

```
TCTATGCTCAGTGGGATGCGAAAGAAGCAGGCCAGGCGAAAGAATCCGCATGGAACGAGAAA

TTCGCTGCTTACGCGAAAGCTTATCCGCAGGAAGCCGCTGAATTTACCCGCCGTATGAAGG

CGAAATGCCGTCTGACTTCGACGCTAAAGCGAAAGAGTTCATCGCTAAACTGCAGGCTAATC

CGGCGAAAATCGCCAGCCGTAAAGCGTCTCAGAATGCTATCGAAGCGTTCGGTCCGCTGTTG

CCGGAATTCCTCGGCGGTTCTGCTGACCTGGCGCCGTCTAACCTGACCCTGTGGTCTGGTTC

TAAAGCAATCAACGAAGATGCTGCGGGTAACTACATCCACTACGGTGTTCGCGAGTTCGGTA

TGACCGCGATTGCTAACGGTATCTCCCTGCACGGTGGCTTCCTGCCGTACACCTCCACCTTC

CTGATGTTCGTGGAATACGCACGTAACGCCGTACGTATGGCTGCGCTGATGAAACAGCGTCA

GGTGATGGTTTACACCCACGACTCCATCGGTCTGGGCGAAGACGGCCCGACTCACCAGCCGG

TTGAGCAGGTCGCTTCTCTGCGCGTAACCCCGAACATGTCTACATGGCGTCCGTGTGACCAG

GTTGAATCCGCGGTCGCGTGGAAATACGGTGTTGAGCGTCAGGACGGCCCGACCGCACTGAT

CCTCTCCCGTCAGAACCTGGCGCAGCAGGAACGAACTGAAGAGCAACTGGCAAACATCGCGC

GCGGTGGTTATGTGCTGAAAGACTGCGCCGGTCAGCCGGAACTGATTTTCATCGCTACCGGT

TCAGAAGTTGAACTGGCTGTTGCTGCCTACGAAAAACTGACTGCCGAAGGCGTGAAAGCGCG

CGTGGTGTCCATGCCGTCTACCGACGCATTTGACAAGCAGGATGCTGCTTACCGTGAATCCG

TACTGCCGAAAGCGGTTACTGCACGCGTTGCTGTAGAAGCGGGTATTGCTGACTACTGGTAC

AAGTATGTTGGCCTGAACGGTGCTATCGTCGGTATGACCACCTTCGGTGAATCTCTGGAAGT

GCTGTTTCAGGGTCCGGCTCCGGCAGAGCTGCTGTTTGAAGAGTTCGGCTTCACTGTTGATA

ACGTTGTTGCGAAAGCAAAAGAACTGCTGTAA
```

SEQ ID NO: 62

```
ATGTCCTCACGTAAAGAGCTTGCCAATGCTATTCGTGCGCTGAGCATGGACGCAGTACAGAA

AGCCAAATCCGGTCACCCGGGTGCCCCTATGGGTATGGCTGACATTGCCGAAGTCCTGTGGC

GTGATTTCCTGAAACACAACCCGCAGAATCCGTCCTGGGCTGACCGTGACCGCTTCGTGCTG

TCCAACGGCCACGGCTCCATGCTGATCTACAGCCTGCTGCACCTCACCGGTTACGATCTGCC

GATGGAAGAACTGAAAAACTTCCGTCAGCTGCACTCTAAAACTCCGGGTCACCCGGAAGTGG

GTTACACCGCTGGTGTGGAAACCACCACCGGTCCGCTGGGTCAGGGTATTGCCAACGCAGTC

GGTATGGCGATTGCAGAAAAAACGCTGGCGGCGCAGTTTAACCGTCCGGGCCACGACATTGT

CGACCACTACACCTACGCCTTCATGGGCGACGGCTGCATGATGGAAGGCATCTCCCACGAAG

TTTGCTCTCTGGCGGGTACGCTGAAGCTGGGTAAACTGATTGCATTCTACGATGACAACGGT

ATTTCTATCGATGGTCACGTTGAAGGCTGGTTCACCGACGACACCGCAATGCGTTTCGAAGC

TTACGGCTGGCACGTTATTCGCGACATCGACGGTCATGACGCGGCATCTATCAAACGCGCAG

TAGAAGAAGCGCGCGCAGTGACTGACAAACCTTCCCTGCTGATGTGCAAAACCATCATCGGT

TTCGGTTCCCCGAACAAAGCCGGTACCCACGACTCCCACGGTGCGCCGCTGGGCGACGCTGA

AATTGCCCTGACCCGCGAACAACTGGGCTGGAAATATGCGCCGTTCGAAATCCCGTCTGAAA

TCTATGCTCAGTGGGATGCGAAAGAAGCAGGCCAGGCGAAAGAATCCGCATGGAACGAGAAA

TTCGCTGCTTACGCGAAAGCTTATCCGCAGGAAGCCGCTGAATTTACCCGCCGTATGAAGG

CGAAATGCCGTCTGACTTCGACGCTAAAGCGAAAGAGTTCATCGCTAAACTGCAGGCTAATC

CGGCGAAAATCGCCAGCCGTAAAGCGTCTCAGAATGCTATCGAAGCGTTCGGTCCGCTGTTG

CCGGAATTCCTCGGCGGTTCTGCTGACCTGGCGCCGTCTAACCTGACCCTGTGGTCTGGTTC
```

-continued

SEQUENCE LISTING

TAAAGCAATCAACGAAGATGCTGCGGGTAACTACATCCACTACGGTGTTCGCGAGTTCGGTA

TGACCGCGATTGCTAACGGTATCTCCCTGCACGGTGGCTTCCTGCCGTACACCTCCACCTTC

CTGATGTTCGTGGAATACGCACGTAACGCCGTACGTATGGCTGCGCTGATGAAACAGCGTCA

GGTGATGGTTTACACCCACGACTCCATCGGTCTGGGCGAAGACGGCCCGACTCACCAGCCGG

TTGAGCAGGTCGCTTCTCTGCGCGTAACCCCGAACATGTCTACATGGCGTCCGTGTGACCAG

GTTGAATCCGCGGTCGCGTGGAAATACGGTGTTGAGCGTCAGGACGGCCCGACCGCACTGAT

CCTCTCCCGTCAGAACCTGGCGCAGCAGGAACGAACTGAAGAGCAACTGGCAAACATCGCGC

GCGGTGGTTATGTGCTGAAAGACTGCGCCGGTCAGCCGGAACTGATTTTCATCGCTACCGGT

TCAGAAGTTGAACTGGCTGTTGCTGCCTACGAAAAACTGACTGCCGAAGGCGTGAAAGCGCG

CGTGGTGTCCATGCCGTCTACCGACGCATTTGACAAGCAGGATGCTGCTTACCGTGAATCCG

TACTGCCGAAAGCGGTTACTGCACGCGTTGCTGTAGAAGCGGGTATTGCTGACTACTGGTAC

AAGTATGTTGGCCTGAACGGTGCTATCGTCGGTATGACCACCTTCGGTGAATCTGCTCCGCT

GGAAGTGCTGTTTCAGGGTCCGGCAGAGCTGCTGTTTGAAGAGTTCGGCTTCACTGTTGATA

ACGTTGTTGCGAAAGCAAAAGAACTGCTGTAA

SEQ ID NO: 63
MSSRKELANAIRALSMDAVQKAKSGHPGAPMGMADIAEVLWRDFLKHNPQNPSWADRDRFVL

SNGHGSMLIYSLLHLTGYDLPMEELKNFRQLHSKTPGHPEVGYTAGVETTTGPLGQGIANAV

GMAIAEKTLAAQFNRPGHDIVDHYTYAFMGDCMMEGISHEVCSLAGTLKLGKLIAFYDDNG

ISIDGHVEGWFTDDTAMRFEAYGWHVIRDIDGHDAASIKRAVEEARAVTDKPSLLMCKTIIG

FGSPNKAGTHDSHGAPLGDAEIALTREQLGWKYAPFEIPSEIYAQWDAKEAGQAKESAWNEK

FAAYAKAYPQEAAEFTRRMKGEMPSDFDAKAKEFIAKLQANPAKIASRKASQNAIEAFGPLL

PEFLGGSADLAPSNLTLWSGSKAINEDAAGNYIHYGVREFGMTAIANGISLHGGFLPYTSTF

LMFVEYARNAVRMAALMKQRQVMVYTHDSIGLGEDGPTHQPVEQIASLRVTPNMSTWRPCDQ

VESAVAWKYGVERQDGPTALILSRQNLAQQERTEEQLANIARGGYVLKDCAGQPELIFIATG

SEVELAVAAYEKLTAEGVKARVVSMPSTDAFDKQDAAYRESVLPKAVTARVAVEAGIADYWY

KYVGLNGAIVGMTTFGESAPAEQLFEEFGFTVDNVVAKAKALL

SEQ ID NO: 64
MSSRKELANAIRALSMDAVQKAKSGHPGAPMGMADIAEVLWRDFLKHNPQNPSWADRDRFVL

SNGHGSMLIYSLLHLTGYDLPMEELKNFRQLHSKTPGHPEVGYTAGVETTTGPLGQGIANAV

GMAIAEKTLAAQFNRPGHDIVDHYTYAFMGDCMMEGISHEVCSLAGTLKLGKLIAFYDDNG

ISIDGHVEGWFTDDTAMRFEAYGWHVIRDIDGHDAASIKRAVEEARAVTDKPSLLMCKTIIG

FGSPNKAGTHDSHGAPLGDAEIALTREQLGWKYAPFEIPSEIYAQWDAKEAGQAKESAWNEK

FAAYAKAYPQEAAEFTRRMKGEMPSDFDAKAKEFIAKLQANPAKIASRKASQNAIEAFGPLL

PEFLGGSADLAPSNLTLWSGSKAINEDAAGNYIHYGVREFGMTAIANGISLHGGFLPYTSTF

LMFVEYARNAVRMAALMKQRQVMVYTHDSIGLGEDGPTHQPVEQVASLRVTPNMSTWRPCDQ

VESAVAWKYGVERQDGPTALILSRQNLAQQERTEEQLANIARGGYVLKDCAGQPELIFIATG

SEVELAVAAYEKLTAEGVKARVVSMPSTDAFDKQDAAYRESVLPKAVTARVAVEAGIADYWY

KYVGLNGAIVGMTTFLEVLFQGPGESAPAELLFEEFGFTVDNVVAKAKELL

SEQUENCE LISTING

SEQ ID NO: 65
MSSRKELANAIRALSMDAVQKAKSGHPGAPMGMADIAEVLWRDFLKHNPQNPSWADRDRFVL

SNGHGSMLIYSLLHLTGYDLPMEELKNFRQLHSKTPGHPEVGYTAGVETTTGPLGQGIANAV

GMAIAEKTLAAQFNRPGHDIVDHYTYAFMGDGCMMEGISHEVCSLAGTLKLGKLIAFYDDNG

ISIDGHVEGWFTDDTAMRFEAYGWHVIRDIDGHDAASIKRAVEEARAVTDKPSLLMCKTIIG

FGSPNKAGTHDSHGAPLGDAEIALTREQLGWKYAPFEIPSEIYAQWDAKEAGQAKESAWNEK

FAAYAKAYPQEAAEFTRRMKGEMPSDFDAKAKEFIAKLQANPAKIASRKASQNAIEAFGPLL

PEFLGGSADLAPSNLTLWSGSKAINEDAAGNYIHYGVREFGMTAIANGISLHGGFLPYTSTF

LMFVEYARNAVRMAALMKQRQVMVYTHDSIGLGEDGPTHQPVEQVASLRVTPNMSTWRPCDQ

VESAVAWKYGVERQDGPTALILSRQNLAQQERTEEQLANIARGGYVLKDCAGQPELIFIATG

SEVELAVAAYEKLTAEGVKARVVSMPSTDAFDKQDAAYRESVLPKAVTARVAVEAGIADYWY

KYVGLNGAIVGMTTFGLEVLFQGPESAPAELLFEEFGFTVDNVVAKAKELL

SEQ ID NO: 66
MSSRKELANAIRALSMDAVQKAKSGHPGAPMGMADIAEVLWRDFLKHNPQNPSWADRDRFVL

SNGHGSMLIYSLLHLTGYDLPMEELKNFRQLHSKTPGHPEVGYTAGVETTTGPLGQGIANAV

GMAIAEKTLAAQFNRPGHDIVDHYTYAFMGDGCMMEGISHEVCSLAGTLKLGKLIAFYDDNG

ISIDGHVEGWFTDDTAMRFEAYGWHVIRDIDGHDAASIKRAVEEARAVTDKPSLLMCKTIIG

FGSPNKAGTHDSHGAPLGDAEIALTREQLGWKYAPFEIPSEIYAQWDAKEAGQAKESAWNEK

FAAYAKAYPQEAAEFTRRMKGEMPSDFDAKAKEFIAKLQANPAKIASRKASQNAIEAFGPLL

PEFLGGSADLAPSNLTLWSGSKAINEDAAGNYIHYGVREFGMTAIANGISLHGGFLPYTSTF

LMFVEYARNAVRMAALMKQRQVMVYTHDSIGLGEDGPTHQPVEQVASLRVTPNMSTWRPCDQ

VESAVAWKYGVERQDGPTALILSRQNLAQQERTEEQLANIARGGYVLKDCAGQPELIFIATG

SEVELAVAAYEKLTAEGVKARVVSMPSTDAFDKQDAAYRESVLPKAVTARVAVEAGIADYWY

KYVGLNGAIVGMTTFGELEVLFQGPSAPAELLFEEFGFTVDNVVAKAKELL

SEQ ID NO: 67
MSSRKELANAIRALSMDAVQKAKSGHPGAPMGMADIAEVLWRDFLKHNPQNPSWADRDRFVL

SNGHGSMLIYSLLHLTGYDLPMEELKNFRQLHSKTPGHPEVGYTAGVETTTGPLGQGIANAV

GMAIAEKTLAAQFNRPGHDIVDHYTYAFMGDGCMMEGISHEVCSLAGTLKLGKLIAFYDDNG

ISIDGHVEGWFTDDTAMRFEAYGWHVIRDIDGHDAASIKRAVEEARAVTDKPSLLMCKTIIG

FGSPNKAGTHDSHGAPLGDAEIALTREQLGWKYAPFEIPSEIYAQWDAKEAGQAKESAWNEK

FAAYAKAYPQEAAEFTRRMKGEMPSDFDAKAKEFIAKLQANPAKIASRKASQNAIEAFGPLL

PEFLGGSADLAPSNLTLWSGSKAINEDAAGNYIHYGVREFGMTAIANGISLHGGFLPYTSTF

LMFVEYARNAVRMAALMKQRQVMVYTHDSIGLGEDGPTHQPVEQVASLRVTPNMSTWRPCDQ

VESAVAWKYGVERQDGPTALILSRQNLAQQERTEEQLANIARGGYVLKDCAGQPELIFIATG

SEVELAVAAYEKLTAEGVKARVVSMPSTDAFDKQDAAYRESVLPKAVTARVAVEAGIADYWY

KYVGLNGAIVGMTTFGESLEVLFQGPAPAELLFEEFGFTVDNVVAKAKELL

SEQ ID NO: 68
MSSRKELANAIRALSMDAVQKAKSGHPGAPMGMADIAEVLWRDFLKHNPQNPSWADRDRFVL

SNGHGSMLIYSLLHLTGYDLPMEELKNFRQLHSKTPGHPEVGYTAGVETTTGPLGQGIANAV

GMAIAEKTLAAQFNRPGHDIVDHYTYAFMGDGCMMEGISHEVCSLAGTLKLGKLIAFYDDNG

SEQUENCE LISTING

-continued

ISIDGHVEGWFTDDTAMRFEAYGWHVIRDIDGHDAASIKRAVEEARAVTDKPSLLMCKTIIG

FGSPNKAGTHDSHGAPLGDAEIALTREQLGWKYAPFEIPSEIYAQWDAKEAGQAKESAWNEK

FAAYAKAYPQEAAEFTRRMKGEMPSDFDAKAKEFIAKLQANPAKIASRKASQNAIEAFGPLL

PEFLGGSADLAPSNLTLWSGSKAINEDAAGNYIHYGVREFGMTAIANGISLHGGFLPYTSTF

LMFVEYARNAVRMAALMKQRQVMVYTHDSIGLGEDGPTHQPVEQVASLRVTPNMSTWRPCDQ

VESAVAWKYGVERQDGPTALILSRQNLAQQERTEEQLANIARGGYVLKDCAGQPELIFIATG

SEVELAVAAYEKLTAEGVKARVVSMPSTDAFDKQDAAYRESVLPKAVTARVAVEAGIADYWY

KYVGLNGAIVGMTTFGESAPLEVLFQGPAELLFEEFGFTVDNVVAKAKELL

SEQ ID NO: 69
CTGGAAGTGCTGTTTCAGGGTCCG

SEQ ID NO: 70
MKNINPTQTAA

SEQ ID NO: 71
ATGAAAAACATCAATCCAACGCAGACCGCTGCC

SEQ ID NO: 72
MLEVLFQGPKNINPTQTAA

SEQ ID NO: 73
ATGCTGGAAGTGCTGTTTCAGGGTCCGAAAAACATCAATCCAACGCAGACCGCTGCC

SEQ ID NO: 74
MKLEVLFQGPNINPTQTAA

SEQ ID NO: 75
ATGAAACTGGAAGTGCTGTTTCAGGGTCCGAACATCAATCCAACGCAGACCGCTGCC

SEQ ID NO: 76
MKNLEVLFQGPINPTQTAA

SEQ ID NO: 77
ATGAAAAACCTGGAAGTGCTGTTTCAGGGTCCGATCAATCCAACGCAGACCGCTGCC

SEQ ID NO: 78
MLEVLFQGPAA

SEQ ID NO: 79
ATGCTGGAAGTGCTGTTTCAGGGTCCGGCTGCC

SEQ ID NO: 80
MKLEVLFQGPA

SEQ ID NO: 81
ATGAAACTGGAAGTGCTGTTTCAGGGTCCGGCC

SEQ ID NO: 82
MKNLEVLFQGP

SEQ ID NO: 83
ATGAAAAACCTGGAAGTGCTGTTTCAGGGTCCG

SEQ ID NO: 84
MKNINLEVLFQGPTQTAA

SEQ ID NO: 85
ATGAAAAACATCAATCTGGAAGTGCTGTTTCAGGGTCCAACGCAGACCGCTGCC

SEQ ID NO: 86
TAAWQALEVLFQGPQKH

SEQ ID NO: 87
ACCGCTGCCTGGCAGGCACTAGAAGTGCTGTTTCAGGGTCCGCAGAAACAC

What is claimed is:

1. A recombinant protein comprising a polypeptide derived from SEQ ID NO: 17, said polypeptide comprising a human rhinovirus 3C protease recognition sequence located between amino acids 526 and 527 of SEQ ID NO:17 wherein, said polypeptide has at least 95% identity with SEQ ID NO: 25 and has phosphoglucose isomerase activity.

2. The recombinant protein of claim 1, wherein the protease recognition sequence comprises the amino acid sequence of SEQ ID NO:38.

3. The recombinant protein of claim 1, wherein the recombinant protein comprises the amino acid sequence of SEQ ID NO:25.

4. The recombinant protein of claim 1, wherein the protease recognition sequence comprises the amino acid sequence of SEQ ID NO:39, SEQ ID NO:40, SEQ ID NO:41, SEQ ID NO:42, SEQ ID NO:43, SEQ ID NO:44, or SEQ ID NO:45.

* * * * *

SEQUENCE LISTING

<160> NUMBER OF SEQ ID NOS: 87

<210> SEQ ID NO 1
<211> LENGTH: 1650
<212> TYPE: DNA
<213> ORGANISM: Artificial Sequence
<220> FEATURE:
<223> OTHER INFORMATION: Synthetic Oligonucleoide

<400> SEQUENCE: 1

| | | | | |
|---|---|---|---|---|
| atgaaaaaca tcaatccaac gcagaccgct gcctggcagg cactacagaa acacttcgat | 60 |
| gaaatgaaag acgttacgat cgccgatctt tttgctaaag acggcgatcg tttttctaag | 120 |
| ttctccgcaa ccttcgacga tcagatgctg gtggattact ccaaaaaccg catcactgaa | 180 |
| gagacgctgg cgaaattaca ggatctggcg aaagagtgcg atctggcggg cgcgattaag | 240 |
| tcgatgttct ctggcgagaa gatcaaccgc actgaaaaacc gcgccgtgct gcacgtagcg | 300 |
| ctgcgtaacc gtagcaatac cccgattttg gttgatggca agacgtaat gccggaagtc | 360 |
| aacgcggtgc tggagaagat gaaaaccttc tcagaagcga ttatttccgg tgagtggaaa | 420 |
| ggttataccg gcaaagcaat cactgacgta gtgaacatcg ggatcggcgg ttctgacctc | 480 |
| ggcccataca tggtgaccga agctctgcgt ccgtacaaaa accacctgaa catgcacttt | 540 |
| gtttctaacg tcgatgggac tcacatcgcg gaagtgctga aaaaagtaaa cccggaaacc | 600 |
| acgctgttct ggtagcatc taaaaccttc accactcagg aaactatgac caacgcccat | 660 |
| agcgcgcgtg actggttcct gaaagcggca ggtgatgaaa acacgttgc aaaacacttt | 720 |
| gcggcgcttt ccaccaatgc caaagccgtt ggcgagtttg gtattgatac tgccaacatg | 780 |
| ttcgagttct gggactgggt tggcggccgt tactctttgt ggtcagcgat tggcctgtcg | 840 |
| attgttctct ccatcggctt tgataacttc gttgaactgc tttccggcgc acacgcgatg | 900 |
| gacaagcatt tctccaccac gcctgccgag aaaaacctgc ctgtactgct ggcgctgatt | 960 |
| ggcatctggt acaacaattt cttggtgcg gaaactgaag cgattctgcc gtatgaccag | 1020 |
| tatatgcacc gttcgcggc gtacttccag cagggcaata tggagtccaa cggtaagtat | 1080 |
| gttgaccgta acggtaacgt tgtggattac cagactggcc cgattatctg gggtgaacca | 1140 |
| ggcactaacg gtcagcacgc gttctaccag ctgatccacc agggaaccaa aatggtaccg | 1200 |
| tgcgatttca tcgctccggc tatcacccat aaccgctct ctgatcatca ccagaaactg | 1260 |
| ctgtctaact cttcgcccca gaccgaagcg ctggcgtttg gtaaatcccg cgaagtggtt | 1320 |
| gagcaggaat atcgtgatca gggtaaagat ccggcaacgc ttgactacgt ggtgccgttc | 1380 |
| aaagtattcg aaggtaaccg cccgaccaac tccatcctgc tgcgtgaaat cactccgttc | 1440 |
| agcctgggtg cgttgattgc gctgtatgag cacaaaatct ttactcaggg cgtgatcctg | 1500 |
| aacatcttca ccttcgacca gtggggcgtg gaactgggta acagctggc gaaccgtatt | 1560 |
| ctgccagagc tgaaagatga taagaaatc agcagccacg atagctcgac caatggtctg | 1620 |
| attaaccgct ataaagcgtg gcgcggttaa | 1650 |

<210> SEQ ID NO 2
<211> LENGTH: 1674
<212> TYPE: DNA
<213> ORGANISM: Artificial Sequence
<220> FEATURE:
<223> OTHER INFORMATION: Synthetic Oligonucleotide

<400> SEQUENCE: 2
atgaaaaaca tcaatccaac gcagaccgct gcctggcagg cactacagaa acacttcgat    60

```
gaaatgaaag acgttacgat cgccgatctt tttgctaaag atggtgatcg ttttcctaag    120
ttctccgcaa ccttcgacga tcagatgctg gtggattact ccaaaaaccg catcactgaa    180
gagacgctgg cgaaattaca ggatctggcg aaagagtgcg atctggcggg cgcgattaag    240
tcgatgttct ctggcgagaa gatcaaccgc actgaaaacc gcgccgtgct gcacgtagcg    300
ctgcgtaacc gtagcaatac cccgctggaa gtgctgtttc agggtccgat tttggttgat    360
ggcaaagacg taatgccgga agtcaacgcg gtgctggaga agatgaaaac cttctcagaa    420
gcgattattt ccggtgagtg aaaggttat accggcaaag caatcactga cgtagtgaac    480
atcgggatcg gcggttctga cctcggccca tacatggtga ccgaagctct gcgtccgtac    540
aaaaaccacc tgaacatgca ctttgtttct aacgtcgatg ggactcacat cgcggaagtg    600
ctgaaaaaag taaacccgga aaccacgctg ttcttggtag catctaaaac cttcaccact    660
caggaaacta tgaccaacgc ccatagcgcg cgtgactggt tcctgaaagc ggcaggtgat    720
gagaagcacg ttgcaaaaca cttttgcggcg ctttccacca atgccaaagc cgttggcgag    780
tttggtattg atactgccaa catgttcgag ttctgggact gggttggcgg ccgttactct    840
ttgtggtcag cgattggcct gtcgattgtt ctctccatcg gctttgataa cttcgttgaa    900
ctgctttccg gcgcacacgc gatggacaag catttctcca ccacgcctgc cgagaaaaac    960
ctgcctgtac tgctggcgct gattggcatc tggtacaaca atttctttgg tgcggaaact   1020
gaagcgattc tgccgtatga ccagtatatg caccgtttcg cggcgtactt ccagcagggc   1080
aatatggagt ccaacggtaa gtatgttgac cgtaacggta acgttgtgga ttaccagact   1140
ggcccgatta tctggggtga accaggcact aacggtcagc acgcgttcta ccagctgatc   1200
caccagggaa ccaaaatggt accgtgcgat ttcatcgctc cggctatcac ccataacccg   1260
ctctctgatc atcaccagaa actgctgtct aacttcttcg cccagaccga agcgctggcg   1320
tttggtaaat cccgcgaagt ggttgagcag gaatatcgtg atcagggtaa agatccggca   1380
acgcttgact acgtggtgcc gttcaaagta ttcgaaggta accgcccgac caactccatc   1440
ctgctgcgtg aaatcactcc gttcagcctg ggtgcgttga ttgcgctgta tgagcacaaa   1500
atctttactc agggcgtgat cctgaacatc ttccccttcg accagtgggg cgtggaactg   1560
ggtaaacagc tggcgaaccg tattctgcca gagctgaaag atgataaaga aatcagcagc   1620
cacgatagct cgaccaatgg tctgattaac cgctataaag cgtggcgcgg ttaa         1674
```

<210> SEQ ID NO 3
<211> LENGTH: 1674
<212> TYPE: DNA
<213> ORGANISM: Artificial Sequence
<220> FEATURE:
<223> OTHER INFORMATION: Synthetic Oligonucleotide

<400> SEQUENCE: 3

```
atgaaaaaca tcaatccaac gcagaccgct gcctggcagg cactacagaa acacttcgat     60
gaaatgaaag acgttacgat cgccgatctt tttgctaaag atggtgatcg ttttcctaag    120
ttctccgcaa ccttcgacga tcagatgctg gtggattact ccaaaaaccg catcactgaa    180
gagacgctgg cgaaattaca ggatctggcg aaagagtgcg atctggcggg cgcgattaag    240
tcgatgttct ctggcgagaa gatcaaccgc actgaaaacc gcgccgtgct gcacgtagcg    300
ctgcgtaacc gtagcaatac cccgattctg aagtgctgtt tcagggtcc gttggttgat    360 ggcaaagacg taatgccgga agtcaacgcg gtgctggaga agatgaaaac cttctcagaa    420
```

```
gcgattattt ccggtgagtg gaaaggttat accggcaaag caatcactga cgtagtgaac      480
atcgggatcg gcggttctga cctcggccca tacatggtga ccgaagctct gcgtccgtac      540
aaaaaccacc tgaacatgca ctttgtttct aacgtcgatg ggactcacat cgcggaagtg      600
ctgaaaaaag taaacccgga aaccacgctg ttcttggtag catctaaaac cttcaccact      660
caggaaacta tgaccaacgc ccatagcgcg cgtgactggt tcctgaaagc ggcaggtgat      720
gagaagcacg ttgcaaaaca ctttgcggcg ctttccacca atgccaaagc cgttggcgag      780
tttggtattg atactgccaa catgttcgag ttctgggact gggttggcgg ccgttactct      840
ttgtggtcag cgattggcct gtcgattgtt ctctccatcg gctttgataa cttcgttgaa      900
ctgctttccg gcgcacacgc gatggacaag catttctcca ccacgcctgc cgagaaaaac      960
ctgcctgtac tgctggcgct gattggcatc tggtacaaca atttctttgg tgcggaaact     1020
gaagcgattc tgccgtatga ccagtatatg caccgtttcg cggcgtactt ccagcagggc     1080
aatatggagt ccaacggtaa gtatgttgac cgtaacggta acgttgtgga ttaccagact     1140
ggcccgatta tctggggtga accaggcact aacggtcagc acgcgttcta ccagctgatc     1200
caccagggaa ccaaaatggt accgtgcgat ttcatcgctc cggctatcac ccataacccg     1260
ctctctgatc atcaccagaa actgctgtct aacttcttcg cccagaccga agcgctggcg     1320
tttggtaaat cccgcgaagt ggttgagcag gaatatcgtg atcagggtaa agatccggca     1380
acgcttgact acgtggtgcc gttcaaagta ttcgaaggta accgcccgac caactccatc     1440
ctgctgcgtg aaatcactcc gttcagcctg ggtgcgttga ttgcgctgta tgagcacaaa     1500
atctttactc agggcgtgat cctgaacatc ttcaccttcg accagtgggg cgtggaactg     1560
ggtaaacagc tggcgaaccg tattctgcca gagctgaaag atgataaaga aatcagcagc     1620
cacgatagct cgaccaatgg tctgattaac cgctataaag cgtggcgcgg ttaa           1674

<210> SEQ ID NO 4
<211> LENGTH: 1671
<212> TYPE: DNA
<213> ORGANISM: Artificial Sequence
<220> FEATURE:
<223> OTHER INFORMATION: Synthetic Oligonucleotide

<400> SEQUENCE: 4
atgaaaaaca tcaatccaac gcagaccgct gcctggcagg cactacagaa acacttcgat       60
gaaatgaaag acgttacgat cgccgatctt tttgctaaag atggtgatcg ttttttctaag     120 ttctccgcaa ccttcgacga tcagatgctg gtggattact ccaaaaaccg catcactgaa      180
gagacgctgg cgaaattaca ggatctggcg aaagagtgcg atctggcggg cgcgattaag      240
tcgatgttct ctggcgagaa gatcaaccgc actgaaaacc gcgccgtgct gcacgtagcg      300
ctgcgtaacc gtagcaatac cccgattttg gaagtgctgt tcagggtcc ggttgatggc       360 aaagacgtaa tgccggaagt caacgcggtg ctggagaaga tgaaaacctt ctcagaagcg      420
attatttccg gtgagtggaa aggttatacc ggcaaagcaa tcactgacgt agtgaacatc      480
gggatcggcg gttctgacct cggcccatac atggtgaccg aagctctgcg tccgtacaaa      540
aaccacctga acatgcactt tgtttctaac gtcgatggga ctcacatcgc ggaagtgctg      600 aaaaagtaa acccggaaac cacgctgttc ttggtagcat ctaaaacctt caccactcag       660
gaaactatga ccaacgccca tagcgcgcgt gactggttcc tgaaagcggc aggtgatgag      720
aagcacgttg caaaacactt tgcggcgctt tccaccaatg ccaaagccgt tggcgagttt      780
ggtattgata ctgccaacat gttcgagttc tgggactggg ttggcggccg ttactctttg      840
```

-continued

```
tggtcagcga ttggcctgtc gattgttctc tccatcggct ttgataactt cgttgaactg      900
ctttccggcg cacacgcgat ggacaagcat ttctccacca cgcctgccga aaaaacctg      960 cctgtactgc tggcgctgat tggcatctgg tacaacaatt tctttggtgc ggaaactgaa    1020
gcgattctgc cgtatgacca gtatatgcac cgtttcgcgg cgtacttcca gcagggcaat    1080
atggagtcca acggtaagta tgttgaccgt aacggtaacg ttgtggatta ccagactggc    1140
ccgattatct ggggtgaacc aggcactaac ggtcagcacg cgttctacca gctgatccac    1200
cagggaacca aaatggtacc gtgcgatttc atcgctccgg ctatcaccca taacccgctc    1260
tctgatcatc accagaaact gctgtctaac ttcttcgccc agaccgaagc gctggcgttt    1320
ggtaaatccc gcgaagtggt tgagcaggaa tatcgtgatc agggtaaaga tccggcaacg    1380
cttgactacg tggtgccgtt caaagtattc gaaggtaacc gcccgaccaa ctccatcctg    1440
ctgcgtgaaa tcactccgtt cagcctgggt gcgttgattg cgctgtatga gcacaaaatc    1500
tttactcagg gcgtgatcct gaacatcttc accttcgacc agtggggcgt ggaactgggt    1560
aaacagctgg cgaaccgtat tctgccagag ctgaaagatg ataaagaaat cagcagccac    1620
gatagctcga ccaatggtct gattaaccgc tataaagcgt ggcgcggtta a              1671
```

<210> SEQ ID NO 5
<211> LENGTH: 1674
<212> TYPE: DNA
<213> ORGANISM: Artificial Sequence
<220> FEATURE:
<223> OTHER INFORMATION: Synthetic Oligonucleotide

<400> SEQUENCE: 5

```
atgaaaaaca tcaatccaac gcagaccgct gcctggcagg cactacagaa acacttcgat       60
gaaatgaaag acgttacgat cgccgatctt tttgctaaag atggtgatcg tttttctaag      120
ttctccgcaa ccttcgacga tcagatgctg gtggattact ccaaaaaccg catcactgaa      180
gagacgctgg cgaaattaca ggatctggcg aaagagtgcg atctggcggg cgcgattaag      240
tcgatgttct ctggcgagaa gatcaaccgc actgaaaaacc gcgccgtgct gcacgtagcg      300
ctgcgtaacc gtagcaatac cccgattttg gttgatggca aagacgtaat gccggaagtc      360
aacgcggtgc tggagaagat gaaaaccttc tcagaagcga ttatttccgg tgagctggaa      420
gtgctgtttc agggtccgtg gaaaggttat accggcaaag caatcactga cgtagtgaac      480
atcgggatcg gcggttctga cctcggccca tacatggtga ccgaagctct cgtccgtac      540 aaaaaccacc tgaacatgca ctttgtttct aacgtcgatg ggactcacat cgcggaagtg      600
ctgaaaaaag taaacccgga aaccacgctg ttcttggtag catctaaaac cttcaccact      660
caggaaacta tgaccaacgc ccatagcgcg cgtgactggt tcctgaaagc ggcaggtgat      720
gagaagcacg ttgcaaaaca ctttgcggcg ctttccacca tgccaaagc cgttggcgag      780 tttggtattg atactgccaa catgttcgag ttctgggact gggttggcgg ccgttactct      840
ttgtggtcag cgattggcct gtcgattgtt ctctccatcg gctttgataa cttcgttgaa      900
ctgctttccg gcgcacacgc gatggacaag catttctcca ccacgcctgc cgagaaaaac      960
ctgcctgtac tgctggcgct gattggcatc tggtacaaca atttctttgg tgcggaaact     1020
gaagcgattc tgccgtatga ccagtatatg caccgtttcg cggcgtactt ccagcagggc    1080
aatatggagt ccaacggtaa gtatgttgac cgtaacggta acgttgtgga ttaccagact    1140
ggcccgatta tctggggtga accaggcact aacggtcagc acgcgttcta ccagctgatc    1200
```

| | |
|---|---|
| caccagggaa ccaaaatggt accgtgcgat ttcatcgctc cggctatcac ccataacccg | 1260 |
| ctctctgatc atcaccagaa actgctgtct aacttcttcg cccagaccga agcgctggcg | 1320 |
| tttggtaaat cccgcgaagt ggttgagcag gaatatcgtg atcagggtaa agatccggca | 1380 |
| acgcttgact acgtggtgcc gttcaaagta ttcgaaggta accgcccgac caactccatc | 1440 |
| ctgctgcgtg aaatcactcc gttcagcctg ggtgcgttga ttgcgctgta tgagcacaaa | 1500 |
| atctttactc agggcgtgat cctgaacatc ttcaccttcg accagtgggg cgtggaactg | 1560 |
| ggtaaacagc tggcgaaccg tattctgcca gagctgaaag atgataaaga aatcagcagc | 1620 |
| cacgatagct cgaccaatgg tctgattaac cgctataaag cgtggcgcgg ttaa | 1674 |

<210> SEQ ID NO 6
<211> LENGTH: 1674
<212> TYPE: DNA
<213> ORGANISM: Artificial Sequence
<220> FEATURE:
<223> OTHER INFORMATION: Synthetic Oligonucleotide

<400> SEQUENCE: 6

| | |
|---|---|
| atgaaaaaca tcaatccaac gcagaccgct gcctggcagg cactacagaa acacttcgat | 60 |
| gaaatgaaag acgttacgat cgccgatctt tttgctaaag atggtgatcg ttttttctaag | 120 |
| ttctccgcaa ccttcgacga tcagatgctg gtggattact ccaaaaaccg catcactgaa | 180 |
| gagacgctgg cgaaattaca ggatctggcg aaagagtgcg atctggcggg cgcgattaag | 240 |
| tcgatgttct ctggcgagaa gatcaaccgc actgaaaacc gcgccgtgct gcacgtagcg | 300 |
| ctgcgtaacc gtagcaatac cccgattttg gttgatggca aagacgtaat gccggaagtc | 360 |
| aacgcggtgc tggagaagat gaaaaccttc tcagaagcga ttatttccgg tgagtggaaa | 420 |
| ggttataccg gcaaagcaat cactgacgta gtgaacatcg gatcggcgg ttctgacctc | 480 |
| ggcccataca tggtgaccga agctctgcgt ccgtacaaaa accacctgaa catgcacttt | 540 |
| gtttctaacg tcgatgggac tcacatcgcg gaagtgctga aaaagtaaa cccggaaacc | 600 |
| acgctgttct tggtagcatc taaaaccttc accactcagg aaactatgac caacgcccat | 660 |
| agcgcgcgtg actggttcct gaaagcggca ggtgatgaga agcacgttgc aaaacacttt | 720 |
| gcggcgcttt ccaccaatgc caaagccgtt ggcgagtttg gtattgatac tgccaacatg | 780 |
| ttcgagttct gggactgggt tggcggccgt tactcttgt ggtcagcgat ggcctgtcg | 840 |
| attgttctct ccatcggctt tgataacttc gttgaactgc tttccggcgc acacgcgatg | 900 |
| gacaagcatt tctccaccac gcctgccgag aaaaacctgc ctgtactgct ggcgctgatt | 960 |
| ggcatctggt acaacaattt ctttggtgcg gaaactgaag cgattctgcc gtatgaccag | 1020 |
| tatatgcacc gtttcgcggc gtacttccag cagggcaata tggagtccaa cggtaagtat | 1080 |
| gttgaccgta acggtaacgt tgtggattac cagactggcc cgattatctg gggtgaacca | 1140 |
| ggcactaacg tcagcacgc gttctaccag ctgatccacc agggaaccaa aatggtaccg | 1200 |
| tgcgatttca tcgctccggc tatcacccat ctggaagtgc tgtttcaggg tccgaacccg | 1260 |
| ctctctgatc atcaccagaa actgctgtct aacttcttcg cccagaccga agcgctggcg | 1320 |
| tttggtaaat cccgcgaagt ggttgagcag gaatatcgtg atcagggtaa agatccggca | 1380 |
| acgcttgact acgtggtgcc gttcaaagta ttcgaaggta accgcccgac caactccatc | 1440 |
| ctgctgcgtg aaatcactcc gttcagcctg ggtgcgttga ttgcgctgta tgagcacaaa | 1500 |
| atctttactc agggcgtgat cctgaacatc ttcaccttcg accagtgggg cgtggaactg | 1560 |
| ggtaaacagc tggcgaaccg tattctgcca gagctgaaag atgataaaga aatcagcagc | 1620 |

<210> SEQ ID NO 7
<211> LENGTH: 1671
<212> TYPE: DNA
<213> ORGANISM: Artificial Sequence
<220> FEATURE:
<223> OTHER INFORMATION: Synthetic Oligonucleotide

<400> SEQUENCE: 7

```
cacgatagct cgaccaatgg tctgattaac cgctataaag cgtggcgcgg ttaa            1674
```

<210> SEQ ID NO 7
<211> LENGTH: 1671
<212> TYPE: DNA
<213> ORGANISM: Artificial Sequence
<220> FEATURE:
<223> OTHER INFORMATION: Synthetic Oligonucleotide

<400> SEQUENCE: 7

```
atgaaaaaca tcaatccaac gcagaccgct gcctggcagg cactacagaa acacttcgat      60
gaaatgaaag acgttacgat cgccgatctt tttgctaaag atggtgatcg tttttctaag     120
ttctccgcaa ccttcgacga tcagatgctg gtggattact ccaaaaaccg catcactgaa     180
gagacgctgg cgaaattaca ggatctggcg aaagagtgcg atctggcggg cgcgattaag     240
tcgatgttct ctggcgagaa gatcaaccgc actgaaaacc gcgccgtgct gcacgtagcg     300
ctgcgtaacc gtagcaatac cccgattttg gttgatggca agacgtaat gccggaagtc      360
aacgcggtgc tggagaagat gaaaaccttc tcagaagcga ttatttccgg tgagtggaaa     420
ggttataccg gcaaagcaat cactgacgta gtgaacatcg gatcggcgg ttctgacctc      480
ggcccataca tggtgaccga agctctgcgt ccgtacaaaa accacctgaa catgcacttt     540
gtttctaacg tcgatgggac tcacatcgcg gaagtgctga aaaagtaaa cccggaaacc      600
acgctgttct tggtagcatc taaaaccttc accactcagg aaactatgac caacgcccat     660
agcgcgcgtg actggttcct gaaagcggca ggtgatgaga agcacgttgc aaaacacttt     720
gcggcgcttt ccaccaatgc caaagccgtt ggcgagtttg gtattgatac tgccaacatg     780
ttcgagttct gggactgggt tggcggccgt tactctttgt ggtcagcgat tggcctgtcg     840
attgttctct ccatcggctt tgataacttc gttgaactgc tttccggcgc acacgcgatg     900
gacaagcatt tctccaccac gcctgccgag aaaaacctgc ctgtactgct ggcgctgatt     960
ggcatctggt acaacaattt ctttggtgcg gaaactgaag cgattctgcc gtatgaccag    1020
tatatgcacc gtttcgcggc gtacttccag cagggcaata tggagtccaa cggtaagtat    1080
gttgaccgta acgtaacgt tgtggattac cagactggcc cgattatctg gggtgaacca    1140
ggcactaacg tcagcacgc gttctaccag ctgatccacc agggaaccaa aatggtaccg    1200
tgcgatttca tcgctccggc tatcacccat aacccgctct ctgatcatca ccagaaactg    1260
ctgtctaact tcttcgccca gaccgaagcg ctggcgtttg gtaaatcccg cgaagtggtt    1320
gagcaggaat atcgtgatca gggtaaagat ccggcaacgc ttgactacgt ggtgccgttc    1380
aaagtattcg aaggtaaccg cccgaccaac tccatcctgc tgcgtgaaat cactccgttc    1440
agcctgggtg cgttgattgc gctgtatgag cacaaaatct ttactcaggg cgtgatcctg    1500
aacatcttca ccttcgacca gtggggcgtg gaactgggta acagctggc gaaccgtatt    1560
ctgccagagc tggaagtgct gtttcagggt ccgaaagatg ataaagaaat cagcagccac    1620
gatagctcga ccaatggtct gattaaccgc tataaagcgt ggcgcggtta a             1671
```

<210> SEQ ID NO 8
<211> LENGTH: 1674
<212> TYPE: DNA
<213> ORGANISM: Artificial Sequence
<220> FEATURE:
<223> OTHER INFORMATION: Synthetic Oligonucleotide

<400> SEQUENCE: 8

```
atgaaaaaca tcaatccaac gcagaccgct gcctggcagg cactacagaa acacttcgat      60
gaaatgaaag acgttacgat cgccgatctt tttgctaaag atggtgatcg ttttttctaag    120
ttctccgcaa ccttcgacga tcagatgctg gtggattact ccaaaaaccg catcactgaa    180
gagacgctgg cgaaattaca ggatctggcg aaagagtgcg atctggcggg cgcgattaag    240
tcgatgttct ctggcgagaa gatcaaccgc actgaaaacc gcgccgtgct gcacgtagcg    300
ctgcgtaacc gtagcaatac cccgattttg gttgatggca agacgtaat gccggaagtc     360
aacgcggtgc tggagaagat gaaaaccttc tcagaagcga ttatttccgg tgagtggaaa    420
ggttataccg gcaaagcaat cactgacgta gtgaacatcg gatcggcgg ttctgacctc     480
ggcccataca tggtgaccga agctctgcgt ccgtacaaaa accacctgaa catgcacttt    540
gtttctaacg tcgatgggac tcacatcgcg gaagtgctga aaaaagtaaa cccggaaacc    600
acgctgttct tggtagcatc taaaaccttc accactcagg aaactatgac caacgcccat    660
agcgcgcgtg actggttcct gaaagcggca ggtgatgaga agcacgttgc aaaacacttt    720
gcggcgcttt ccaccaatgc caaagccgtt ggcgagtttg gtattgatac tgccaacatg    780
ttcgagttct gggactgggt tggcggccgt tactctttgt ggtcagcgat tggcctgtcg    840
attgttctct ccatcggctt tgataacttc gttgaactgc tttccggcgc acacgcgatg    900
gacaagcatt tctccaccac gcctgccgag aaaaacctgc ctgtactgct ggcgctgatt    960
ggcatctggt acaacaattt ctttggtgcg gaaactgaag cgattctgcc gtatgaccag   1020
tatatgcacc gtttcgcggc gtacttccag cagggcaata tggagtccaa cggtaagtat   1080
gttgaccgta acgtaacgt tgtggattac cagactggcc cgattatctg gggtgaacca   1140
ggcactaacg gtcagcacgc gttctaccag ctgatccacc agggaaccaa aatggtaccg   1200
tgcgatttca tcgctccggc tatcacccat aacccgctct ctgatcatca ccagaaactg   1260
ctgtctaact tcttcgccca gaccgaagcg ctggcgtttg gtaaatcccg cgaagtggtt   1320
gagcaggaat atcgtgatca gggtaaagat ccggcaacgc ttgactacgt ggtgccgttc   1380
aaagtattcg aaggtaaccg cccgaccaac tccatcctgc tgcgtgaaat cactccgttc   1440
agcctgggtg cgttgattgc gctgtatgag cacaaaatct ttactcaggg cgtgatcctg   1500
aacatcttca ccttcgacca gtggggcgtg aactgggta acagctggc gaaccgtatt    1560
ctgccagagc tgaaactgga agtgctgttt cagggtccgg atgataaaga aatcagcagc   1620
cacgatagct cgaccaatgg tctgattaac cgctataaag cgtggcgcgg ttaa          1674
```

<210> SEQ ID NO 9
<211> LENGTH: 1674
<212> TYPE: DNA
<213> ORGANISM: Artificial Sequence
<220> FEATURE:
<223> OTHER INFORMATION: Synthetic Oligonucleotide

<400> SEQUENCE: 9

```
atgaaaaaca tcaatccaac gcagaccgct gcctggcagg cactacagaa acacttcgat      60
gaaatgaaag acgttacgat cgccgatctt tttgctaaag atggtgatcg ttttttctaag    120
ttctccgcaa ccttcgacga tcagatgctg gtggattact ccaaaaaccg catcactgaa    180
gagacgctgg cgaaattaca ggatctggcg aaagagtgcg atctggcggg cgcgattaag    240
tcgatgttct ctggcgagaa gatcaaccgc actgaaaacc gcgccgtgct gcacgtagcg    300
ctgcgtaacc gtagcaatac cccgattttg gttgatggca agacgtaat gccggaagtc     360
aacgcggtgc tggagaagat gaaaaccttc tcagaagcga ttatttccgg tgagtggaaa    420
```

```
ggttataccg gcaaagcaat cactgacgta gtgaacatcg ggatcggcgg ttctgacctc      480
ggcccataca tggtgaccga agctctgcgt ccgtacaaaa accacctgaa catgcacttt      540
gtttctaacg tcgatgggac tcacatcgcg gaagtgctga aaaagtaaa cccggaaacc      600 acgctgttct tggtagcatc taaaaccttc accactcagg aaactatgac caacgcccat      660
agcgcgcgtg actggttcct gaaagcggca ggtgatgaga agcacgttgc aaaacacttt      720
gcggcgcttt ccaccaatgc caaagccgtt ggcgagtttg gtattgatac tgccaacatg      780
ttcgagttct gggactgggt tggcggccgt tactctttgt ggtcagcgat tggcctgtcg      840
attgttctct ccatcggctt tgataacttc gttgaactgc tttccggcgc acacgcgatg      900
gacaagcatt tctccaccac gcctgccgag aaaaacctgc ctgtactgct ggcgctgatt      960
ggcatctggt acaacaattt ctttggtgcg gaaactgaag cgattctgcc gtatgaccag     1020
tatatgcacc gtttcgcggc gtacttccag cagggcaata tggagtccaa cggtaagtat     1080
gttgaccgta acggtaacgt tgtggattac cagactggcc cgattatctg gggtgaacca     1140
ggcactaacg gtcagcacgc gttctaccag ctgatccacc agggaaccaa aatggtaccg     1200
tgcgatttca tcgctccggc tatcacccat aacccgctct ctgatcatca ccagaaactg     1260
ctgtctaact tcttcgccca gaccgaagcg ctggcgtttg gtaaatcccg cgaagtggtt     1320
gagcaggaat atcgtgatca gggtaaagat ccggcaacgc ttgactacgt ggtgccgttc     1380
aaagtattcg aaggtaaccg cccgaccaac tccatcctgc tgcgtgaaat cactccgttc     1440
agcctgggtg cgttgattgc gctgtatgag cacaaaatct ttactcaggg cgtgatcctg     1500
aacatcttca ccttcgacca gtggggcgtg gaactgggta acagctggc gaaccgtatt     1560 ctgccagagc tgaaagatct ggaagtgctg tttcagggtc cggataaaga aatcagcagc     1620
cacgatagct cgaccaatgg tctgattaac cgctataaag cgtggcgcgg ttaa           1674
```

<210> SEQ ID NO 10
<211> LENGTH: 1674
<212> TYPE: DNA
<213> ORGANISM: Artificial Sequence
<220> FEATURE:
<223> OTHER INFORMATION: Synthetic Oligonucleotide

<400> SEQUENCE: 10

```
atgaaaaaca tcaatccaac gcagaccgct gcctggcagg cactacagaa acacttcgat       60
gaaatgaaag acgttacgat cgccgatctt tttgctaaag atggtgatcg ttttttctaag     120 ttctccgcaa ccttcgacga tcagatgctg gtggattact ccaaaaaccg catcactgaa      180
gagacgctgg cgaaattaca ggatctggcg aaagagtgcg atctggcggg cgcgattaag      240
tcgatgttct ctggcgagaa gatcaaccgc actgaaaaacc gcgccgtgct gcacgtagcg      300
ctgcgtaacc gtagcaatac cccgattttg gttgatggca agacgtaat gccggaagtc      360 aacgcggtgc tggagaagat gaaaaccttc tcagaagcga ttatttccgg tgagtggaaa      420
ggttataccg gcaaagcaat cactgacgta gtgaacatcg ggatcggcgg ttctgacctc      480
ggcccataca tggtgaccga agctctgcgt ccgtacaaaa accacctgaa catgcacttt      540
gtttctaacg tcgatgggac tcacatcgcg gaagtgctga aaaagtaaa cccggaaacc      600 acgctgttct tggtagcatc taaaaccttc accactcagg aaactatgac caacgcccat      660
agcgcgcgtg actggttcct gaaagcggca ggtgatgaga agcacgttgc aaaacacttt      720
gcggcgcttt ccaccaatgc caaagccgtt ggcgagtttg gtattgatac tgccaacatg      780
```

```
ttcgagttct gggactgggt tggcggccgt tactctttgt ggtcagcgat tggcctgtcg    840
attgttctct ccatcggctt tgataacttc gttgaactgc tttccggcgc acacgcgatg    900
gacaagcatt tctccaccac gcctgccgag aaaaacctgc ctgtactgct ggcgctgatt    960
ggcatctggt acaacaattt cttggtgcg aaactgaag cgattctgcc gtatgaccag    1020
tatatgcacc gtttcgcggc gtacttccag cagggcaata tggagtccaa cggtaagtat   1080
gttgaccgta acggtaacgt tgtggattac cagactggcc cgattatctg gggtgaacca   1140
ggcactaacg gtcagcacgc gttctaccag ctgatccacc agggaaccaa aatggtaccg   1200
tgcgatttca tcgctccggc tatcacccat aacccgctct ctgatcatca ccagaaactg   1260
ctgtctaact tcttcgccca gaccgaagcg ctggcgtttg gtaaatcccg cgaagtggtt   1320
gagcaggaat atcgtgatca gggtaaagat ccggcaacgc ttgactacgt ggtgccgttc   1380
aaagtattcg aaggtaaccg cccgaccaac tccatcctgc tgcgtgaaat cactccgttc   1440
agcctgggtg cgttgattgc gctgtatgag cacaaaatct ttactcaggg cgtgatcctg   1500
aacatcttca ccttcgacca gtggggcgtg gaactgggta acagctggc gaaccgtatt   1560 ctgccagagc tgaaagatga tctggaagtg ctgtttcagg gtccgaaaga aatcagcagc   1620
cacgatagct cgaccaatgg tctgattaac cgctataaag cgtggcgcgg ttaa         1674
```

<210> SEQ ID NO 11  
<211> LENGTH: 1674  
<212> TYPE: DNA  
<213> ORGANISM: Artificial Sequence  
<220> FEATURE:  
<223> OTHER INFORMATION: Synthetic Oligonucleotide

<400> SEQUENCE: 11

```
atgaaaaaca tcaatccaac gcagaccgct gcctggcagg cactacagaa acacttcgat    60
gaaatgaaag acgttacgat cgccgatctt tttgctaaag atggtgatcg ttttctaag   120 ttctccgcaa ccttcgacga tcagatgctg gtggattact ccaaaaaccg catcactgaa   180
gagacgctgg cgaaattaca ggatctggcg aaagagtgcg atctggcggg cgcgattaag   240
tcgatgttct ctggcgagaa gatcaaccgc actgaaaaacc gcgccgtgct gcacgtagcg   300
ctgcgtaacc gtagcaatac cccgattttg gttgatggca aagacgtaat gccggaagtc   360
aacgcggtgc tggagaagat gaaaaccttc tcagaagcga ttatttccgg tgagtggaaa   420
ggttataccg gcaaagcaat cactgacgta gtgaacatcg ggatcggcgg ttctgacctc   480
ggcccataca tggtgaccga agctctgcgt ccgtacaaaa accacctgaa catgcacttt   540
gtttctaacg tcgatgggac tcacatcgcg gaagtgctga aaaagtaaa cccggaaacc   600 acgctgttct ggtagcatc taaaaccttc accactcagg aaactatgac caacgcccat   660
agcgcgcgtg actggttcct gaaagcggca ggtgatgaga agcacgttgc aaaacacttt   720
gcggcgcttt ccaccaatgc caaagccgtt ggcgagtttg gtattgatac tgccaacatg   780
ttcgagttct gggactgggt tggcggccgt tactctttgt ggtcagcgat tggcctgtcg   840
attgttctct ccatcggctt tgataacttc gttgaactgc tttccggcgc acacgcgatg    900
gacaagcatt tctccaccac gcctgccgag aaaaacctgc ctgtactgct ggcgctgatt    960
ggcatctggt acaacaattt cttggtgcg aaactgaag cgattctgcc gtatgaccag   1020
tatatgcacc gtttcgcggc gtacttccag cagggcaata tggagtccaa cggtaagtat   1080
gttgaccgta acggtaacgt tgtggattac cagactggcc cgattatctg gggtgaacca   1140
ggcactaacg gtcagcacgc gttctaccag ctgatccacc agggaaccaa aatggtaccg   1200
```

```
tgcgatttca tcgctccggc tatcacccat aacccgctct ctgatcatca ccagaaactg    1260
ctgtctaact tcttcgccca gaccgaagcg ctggcgtttg gtaaatcccg cgaagtggtt    1320
gagcaggaat atcgtgatca gggtaaagat ccggcaacgc ttgactacgt ggtgccgttc    1380
aaagtattcg aaggtaaccg cccgaccaac tccatcctgc tgcgtgaaat cactccgttc    1440
agcctgggtg cgttgattgc gctgtatgag cacaaaatct ttactcaggg cgtgatcctg    1500
aacatcttca ccttcgacca gtggggcgtg gaactgggta acagctggc gaaccgtatt     1560 ctgccagagc tgaaagatga taaactggaa gtgctgtttc agggtccgga atcagcagc     1620 cacgatagct cgaccaatgg tctgattaac cgctataaag cgtggcgcgg ttaa          1674
```

<210> SEQ ID NO 12
<211> LENGTH: 1674
<212> TYPE: DNA
<213> ORGANISM: Artificial Sequence
<220> FEATURE:
<223> OTHER INFORMATION: Synthetic Oligonucleotide

<400> SEQUENCE: 12

```
atgaaaaaca tcaatccaac gcagaccgct gcctggcagg cactacagaa acacttcgat      60
gaaatgaaag acgttacgat cgccgatctt tttgctaaag atggtgatcg ttttttctaag    120 ttctccgcaa ccttcgacga tcagatgctg gtggattact ccaaaaaccg catcactgaa    180
gagacgctgg cgaaattaca ggatctggcg aaagagtgcg atctggcggg cgcgattaag    240
tcgatgttct ctggcgagaa gatcaaccgc actgaaaaacc gcgccgtgct gcacgtagcg    300
ctgcgtaacc gtagcaatac cccgattttg gttgatggca agacgtaat gccggaagtc     360 aacgcggtgc tggagaagat gaaaaccttc tcagaagcga ttatttccgg tgagtggaaa    420
ggttataccg gcaaagcaat cactgacgta gtgaacatcg ggatcggcgg ttctgacctc    480
ggcccataca tggtgaccga agctctgcgt ccgtacaaaa accacctgaa catgcacttt    540
gtttctaacg tcgatgggac tcacatcgcg gaagtgctga aaaaagtaaa cccggaaacc    600
acgctgttct ggtagcatc taaaaccttc accactcagg aaactatgac caacgcccat     660
agcgcgcgtg actggttcct gaaagcggca ggtgatgaga agcacgttgc aaaacacttt    720
gcggcgcttt ccaccaatgc caaagccgtt ggcgagtttg gtattgatac tgccaacatg    780
ttcgagttct gggactgggt tggcggccgt tactcttgt ggtcagcgat ggcctgtcg      840 attgttctct ccatcggctt tgataacttc gttgaactgc tttccggcgc acacgcgatg    900
gacaagcatt tctccaccac gcctgccgag aaaaacctgc ctgtactgct ggcgctgatt    960
ggcatctggt acaacaattt ctttggtgcg gaaactgaag cgattctgcc gtatgaccag   1020
tatatgcacc gttcgcgcc gtacttccag cagggcaata tggagtccaa cggtaagtat    1080
gttgaccgta acggtaacgt tgtggattac cagactggcc cgattatctg gggtgaacca    1140
ggcactaacg gtcagcacgc gttctaccag ctgatccacc agggaaccaa aatggtaccg    1200
tgcgatttca tcgctccggc tatcacccat aacccgctct ctgatcatca ccagaaactg    1260
ctgtctaact tcttcgccca gaccgaagcg ctggcgtttg gtaaatcccg cgaagtggtt    1320
gagcaggaat atcgtgatca gggtaaagat ccggcaacgc ttgactacgt ggtgccgttc    1380
aaagtattcg aaggtaaccg cccgaccaac tccatcctgc tgcgtgaaat cactccgttc    1440
agcctgggtg cgttgattgc gctgtatgag cacaaaatct ttactcaggg cgtgatcctg    1500
aacatcttca ccttcgacca gtggggcgtg gaactgggta acagctggc gaaccgtatt     1560
```
ctgccagagc tgaaagatga taaagaactg gaagtgctgt ttcagggtcc gatcagcagc     1620
cacgatagct cgaccaatgg tctgattaac cgctataaag cgtggcgcgg ttaa          1674

<210> SEQ ID NO 13
<211> LENGTH: 1674
<212> TYPE: DNA
<213> ORGANISM: Artificial Sequence
<220> FEATURE:
<223> OTHER INFORMATION: Synthetic Oligonucleotide

<400> SEQUENCE: 13
atgaaaaaca tcaatccaac gcagaccgct gcctggcagg cactacagaa acacttcgat     60
gaaatgaaag acgttacgat cgccgatctt tttgctaaag atggtgatcg tttttctaag    120
ttctccgcaa ccttcgacga tcagatgctg gtgattact ccaaaaaccg catcactgaa     180
gagacgctgg cgaaattaca ggatctggcg aaagagtgcg atctggcggg cgcgattaag    240
tcgatgttct ctggcgagaa gatcaaccgc actgaaaacc gcgccgtgct gcacgtagcg    300
ctgcgtaacc gtagcaatac cccgattttg gttgatggca agacgtaat gccggaagtc     360 aacgcggtgc tggagaagat gaaaaccttc tcagaagcga ttatttccgg tgagtggaaa    420
ggttataccg gcaaagcaat cactgacgta gtgaacatcg gatcggcgg ttctgacctc     480 ggcccataca tggtgaccga agctctgcgt ccgtacaaaa accacctgaa catgcacttt    540
gtttctaacg tcgatgggac tcacatcgcg gaagtgctga aaaaagtaaa cccggaaacc    600
acgctgttct tggtagcatc taaaaccttc accactcagg aaactatgac caacgcccat    660
agcgcgcgtg actggttcct gaaagcggca ggtgatgaga gcacgttgc aaaacacttt    720 gcggcgcttt ccaccaatgc caaagccgtt ggcgagtttg gtattgatac tgccaacatg    780
ttcgagttct gggactgggt tggcggccgt tactctttgt ggtcagcgat tggcctgtcg    840
attgttctct ccatcggctt tgataacttc gttgaactgc tttccggcgc acacgcgatg    900
gacaagcatt tctccaccac gcctgccgag aaaaacctgc ctgtactgct ggcgctgatt    960
ggcatctggt acaacaattt ctttggtgcg gaaactgaag cgattctgcc gtatgaccag   1020
tatatgcacc gttcgcggc gtacttccag cagggcaata tggagtccaa cggtaagtat   1080
gttgaccgta acggtaacgt tgtggattac cagactggcc cgattatctg gggtgaacca   1140
ggcactaacg tcagcacgc gttctaccag ctgatccacc agggaaccaa aatggtaccg   1200
tgcgatttca tcgctccggc tatcacccat aacccgctct ctgatcatca ccagaaactg   1260
ctgtctaact tcttcgccca gaccgaagcg ctggcgtttg gtaaatcccg cgaagtggtt   1320
gagcaggaat atcgtgatca gggtaaagat ccggcaacgc ttgactacgt ggtgccgttc   1380
aaagtattcg aaggtaaccg cccgaccaac tccatcctgc tgcgtgaaat cactccgttc   1440
agcctgggtg cgttgattgc gctgtatgag cacaaaatct ttactcaggg cgtgatcctg   1500
aacatcttca ccttcgacca gtggggcgtg gaactgggta acagctggc gaaccgtatt   1560 ctgccagagc tgaaagatga taaagaaatc tggaagtgc tgtttcaggg tccgagcagc   1620
cacgatagct cgaccaatgg tctgattaac cgctataaag cgtggcgcgg ttaa          1674

<210> SEQ ID NO 14
<211> LENGTH: 1674
<212> TYPE: DNA
<213> ORGANISM: Artificial Sequence
<220> FEATURE:
<223> OTHER INFORMATION: Synthetic Oligonucleotide

<400> SEQUENCE: 14

```
atgaaaaaca tcaatccaac gcagaccgct gcctggcagg cactacagaa acacttcgat    60
gaaatgaaag acgttacgat cgccgatctt tttgctaaag atggtgatcg ttttttctaag   120
ttctccgcaa ccttcgacga tcagatgctg gtggattact ccaaaaaccg catcactgaa   180
gagacgctgg cgaaattaca ggatctggcg aaagagtgcg atctggcggg cgcgattaag   240
tcgatgttct ctggcgagaa gatcaaccgc actgaaaacc gcgccgtgct gcacgtagcg   300
ctgcgtaacc gtagcaatac cccgattttg gttgatggca aagacgtaat gccggaagtc   360
aacgcggtgc tggagaagat gaaaaccttc tcagaagcga ttatttccgg tgagtggaaa   420
ggttataccg gcaaagcaat cactgacgta gtgaacatcg gatcggcgg ttctgacctc    480
ggcccataca tggtgaccga agctctgcgt ccgtacaaaa accacctgaa catgcacttt   540
gtttctaacg tcgatgggac tcacatcgcg gaagtgctga aaaagtaaa cccggaaacc    600
acgctgttct tggtagcatc taaaaccttc accactcagg aaactatgac caacgcccat   660
agcgcgcgtg actggttcct gaaagcggca ggtgatgaga agcacgttgc aaaacacttt   720
gcggcgcttt ccaccaatgc caaagccgtt ggcgagtttg gtattgatac tgccaacatg   780
ttcgagttct gggactgggt tggcggccgt tactctttgt ggtcagcgat tggcctgtcg   840
attgttctct ccatcggctt tgataacttc gttgaactgc tttccggcgc acacgcgatg   900
gacaagcatt tctccaccac gcctgccgag aaaaacctgc ctgtactgct ggcgctgatt   960
ggcatctggt acaacaattt ctttggtgcg gaaactgaag cgattctgcc gtatgaccag  1020
tatatgcacc gtttcgcggc gtacttccag cagggcaata tggagtccaa cggtaagtat  1080
gttgaccgta acggtaacgt tgtggattac cagactggcc cgattatctg gggtgaacca  1140
ggcactaacg gtcagcacgc gttctaccag ctgatccacc agggaaccaa aatggtaccg  1200
tgcgatttca tcgctccggc tatcacccat aacccgctct ctgatcatca ccagaaactg  1260
ctgtctaact tcttcgccca gaccgaagcg ctggcgtttg gtaaatcccg cgaagtggtt  1320
gagcaggaat atcgtgatca gggtaaagat ccggcaacgc ttgactacgt ggtgccgttc  1380
aaagtattcg aaggtaaccg cccgaccaac tccatcctgc tgcgtgaaat cactccgttc  1440
agcctgggtg cgttgattgc gctgtatgag cacaaaatct ttactcaggg cgtgatcctg  1500
aacatcttca ccttcgacca gtggggcgtg gaactgggta acagctggc gaaccgtatt   1560
ctgccagagc tgaaagatga taaagaaatc agcctggaag tgctgtttca gggtccgagc  1620
cacgatagct cgaccaatgg tctgattaac cgctataaag cgtggcgcgg ttaa         1674
```

<210> SEQ ID NO 15
<211> LENGTH: 1674
<212> TYPE: DNA
<213> ORGANISM: Artificial Sequence
<220> FEATURE:
<223> OTHER INFORMATION: Synthetic Oligonucleotide

<400> SEQUENCE: 15

```
atgaaaaaca tcaatccaac gcagaccgct gcctggcagg cactacagaa acacttcgat    60
gaaatgaaag acgttacgat cgccgatctt tttgctaaag atggtgatcg ttttttctaag   120
ttctccgcaa ccttcgacga tcagatgctg gtggattact ccaaaaaccg catcactgaa   180
gagacgctgg cgaaattaca ggatctggcg aaagagtgcg atctggcggg cgcgattaag   240
tcgatgttct ctggcgagaa gatcaaccgc actgaaaacc gcgccgtgct gcacgtagcg   300
ctgcgtaacc gtagcaatac cccgattttg gttgatggca aagacgtaat gccggaagtc   360
```

```
aacgcggtgc tggagaagat gaaaaccttc tcagaagcga ttatttccgg tgagtggaaa      420
ggttataccg gcaaagcaat cactgacgta gtgaacatcg ggatcggcgg ttctgacctc      480
ggcccataca tggtgaccga agctctgcgt ccgtacaaaa accacctgaa catgcacttt      540
gtttctaacg tcgatgggac tcacatcgcg gaagtgctga aaaagtaaa cccggaaacc       600 acgctgttct tggtagcatc taaaaccttc accactcagg aaactatgac caacgcccat      660
agcgcgcgtg actggttcct gaaagcggca ggtgatgaga agcacgttgc aaaacacttt      720
gcggcgcttt ccaccaatgc caaagccgtt ggcgagtttg gtattgatac tgccaacatg      780
ttcgagttct gggactgggt tggcggccgt tactctttgt ggtcagcgat tggcctgtcg      840
attgttctct ccatcggctt tgataacttc gttgaactgc tttccggcgc acacgcgatg      900
gacaagcatt tctccaccac gcctgccgag aaaaacctgc ctgtactgct ggcgctgatt      960
ggcatctggt acaacaattt ctttggtgcg gaaactgaag cgattctgcc gtatgaccag     1020
tatatgcacc gtttcgcggc gtacttccag cagggcaata tggagtccaa cggtaagtat     1080
gttgaccgta acgtaacgt tgtggattac cagactggcc cgattatctg gggtgaacca      1140
ggcactaacg gtcagcacgc gttctaccag ctgatccacc agggaaccaa aatggtaccg     1200
tgcgatttca tcgctccggc tatcacccat aacccgctct ctgatcatca ccagaaactg     1260
ctgtctaact tcttcgccca gaccgaagcg ctggcgtttg gtaaatcccg cgaagtggtt     1320
gagcaggaat atcgtgatca gggtaaagat ccggcaacgc ttgactacgt ggtgccgttc     1380
aaagtattcg aaggtaaccg cccgaccaac tccatcctgc tgcgtgaaat cactccgttc     1440
agcctgggtg cgttgattgc gctgtatgag cacaaaatct ttactcaggg cgtgatcctg     1500
aacatcttca ccttcgacca gtggggcgtg gaactgggta acagctggc gaaccgtatt      1560 ctgccagagc tgaaagatga taagaaatc agcagcctgg aagtgctgtt tcagggtccg     1620
cacgatagct cgaccaatgg tctgattaac cgctataaag cgtggcgcgg ttaa           1674

<210> SEQ ID NO 16
<211> LENGTH: 1674
<212> TYPE: DNA
<213> ORGANISM: Artificial Sequence
<220> FEATURE:
<223> OTHER INFORMATION: Synthetic Oligonucleotide

<400> SEQUENCE: 16
atgaaaaaca tcaatccaac gcagaccgct gcctggcagg cactacagaa acacttcgat       60
gaaatgaaag acgttacgat cgccgatctt tttgctaaag atggtgatcg tttttctaag      120
ttctccgcaa ccttcgacga tcagatgctg gtggattact ccaaaaaccg catcactgaa      180
gagacgctgg cgaaattaca ggatctggcg aaagagtgcg atctggcggg cgcgattaag      240
tcgatgttct ctggcgagaa gatcaaccgc actgaaaacc gcgccgtgct gcacgtagcg      300
ctgcgtaacc gtagcaatac cccgattttg gttgatggca agacgtaat gccggaagtc      360 aacgcggtgc tggagaagat gaaaaccttc tcagaagcga ttatttccgg tgagtggaaa      420
ggttataccg gcaaagcaat cactgacgta gtgaacatcg ggatcggcgg ttctgacctc      480
ggcccataca tggtgaccga agctctgcgt ccgtacaaaa accacctgaa catgcacttt      540
gtttctaacg tcgatgggac tcacatcgcg gaagtgctga aaaagtaaa cccggaaacc       600 acgctgttct tggtagcatc taaaaccttc accactcagg aaactatgac caacgcccat      660
agcgcgcgtg actggttcct gaaagcggca ggtgatgaga agcacgttgc aaaacacttt      720
gcggcgcttt ccaccaatgc caaagccgtt ggcgagtttg gtattgatac tgccaacatg      780
```

```
ttcgagttct gggactgggt tggcggccgt tactctttgt ggtcagcgat tggcctgtcg    840
attgttctct ccatcggctt tgataacttc gttgaactgc tttccggcgc acacgcgatg    900
gacaagcatt tctccaccac gcctgccgag aaaaacctgc ctgtactgct ggcgctgatt    960
ggcatctggt acaacaattt ctttggtgcg gaaactgaag cgattctgcc gtatgaccag   1020
tatatgcacc gtttcgcggc gtacttccag cagggcaata tggagtccaa cggtaagtat   1080
gttgaccgta acgtaacgt tgtggattac cagactggcc cgattatctg ggtgaacca    1140 ggcactaacg gtcagcacgc gttctaccag ctgatccacc agggaaccaa aatggtaccg   1200
tgcgatttca tcgctccggc tatcacccat aacccgctct ctgatcatca ccagaaactg   1260
ctgtctaact tcttcgccca gaccgaagcg ctggcgtttg gtaaatcccg cgaagtggtt   1320
gagcaggaat atcgtgatca gggtaaagat ccggcaacgc ttgactacgt ggtgccgttc   1380
aaagtattcg aaggtaaccg cccgaccaac tccatcctgc tgcgtgaaat cactccgttc   1440
agcctgggtg cgttgattgc gctgtatgag cacaaaatct ttactcaggg cgtgatcctg   1500
aacatcttca ccttcgacca gtggggcgtg gaactgggta acagctggc gaaccgtatt    1560 ctgccagagc tgaaagatga taagaaaatc agcagccacg atagctcgac caatggtctg   1620
attaaccgct ataaactgga agtgctgttt cagggtccgg cgtggcgcgg ttaa        1674
```

<210> SEQ ID NO 17
<211> LENGTH: 549
<212> TYPE: PRT
<213> ORGANISM: Artificial Sequence
<220> FEATURE:
<223> OTHER INFORMATION: Synthetic Polypeptide

<400> SEQUENCE: 17

```
Met Lys Asn Ile Asn Pro Thr Gln Thr Ala Ala Trp Gln Ala Leu Gln
1               5                   10                  15

Lys His Phe Asp Glu Met Lys Asp Val Thr Ile Ala Asp Leu Phe Ala
            20                  25                  30

Lys Asp Gly Asp Arg Phe Ser Lys Phe Ser Ala Thr Phe Asp Asp Gln
        35                  40                  45

Met Leu Val Asp Tyr Ser Lys Asn Arg Ile Thr Glu Glu Thr Leu Ala
    50                  55                  60

Lys Leu Gln Asp Leu Ala Lys Glu Cys Asp Leu Ala Gly Ala Ile Lys
65                  70                  75                  80

Ser Met Phe Ser Gly Glu Lys Ile Asn Arg Thr Glu Asn Arg Ala Val
                85                  90                  95

Leu His Val Ala Leu Arg Asn Arg Ser Asn Thr Pro Ile Leu Val Asp
            100                 105                 110

Gly Lys Asp Val Met Pro Glu Val Asn Ala Val Leu Glu Lys Met Lys
        115                 120                 125

Thr Phe Ser Glu Ala Ile Ile Ser Gly Glu Trp Lys Gly Tyr Thr Gly
    130                 135                 140

Lys Ala Ile Thr Asp Val Val Asn Ile Gly Ile Gly Gly Ser Asp Leu
145                 150                 155                 160

Gly Pro Tyr Met Val Thr Glu Ala Leu Arg Pro Tyr Lys Asn His Leu
                165                 170                 175

Asn Met His Phe Val Ser Asn Val Asp Gly Thr His Ile Ala Glu Val
            180                 185                 190

Leu Lys Lys Val Asn Pro Glu Thr Thr Leu Phe Leu Val Ala Ser Lys
        195                 200                 205
```

```
Thr Phe Thr Thr Gln Glu Thr Met Thr Asn Ala His Ser Ala Arg Asp
    210                 215                 220

Trp Phe Leu Lys Ala Ala Gly Asp Glu Lys His Val Ala Lys His Phe
225                 230                 235                 240

Ala Ala Leu Ser Thr Asn Ala Lys Ala Val Gly Glu Phe Gly Ile Asp
                245                 250                 255

Thr Ala Asn Met Phe Glu Phe Trp Asp Trp Val Gly Gly Arg Tyr Ser
                260                 265                 270

Leu Trp Ser Ala Ile Gly Leu Ser Ile Val Leu Ser Ile Gly Phe Asp
            275                 280                 285

Asn Phe Val Glu Leu Leu Ser Gly Ala His Ala Met Asp Lys His Phe
    290                 295                 300

Ser Thr Thr Pro Ala Glu Lys Asn Leu Pro Val Leu Ala Leu Ile
305                 310                 315                 320

Gly Ile Trp Tyr Asn Asn Phe Phe Gly Ala Glu Thr Glu Ala Ile Leu
                325                 330                 335

Pro Tyr Asp Gln Tyr Met His Arg Phe Ala Ala Tyr Phe Gln Gln Gly
                340                 345                 350

Asn Met Glu Ser Asn Gly Lys Tyr Val Asp Arg Asn Gly Asn Val Val
            355                 360                 365

Asp Tyr Gln Thr Gly Pro Ile Ile Trp Gly Glu Pro Gly Thr Asn Gly
    370                 375                 380

Gln His Ala Phe Tyr Gln Leu Ile His Gln Gly Thr Lys Met Val Pro
385                 390                 395                 400

Cys Asp Phe Ile Ala Pro Ala Ile Thr His Asn Pro Leu Ser Asp His
                405                 410                 415

His Gln Lys Leu Leu Ser Asn Phe Phe Ala Gln Thr Glu Ala Leu Ala
            420                 425                 430

Phe Gly Lys Ser Arg Glu Val Val Glu Gln Glu Tyr Arg Asp Gln Gly
            435                 440                 445

Lys Asp Pro Ala Thr Leu Asp Tyr Val Val Pro Phe Lys Val Phe Glu
450                 455                 460

Gly Asn Arg Pro Thr Asn Ser Ile Leu Leu Arg Glu Ile Thr Pro Phe
465                 470                 475                 480

Ser Leu Gly Ala Leu Ile Ala Leu Tyr Glu His Lys Ile Phe Thr Gln
                485                 490                 495

Gly Val Ile Leu Asn Ile Phe Thr Phe Asp Gln Trp Gly Val Glu Leu
            500                 505                 510

Gly Lys Gln Leu Ala Asn Arg Ile Leu Pro Glu Leu Lys Asp Asp Lys
            515                 520                 525

Glu Ile Ser Ser His Asp Ser Ser Thr Asn Gly Leu Ile Asn Arg Tyr
    530                 535                 540

Lys Ala Trp Arg Gly
545

<210> SEQ ID NO 18
<211> LENGTH: 557
<212> TYPE: PRT
<213> ORGANISM: Artificial Sequence
<220> FEATURE:
<223> OTHER INFORMATION: Synthetic Polypeptide

<400> SEQUENCE: 18

Met Lys Asn Ile Asn Pro Thr Gln Thr Ala Ala Trp Gln Ala Leu Gln
1               5                   10                  15
```

-continued

```
Lys His Phe Asp Glu Met Lys Asp Val Thr Ile Ala Asp Leu Phe Ala
                 20                  25                  30
Lys Asp Gly Asp Arg Phe Ser Lys Phe Ser Ala Thr Phe Asp Asp Gln
         35                  40                  45
Met Leu Val Asp Tyr Ser Lys Asn Arg Ile Thr Glu Glu Thr Leu Ala
     50                  55                  60
Lys Leu Gln Asp Leu Ala Lys Glu Cys Asp Leu Ala Gly Ala Ile Lys
 65                  70                  75                  80
Ser Met Phe Ser Gly Glu Lys Ile Asn Arg Thr Glu Asn Arg Ala Val
                 85                  90                  95
Leu His Val Ala Leu Arg Asn Arg Ser Asn Thr Pro Leu Glu Val Leu
                100                 105                 110
Phe Gln Gly Pro Ile Leu Val Asp Gly Lys Asp Val Met Pro Glu Val
            115                 120                 125
Asn Ala Val Leu Glu Lys Met Lys Thr Phe Ser Glu Ala Ile Ile Ser
130                 135                 140
Gly Glu Trp Lys Gly Tyr Thr Gly Lys Ala Ile Thr Asp Val Val Asn
145                 150                 155                 160
Ile Gly Ile Gly Gly Ser Asp Leu Gly Pro Tyr Met Val Thr Glu Ala
                165                 170                 175
Leu Arg Pro Tyr Lys Asn His Leu Asn Met His Phe Val Ser Asn Val
            180                 185                 190
Asp Gly Thr His Ile Ala Glu Val Leu Lys Lys Val Asn Pro Glu Thr
        195                 200                 205
Thr Leu Phe Leu Val Ala Ser Lys Thr Phe Thr Thr Gln Glu Thr Met
    210                 215                 220
Thr Asn Ala His Ser Ala Arg Asp Trp Phe Leu Lys Ala Ala Gly Asp
225                 230                 235                 240
Glu Lys His Val Ala Lys His Phe Ala Ala Leu Ser Thr Asn Ala Lys
                245                 250                 255
Ala Val Gly Glu Phe Gly Ile Asp Thr Ala Asn Met Phe Glu Phe Trp
            260                 265                 270
Asp Trp Val Gly Gly Arg Tyr Ser Leu Trp Ser Ala Ile Gly Leu Ser
        275                 280                 285
Ile Val Leu Ser Ile Gly Phe Asp Asn Phe Val Glu Leu Leu Ser Gly
    290                 295                 300
Ala His Ala Met Asp Lys His Phe Ser Thr Thr Pro Ala Glu Lys Asn
305                 310                 315                 320
Leu Pro Val Leu Leu Ala Leu Ile Gly Ile Trp Tyr Asn Asn Phe Phe
                325                 330                 335
Gly Ala Glu Thr Glu Ala Ile Leu Pro Tyr Asp Gln Tyr Met His Arg
            340                 345                 350
Phe Ala Ala Tyr Phe Gln Gln Gly Asn Met Glu Ser Asn Gly Lys Tyr
        355                 360                 365
Val Asp Arg Asn Gly Asn Val Asp Tyr Gln Thr Gly Pro Ile Ile
    370                 375                 380
Trp Gly Glu Pro Gly Thr Asn Gly Gln His Ala Phe Tyr Gln Leu Ile
385                 390                 395                 400
His Gln Gly Thr Lys Met Val Pro Cys Asp Phe Ile Ala Pro Ala Ile
                405                 410                 415
Thr His Asn Pro Leu Ser Asp His Gln Lys Leu Leu Ser Asn Phe
            420                 425                 430
```

```
Phe Ala Gln Thr Glu Ala Leu Ala Phe Gly Lys Ser Arg Glu Val Val
            435                 440                 445
Glu Gln Glu Tyr Arg Asp Gln Gly Lys Asp Pro Ala Thr Leu Asp Tyr
450                 455                 460
Val Val Pro Phe Lys Val Phe Glu Gly Asn Arg Pro Thr Asn Ser Ile
465                 470                 475                 480
Leu Leu Arg Glu Ile Thr Pro Phe Ser Leu Gly Ala Leu Ile Ala Leu
                485                 490                 495
Tyr Glu His Lys Ile Phe Thr Gln Gly Val Ile Leu Asn Ile Phe Thr
            500                 505                 510
Phe Asp Gln Trp Gly Val Glu Leu Gly Lys Gln Leu Ala Asn Arg Ile
        515                 520                 525
Leu Pro Glu Leu Lys Asp Asp Lys Glu Ile Ser Ser His Asp Ser Ser
530                 535                 540
Thr Asn Gly Leu Ile Asn Arg Tyr Lys Ala Trp Arg Gly
545                 550                 555
```

<210> SEQ ID NO 19
<211> LENGTH: 557
<212> TYPE: PRT
<213> ORGANISM: Artificial Sequence
<220> FEATURE:
<223> OTHER INFORMATION: Synthetic Polypeptide

<400> SEQUENCE: 19

```
Met Lys Asn Ile Asn Pro Thr Gln Thr Ala Ala Trp Gln Ala Leu Gln
1               5                   10                  15
Lys His Phe Asp Glu Met Lys Asp Val Thr Ile Ala Asp Leu Phe Ala
            20                  25                  30
Lys Asp Gly Asp Arg Phe Ser Lys Phe Ser Ala Thr Phe Asp Asp Gln
        35                  40                  45
Met Leu Val Asp Tyr Ser Lys Asn Arg Ile Thr Glu Glu Thr Leu Ala
    50                  55                  60
Lys Leu Gln Asp Leu Ala Lys Glu Cys Asp Leu Ala Gly Ala Ile Lys
65                  70                  75                  80
Ser Met Phe Ser Gly Glu Lys Ile Asn Arg Thr Glu Asn Arg Ala Val
                85                  90                  95
Leu His Val Ala Leu Arg Asn Arg Ser Asn Thr Pro Ile Leu Glu Val
            100                 105                 110
Leu Phe Gln Gly Pro Leu Val Asp Gly Lys Asp Val Met Pro Glu Val
        115                 120                 125
Asn Ala Val Leu Glu Lys Met Lys Thr Phe Ser Glu Ala Ile Ile Ser
    130                 135                 140
Gly Glu Trp Lys Gly Tyr Thr Gly Lys Ala Ile Thr Asp Val Val Asn
145                 150                 155                 160
Ile Gly Ile Gly Gly Ser Asp Leu Gly Pro Tyr Met Val Thr Glu Ala
                165                 170                 175
Leu Arg Pro Tyr Lys Asn His Leu Asn Met His Phe Val Ser Asn Val
            180                 185                 190
Asp Gly Thr His Ile Ala Glu Val Leu Lys Lys Val Asn Pro Glu Thr
        195                 200                 205
Thr Leu Phe Leu Val Ala Ser Lys Thr Phe Thr Thr Gln Glu Thr Met
    210                 215                 220
Thr Asn Ala His Ser Ala Arg Asp Trp Phe Leu Lys Ala Ala Gly Asp
225                 230                 235                 240
```

```
Glu Lys His Val Ala Lys His Phe Ala Ala Leu Ser Thr Asn Ala Lys
            245                 250                 255

Ala Val Gly Glu Phe Gly Ile Asp Thr Ala Asn Met Phe Glu Phe Trp
        260                 265                 270

Asp Trp Val Gly Gly Arg Tyr Ser Leu Trp Ser Ala Ile Gly Leu Ser
    275                 280                 285

Ile Val Leu Ser Ile Gly Phe Asp Asn Phe Val Glu Leu Leu Ser Gly
290                 295                 300

Ala His Ala Met Asp Lys His Phe Ser Thr Thr Pro Ala Glu Lys Asn
305                 310                 315                 320

Leu Pro Val Leu Leu Ala Leu Ile Gly Ile Trp Tyr Asn Asn Phe Phe
                325                 330                 335

Gly Ala Glu Thr Glu Ala Ile Leu Pro Tyr Asp Gln Tyr Met His Arg
            340                 345                 350

Phe Ala Ala Tyr Phe Gln Gln Gly Asn Met Glu Ser Asn Gly Lys Tyr
        355                 360                 365

Val Asp Arg Asn Gly Asn Val Val Asp Tyr Gln Thr Gly Pro Ile Ile
    370                 375                 380

Trp Gly Glu Pro Gly Thr Asn Gly Gln His Ala Phe Tyr Gln Leu Ile
385                 390                 395                 400

His Gln Gly Thr Lys Met Val Pro Cys Asp Phe Ile Ala Pro Ala Ile
                405                 410                 415

Thr His Asn Pro Leu Ser Asp His His Gln Lys Leu Leu Ser Asn Phe
            420                 425                 430

Phe Ala Gln Thr Glu Ala Leu Ala Phe Gly Lys Ser Arg Glu Val Val
        435                 440                 445

Glu Gln Glu Tyr Arg Asp Gln Gly Lys Asp Pro Ala Thr Leu Asp Tyr
    450                 455                 460

Val Val Pro Phe Lys Val Phe Glu Gly Asn Arg Pro Thr Asn Ser Ile
465                 470                 475                 480

Leu Leu Arg Glu Ile Thr Pro Phe Ser Leu Gly Ala Leu Ile Ala Leu
                485                 490                 495

Tyr Glu His Lys Ile Phe Thr Gln Gly Val Ile Leu Asn Ile Phe Thr
            500                 505                 510

Phe Asp Gln Trp Gly Val Glu Leu Gly Lys Gln Leu Ala Asn Arg Ile
        515                 520                 525

Leu Pro Glu Leu Lys Asp Asp Lys Glu Ile Ser Ser His Asp Ser Ser
    530                 535                 540

Thr Asn Gly Leu Ile Asn Arg Tyr Lys Ala Trp Arg Gly
545                 550                 555

<210> SEQ ID NO 20
<211> LENGTH: 556
<212> TYPE: PRT
<213> ORGANISM: Artificial Sequence
<220> FEATURE:
<223> OTHER INFORMATION: Synthetic Polypeptide

<400> SEQUENCE: 20

Met Lys Asn Ile Asn Pro Thr Gln Thr Ala Ala Trp Gln Ala Leu Gln
1               5                   10                  15

Lys His Phe Asp Glu Met Lys Asp Val Thr Ile Ala Asp Leu Phe Ala
            20                  25                  30

Lys Asp Gly Asp Arg Phe Ser Lys Phe Ser Ala Thr Phe Asp Asp Gln
        35                  40                  45
```

-continued

```
Met Leu Val Asp Tyr Ser Lys Asn Arg Ile Thr Glu Glu Thr Leu Ala
    50                  55                  60
Lys Leu Gln Asp Leu Ala Lys Glu Cys Asp Leu Ala Gly Ala Ile Lys
 65                  70                  75                  80
Ser Met Phe Ser Gly Glu Lys Ile Asn Arg Thr Glu Asn Arg Ala Val
                 85                  90                  95
Leu His Val Ala Leu Arg Asn Arg Ser Asn Thr Pro Ile Leu Glu Val
                100                 105                 110
Leu Phe Gln Gly Pro Val Asp Gly Lys Asp Val Met Pro Glu Val Asn
            115                 120                 125
Ala Val Leu Glu Lys Met Lys Thr Phe Ser Glu Ala Ile Ile Ser Gly
        130                 135                 140
Glu Trp Lys Gly Tyr Thr Gly Lys Ala Ile Thr Asp Val Val Asn Ile
145                 150                 155                 160
Gly Ile Gly Gly Ser Asp Leu Gly Pro Tyr Met Val Thr Glu Ala Leu
                165                 170                 175
Arg Pro Tyr Lys Asn His Leu Asn Met His Phe Val Ser Asn Val Asp
            180                 185                 190
Gly Thr His Ile Ala Glu Val Leu Lys Lys Val Asn Pro Glu Thr Thr
        195                 200                 205
Leu Phe Leu Val Ala Ser Lys Thr Phe Thr Thr Gln Glu Thr Met Thr
210                 215                 220
Asn Ala His Ser Ala Arg Asp Trp Phe Leu Lys Ala Ala Gly Asp Glu
225                 230                 235                 240
Lys His Val Ala Lys His Phe Ala Ala Leu Ser Thr Asn Ala Lys Ala
                245                 250                 255
Val Gly Glu Phe Gly Ile Asp Thr Ala Asn Met Phe Glu Phe Trp Asp
            260                 265                 270
Trp Val Gly Gly Arg Tyr Ser Leu Trp Ser Ala Ile Gly Leu Ser Ile
        275                 280                 285
Val Leu Ser Ile Gly Phe Asp Asn Phe Val Glu Leu Leu Ser Gly Ala
290                 295                 300
His Ala Met Asp Lys His Phe Ser Thr Thr Pro Ala Glu Lys Asn Leu
305                 310                 315                 320
Pro Val Leu Leu Ala Leu Ile Gly Ile Trp Tyr Asn Asn Phe Phe Gly
                325                 330                 335
Ala Glu Thr Glu Ala Ile Leu Pro Tyr Asp Gln Tyr Met His Arg Phe
            340                 345                 350
Ala Ala Tyr Phe Gln Gln Gly Asn Met Glu Ser Asn Gly Lys Tyr Val
        355                 360                 365
Asp Arg Asn Gly Asn Val Val Asp Tyr Gln Thr Gly Pro Ile Ile Trp
370                 375                 380
Gly Glu Pro Gly Thr Asn Gly Gln His Ala Phe Tyr Gln Leu Ile His
385                 390                 395                 400
Gln Gly Thr Lys Met Val Pro Cys Asp Phe Ile Ala Pro Ala Ile Thr
                405                 410                 415
His Asn Pro Leu Ser Asp His His Gln Lys Leu Leu Ser Asn Phe Phe
            420                 425                 430
Ala Gln Thr Glu Ala Leu Ala Phe Gly Lys Ser Arg Glu Val Val Glu
        435                 440                 445
Gln Glu Tyr Arg Asp Gln Gly Lys Asp Pro Ala Thr Leu Asp Tyr Val
450                 455                 460
Val Pro Phe Lys Val Phe Glu Gly Asn Arg Pro Thr Asn Ser Ile Leu
```

```
                465                 470                 475                 480
Leu Arg Glu Ile Thr Pro Phe Ser Leu Gly Ala Leu Ile Ala Leu Tyr
                    485                 490                 495
Glu His Lys Ile Phe Thr Gln Gly Val Ile Leu Asn Ile Phe Thr Phe
                    500                 505                 510
Asp Gln Trp Gly Val Glu Leu Gly Lys Gln Leu Ala Asn Arg Ile Leu
                    515                 520                 525
Pro Glu Leu Lys Asp Asp Lys Glu Ile Ser Ser His Asp Ser Ser Thr
530                 535                 540
Asn Gly Leu Ile Asn Arg Tyr Lys Ala Trp Arg Gly
545                 550                 555

<210> SEQ ID NO 21
<211> LENGTH: 557
<212> TYPE: PRT
<213> ORGANISM: Artificial Sequence
<220> FEATURE:
<223> OTHER INFORMATION: Synthetic Polypeptide

<400> SEQUENCE: 21

Met Lys Asn Ile Asn Pro Thr Gln Thr Ala Ala Trp Gln Ala Leu Gln
1               5                   10                  15
Lys His Phe Asp Glu Met Lys Asp Val Thr Ile Ala Asp Leu Phe Ala
                    20                  25                  30
Lys Asp Gly Asp Arg Phe Ser Lys Phe Ser Ala Thr Phe Asp Asp Gln
                35                  40                  45
Met Leu Val Asp Tyr Ser Lys Asn Arg Ile Thr Glu Glu Thr Leu Ala
50                  55                  60
Lys Leu Gln Asp Leu Ala Lys Glu Cys Asp Leu Ala Gly Ala Ile Lys
65                  70                  75                  80
Ser Met Phe Ser Gly Glu Lys Ile Asn Arg Thr Glu Asn Arg Ala Val
                    85                  90                  95
Leu His Val Ala Leu Arg Asn Arg Ser Asn Thr Pro Ile Leu Val Asp
                100                 105                 110
Gly Lys Asp Val Met Pro Glu Val Asn Ala Val Leu Glu Lys Met Lys
            115                 120                 125
Thr Phe Ser Glu Ala Ile Ile Ser Gly Glu Leu Glu Val Leu Phe Gln
130                 135                 140
Gly Pro Trp Lys Gly Tyr Thr Gly Lys Ala Ile Thr Asp Val Val Asn
145                 150                 155                 160
Ile Gly Ile Gly Gly Ser Asp Leu Gly Pro Tyr Met Val Thr Glu Ala
                165                 170                 175
Leu Arg Pro Tyr Lys Asn His Leu Asn Met His Phe Val Ser Asn Val
                180                 185                 190
Asp Gly Thr His Ile Ala Glu Val Leu Lys Lys Val Asn Pro Glu Thr
            195                 200                 205
Thr Leu Phe Leu Val Ala Ser Lys Thr Phe Thr Thr Gln Glu Thr Met
        210                 215                 220
Thr Asn Ala His Ser Ala Arg Asp Trp Phe Leu Lys Ala Ala Gly Asp
225                 230                 235                 240
Glu Lys His Val Ala Lys His Phe Ala Ala Leu Ser Thr Asn Ala Lys
                    245                 250                 255
Ala Val Gly Glu Phe Gly Ile Asp Thr Ala Asn Met Phe Glu Phe Trp
                260                 265                 270
Asp Trp Val Gly Gly Arg Tyr Ser Leu Trp Ser Ala Ile Gly Leu Ser
```

```
              275                 280                 285
Ile Val Leu Ser Ile Gly Phe Asp Asn Phe Val Glu Leu Leu Ser Gly
            290                 295                 300
Ala His Ala Met Asp Lys His Phe Ser Thr Thr Pro Ala Glu Lys Asn
305                 310                 315                 320
Leu Pro Val Leu Leu Ala Leu Ile Gly Ile Trp Tyr Asn Asn Phe Phe
                325                 330                 335
Gly Ala Glu Thr Glu Ala Ile Leu Pro Tyr Asp Gln Tyr Met His Arg
            340                 345                 350
Phe Ala Ala Tyr Phe Gln Gln Gly Asn Met Glu Ser Asn Gly Lys Tyr
            355                 360                 365
Val Asp Arg Asn Gly Asn Val Val Asp Tyr Gln Thr Gly Pro Ile Ile
        370                 375                 380
Trp Gly Glu Pro Gly Thr Asn Gly Gln His Ala Phe Tyr Gln Leu Ile
385                 390                 395                 400
His Gln Gly Thr Lys Met Val Pro Cys Asp Phe Ile Ala Pro Ala Ile
                405                 410                 415
Thr His Asn Pro Leu Ser Asp His His Gln Lys Leu Leu Ser Asn Phe
            420                 425                 430
Phe Ala Gln Thr Glu Ala Leu Ala Phe Gly Lys Ser Arg Glu Val Val
            435                 440                 445
Glu Gln Glu Tyr Arg Asp Gln Gly Lys Asp Pro Ala Thr Leu Asp Tyr
        450                 455                 460
Val Val Pro Phe Lys Val Phe Glu Gly Asn Arg Pro Thr Asn Ser Ile
465                 470                 475                 480
Leu Leu Arg Glu Ile Thr Pro Phe Ser Leu Gly Ala Leu Ile Ala Leu
                485                 490                 495
Tyr Glu His Lys Ile Phe Thr Gln Gly Val Ile Leu Asn Ile Phe Thr
            500                 505                 510
Phe Asp Gln Trp Gly Val Glu Leu Gly Lys Gln Leu Ala Asn Arg Ile
            515                 520                 525
Leu Pro Glu Leu Lys Asp Asp Lys Glu Ile Ser Ser His Asp Ser Ser
        530                 535                 540
Thr Asn Gly Leu Ile Asn Arg Tyr Lys Ala Trp Arg Gly
545                 550                 555
```

<210> SEQ ID NO 22
<211> LENGTH: 557
<212> TYPE: PRT
<213> ORGANISM: Artificial Sequence
<220> FEATURE:
<223> OTHER INFORMATION: Synthetic Polypeptide

<400> SEQUENCE: 22

```
Met Lys Asn Ile Asn Pro Thr Gln Thr Ala Ala Trp Gln Ala Leu Gln
1               5                   10                  15
Lys His Phe Asp Glu Met Lys Asp Val Thr Ile Ala Asp Leu Phe Ala
            20                  25                  30
Lys Asp Gly Asp Arg Phe Ser Lys Phe Ser Ala Thr Phe Asp Asp Gln
        35                  40                  45
Met Leu Val Asp Tyr Ser Lys Asn Arg Ile Thr Glu Glu Thr Leu Ala
    50                  55                  60
Lys Leu Gln Asp Leu Ala Lys Glu Cys Asp Leu Ala Gly Ala Ile Lys
65                  70                  75                  80
Ser Met Phe Ser Gly Glu Lys Ile Asn Arg Thr Glu Asn Arg Ala Val
```

```
            85                  90                  95
Leu His Val Ala Leu Arg Asn Arg Ser Asn Thr Pro Ile Leu Val Asp
            100                 105                 110

Gly Lys Asp Val Met Pro Glu Val Asn Ala Val Leu Glu Lys Met Lys
            115                 120                 125

Thr Phe Ser Glu Ala Ile Ile Ser Gly Glu Trp Lys Gly Tyr Thr Gly
            130                 135                 140

Lys Ala Ile Thr Asp Val Val Asn Ile Gly Ile Gly Gly Ser Asp Leu
145                 150                 155                 160

Gly Pro Tyr Met Val Thr Glu Ala Leu Arg Pro Tyr Lys Asn His Leu
            165                 170                 175

Asn Met His Phe Val Ser Asn Val Asp Gly Thr His Ile Ala Glu Val
            180                 185                 190

Leu Lys Lys Val Asn Pro Glu Thr Thr Leu Phe Leu Val Ala Ser Lys
            195                 200                 205

Thr Phe Thr Thr Gln Glu Thr Met Thr Asn Ala His Ser Ala Arg Asp
            210                 215                 220

Trp Phe Leu Lys Ala Ala Gly Asp Glu Lys His Val Ala Lys His Phe
225                 230                 235                 240

Ala Ala Leu Ser Thr Asn Ala Lys Ala Val Gly Glu Phe Gly Ile Asp
            245                 250                 255

Thr Ala Asn Met Phe Glu Phe Trp Asp Trp Val Gly Gly Arg Tyr Ser
            260                 265                 270

Leu Trp Ser Ala Ile Gly Leu Ser Ile Val Leu Ser Ile Gly Phe Asp
            275                 280                 285

Asn Phe Val Glu Leu Leu Ser Gly Ala His Ala Met Asp Lys His Phe
            290                 295                 300

Ser Thr Thr Pro Ala Glu Lys Asn Leu Pro Val Leu Leu Ala Leu Ile
305                 310                 315                 320

Gly Ile Trp Tyr Asn Asn Phe Phe Gly Ala Glu Thr Glu Ala Ile Leu
            325                 330                 335

Pro Tyr Asp Gln Tyr Met His Arg Phe Ala Ala Tyr Phe Gln Gln Gly
            340                 345                 350

Asn Met Glu Ser Asn Gly Lys Tyr Val Asp Arg Asn Gly Asn Val Val
            355                 360                 365

Asp Tyr Gln Thr Gly Pro Ile Ile Trp Gly Glu Pro Gly Thr Asn Gly
            370                 375                 380

Gln His Ala Phe Tyr Gln Leu Ile His Gln Gly Thr Lys Met Val Pro
385                 390                 395                 400

Cys Asp Phe Ile Ala Pro Ala Ile Thr His Leu Glu Val Leu Phe Gln
            405                 410                 415

Gly Pro Asn Pro Leu Ser Asp His His Gln Lys Leu Leu Ser Asn Phe
            420                 425                 430

Phe Ala Gln Thr Glu Ala Leu Ala Phe Gly Lys Ser Arg Glu Val Val
            435                 440                 445

Glu Gln Glu Tyr Arg Asp Gln Gly Lys Asp Pro Ala Thr Leu Asp Tyr
            450                 455                 460

Val Val Pro Phe Lys Val Phe Glu Gly Asn Arg Pro Thr Asn Ser Ile
465                 470                 475                 480

Leu Leu Arg Glu Ile Thr Pro Phe Ser Leu Gly Ala Leu Ile Ala Leu
            485                 490                 495

Tyr Glu His Lys Ile Phe Thr Gln Gly Val Ile Leu Asn Ile Phe Thr
            500                 505                 510
```

```
Phe Asp Gln Trp Gly Val Glu Leu Gly Lys Gln Leu Ala Asn Arg Ile
        515                 520                 525

Leu Pro Glu Leu Lys Asp Asp Lys Glu Ile Ser Ser His Asp Ser Ser
    530                 535                 540

Thr Asn Gly Leu Ile Asn Arg Tyr Lys Ala Trp Arg Gly
545                 550                 555

<210> SEQ ID NO 23
<211> LENGTH: 556
<212> TYPE: PRT
<213> ORGANISM: Artificial Sequence
<220> FEATURE:
<223> OTHER INFORMATION: Synthetic Polypeptide

<400> SEQUENCE: 23

Met Lys Asn Ile Asn Pro Thr Gln Thr Ala Ala Trp Gln Ala Leu Gln
1               5                   10                  15

Lys His Phe Asp Glu Met Lys Asp Val Thr Ile Ala Asp Leu Phe Ala
            20                  25                  30

Lys Asp Gly Asp Arg Phe Ser Lys Phe Ser Ala Thr Phe Asp Asp Gln
        35                  40                  45

Met Leu Val Asp Tyr Ser Lys Asn Arg Ile Thr Glu Glu Thr Leu Ala
    50                  55                  60

Lys Leu Gln Asp Leu Ala Lys Glu Cys Asp Leu Ala Gly Ala Ile Lys
65                  70                  75                  80

Ser Met Phe Ser Gly Glu Lys Ile Asn Arg Thr Glu Asn Arg Ala Val
                85                  90                  95

Leu His Val Ala Leu Arg Asn Arg Ser Asn Thr Pro Ile Leu Val Asp
            100                 105                 110

Gly Lys Asp Val Met Pro Glu Val Asn Ala Val Leu Glu Lys Met Lys
        115                 120                 125

Thr Phe Ser Glu Ala Ile Ile Ser Gly Glu Trp Lys Gly Tyr Thr Gly
    130                 135                 140

Lys Ala Ile Thr Asp Val Val Asn Ile Gly Ile Gly Gly Ser Asp Leu
145                 150                 155                 160

Gly Pro Tyr Met Val Thr Glu Ala Leu Arg Pro Tyr Lys Asn His Leu
                165                 170                 175

Asn Met His Phe Val Ser Asn Val Asp Gly Thr His Ile Ala Glu Val
            180                 185                 190

Leu Lys Lys Val Asn Pro Glu Thr Thr Leu Phe Leu Val Ala Ser Lys
        195                 200                 205

Thr Phe Thr Thr Gln Glu Thr Met Thr Asn Ala His Ser Ala Arg Asp
    210                 215                 220

Trp Phe Leu Lys Ala Ala Gly Asp Glu Lys His Val Ala Lys His Phe
225                 230                 235                 240

Ala Ala Leu Ser Thr Asn Ala Lys Ala Val Gly Glu Phe Gly Ile Asp
                245                 250                 255

Thr Ala Asn Met Phe Glu Phe Trp Asp Trp Val Gly Gly Arg Tyr Ser
            260                 265                 270

Leu Trp Ser Ala Ile Gly Leu Ser Ile Val Leu Ser Ile Gly Phe Asp
        275                 280                 285

Asn Phe Val Glu Leu Leu Ser Gly Ala His Ala Met Asp Lys His Phe
    290                 295                 300

Ser Thr Thr Pro Ala Glu Lys Asn Leu Pro Val Leu Leu Ala Leu Ile
305                 310                 315                 320
```

```
Gly Ile Trp Tyr Asn Asn Phe Phe Gly Ala Glu Thr Glu Ala Ile Leu
            325                 330                 335

Pro Tyr Asp Gln Tyr Met His Arg Phe Ala Ala Tyr Phe Gln Gln Gly
        340                 345                 350

Asn Met Glu Ser Asn Gly Lys Tyr Val Asp Arg Asn Gly Asn Val Val
            355                 360                 365

Asp Tyr Gln Thr Gly Pro Ile Ile Trp Gly Glu Pro Gly Thr Asn Gly
        370                 375                 380

Gln His Ala Phe Tyr Gln Leu Ile His Gln Gly Thr Lys Met Val Pro
385                 390                 395                 400

Cys Asp Phe Ile Ala Pro Ala Ile Thr His Asn Pro Leu Ser Asp His
                405                 410                 415

His Gln Lys Leu Leu Ser Asn Phe Phe Ala Gln Thr Glu Ala Leu Ala
            420                 425                 430

Phe Gly Lys Ser Arg Glu Val Val Glu Gln Glu Tyr Arg Asp Gln Gly
        435                 440                 445

Lys Asp Pro Ala Thr Leu Asp Tyr Val Val Pro Phe Lys Val Phe Glu
    450                 455                 460

Gly Asn Arg Pro Thr Asn Ser Ile Leu Leu Arg Glu Ile Thr Pro Phe
465                 470                 475                 480

Ser Leu Gly Ala Leu Ile Ala Leu Tyr Glu His Lys Ile Phe Thr Gln
            485                 490                 495

Gly Val Ile Leu Asn Ile Phe Thr Phe Asp Gln Trp Gly Val Glu Leu
            500                 505                 510

Gly Lys Gln Leu Ala Asn Arg Ile Leu Pro Glu Leu Glu Val Leu Phe
        515                 520                 525

Gln Gly Pro Lys Asp Asp Lys Glu Ile Ser Ser His Asp Ser Ser Thr
    530                 535                 540

Asn Gly Leu Ile Asn Arg Tyr Lys Ala Trp Arg Gly
545                 550                 555

<210> SEQ ID NO 24
<211> LENGTH: 557
<212> TYPE: PRT
<213> ORGANISM: Artificial Sequence
<220> FEATURE:
<223> OTHER INFORMATION: Synthetic Polypeptide

<400> SEQUENCE: 24

Met Lys Asn Ile Asn Pro Thr Gln Thr Ala Ala Trp Gln Ala Leu Gln
1               5                   10                  15

Lys His Phe Asp Glu Met Lys Asp Val Thr Ile Ala Asp Leu Phe Ala
            20                  25                  30

Lys Asp Gly Asp Arg Phe Ser Lys Phe Ser Ala Thr Phe Asp Asp Gln
        35                  40                  45

Met Leu Val Asp Tyr Ser Lys Asn Arg Ile Thr Glu Glu Thr Leu Ala
    50                  55                  60

Lys Leu Gln Asp Leu Ala Lys Glu Cys Asp Leu Ala Gly Ala Ile Lys
65                  70                  75                  80

Ser Met Phe Ser Gly Glu Lys Ile Asn Arg Thr Glu Asn Arg Ala Val
                85                  90                  95

Leu His Val Ala Leu Arg Asn Arg Ser Asn Thr Pro Ile Leu Val Asp
            100                 105                 110

Gly Lys Asp Val Met Pro Glu Val Asn Ala Val Leu Glu Lys Met Lys
        115                 120                 125
```

```
Thr Phe Ser Glu Ala Ile Ile Ser Gly Glu Trp Lys Gly Tyr Thr Gly
    130                 135                 140

Lys Ala Ile Thr Asp Val Val Asn Ile Gly Ile Gly Gly Ser Asp Leu
145                 150                 155                 160

Gly Pro Tyr Met Val Thr Glu Ala Leu Arg Pro Tyr Lys Asn His Leu
                165                 170                 175

Asn Met His Phe Val Ser Asn Val Asp Gly Thr His Ile Ala Glu Val
            180                 185                 190

Leu Lys Lys Val Asn Pro Glu Thr Thr Leu Phe Leu Val Ala Ser Lys
        195                 200                 205

Thr Phe Thr Thr Gln Glu Thr Met Thr Asn Ala His Ser Ala Arg Asp
210                 215                 220

Trp Phe Leu Lys Ala Ala Gly Asp Glu Lys His Val Ala Lys His Phe
225                 230                 235                 240

Ala Ala Leu Ser Thr Asn Ala Lys Ala Val Gly Glu Phe Gly Ile Asp
                245                 250                 255

Thr Ala Asn Met Phe Glu Phe Trp Asp Trp Val Gly Gly Arg Tyr Ser
            260                 265                 270

Leu Trp Ser Ala Ile Gly Leu Ser Ile Val Leu Ser Ile Gly Phe Asp
        275                 280                 285

Asn Phe Val Glu Leu Leu Ser Gly Ala His Ala Met Asp Lys His Phe
290                 295                 300

Ser Thr Thr Pro Ala Glu Lys Asn Leu Pro Val Leu Leu Ala Leu Ile
305                 310                 315                 320

Gly Ile Trp Tyr Asn Asn Phe Phe Gly Ala Thr Glu Ala Ile Leu
                325                 330                 335

Pro Tyr Asp Gln Tyr Met His Arg Phe Ala Ala Tyr Phe Gln Gln Gly
            340                 345                 350

Asn Met Glu Ser Asn Gly Lys Tyr Val Asp Arg Asn Gly Asn Val Val
        355                 360                 365

Asp Tyr Gln Thr Gly Pro Ile Ile Trp Gly Glu Pro Gly Thr Asn Gly
370                 375                 380

Gln His Ala Phe Tyr Gln Leu Ile His Gln Gly Thr Lys Met Val Pro
385                 390                 395                 400

Cys Asp Phe Ile Ala Pro Ala Ile Thr His Asn Pro Leu Ser Asp His
                405                 410                 415

His Gln Lys Leu Leu Ser Asn Phe Phe Ala Gln Thr Glu Ala Leu Ala
            420                 425                 430

Phe Gly Lys Ser Arg Glu Val Val Glu Gln Glu Tyr Arg Asp Gln Gly
        435                 440                 445

Lys Asp Pro Ala Thr Leu Asp Tyr Val Val Pro Phe Lys Val Phe Glu
450                 455                 460

Gly Asn Arg Pro Thr Asn Ser Ile Leu Leu Arg Glu Ile Thr Pro Phe
465                 470                 475                 480

Ser Leu Gly Ala Leu Ile Ala Leu Tyr Glu His Lys Ile Phe Thr Gln
                485                 490                 495

Gly Val Ile Leu Asn Ile Phe Thr Phe Asp Gln Trp Gly Val Glu Leu
            500                 505                 510

Gly Lys Gln Leu Ala Asn Arg Ile Leu Pro Glu Leu Lys Leu Glu Val
        515                 520                 525

Leu Phe Gln Gly Pro Asp Asp Lys Glu Ile Ser Ser His Asp Ser Ser
530                 535                 540
```

```
Thr Asn Gly Leu Ile Asn Arg Tyr Lys Ala Trp Arg Gly
545                 550                 555
```

<210> SEQ ID NO 25
<211> LENGTH: 557
<212> TYPE: PRT
<213> ORGANISM: Artificial Sequence
<220> FEATURE:
<223> OTHER INFORMATION: Synthetic Polypeptide

<400> SEQUENCE: 25

```
Met Lys Asn Ile Asn Pro Thr Gln Thr Ala Ala Trp Gln Ala Leu Gln
1               5                   10                  15

Lys His Phe Asp Glu Met Lys Asp Val Thr Ile Ala Asp Leu Phe Ala
            20                  25                  30

Lys Asp Gly Asp Arg Phe Ser Lys Phe Ser Ala Thr Phe Asp Asp Gln
        35                  40                  45

Met Leu Val Asp Tyr Ser Lys Asn Arg Ile Thr Glu Glu Thr Leu Ala
    50                  55                  60

Lys Leu Gln Asp Leu Ala Lys Glu Cys Asp Leu Ala Gly Ala Ile Lys
65                  70                  75                  80

Ser Met Phe Ser Gly Glu Lys Ile Asn Arg Thr Glu Asn Arg Ala Val
                85                  90                  95

Leu His Val Ala Leu Arg Asn Arg Ser Asn Thr Pro Ile Leu Val Asp
            100                 105                 110

Gly Lys Asp Val Met Pro Glu Val Asn Ala Val Leu Glu Lys Met Lys
        115                 120                 125

Thr Phe Ser Glu Ala Ile Ile Ser Gly Glu Trp Lys Gly Tyr Thr Gly
    130                 135                 140

Lys Ala Ile Thr Asp Val Val Asn Ile Gly Ile Gly Gly Ser Asp Leu
145                 150                 155                 160

Gly Pro Tyr Met Val Thr Glu Ala Leu Arg Pro Tyr Lys Asn His Leu
                165                 170                 175

Asn Met His Phe Val Ser Asn Val Asp Gly Thr His Ile Ala Glu Val
            180                 185                 190

Leu Lys Lys Val Asn Pro Glu Thr Thr Leu Phe Leu Val Ala Ser Lys
        195                 200                 205

Thr Phe Thr Thr Gln Glu Thr Met Thr Asn Ala His Ser Ala Arg Asp
    210                 215                 220

Trp Phe Leu Lys Ala Ala Gly Asp Glu Lys His Val Ala Lys His Phe
225                 230                 235                 240

Ala Ala Leu Ser Thr Asn Ala Lys Ala Val Gly Glu Phe Gly Ile Asp
                245                 250                 255

Thr Ala Asn Met Phe Glu Phe Trp Asp Trp Val Gly Gly Arg Tyr Ser
            260                 265                 270

Leu Trp Ser Ala Ile Gly Leu Ser Ile Val Leu Ser Ile Gly Phe Asp
        275                 280                 285

Asn Phe Val Glu Leu Leu Ser Gly Ala His Ala Met Asp Lys His Phe
    290                 295                 300

Ser Thr Thr Pro Ala Glu Lys Asn Leu Pro Val Leu Leu Ala Leu Ile
305                 310                 315                 320

Gly Ile Trp Tyr Asn Asn Phe Phe Gly Ala Glu Thr Glu Ala Ile Leu
                325                 330                 335

Pro Tyr Asp Gln Tyr Met His Arg Phe Ala Ala Tyr Phe Gln Gln Gly
            340                 345                 350
```

```
Asn Met Glu Ser Asn Gly Lys Tyr Val Asp Arg Asn Gly Asn Val Val
            355                 360                 365

Asp Tyr Gln Thr Gly Pro Ile Ile Trp Gly Pro Gly Thr Asn Gly
    370                 375                 380

Gln His Ala Phe Tyr Gln Leu Ile His Gln Gly Thr Lys Met Val Pro
385                 390                 395                 400

Cys Asp Phe Ile Ala Pro Ala Ile Thr His Asn Pro Leu Ser Asp His
                405                 410                 415

His Gln Lys Leu Leu Ser Asn Phe Phe Ala Gln Thr Glu Ala Leu Ala
            420                 425                 430

Phe Gly Lys Ser Arg Glu Val Val Glu Gln Glu Tyr Arg Asp Gln Gly
        435                 440                 445

Lys Asp Pro Ala Thr Leu Asp Tyr Val Val Pro Phe Lys Val Phe Glu
    450                 455                 460

Gly Asn Arg Pro Thr Asn Ser Ile Leu Leu Arg Glu Ile Thr Pro Phe
465                 470                 475                 480

Ser Leu Gly Ala Leu Ile Ala Leu Tyr Glu His Lys Ile Phe Thr Gln
                485                 490                 495

Gly Val Ile Leu Asn Ile Phe Thr Phe Asp Gln Trp Gly Val Glu Leu
            500                 505                 510

Gly Lys Gln Leu Ala Asn Arg Ile Leu Pro Glu Leu Lys Asp Leu Glu
        515                 520                 525

Val Leu Phe Gln Gly Pro Asp Lys Glu Ile Ser Ser His Asp Ser Ser
    530                 535                 540

Thr Asn Gly Leu Ile Asn Arg Tyr Lys Ala Trp Arg Gly
545                 550                 555

<210> SEQ ID NO 26
<211> LENGTH: 557
<212> TYPE: PRT
<213> ORGANISM: Artificial Sequence
<220> FEATURE:
<223> OTHER INFORMATION: Synthetic Polypeptide

<400> SEQUENCE: 26

Met Lys Asn Ile Asn Pro Thr Gln Thr Ala Ala Trp Gln Ala Leu Gln
1               5                   10                  15

Lys His Phe Asp Glu Met Lys Asp Val Thr Ile Ala Asp Leu Phe Ala
            20                  25                  30

Lys Asp Gly Asp Arg Phe Ser Lys Phe Ser Ala Thr Phe Asp Asp Gln
        35                  40                  45

Met Leu Val Asp Tyr Ser Lys Asn Arg Ile Thr Glu Glu Thr Leu Ala
    50                  55                  60

Lys Leu Gln Asp Leu Ala Lys Glu Cys Asp Leu Ala Gly Ala Ile Lys
65                  70                  75                  80

Ser Met Phe Ser Gly Glu Lys Ile Asn Arg Thr Glu Asn Arg Ala Val
                85                  90                  95

Leu His Val Ala Leu Arg Asn Arg Ser Asn Thr Pro Ile Leu Val Asp
            100                 105                 110

Gly Lys Asp Val Met Pro Glu Val Asn Ala Val Leu Glu Lys Met Lys
        115                 120                 125

Thr Phe Ser Glu Ala Ile Ile Ser Gly Glu Trp Lys Gly Tyr Thr Gly
    130                 135                 140

Lys Ala Ile Thr Asp Val Val Asn Ile Gly Ile Gly Gly Ser Asp Leu
145                 150                 155                 160
```

```
Gly Pro Tyr Met Val Thr Glu Ala Leu Arg Pro Tyr Lys Asn His Leu
            165                 170                 175

Asn Met His Phe Val Ser Asn Val Asp Gly Thr His Ile Ala Glu Val
            180                 185                 190

Leu Lys Lys Val Asn Pro Glu Thr Thr Leu Phe Leu Val Ala Ser Lys
            195                 200                 205

Thr Phe Thr Thr Gln Glu Thr Met Thr Asn Ala His Ser Ala Arg Asp
            210                 215                 220

Trp Phe Leu Lys Ala Ala Gly Asp Glu Lys His Val Ala Lys His Phe
225                 230                 235                 240

Ala Ala Leu Ser Thr Asn Ala Lys Ala Val Gly Glu Phe Gly Ile Asp
            245                 250                 255

Thr Ala Asn Met Phe Glu Phe Trp Asp Trp Val Gly Gly Arg Tyr Ser
            260                 265                 270

Leu Trp Ser Ala Ile Gly Leu Ser Ile Val Leu Ser Ile Gly Phe Asp
            275                 280                 285

Asn Phe Val Glu Leu Leu Ser Gly Ala His Ala Met Asp Lys His Phe
            290                 295                 300

Ser Thr Thr Pro Ala Glu Lys Asn Leu Pro Val Leu Ala Leu Ile
305                 310                 315                 320

Gly Ile Trp Tyr Asn Asn Phe Phe Gly Ala Glu Thr Glu Ala Ile Leu
            325                 330                 335

Pro Tyr Asp Gln Tyr Met His Arg Phe Ala Ala Tyr Phe Gln Gln Gly
            340                 345                 350

Asn Met Glu Ser Asn Gly Lys Tyr Val Asp Arg Asn Gly Asn Val Val
            355                 360                 365

Asp Tyr Gln Thr Gly Pro Ile Ile Trp Gly Glu Pro Gly Thr Asn Gly
            370                 375                 380

Gln His Ala Phe Tyr Gln Leu Ile His Gln Gly Thr Lys Met Val Pro
385                 390                 395                 400

Cys Asp Phe Ile Ala Pro Ala Ile Thr His Asn Pro Leu Ser Asp His
            405                 410                 415

His Gln Lys Leu Leu Ser Asn Phe Phe Ala Gln Thr Glu Ala Leu Ala
            420                 425                 430

Phe Gly Lys Ser Arg Glu Val Val Glu Gln Glu Tyr Arg Asp Gln Gly
            435                 440                 445

Lys Asp Pro Ala Thr Leu Asp Tyr Val Val Pro Phe Lys Val Phe Glu
            450                 455                 460

Gly Asn Arg Pro Thr Asn Ser Ile Leu Leu Arg Glu Ile Thr Pro Phe
465                 470                 475                 480

Ser Leu Gly Ala Leu Ile Ala Leu Tyr Glu His Lys Ile Phe Thr Gln
            485                 490                 495

Gly Val Ile Leu Asn Ile Phe Thr Phe Asp Gln Trp Gly Val Glu Leu
            500                 505                 510

Gly Lys Gln Leu Ala Asn Arg Ile Leu Pro Glu Leu Lys Asp Asp Leu
            515                 520                 525

Glu Val Leu Phe Gln Gly Pro Lys Glu Ile Ser Ser His Asp Ser Ser
            530                 535                 540

Thr Asn Gly Leu Ile Asn Arg Tyr Lys Ala Trp Arg Gly
545                 550                 555

<210> SEQ ID NO 27
<211> LENGTH: 557
<212> TYPE: PRT
```

<213> ORGANISM: Artificial Sequence
<220> FEATURE:
<223> OTHER INFORMATION: Synthetic Polypeptide

<400> SEQUENCE: 27

```
Met Lys Asn Ile Asn Pro Thr Gln Thr Ala Ala Trp Gln Ala Leu Gln
1               5                   10                  15

Lys His Phe Asp Glu Met Lys Asp Val Thr Ile Ala Asp Leu Phe Ala
            20                  25                  30

Lys Asp Gly Asp Arg Phe Ser Lys Phe Ser Ala Thr Phe Asp Asp Gln
        35                  40                  45

Met Leu Val Asp Tyr Ser Lys Asn Arg Ile Thr Glu Glu Thr Leu Ala
    50                  55                  60

Lys Leu Gln Asp Leu Ala Lys Glu Cys Asp Leu Ala Gly Ala Ile Lys
65                  70                  75                  80

Ser Met Phe Ser Gly Glu Lys Ile Asn Arg Thr Glu Asn Arg Ala Val
                85                  90                  95

Leu His Val Ala Leu Arg Asn Arg Ser Asn Thr Pro Ile Leu Val Asp
            100                 105                 110

Gly Lys Asp Val Met Pro Glu Val Asn Ala Val Leu Glu Lys Met Lys
        115                 120                 125

Thr Phe Ser Glu Ala Ile Ile Ser Gly Glu Trp Lys Gly Tyr Thr Gly
    130                 135                 140

Lys Ala Ile Thr Asp Val Val Asn Ile Gly Ile Gly Ser Asp Leu
145                 150                 155                 160

Gly Pro Tyr Met Val Thr Glu Ala Leu Arg Pro Tyr Lys Asn His Leu
                165                 170                 175

Asn Met His Phe Val Ser Asn Val Asp Gly Thr His Ile Ala Glu Val
            180                 185                 190

Leu Lys Lys Val Asn Pro Glu Thr Thr Leu Phe Leu Val Ala Ser Lys
        195                 200                 205

Thr Phe Thr Thr Gln Glu Thr Met Thr Asn Ala His Ser Ala Arg Asp
    210                 215                 220

Trp Phe Leu Lys Ala Ala Gly Asp Glu Lys His Val Ala Lys His Phe
225                 230                 235                 240

Ala Ala Leu Ser Thr Asn Ala Lys Ala Val Gly Glu Phe Gly Ile Asp
                245                 250                 255

Thr Ala Asn Met Phe Glu Phe Trp Asp Trp Val Gly Gly Arg Tyr Ser
            260                 265                 270

Leu Trp Ser Ala Ile Gly Leu Ser Ile Val Leu Ser Ile Gly Phe Asp
        275                 280                 285

Asn Phe Val Glu Leu Leu Ser Gly Ala His Ala Met Asp Lys His Phe
    290                 295                 300

Ser Thr Thr Pro Ala Glu Lys Asn Leu Pro Val Leu Leu Ala Leu Ile
305                 310                 315                 320

Gly Ile Trp Tyr Asn Asn Phe Phe Gly Ala Glu Thr Glu Ala Ile Leu
                325                 330                 335

Pro Tyr Asp Gln Tyr Met His Arg Phe Ala Ala Tyr Phe Gln Gln Gly
            340                 345                 350

Asn Met Glu Ser Asn Gly Lys Tyr Val Asp Arg Asn Gly Asn Val Val
        355                 360                 365

Asp Tyr Gln Thr Gly Pro Ile Ile Trp Gly Glu Pro Gly Thr Asn Gly
    370                 375                 380

Gln His Ala Phe Tyr Gln Leu Ile His Gln Gly Thr Lys Met Val Pro
```

```
                385                 390                 395                 400
Cys Asp Phe Ile Ala Pro Ala Ile Thr His Asn Pro Leu Ser Asp His
                    405                 410                 415

His Gln Lys Leu Leu Ser Asn Phe Phe Ala Gln Thr Glu Ala Leu Ala
            420                 425                 430

Phe Gly Lys Ser Arg Glu Val Val Gln Glu Tyr Arg Asp Gln Gly
        435                 440                 445

Lys Asp Pro Ala Thr Leu Asp Tyr Val Val Pro Phe Lys Val Phe Glu
450                 455                 460

Gly Asn Arg Pro Thr Asn Ser Ile Leu Leu Arg Glu Ile Thr Pro Phe
465                 470                 475                 480

Ser Leu Gly Ala Leu Ile Ala Leu Tyr Glu His Lys Ile Phe Thr Gln
                485                 490                 495

Gly Val Ile Leu Asn Ile Phe Thr Phe Asp Gln Trp Gly Val Glu Leu
                500                 505                 510

Gly Lys Gln Leu Ala Asn Arg Ile Leu Pro Glu Leu Lys Asp Asp Lys
            515                 520                 525

Leu Glu Val Leu Phe Gln Gly Pro Glu Ile Ser Ser His Asp Ser Ser
        530                 535                 540

Thr Asn Gly Leu Ile Asn Arg Tyr Lys Ala Trp Arg Gly
545                 550                 555
```

<210> SEQ ID NO 28
<211> LENGTH: 557
<212> TYPE: PRT
<213> ORGANISM: Artificial Sequence
<220> FEATURE:
<223> OTHER INFORMATION: Synthetic Polypeptide

<400> SEQUENCE: 28

```
Met Lys Asn Ile Asn Pro Thr Gln Thr Ala Ala Trp Gln Ala Leu Gln
1               5                   10                  15

Lys His Phe Asp Glu Met Lys Asp Val Thr Ile Ala Asp Leu Phe Ala
                20                  25                  30

Lys Asp Gly Asp Arg Phe Ser Lys Phe Ser Ala Thr Phe Asp Asp Gln
            35                  40                  45

Met Leu Val Asp Tyr Ser Lys Asn Arg Ile Thr Glu Glu Thr Leu Ala
        50                  55                  60

Lys Leu Gln Asp Leu Ala Lys Glu Cys Asp Leu Ala Gly Ala Ile Lys
65                  70                  75                  80

Ser Met Phe Ser Gly Glu Lys Ile Asn Arg Thr Glu Asn Arg Ala Val
                85                  90                  95

Leu His Val Ala Leu Arg Asn Arg Ser Asn Thr Pro Ile Leu Val Asp
                100                 105                 110

Gly Lys Asp Val Met Pro Glu Val Asn Ala Val Leu Glu Lys Met Lys
            115                 120                 125

Thr Phe Ser Glu Ala Ile Ile Ser Gly Glu Trp Lys Gly Tyr Thr Gly
        130                 135                 140

Lys Ala Ile Thr Asp Val Val Asn Ile Gly Ile Gly Gly Ser Asp Leu
145                 150                 155                 160

Gly Pro Tyr Met Val Thr Glu Ala Leu Arg Pro Tyr Lys Asn His Leu
                165                 170                 175

Asn Met His Phe Val Ser Asn Val Asp Gly Thr His Ile Ala Glu Val
                180                 185                 190

Leu Lys Lys Val Asn Pro Glu Thr Thr Leu Phe Leu Val Ala Ser Lys
```

-continued

```
                195                 200                 205
Thr Phe Thr Thr Gln Glu Thr Met Thr Asn Ala His Ser Ala Arg Asp
    210                 215                 220

Trp Phe Leu Lys Ala Ala Gly Asp Glu Lys His Val Ala Lys His Phe
225                 230                 235                 240

Ala Ala Leu Ser Thr Asn Ala Lys Ala Val Gly Glu Phe Gly Ile Asp
                245                 250                 255

Thr Ala Asn Met Phe Glu Phe Trp Asp Trp Val Gly Gly Arg Tyr Ser
            260                 265                 270

Leu Trp Ser Ala Ile Gly Leu Ser Ile Val Leu Ser Ile Gly Phe Asp
        275                 280                 285

Asn Phe Val Glu Leu Leu Ser Gly Ala His Ala Met Asp Lys His Phe
    290                 295                 300

Ser Thr Thr Pro Ala Glu Lys Asn Leu Pro Val Leu Ala Leu Ile
305                 310                 315                 320

Gly Ile Trp Tyr Asn Asn Phe Phe Gly Ala Glu Thr Glu Ala Ile Leu
                325                 330                 335

Pro Tyr Asp Gln Tyr Met His Arg Phe Ala Ala Tyr Phe Gln Gln Gly
            340                 345                 350

Asn Met Glu Ser Asn Gly Lys Tyr Val Asp Arg Asn Gly Asn Val Val
        355                 360                 365

Asp Tyr Gln Thr Gly Pro Ile Ile Trp Gly Pro Gly Thr Asn Gly
    370                 375                 380

Gln His Ala Phe Tyr Gln Leu Ile His Gln Gly Thr Lys Met Val Pro
385                 390                 395                 400

Cys Asp Phe Ile Ala Pro Ala Ile Thr His Asn Pro Leu Ser Asp His
                405                 410                 415

His Gln Lys Leu Leu Ser Asn Phe Phe Ala Gln Thr Glu Ala Leu Ala
            420                 425                 430

Phe Gly Lys Ser Arg Glu Val Val Glu Gln Glu Tyr Arg Asp Gln Gly
        435                 440                 445

Lys Asp Pro Ala Thr Leu Asp Tyr Val Val Pro Phe Lys Val Phe Glu
    450                 455                 460

Gly Asn Arg Pro Thr Asn Ser Ile Leu Leu Arg Glu Ile Thr Pro Phe
465                 470                 475                 480

Ser Leu Gly Ala Leu Ile Ala Leu Tyr Glu His Lys Ile Phe Thr Gln
                485                 490                 495

Gly Val Ile Leu Asn Ile Phe Thr Phe Asp Gln Trp Gly Val Glu Leu
            500                 505                 510

Gly Lys Gln Leu Ala Asn Arg Ile Leu Pro Glu Leu Lys Asp Asp Lys
        515                 520                 525

Glu Leu Glu Val Leu Phe Gln Gly Pro Ile Ser Ser His Asp Ser Ser
    530                 535                 540

Thr Asn Gly Leu Ile Asn Arg Tyr Lys Ala Trp Arg Gly
545                 550                 555

<210> SEQ ID NO 29
<211> LENGTH: 557
<212> TYPE: PRT
<213> ORGANISM: Artificial Sequence
<220> FEATURE:
<223> OTHER INFORMATION: Synthetic Polypeptide

<400> SEQUENCE: 29

Met Lys Asn Ile Asn Pro Thr Gln Thr Ala Ala Trp Gln Ala Leu Gln
```

```
 1               5                   10                  15
Lys His Phe Asp Glu Met Lys Asp Val Thr Ile Ala Asp Leu Phe Ala
             20                  25                  30

Lys Asp Gly Asp Arg Phe Ser Lys Phe Ser Ala Thr Phe Asp Asp Gln
             35                  40                  45

Met Leu Val Asp Tyr Ser Lys Asn Arg Ile Thr Glu Glu Thr Leu Ala
             50                  55                  60

Lys Leu Gln Asp Leu Ala Lys Glu Cys Asp Leu Ala Gly Ala Ile Lys
 65                  70                  75                  80

Ser Met Phe Ser Gly Glu Lys Ile Asn Arg Thr Glu Asn Arg Ala Val
                 85                  90                  95

Leu His Val Ala Leu Arg Asn Arg Ser Asn Thr Pro Ile Leu Val Asp
             100                 105                 110

Gly Lys Asp Val Met Pro Glu Val Asn Ala Val Leu Glu Lys Met Lys
             115                 120                 125

Thr Phe Ser Glu Ala Ile Ile Ser Gly Glu Trp Lys Gly Tyr Thr Gly
             130                 135                 140

Lys Ala Ile Thr Asp Val Val Asn Ile Gly Ile Gly Gly Ser Asp Leu
145                 150                 155                 160

Gly Pro Tyr Met Val Thr Glu Ala Leu Arg Pro Tyr Lys Asn His Leu
                 165                 170                 175

Asn Met His Phe Val Ser Asn Val Asp Gly Thr His Ile Ala Glu Val
             180                 185                 190

Leu Lys Lys Val Asn Pro Glu Thr Thr Leu Phe Leu Val Ala Ser Lys
             195                 200                 205

Thr Phe Thr Thr Gln Glu Thr Met Thr Asn Ala His Ser Ala Arg Asp
             210                 215                 220

Trp Phe Leu Lys Ala Ala Gly Asp Glu Lys His Val Ala Lys His Phe
225                 230                 235                 240

Ala Ala Leu Ser Thr Asn Ala Lys Ala Val Gly Glu Phe Gly Ile Asp
                 245                 250                 255

Thr Ala Asn Met Phe Glu Phe Trp Asp Trp Val Gly Gly Arg Tyr Ser
             260                 265                 270

Leu Trp Ser Ala Ile Gly Leu Ser Ile Val Leu Ser Ile Gly Phe Asp
             275                 280                 285

Asn Phe Val Glu Leu Leu Ser Gly Ala His Ala Met Asp Lys His Phe
             290                 295                 300

Ser Thr Thr Pro Ala Glu Lys Asn Leu Pro Val Leu Leu Ala Leu Ile
305                 310                 315                 320

Gly Ile Trp Tyr Asn Asn Phe Phe Gly Ala Glu Thr Glu Ala Ile Leu
                 325                 330                 335

Pro Tyr Asp Gln Tyr Met His Arg Phe Ala Ala Tyr Phe Gln Gln Gly
             340                 345                 350

Asn Met Glu Ser Asn Gly Lys Tyr Val Asp Arg Asn Gly Asn Val Val
             355                 360                 365

Asp Tyr Gln Thr Gly Pro Ile Ile Trp Gly Glu Pro Gly Thr Asn Gly
             370                 375                 380

Gln His Ala Phe Tyr Gln Leu Ile His Gln Gly Thr Lys Met Val Pro
385                 390                 395                 400

Cys Asp Phe Ile Ala Pro Ala Ile Thr His Asn Pro Leu Ser Asp His
                 405                 410                 415

His Gln Lys Leu Leu Ser Asn Phe Phe Ala Gln Thr Glu Ala Leu Ala
             420                 425                 430
```

```
Phe Gly Lys Ser Arg Glu Val Glu Gln Glu Tyr Arg Asp Gln Gly
        435                 440                 445

Lys Asp Pro Ala Thr Leu Asp Tyr Val Val Pro Phe Lys Val Phe Glu
    450                 455                 460

Gly Asn Arg Pro Thr Asn Ser Ile Leu Arg Glu Ile Thr Pro Phe
465                 470                 475                 480

Ser Leu Gly Ala Leu Ile Ala Leu Tyr Glu His Lys Ile Phe Thr Gln
                485                 490                 495

Gly Val Ile Leu Asn Ile Phe Thr Phe Asp Gln Trp Gly Val Glu Leu
                500                 505                 510

Gly Lys Gln Leu Ala Asn Arg Ile Leu Pro Glu Leu Lys Asp Asp Lys
            515                 520                 525

Glu Ile Leu Glu Val Leu Phe Gln Gly Pro Ser Ser His Asp Ser Ser
    530                 535                 540

Thr Asn Gly Leu Ile Asn Arg Tyr Lys Ala Trp Arg Gly
545                 550                 555

<210> SEQ ID NO 30
<211> LENGTH: 557
<212> TYPE: PRT
<213> ORGANISM: Artificial Sequence
<220> FEATURE:
<223> OTHER INFORMATION: Synthetic Polypeptide

<400> SEQUENCE: 30

Met Lys Asn Ile Asn Pro Thr Gln Thr Ala Ala Trp Gln Ala Leu Gln
1               5                   10                  15

Lys His Phe Asp Glu Met Lys Asp Val Thr Ile Ala Asp Leu Phe Ala
                20                  25                  30

Lys Asp Gly Asp Arg Phe Ser Lys Phe Ser Ala Thr Phe Asp Asp Gln
            35                  40                  45

Met Leu Val Asp Tyr Ser Lys Asn Arg Ile Thr Glu Glu Thr Leu Ala
        50                  55                  60

Lys Leu Gln Asp Leu Ala Lys Glu Cys Asp Leu Ala Gly Ala Ile Lys
65                  70                  75                  80

Ser Met Phe Ser Gly Glu Lys Ile Asn Arg Thr Glu Asn Arg Ala Val
                85                  90                  95

Leu His Val Ala Leu Arg Asn Arg Ser Asn Thr Pro Ile Leu Val Asp
                100                 105                 110

Gly Lys Asp Val Met Pro Glu Val Asn Ala Val Leu Glu Lys Met Lys
            115                 120                 125

Thr Phe Ser Glu Ala Ile Ile Ser Gly Glu Trp Lys Gly Tyr Thr Gly
        130                 135                 140

Lys Ala Ile Thr Asp Val Val Asn Ile Gly Ile Gly Gly Ser Asp Leu
145                 150                 155                 160

Gly Pro Tyr Met Val Thr Glu Ala Leu Arg Pro Tyr Lys Asn His Leu
                165                 170                 175

Asn Met His Phe Val Ser Asn Val Asp Gly Thr His Ile Ala Glu Val
                180                 185                 190

Leu Lys Lys Val Asn Pro Glu Thr Thr Leu Phe Leu Val Ala Ser Lys
            195                 200                 205

Thr Phe Thr Thr Gln Glu Thr Met Thr Asn Ala His Ser Ala Arg Asp
        210                 215                 220

Trp Phe Leu Lys Ala Ala Gly Asp Glu Lys His Val Ala Lys His Phe
225                 230                 235                 240
```

-continued

```
Ala Ala Leu Ser Thr Asn Ala Lys Ala Val Gly Glu Phe Gly Ile Asp
            245                 250                 255

Thr Ala Asn Met Phe Glu Phe Trp Asp Trp Val Gly Gly Arg Tyr Ser
        260                 265                 270

Leu Trp Ser Ala Ile Gly Leu Ser Ile Val Leu Ser Ile Gly Phe Asp
    275                 280                 285

Asn Phe Val Glu Leu Leu Ser Gly Ala His Ala Met Asp Lys His Phe
290                 295                 300

Ser Thr Thr Pro Ala Glu Lys Asn Leu Pro Val Leu Leu Ala Leu Ile
305                 310                 315                 320

Gly Ile Trp Tyr Asn Asn Phe Gly Ala Thr Glu Ala Ile Leu
                325                 330                 335

Pro Tyr Asp Gln Tyr Met His Arg Phe Ala Ala Tyr Phe Gln Gln Gly
            340                 345                 350

Asn Met Glu Ser Asn Gly Lys Tyr Val Asp Arg Asn Gly Asn Val Val
        355                 360                 365

Asp Tyr Gln Thr Gly Pro Ile Ile Trp Gly Glu Pro Gly Thr Asn Gly
    370                 375                 380

Gln His Ala Phe Tyr Gln Leu Ile His Gln Gly Thr Lys Met Val Pro
385                 390                 395                 400

Cys Asp Phe Ile Ala Pro Ala Ile Thr His Asn Pro Leu Ser Asp His
                405                 410                 415

His Gln Lys Leu Leu Ser Asn Phe Phe Ala Gln Thr Glu Ala Leu Ala
            420                 425                 430

Phe Gly Lys Ser Arg Glu Val Val Glu Gln Glu Tyr Arg Asp Gln Gly
        435                 440                 445

Lys Asp Pro Ala Thr Leu Asp Tyr Val Val Pro Phe Lys Val Phe Glu
    450                 455                 460

Gly Asn Arg Pro Thr Asn Ser Ile Leu Leu Arg Glu Ile Thr Pro Phe
465                 470                 475                 480

Ser Leu Gly Ala Leu Ile Ala Leu Tyr Glu His Lys Ile Phe Thr Gln
                485                 490                 495

Gly Val Ile Leu Asn Ile Phe Thr Phe Asp Gln Trp Gly Val Glu Leu
            500                 505                 510

Gly Lys Gln Leu Ala Asn Arg Ile Leu Pro Glu Leu Lys Asp Asp Lys
        515                 520                 525

Glu Ile Ser Leu Glu Val Leu Phe Gln Gly Pro Ser His Asp Ser Ser
    530                 535                 540

Thr Asn Gly Leu Ile Asn Arg Tyr Lys Ala Trp Arg Gly
545                 550                 555
```

<210> SEQ ID NO 31
<211> LENGTH: 557
<212> TYPE: PRT
<213> ORGANISM: Artificial Sequence
<220> FEATURE:
<223> OTHER INFORMATION: Synthetic Polypeptide

<400> SEQUENCE: 31

```
Met Lys Asn Ile Asn Pro Thr Gln Thr Ala Ala Trp Gln Ala Leu Gln
1               5                   10                  15

Lys His Phe Asp Glu Met Lys Asp Val Thr Ile Ala Asp Leu Phe Ala
            20                  25                  30

Lys Asp Gly Asp Arg Phe Ser Lys Phe Ser Ala Thr Phe Asp Asp Gln
        35                  40                  45
```

-continued

```
Met Leu Val Asp Tyr Ser Lys Asn Arg Ile Thr Glu Glu Thr Leu Ala
     50                  55                  60
Lys Leu Gln Asp Leu Ala Lys Glu Cys Asp Leu Ala Gly Ala Ile Lys
 65                  70                  75                  80
Ser Met Phe Ser Gly Glu Lys Ile Asn Arg Thr Glu Asn Arg Ala Val
                 85                  90                  95
Leu His Val Ala Leu Arg Asn Arg Ser Asn Thr Pro Ile Leu Val Asp
             100                 105                 110
Gly Lys Asp Val Met Pro Glu Val Asn Ala Val Leu Glu Lys Met Lys
         115                 120                 125
Thr Phe Ser Glu Ala Ile Ile Ser Gly Glu Trp Lys Gly Tyr Thr Gly
     130                 135                 140
Lys Ala Ile Thr Asp Val Val Asn Ile Gly Ile Gly Gly Ser Asp Leu
145                 150                 155                 160
Gly Pro Tyr Met Val Thr Glu Ala Leu Arg Pro Tyr Lys Asn His Leu
                 165                 170                 175
Asn Met His Phe Val Ser Asn Val Asp Gly Thr His Ile Ala Glu Val
             180                 185                 190
Leu Lys Lys Val Asn Pro Glu Thr Thr Leu Phe Leu Val Ala Ser Lys
         195                 200                 205
Thr Phe Thr Thr Gln Glu Thr Met Thr Asn Ala His Ser Ala Arg Asp
     210                 215                 220
Trp Phe Leu Lys Ala Ala Gly Asp Glu Lys His Val Ala Lys His Phe
225                 230                 235                 240
Ala Ala Leu Ser Thr Asn Ala Lys Ala Val Gly Glu Phe Gly Ile Asp
                 245                 250                 255
Thr Ala Asn Met Phe Glu Phe Trp Asp Trp Val Gly Gly Arg Tyr Ser
             260                 265                 270
Leu Trp Ser Ala Ile Gly Leu Ser Ile Val Leu Ser Ile Gly Phe Asp
         275                 280                 285
Asn Phe Val Glu Leu Leu Ser Gly Ala His Ala Met Asp Lys His Phe
     290                 295                 300
Ser Thr Thr Pro Ala Glu Lys Asn Leu Pro Val Leu Leu Ala Leu Ile
305                 310                 315                 320
Gly Ile Trp Tyr Asn Asn Phe Phe Gly Ala Glu Thr Glu Ala Ile Leu
                 325                 330                 335
Pro Tyr Asp Gln Tyr Met His Arg Phe Ala Ala Tyr Phe Gln Gln Gly
             340                 345                 350
Asn Met Glu Ser Asn Gly Lys Tyr Val Asp Arg Asn Gly Asn Val Val
         355                 360                 365
Asp Tyr Gln Thr Gly Pro Ile Ile Trp Gly Glu Pro Gly Thr Asn Gly
     370                 375                 380
Gln His Ala Phe Tyr Gln Leu Ile His Gln Gly Thr Lys Met Val Pro
385                 390                 395                 400
Cys Asp Phe Ile Ala Pro Ala Ile Thr His Asn Pro Leu Ser Asp His
                 405                 410                 415
His Gln Lys Leu Leu Ser Asn Phe Phe Ala Gln Thr Glu Ala Leu Ala
             420                 425                 430
Phe Gly Lys Ser Arg Glu Val Val Glu Gln Glu Tyr Arg Asp Gln Gly
         435                 440                 445
Lys Asp Pro Ala Thr Leu Asp Tyr Val Val Pro Phe Lys Val Phe Glu
     450                 455                 460
```

Gly Asn Arg Pro Thr Asn Ser Ile Leu Leu Arg Glu Ile Thr Pro Phe
465                 470                 475                 480

Ser Leu Gly Ala Leu Ile Ala Leu Tyr Glu His Lys Ile Phe Thr Gln
            485                 490                 495

Gly Val Ile Leu Asn Ile Phe Thr Phe Asp Gln Trp Gly Val Glu Leu
        500                 505                 510

Gly Lys Gln Leu Ala Asn Arg Ile Leu Pro Glu Leu Lys Asp Asp Lys
    515                 520                 525

Glu Ile Ser Ser Leu Glu Val Leu Phe Gln Gly Pro His Asp Ser Ser
530                 535                 540

Thr Asn Gly Leu Ile Asn Arg Tyr Lys Ala Trp Arg Gly
545                 550                 555

<210> SEQ ID NO 32
<211> LENGTH: 557
<212> TYPE: PRT
<213> ORGANISM: Artificial Sequence
<220> FEATURE:
<223> OTHER INFORMATION: Synthetic Polypeptide

<400> SEQUENCE: 32

Met Lys Asn Ile Asn Pro Thr Gln Thr Ala Ala Trp Gln Ala Leu Gln
1               5                   10                  15

Lys His Phe Asp Glu Met Lys Asp Val Thr Ile Ala Asp Leu Phe Ala
            20                  25                  30

Lys Asp Gly Asp Arg Phe Ser Lys Phe Ser Ala Thr Phe Asp Asp Gln
        35                  40                  45

Met Leu Val Asp Tyr Ser Lys Asn Arg Ile Thr Glu Glu Thr Leu Ala
50                  55                  60

Lys Leu Gln Asp Leu Ala Lys Glu Cys Asp Leu Ala Gly Ala Ile Lys
65                  70                  75                  80

Ser Met Phe Ser Gly Glu Lys Ile Asn Arg Thr Glu Asn Arg Ala Val
                85                  90                  95

Leu His Val Ala Leu Arg Asn Arg Ser Asn Thr Pro Ile Leu Val Asp
            100                 105                 110

Gly Lys Asp Val Met Pro Glu Val Asn Ala Val Leu Glu Lys Met Lys
        115                 120                 125

Thr Phe Ser Glu Ala Ile Ile Ser Gly Glu Trp Lys Gly Tyr Thr Gly
130                 135                 140

Lys Ala Ile Thr Asp Val Val Asn Ile Gly Ile Gly Gly Ser Asp Leu
145                 150                 155                 160

Gly Pro Tyr Met Val Thr Glu Ala Leu Arg Pro Tyr Lys Asn His Leu
                165                 170                 175

Asn Met His Phe Val Ser Asn Val Asp Gly Thr His Ile Ala Glu Val
            180                 185                 190

Leu Lys Lys Val Asn Pro Glu Thr Thr Leu Phe Leu Val Ala Ser Lys
        195                 200                 205

Thr Phe Thr Thr Gln Glu Thr Met Thr Asn Ala His Ser Ala Arg Asp
210                 215                 220

Trp Phe Leu Lys Ala Ala Gly Asp Glu Lys His Val Ala Lys His Phe
225                 230                 235                 240

Ala Ala Leu Ser Thr Asn Ala Lys Ala Val Gly Glu Phe Gly Ile Asp
                245                 250                 255

Thr Ala Asn Met Phe Glu Phe Trp Asp Trp Val Gly Gly Arg Tyr Ser
            260                 265                 270

```
Leu Trp Ser Ala Ile Gly Leu Ser Ile Val Leu Ser Ile Gly Phe Asp
            275                 280                 285

Asn Phe Val Glu Leu Leu Ser Gly Ala His Ala Met Asp Lys His Phe
        290                 295                 300

Ser Thr Thr Pro Ala Glu Lys Asn Leu Pro Val Leu Ala Leu Ile
305                 310                 315                 320

Gly Ile Trp Tyr Asn Asn Phe Phe Gly Ala Glu Thr Glu Ala Ile Leu
                325                 330                 335

Pro Tyr Asp Gln Tyr Met His Arg Phe Ala Ala Tyr Phe Gln Gln Gly
            340                 345                 350

Asn Met Glu Ser Asn Gly Lys Tyr Val Asp Arg Asn Gly Asn Val Val
        355                 360                 365

Asp Tyr Gln Thr Gly Pro Ile Ile Trp Gly Glu Pro Gly Thr Asn Gly
    370                 375                 380

Gln His Ala Phe Tyr Gln Leu Ile His Gln Gly Thr Lys Met Val Pro
385                 390                 395                 400

Cys Asp Phe Ile Ala Pro Ala Ile Thr His Asn Pro Leu Ser Asp His
                405                 410                 415

His Gln Lys Leu Leu Ser Asn Phe Phe Ala Gln Thr Glu Ala Leu Ala
            420                 425                 430

Phe Gly Lys Ser Arg Glu Val Val Glu Gln Glu Tyr Arg Asp Gln Gly
        435                 440                 445

Lys Asp Pro Ala Thr Leu Asp Tyr Val Val Pro Phe Lys Val Phe Glu
    450                 455                 460

Gly Asn Arg Pro Thr Asn Ser Ile Leu Leu Arg Glu Ile Thr Pro Phe
465                 470                 475                 480

Ser Leu Gly Ala Leu Ile Ala Leu Tyr Glu His Lys Ile Phe Thr Gln
                485                 490                 495

Gly Val Ile Leu Asn Ile Phe Thr Phe Asp Gln Trp Gly Val Glu Leu
            500                 505                 510

Gly Lys Gln Leu Ala Asn Arg Ile Leu Pro Glu Leu Lys Asp Asp Lys
        515                 520                 525

Glu Ile Ser Ser His Asp Ser Ser Thr Asn Gly Leu Ile Asn Arg Tyr
    530                 535                 540

Lys Leu Glu Val Leu Phe Gln Gly Pro Ala Trp Arg Gly
545                 550                 555

<210> SEQ ID NO 33
<211> LENGTH: 558
<212> TYPE: DNA
<213> ORGANISM: Artificial Sequence
<220> FEATURE:
<223> OTHER INFORMATION: Synthetic Oligonucleotide

<400> SEQUENCE: 33
atgggcccag aagaagaatt cggcatgagc ctgatcaagc ataactcttg cgtcattacc        60
acggagaatg gtaagttcac gggcttgggc gtttatgacc gtttcgtcgt ggttccgacc       120
cacgctgacc cgggtaaaga atccaggtt gacggtatca cgaccaaagt gattgatagc        180
tatgatctct ataataagaa cggcatcaag ctggaaatca cggtgctgaa actggaccgt       240
aatgaaaagt tcgtgatat ccgtcgctat attccgaata cgaggatga ctacccaaat         300 tgcaatctgg cgctgctggc aaatcagccg gaaccgacga tcatcaacgt gggtgacgtg       360
gtgagctatg caatatcct gctgagcggt aaccagaccg cgcgtatgct gaagtattcc        420
tatccgacga aaagcggcta ttgcggcggc gtgctctata agattggtca gtcctgggc        480
```
atccacgtcg gcggtaatgg ccgcgatggt ttcagcgcga tgctgctgcg tagctatttc     540
accgacgtcc agtgataa                                                   558

<210> SEQ ID NO 34
<211> LENGTH: 184
<212> TYPE: PRT
<213> ORGANISM: Artificial Sequence
<220> FEATURE:
<223> OTHER INFORMATION: Synthetic Polypeptide

<400> SEQUENCE: 34

Met Gly Pro Glu Glu Phe Gly Met Ser Leu Ile Lys His Asn Ser
1               5                   10                  15

Cys Val Ile Thr Thr Glu Asn Gly Lys Phe Thr Gly Leu Gly Val Tyr
                20                  25                  30

Asp Arg Phe Val Val Pro Thr His Ala Asp Pro Gly Lys Glu Ile
            35                  40                  45

Gln Val Asp Gly Ile Thr Thr Lys Val Ile Asp Ser Tyr Asp Leu Tyr
    50                  55                  60

Asn Lys Asn Gly Ile Lys Leu Glu Ile Thr Val Leu Lys Leu Asp Arg
65                  70                  75                  80

Asn Glu Lys Phe Arg Asp Ile Arg Arg Tyr Ile Pro Asn Asn Glu Asp
                85                  90                  95

Asp Tyr Pro Asn Cys Asn Leu Ala Leu Leu Ala Asn Gln Pro Glu Pro
            100                 105                 110

Thr Ile Ile Asn Val Gly Asp Val Val Ser Tyr Gly Asn Ile Leu Leu
        115                 120                 125

Ser Gly Asn Gln Thr Ala Arg Met Leu Lys Tyr Ser Tyr Pro Thr Lys
    130                 135                 140

Ser Gly Tyr Cys Gly Gly Val Leu Tyr Lys Ile Gly Gln Val Leu Gly
145                 150                 155                 160

Ile His Val Gly Gly Asn Gly Arg Asp Gly Phe Ser Ala Met Leu Leu
                165                 170                 175

Arg Ser Tyr Phe Thr Asp Val Gln
            180

<210> SEQ ID NO 35
<211> LENGTH: 618
<212> TYPE: DNA
<213> ORGANISM: Artificial Sequence
<220> FEATURE:
<223> OTHER INFORMATION: Synthetic Oligonucleotide

<400> SEQUENCE: 35
atgaaaaaaa cggcaattgc gatagcggtt gcgctagctg ttttgccac ggtggcgcag      60 gctggcccag aagaagaatt cggcatgagc ctgatcaagc ataactcttg cgtcattacc    120
acggagaatg gtaagttcac gggcttgggc gtttatgacc gtttcgtcgt ggttccgacc    180
cacgctgacc cgggtaaaga aatccaggtt gacggtatca cgaccaaagt gattgatagc    240
tatgatctct ataataagaa cggcatcaag ctggaaatca cggtgctgaa actggaccgt    300
aatgaaaagt ttcgtgatat ccgtcgctat attccgaata cgaggatga ctacccaaat     360 tgcaatctgg cgctgctggc aaatcagccg gaaccgacga tcatcaacgt gggtgacgtg    420
gtgagctatg gcaatatcct gctgagcggt aaccagaccg cgcgtatgct gaagtattcc    480
tatccgacga aaagcggcta ttgcggcggc gtgctctata agattggtca agtcctgggc    540

-continued

```
atccacgtcg gcggtaatgg ccgcgatggt ttcagcgcga tgctgctgcg tagctatttc    600
accgacgtcc agtgataa                                                  618
```

<210> SEQ ID NO 36
<211> LENGTH: 204
<212> TYPE: PRT
<213> ORGANISM: Artificial Sequence
<220> FEATURE:
<223> OTHER INFORMATION: Synthetic Polypeptide

<400> SEQUENCE: 36

```
Met Lys Lys Thr Ala Ile Ala Ile Ala Val Ala Leu Ala Gly Phe Ala
1               5                   10                  15

Thr Val Ala Gln Ala Gly Pro Glu Glu Phe Gly Met Ser Leu Ile
            20                  25                  30

Lys His Asn Ser Cys Val Ile Thr Glu Asn Gly Lys Phe Thr Gly
            35                  40                  45

Leu Gly Val Tyr Asp Arg Phe Val Val Pro Thr His Ala Asp Pro
    50                  55                  60

Gly Lys Glu Ile Gln Val Asp Gly Ile Thr Thr Lys Val Ile Asp Ser
65                  70                  75                  80

Tyr Asp Leu Tyr Asn Lys Asn Gly Ile Lys Leu Glu Ile Thr Val Leu
                85                  90                  95

Lys Leu Asp Arg Asn Glu Lys Phe Arg Asp Ile Arg Arg Tyr Ile Pro
                100                 105                 110

Asn Asn Glu Asp Asp Tyr Pro Asn Cys Asn Leu Ala Leu Leu Ala Asn
            115                 120                 125

Gln Pro Glu Pro Thr Ile Ile Asn Val Gly Asp Val Val Ser Tyr Gly
    130                 135                 140

Asn Ile Leu Leu Ser Gly Asn Gln Thr Ala Arg Met Leu Lys Tyr Ser
145                 150                 155                 160

Tyr Pro Thr Lys Ser Gly Tyr Cys Gly Gly Val Leu Tyr Lys Ile Gly
                165                 170                 175

Gln Val Leu Gly Ile His Val Gly Gly Asn Gly Arg Asp Gly Phe Ser
            180                 185                 190

Ala Met Leu Leu Arg Ser Tyr Phe Thr Asp Val Gln
    195                 200
```

<210> SEQ ID NO 37
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 37

```
ctggaagtgc tgtttcaggg tccg                                           24
```

<210> SEQ ID NO 38
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 38

```
Leu Glu Val Leu Phe Gln Gly Pro
1               5
```

```
<210> SEQ ID NO 39
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 39

Glu Val Leu Phe Gln Gly Pro
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 40

Val Leu Phe Gln Gly Pro
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 41

Leu Phe Gln Gly Pro
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 42

Leu Glu Val Leu Phe Gln Gly
1               5

<210> SEQ ID NO 43
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 43

Leu Glu Val Leu Phe Gln
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 44

Leu Glu Val Leu Phe
1               5

<210> SEQ ID NO 45
```

<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 45

Glu Val Leu Phe Gln Gly
1               5

<210> SEQ ID NO 46
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 46

Met Lys Lys Thr Ala Ile Ala Ile Ala Val Ala Leu Ala Gly Phe Ala
1               5                   10                  15

Thr Val Ala Gln Ala
            20

<210> SEQ ID NO 47
<211> LENGTH: 2145
<212> TYPE: DNA
<213> ORGANISM: Artificial Sequence
<220> FEATURE:
<223> OTHER INFORMATION: Synthetic Oligonucleotide

<400> SEQUENCE: 47

| | |
|---|---:|
| gtgtcccgta ttattatgct gatccctacc ggaaccagcg tcggtctgac cagcgtcagc | 60 |
| cttggcgtga tccgtgcaat ggaacgcaaa ggcgttcgtc tgagcgtttt caaacctatc | 120 |
| gctcagccgc gtaccggtgg cgatgcgccc gatcagacta cgactatcgt gcgtgcgaac | 180 |
| tcttccacca cgacggccgc tgaaccgctg aaaatgagct acgttgaagg tctgctttcc | 240 |
| agcaatcaga aagatgtgct gatggaagag atcgtcgcaa actaccacgc taacaccaaa | 300 |
| gacgctgaag tcgttctggt tgaaggtctg gtcccgacac gtaagcacca gtttgcccag | 360 |
| tctctgaact acgaaatcgc taaaacgctg aatgcggaaa tcgtcttcgt tatgtctcag | 420 |
| ggcactgaca ccccggaaca gctgaaagag cgtatcgaac tgaccgcaa cagcttcggc | 480 |
| ggtgccaaaa acaccaacat caccggcgtt atcgttaaca aactgaacgc accggttgat | 540 |
| gaacagggtc gtactcgccc ggatctgtcc gagattttcg acgactcttc caaagctaaa | 600 |
| gtaaacaatg ttgatccggc gaagctgcaa gaatccagcc cgctgccggt tctcggcgct | 660 |
| gtgccgtgga gctttgacct gatcgcgact cgtgcgatcg atatggctcg ccacctgaat | 720 |
| gcgaccatca tcaacgaagg cgacatcaat actcgccgcg ttaaatccgt cactttctgc | 780 |
| gcacgcagca ttccgcacat gctggagcac ttccgtgccg ttctctgct ggtgacttcc | 840 |
| gcagaccgtc ctgacgtgct ggtggccgct gcctggcag ccatgaacgg cgtagaaatc | 900 |
| ggtgccctgc tgctgactgg cggttacgaa atggacgcgc gcatttctaa actgtgcgaa | 960 |
| cgtgctttcg ctaccggcct gccggtattt atggtgaaca ccaacacctg gcagacctct | 1020 |
| ctgagcctgc agagcttcaa cctggaagtt ccggttgacg atcacgaacg tatcgagaaa | 1080 |
| gttcaggaat acgttgctaa ctacatcaac gctgactgga tcgaatctct gactgccact | 1140 |
| tctgagcgca gccgtcgtct gtctccgcct gcgttccgtt atcagctgac tgaacttgcg | 1200 |
| cgcaaagcgg gcaaacgtat cgtactgccg gaaggtgacg aaccgcgtac cgttaaagca | 1260 |

```
gccgctatct gtgctgaacg tggtatcgca acttgcgtac tgctgggtaa tccggcagag   1320
atcaaccgtg ttgcagcgtc tcagggtgta gaactgggtg cagggattga aatcgttgat   1380
ccagaagtgg ttcgcgaaag ctatgttggt cgtctggtcg aactgcgtaa gaacaaaggc   1440
atgaccgaaa ccgttgcccg cgaacagctg gaagacaacg tggtgctcgg tacgctgatg   1500
ctggaacagg atgaagttga tggtctggtt tccggtgctg ttcacactac cgcaaacacc   1560
atccgtccgc cgctgcagct gatcaaaact gcaccgggca gctccctggt atcttccgtg   1620
ttcttcatgc tgctgccgga acaggtttac gtttacggtg actgtgcgat caacccggat   1680
ccgaccgctg aacagctggc agaaatcgcg attcagtccg ctgattccgc tgcggccttc   1740
ggtatcgaac cgcgcgttgc tatgctctcc tactccaccg gtacttctgg tgcaggtagc   1800
gacgtagaaa aagttcgcga agcaactcgt ctggcgcagg aaaaacgtcc tgacctgatg   1860
atcgacggtc cgctgcagta cgacgctgcg gtaatggctg acgttgcgaa atccaaagcg   1920
ccgaactctc cggttgcagg tcgcgctacc gtgttcatct cccggatct gaacaccggt   1980 aacaccacct acaaagcggt acagcgttct gccgacctga tctccatcgg gccgatgctg   2040
cagggtatgc gcaagccggt taacgacctg tcccgtggcg cactggttga cgatatcgtc   2100
tacaccatcg cgctgactgc gattcagtct gcacagcagc agtaa              2145
```

<210> SEQ ID NO 48
<211> LENGTH: 714
<212> TYPE: PRT
<213> ORGANISM: Artificial Sequence
<220> FEATURE:
<223> OTHER INFORMATION: Synthetic Polypeptide

<400> SEQUENCE: 48

```
Val Ser Arg Ile Ile Met Leu Ile Pro Thr Gly Thr Ser Val Gly Leu
1               5                   10                  15

Thr Ser Val Ser Leu Gly Val Ile Arg Ala Met Glu Arg Lys Gly Val
            20                  25                  30

Arg Leu Ser Val Phe Lys Pro Ile Ala Gln Pro Arg Thr Gly Gly Asp
        35                  40                  45

Ala Pro Asp Gln Thr Thr Thr Ile Val Arg Ala Asn Ser Ser Thr Thr
    50                  55                  60

Thr Ala Ala Glu Pro Leu Lys Met Ser Tyr Val Glu Gly Leu Leu Ser
65                  70                  75                  80

Ser Asn Gln Lys Asp Val Leu Met Glu Glu Ile Val Ala Asn Tyr His
                85                  90                  95

Ala Asn Thr Lys Asp Ala Glu Val Val Leu Val Glu Gly Leu Val Pro
            100                 105                 110

Thr Arg Lys His Gln Phe Ala Gln Ser Leu Asn Tyr Glu Ile Ala Lys
        115                 120                 125

Thr Leu Asn Ala Glu Ile Val Phe Val Met Ser Gln Gly Thr Asp Thr
    130                 135                 140

Pro Glu Gln Leu Lys Glu Arg Ile Glu Leu Thr Arg Asn Ser Phe Gly
145                 150                 155                 160

Gly Ala Lys Asn Thr Asn Ile Thr Gly Val Ile Val Asn Lys Leu Asn
                165                 170                 175

Ala Pro Val Asp Glu Gln Gly Arg Thr Arg Pro Asp Leu Ser Glu Ile
            180                 185                 190

Phe Asp Asp Ser Ser Lys Ala Lys Val Asn Asn Val Asp Pro Ala Lys
        195                 200                 205
```

```
Leu Gln Glu Ser Ser Pro Leu Pro Val Leu Gly Ala Val Pro Trp Ser
        210                 215                 220

Phe Asp Leu Ile Ala Thr Arg Ala Ile Asp Met Ala Arg His Leu Asn
225                 230                 235                 240

Ala Thr Ile Ile Asn Glu Gly Asp Ile Asn Thr Arg Arg Val Lys Ser
                245                 250                 255

Val Thr Phe Cys Ala Arg Ser Ile Pro His Met Leu Glu His Phe Arg
                260                 265                 270

Ala Gly Ser Leu Leu Val Thr Ser Ala Asp Arg Pro Asp Val Leu Val
            275                 280                 285

Ala Ala Cys Leu Ala Ala Met Asn Gly Val Glu Ile Gly Ala Leu Leu
            290                 295                 300

Leu Thr Gly Gly Tyr Glu Met Asp Ala Arg Ile Ser Lys Leu Cys Glu
305                 310                 315                 320

Arg Ala Phe Ala Thr Gly Leu Pro Val Phe Met Val Asn Thr Asn Thr
                325                 330                 335

Trp Gln Thr Ser Leu Ser Leu Gln Ser Phe Asn Leu Glu Val Pro Val
                340                 345                 350

Asp Asp His Glu Arg Ile Glu Lys Val Gln Glu Tyr Val Ala Asn Tyr
            355                 360                 365

Ile Asn Ala Asp Trp Ile Glu Ser Leu Thr Ala Thr Ser Glu Arg Ser
370                 375                 380

Arg Arg Leu Ser Pro Pro Ala Phe Arg Tyr Gln Leu Thr Glu Leu Ala
385                 390                 395                 400

Arg Lys Ala Gly Lys Arg Ile Val Leu Pro Glu Gly Asp Glu Pro Arg
                405                 410                 415

Thr Val Lys Ala Ala Ala Ile Cys Ala Glu Arg Gly Ile Ala Thr Cys
                420                 425                 430

Val Leu Leu Gly Asn Pro Ala Glu Ile Asn Arg Val Ala Ala Ser Gln
            435                 440                 445

Gly Val Glu Leu Gly Ala Gly Ile Glu Ile Val Asp Pro Glu Val Val
            450                 455                 460

Arg Glu Ser Tyr Val Gly Arg Leu Val Glu Leu Arg Lys Asn Lys Gly
465                 470                 475                 480

Met Thr Glu Thr Val Ala Arg Glu Gln Leu Glu Asp Asn Val Val Leu
                485                 490                 495

Gly Thr Leu Met Leu Glu Gln Asp Glu Val Asp Gly Leu Val Ser Gly
            500                 505                 510

Ala Val His Thr Thr Ala Asn Thr Ile Arg Pro Pro Leu Gln Leu Ile
            515                 520                 525

Lys Thr Ala Pro Gly Ser Ser Leu Val Ser Ser Val Phe Phe Met Leu
530                 535                 540

Leu Pro Glu Gln Val Tyr Val Tyr Gly Asp Cys Ala Ile Asn Pro Asp
545                 550                 555                 560

Pro Thr Ala Glu Gln Leu Ala Glu Ile Ala Ile Gln Ser Ala Asp Ser
                565                 570                 575

Ala Ala Ala Phe Gly Ile Glu Pro Arg Val Ala Met Leu Ser Tyr Ser
            580                 585                 590

Thr Gly Thr Ser Gly Ala Gly Ser Asp Val Glu Lys Val Arg Glu Ala
            595                 600                 605

Thr Arg Leu Ala Gln Glu Lys Arg Pro Asp Leu Met Ile Asp Gly Pro
610                 615                 620

Leu Gln Tyr Asp Ala Ala Val Met Ala Asp Val Ala Lys Ser Lys Ala
```

```
                625                 630                 635                 640
Pro Asn Ser Pro Val Ala Gly Arg Ala Thr Val Phe Ile Phe Pro Asp
                    645                 650                 655
Leu Asn Thr Gly Asn Thr Thr Tyr Lys Ala Val Gln Arg Ser Ala Asp
                660                 665                 670
Leu Ile Ser Ile Gly Pro Met Leu Gln Gly Met Arg Lys Pro Val Asn
            675                 680                 685
Asp Leu Ser Arg Gly Ala Leu Val Asp Asp Ile Val Tyr Thr Ile Ala
        690                 695                 700
Leu Thr Ala Ile Gln Ser Ala Gln Gln Gln
705                 710

<210> SEQ ID NO 49
<211> LENGTH: 2169
<212> TYPE: DNA
<213> ORGANISM: Artificial Sequence
<220> FEATURE:
<223> OTHER INFORMATION: Synthetic Oligonucleotide

<400> SEQUENCE: 49
gtgtcccgta ttattatgct gatccctacc ggaaccagcg tcggtctgac cagcgtcagc      60
cttggcgtga tccgtgcaat ggaacgcaaa ggcgttcgtc tgagcgtttt caaacctatc     120
gctcagccgc gtaccggtgg cgatgcgccc gatcagacta cgactatcgt gcgtgcgaac     180
tcttccacca cgacggccgc tgaaccgctg aaaatgagct acgttgaagg tctgctttcc     240
agcaatcaga aagatgtgct gatggaagag atcgtcgcaa actaccacgc taacaccaaa     300
gacgctgaag tcgttctggt tgaaggtctg gtcccgacac gtaagcacca gtttgcccag     360
tctctgaact acgaaatcgc taaaacgctg aatgcggaaa tcgtcttcgt tatgtctcag     420
ggcactgaca ccccggaaca gctgaaagag cgtatcgaac tgacccgcaa cagcttcggc     480
ggtgccaaaa acaccaacat caccggcgtt atcgttaaca aactgaacgc accggttgat     540
gaacagggtc gtactcgccc ggatctgtcc gagattttcg acgactcttc caaagctaaa     600
gtaaacaatg ttgatccggc gaagctgcaa gaatccagcc cgctgccggt tctcggcgct     660
gtgccgtgga gctttgacct gatcgcgact cgtgcgatcg atatggctcg ccacctgaat     720
gcgaccatca tcaacgaagg cgacatcaat actcgccgcg ttaaatccgt cactttctgc     780
gcacgcagca ttccgcacat gctggagcac ttccgtgccg gttctctgct ggtgacttcc     840
gcagaccgtc ctgacgtgct ggtggccgct tgcctggcag ccatgaacgg cgtagaaatc     900
ggtgccctgc tgctgactgg cggttacgaa atggacgcgc gcatttctaa actgtgcgaa     960
cgtgctttcg ctaccggcct gccggtattt atggtgaaca ccaacacctg gcagacctct    1020
ctgagcctgc agagcttcaa cctggaagtt ccggttgacg atcacgaacg tatcgagaaa    1080
gttcaggaat acgttgctaa ctacatcaac gctgactgga tcgaatctct gactgccact    1140
tctctggaag tgctgtttca gggtccggag cgcagccgtc gtctgtctcc gcctgcgttc    1200
cgttatcagc tgactgaact tgcgcgcaaa gcgggcaaac gtatcgtact gccggaaggt    1260
gacgaaccgc gtaccgttaa agcagccgct atctgtgctg aacgtggtat cgcaacttgc    1320
gtactgctgg gtaatccggc agagatcaac cgtgttgcag cgtctcaggg tgtagaactg    1380
ggtgcaggga ttgaaatcgt tgatccagaa gtggttcgcg aaagctatgt tggtcgtctg    1440
gtcgaactgc gtaagaacaa aggcatgacc gaaaccgttg cccgcgaaca gctgaagac     1500
aacgtggtgc tcggtacgct gatgctggaa caggatgaag ttgatggtct ggtttccggt    1560
```

-continued

```
gctgttcaca ctaccgcaaa caccatccgt ccgccgctgc agctgatcaa aactgcaccg    1620
ggcagctccc tggtatcttc cgtgttcttc atgctgctgc cggaacaggt ttacgtttac    1680
ggtgactgtg cgatcaaccc ggatccgacc gctgaacagc tggcagaaat cgcgattcag    1740
tccgctgatt ccgctgcggc cttcggtatc gaaccgcgcg ttgctatgct ctcctactcc    1800
accggtactt ctggtgcagg tagcgacgta gaaaaagttc gcgaagcaac tcgtctggcg    1860
caggaaaaac gtcctgacct gatgatcgac ggtccgctgc agtacgacgc tgcggtaatg    1920
gctgacgttg cgaaatccaa agcgccgaac tctccggttg caggtcgcgc taccgtgttc    1980
atcttcccgg atctgaacac cggtaacacc acctacaaag cggtacagcg ttctgccgac    2040
ctgatctcca tcgggccgat gctgcagggt atgcgcaagc cggttaacga cctgtcccgt    2100
ggcgcactgg ttgacgatat cgtctacacc atcgcgctga ctgcgattca gtctgcacag    2160
cagcagtaa                                                            2169
```

<210> SEQ ID NO 50
<211> LENGTH: 722
<212> TYPE: PRT
<213> ORGANISM: Artificial Sequence
<220> FEATURE:
<223> OTHER INFORMATION: Synthetic Polypeptide

<400> SEQUENCE: 50

```
Val Ser Arg Ile Ile Met Leu Ile Pro Thr Gly Thr Ser Val Gly Leu
1               5                   10                  15

Thr Ser Val Ser Leu Gly Val Ile Arg Ala Met Glu Arg Lys Gly Val
            20                  25                  30

Arg Leu Ser Val Phe Lys Pro Ile Ala Gln Pro Arg Thr Gly Gly Asp
        35                  40                  45

Ala Pro Asp Gln Thr Thr Thr Ile Val Arg Ala Asn Ser Ser Thr Thr
    50                  55                  60

Thr Ala Ala Glu Pro Leu Lys Met Ser Tyr Val Glu Gly Leu Leu Ser
65                  70                  75                  80

Ser Asn Gln Lys Asp Val Leu Met Glu Glu Ile Val Ala Asn Tyr His
                85                  90                  95

Ala Asn Thr Lys Asp Ala Glu Val Val Leu Val Glu Gly Leu Val Pro
            100                 105                 110

Thr Arg Lys His Gln Phe Ala Gln Ser Leu Asn Tyr Glu Ile Ala Lys
        115                 120                 125

Thr Leu Asn Ala Glu Ile Val Phe Val Met Ser Gln Gly Thr Asp Thr
    130                 135                 140

Pro Glu Gln Leu Lys Glu Arg Ile Glu Leu Thr Arg Asn Ser Phe Gly
145                 150                 155                 160

Gly Ala Lys Asn Thr Asn Ile Thr Gly Val Ile Val Asn Lys Leu Asn
                165                 170                 175

Ala Pro Val Asp Glu Gln Gly Arg Thr Arg Pro Asp Leu Ser Glu Ile
            180                 185                 190

Phe Asp Asp Ser Ser Lys Ala Lys Val Asn Asn Val Asp Pro Ala Lys
        195                 200                 205

Leu Gln Glu Ser Ser Pro Leu Pro Val Leu Gly Ala Val Pro Trp Ser
    210                 215                 220

Phe Asp Leu Ile Ala Thr Arg Ala Ile Asp Met Ala Arg His Leu Asn
225                 230                 235                 240

Ala Thr Ile Ile Asn Glu Gly Asp Ile Asn Thr Arg Arg Val Lys Ser
                245                 250                 255
```

```
Val Thr Phe Cys Ala Arg Ser Ile Pro His Met Leu Glu His Phe Arg
            260                 265                 270

Ala Gly Ser Leu Leu Val Thr Ser Ala Asp Arg Pro Asp Val Leu Val
            275                 280                 285

Ala Ala Cys Leu Ala Ala Met Asn Gly Val Glu Ile Gly Ala Leu Leu
            290                 295                 300

Leu Thr Gly Gly Tyr Glu Met Asp Ala Arg Ile Ser Lys Leu Cys Glu
305                 310                 315                 320

Arg Ala Phe Ala Thr Gly Leu Pro Val Phe Met Val Asn Thr Asn Thr
                325                 330                 335

Trp Gln Thr Ser Leu Ser Leu Gln Ser Phe Asn Leu Glu Val Pro Val
            340                 345                 350

Asp Asp His Glu Arg Ile Glu Lys Val Gln Glu Tyr Val Ala Asn Tyr
            355                 360                 365

Ile Asn Ala Asp Trp Ile Glu Ser Leu Thr Ala Thr Ser Leu Glu Val
            370                 375                 380

Leu Phe Gln Gly Pro Glu Arg Ser Arg Arg Leu Ser Pro Pro Ala Phe
385                 390                 395                 400

Arg Tyr Gln Leu Thr Glu Leu Ala Arg Lys Ala Gly Lys Arg Ile Val
                405                 410                 415

Leu Pro Glu Gly Asp Glu Pro Arg Thr Val Lys Ala Ala Ile Cys
                420                 425                 430

Ala Glu Arg Gly Ile Ala Thr Cys Val Leu Leu Gly Asn Pro Ala Glu
            435                 440                 445

Ile Asn Arg Val Ala Ala Ser Gln Gly Val Glu Leu Gly Ala Gly Ile
            450                 455                 460

Glu Ile Val Asp Pro Glu Val Val Arg Glu Ser Tyr Val Gly Arg Leu
465                 470                 475                 480

Val Glu Leu Arg Lys Asn Lys Gly Met Thr Glu Thr Val Ala Arg Glu
                485                 490                 495

Gln Leu Glu Asp Asn Val Val Leu Gly Thr Leu Met Leu Glu Gln Asp
            500                 505                 510

Glu Val Asp Gly Leu Val Ser Gly Ala Val His Thr Thr Ala Asn Thr
            515                 520                 525

Ile Arg Pro Pro Leu Gln Leu Ile Lys Thr Ala Pro Gly Ser Ser Leu
            530                 535                 540

Val Ser Ser Val Phe Phe Met Leu Leu Pro Glu Gln Val Tyr Val Tyr
545                 550                 555                 560

Gly Asp Cys Ala Ile Asn Pro Asp Pro Thr Ala Glu Gln Leu Ala Glu
                565                 570                 575

Ile Ala Ile Gln Ser Ala Asp Ser Ala Ala Phe Gly Ile Glu Pro
            580                 585                 590

Arg Val Ala Met Leu Ser Tyr Ser Thr Gly Thr Ser Gly Ala Gly Ser
            595                 600                 605

Asp Val Glu Lys Val Arg Glu Ala Thr Arg Leu Ala Gln Glu Lys Arg
            610                 615                 620

Pro Asp Leu Met Ile Asp Gly Pro Leu Gln Tyr Asp Ala Ala Val Met
625                 630                 635                 640

Ala Asp Val Ala Lys Ser Lys Ala Pro Asn Ser Pro Val Ala Gly Arg
                645                 650                 655

Ala Thr Val Phe Ile Phe Pro Asp Leu Asn Thr Gly Asn Thr Thr Tyr
            660                 665                 670
```

Lys Ala Val Gln Arg Ser Ala Asp Leu Ile Ser Ile Gly Pro Met Leu
        675                 680                 685

Gln Gly Met Arg Lys Pro Val Asn Asp Leu Ser Arg Gly Ala Leu Val
    690                 695                 700

Asp Asp Ile Val Tyr Thr Ile Ala Leu Thr Ala Ile Gln Ser Ala Gln
705                 710                 715                 720

Gln Gln

<210> SEQ ID NO 51
<211> LENGTH: 2169
<212> TYPE: DNA
<213> ORGANISM: Artificial Sequence
<220> FEATURE:
<223> OTHER INFORMATION: Synthetic Oligonucleotide

<400> SEQUENCE: 51

```
gtgtcccgta ttattatgct gatccctacc ggaaccagcg tcggtctgac cagcgtcagc      60
cttggcgtga tccgtgcaat ggaacgcaaa ggcgttcgtc tgagcgtttt caaacctatc     120
gctcagccgc gtaccggtgg cgatgcgccc gatcagacta cgactatcgt gcgtgcgaac     180
tcttccacca cgacggccgc tgaaccgctg aaaatgagct acgttgaagg tctgctttcc     240
agcaatcaga aagatgtgct gatggaagag atcgtcgcaa actaccacgc taacaccaaa     300
gacgctgaag tcgttctggt tgaaggtctg gtcccgacac gtaagcacca gtttgcccag     360
tctctgaact acgaaatcgc taaaacgctg aatgcggaaa tcgtcttcgt tatgtctcag     420
ggcactgaca ccccggaaca gctgaaagag cgtatcgaac tgaccgcaa cagcttcggc      480
ggtgccaaaa acaccaacat caccggcgtt atcgttaaca aactgaacgc accggttgat     540
gaacagggtc gtactcgccc ggatctgtcc gagattttcg acgactcttc aaagctaaa     600
gtaaacaatg ttgatccggc gaagctgcaa gaatccagcc cgctgccggt tctcggcgct     660
gtgccgtgga gctttgacct gatcgcgact cgtgcgatcg atatggctcg ccacctgaat     720
gcgaccatca tcaacgaagg cgacatcaat actcgccgcg ttaaatccgt cactttctgc     780
gcacgcagca ttccgcacat gctggagcac ttccgtgccg ttctctgct ggtgacttcc      840
gcagaccgtc ctgacgtgct ggtggccgct tgcctggcag ccatgaacgg cgtagaaatc     900
ggtgccctgc tgctgactgg cggttacgaa atggacgcgc gcatttctaa actgtgcgaa     960
cgtgctttcg ctaccggcct gccggtattt atggtgaaca ccaacacctg cagacctct    1020
ctgagcctgc agagcttcaa cctggaagtt ccggttgacg atcacgaacg tatcgagaaa    1080
gttcaggaat acgttgctaa ctacatcaac gctgactgga tcgaatctct gactgccact    1140
tctgagctgg aagtgctgtt tcagggtccg cgcagccgtc gtctgtctcc gcctgcgttc    1200
cgttatcagc tgactgaact tgcgcgcaaa gcgggcaaac gtatcgtact gccggaaggt    1260
gacgaaccgc gtaccgttaa agcagccgct atctgtgctg aacgtggtat cgcaacttgc    1320
gtactgctgg gtaatccggc agagatcaac cgtgttgcag cgtctcaggg tgtagaactg    1380
ggtgcaggga ttgaaatcgt tgatccagaa gtggttcgcg aaagctatgt tggtcgtctg    1440
gtcgaactgc gtaagaacaa aggcatgacc gaaaccgttg cccgcgaaca gctggaagac    1500
aacgtggtgc tcggtacgct gatgctggaa caggatgaag ttgatggtct ggtttccggt    1560
gctgttcaca ctaccgcaaa accatccgt ccgccgctgc agctgatcaa aactgcaccg    1620
ggcagctccc tggtatcttc cgtgttcttc atgctgctgc cggaacaggt ttacgtttac    1680
ggtgactgtg cgatcaaccc ggatccgacc gctgaacagc tggcagaaat cgcgattcag    1740
```

```
tccgctgatt ccgctgcggc cttcggtatc gaaccgcgcg ttgctatgct ctcctactcc    1800
accggtactt ctggtgcagg tagcgacgta gaaaaagttc gcgaagcaac tcgtctggcg    1860
caggaaaaac gtcctgacct gatgatcgac ggtccgctgc agtacgacgc tgcggtaatg    1920
gctgacgttg cgaaatccaa agcgccgaac tctccggttg caggtcgcgc taccgtgttc    1980
atcttcccgg atctgaacac cggtaacacc acctacaaag cggtacagcg ttctgccgac    2040
ctgatctcca tcgggccgat gctgcagggt atgcgcaagc cggttaacga cctgtcccgt    2100
ggcgcactgg ttgacgatat cgtctacacc atcgcgctga ctgcgattca gtctgcacag    2160
cagcagtaa                                                            2169
```

<210> SEQ ID NO 52
<211> LENGTH: 722
<212> TYPE: PRT
<213> ORGANISM: Artificial Sequence
<220> FEATURE:
<223> OTHER INFORMATION: Synthetic Polypeptide

<400> SEQUENCE: 52

```
Val Ser Arg Ile Ile Met Leu Ile Pro Thr Gly Thr Ser Val Gly Leu
1               5                   10                  15

Thr Ser Val Ser Leu Gly Val Ile Arg Ala Met Glu Arg Lys Gly Val
                20                  25                  30

Arg Leu Ser Val Phe Lys Pro Ile Ala Gln Pro Arg Thr Gly Gly Asp
            35                  40                  45

Ala Pro Asp Gln Thr Thr Thr Ile Val Arg Ala Asn Ser Ser Thr Thr
        50                  55                  60

Thr Ala Ala Glu Pro Leu Lys Met Ser Tyr Val Glu Gly Leu Leu Ser
65                  70                  75                  80

Ser Asn Gln Lys Asp Val Leu Met Glu Glu Ile Val Ala Asn Tyr His
                85                  90                  95

Ala Asn Thr Lys Asp Ala Glu Val Val Leu Val Glu Gly Leu Val Pro
            100                 105                 110

Thr Arg Lys His Gln Phe Ala Gln Ser Leu Asn Tyr Glu Ile Ala Lys
        115                 120                 125

Thr Leu Asn Ala Glu Ile Val Phe Val Met Ser Gln Gly Thr Asp Thr
130                 135                 140

Pro Glu Gln Leu Lys Glu Arg Ile Glu Leu Thr Arg Asn Ser Phe Gly
145                 150                 155                 160

Gly Ala Lys Asn Thr Asn Ile Thr Gly Val Ile Val Asn Lys Leu Asn
                165                 170                 175

Ala Pro Val Asp Glu Gln Gly Arg Thr Arg Pro Asp Leu Ser Glu Ile
            180                 185                 190

Phe Asp Asp Ser Ser Lys Ala Lys Val Asn Asn Val Pro Ala Lys
        195                 200                 205

Leu Gln Glu Ser Ser Pro Leu Pro Val Leu Gly Ala Val Pro Trp Ser
210                 215                 220

Phe Asp Leu Ile Ala Thr Arg Ala Ile Asp Met Ala Arg His Leu Asn
225                 230                 235                 240

Ala Thr Ile Ile Asn Glu Gly Asp Ile Asn Thr Arg Arg Val Lys Ser
                245                 250                 255

Val Thr Phe Cys Ala Arg Ser Ile Pro His Met Leu Glu His Phe Arg
            260                 265                 270

Ala Gly Ser Leu Leu Val Thr Ser Ala Asp Arg Pro Asp Val Leu Val
        275                 280                 285
```

```
Ala Ala Cys Leu Ala Ala Met Asn Gly Val Glu Ile Gly Ala Leu Leu
        290                 295                 300

Leu Thr Gly Gly Tyr Glu Met Asp Ala Arg Ile Ser Lys Leu Cys Glu
305                 310                 315                 320

Arg Ala Phe Ala Thr Gly Leu Pro Val Phe Met Val Asn Thr Asn Thr
                325                 330                 335

Trp Gln Thr Ser Leu Ser Leu Gln Ser Phe Asn Leu Glu Val Pro Val
                340                 345                 350

Asp Asp His Glu Arg Ile Glu Lys Val Gln Glu Tyr Val Ala Asn Tyr
            355                 360                 365

Ile Asn Ala Asp Trp Ile Glu Ser Leu Thr Ala Thr Ser Glu Leu Glu
370                 375                 380

Val Leu Phe Gln Gly Pro Arg Ser Arg Arg Leu Ser Pro Pro Ala Phe
385                 390                 395                 400

Arg Tyr Gln Leu Thr Glu Leu Ala Arg Lys Ala Gly Lys Arg Ile Val
                405                 410                 415

Leu Pro Glu Gly Asp Glu Pro Arg Thr Val Lys Ala Ala Ile Cys
                420                 425                 430

Ala Glu Arg Gly Ile Ala Thr Cys Val Leu Leu Gly Asn Pro Ala Glu
            435                 440                 445

Ile Asn Arg Val Ala Ala Ser Gln Gly Val Glu Leu Gly Ala Gly Ile
450                 455                 460

Glu Ile Val Asp Pro Glu Val Val Arg Glu Ser Tyr Val Gly Arg Leu
465                 470                 475                 480

Val Glu Leu Arg Lys Asn Lys Gly Met Thr Glu Thr Val Ala Arg Glu
                485                 490                 495

Gln Leu Glu Asp Asn Val Val Leu Gly Thr Leu Met Leu Glu Gln Asp
                500                 505                 510

Glu Val Asp Gly Leu Val Ser Gly Ala Val His Thr Ala Asn Thr
            515                 520                 525

Ile Arg Pro Pro Leu Gln Leu Ile Lys Thr Ala Pro Gly Ser Ser Leu
530                 535                 540

Val Ser Ser Val Phe Phe Met Leu Leu Pro Glu Gln Val Tyr Val Tyr
545                 550                 555                 560

Gly Asp Cys Ala Ile Asn Pro Asp Pro Thr Ala Glu Gln Leu Ala Glu
                565                 570                 575

Ile Ala Ile Gln Ser Ala Asp Ser Ala Ala Phe Gly Ile Glu Pro
                580                 585                 590

Arg Val Ala Met Leu Ser Tyr Ser Thr Gly Thr Ser Gly Ala Gly Ser
                595                 600                 605

Asp Val Glu Lys Val Arg Glu Ala Thr Arg Leu Ala Gln Glu Lys Arg
610                 615                 620

Pro Asp Leu Met Ile Asp Gly Pro Leu Gln Tyr Asp Ala Ala Val Met
625                 630                 635                 640

Ala Asp Val Ala Lys Ser Lys Ala Pro Asn Ser Pro Val Ala Gly Arg
                645                 650                 655

Ala Thr Val Phe Ile Phe Pro Asp Leu Asn Thr Gly Asn Thr Thr Tyr
                660                 665                 670

Lys Ala Val Gln Arg Ser Ala Asp Leu Ile Ser Ile Gly Pro Met Leu
            675                 680                 685

Gln Gly Met Arg Lys Pro Val Asn Asp Leu Ser Arg Gly Ala Leu Val
            690                 695                 700
```

Asp Asp Ile Val Tyr Thr Ile Ala Leu Thr Ala Ile Gln Ser Ala Gln
705                 710                 715                 720

Gln Gln

<210> SEQ ID NO 53
<211> LENGTH: 2166
<212> TYPE: DNA
<213> ORGANISM: Artificial Sequence
<220> FEATURE:
<223> OTHER INFORMATION: Synthetic Oligonucleotide

<400> SEQUENCE: 53

| | | | | |
|---|---|---|---|---|
| gtgtcccgta | ttattatgct | gatccctacc | ggaaccagcg | tcggtctgac cagcgtcagc | 60 |
| cttggcgtga | tccgtgcaat | ggaacgcaaa | ggcgttcgtc | tgagcgtttt caaacctatc | 120 |
| gctcagccgc | gtaccggtgg | cgatgcgccc | gatcagacta | cgactatcgt gcgtgcgaac | 180 |
| tcttccacca | cgacggccgc | tgaaccgctg | aaaatgagct | acgttgaagg tctgctttcc | 240 |
| agcaatcaga | agatgtgct | gatggaagag | atcgtcgcaa | actaccacgc taacaccaaa | 300 |
| gacgctgaag | tcgttctggt | tgaaggtctg | gtcccgacac | gtaagcacca gtttgcccag | 360 |
| tctctgaact | acgaaatcgc | taaaacgctg | aatgcgaaaa | tcgtcttcgt tatgtctcag | 420 |
| ggcactgaca | ccccggaaca | gctgaaagag | cgtatcgaac | tgacccgcaa cagcttcggc | 480 |
| ggtgccaaaa | acaccaacat | caccggcgtt | atcgttaaca | aactgaacgc accggttgat | 540 |
| gaacagggtc | gtactcgccc | ggatctgtcc | gagattttcg | acgactcttc caaagctaaa | 600 |
| gtaaacaatg | ttgatccggc | gaagctgcaa | gaatccagcc | cgctgccggt tctcggcgct | 660 |
| gtgccgtgga | gctttgacct | gatcgcgact | cgtgcgatcg | atatggctcg ccacctgaat | 720 |
| gcgaccatca | tcaacgaagg | cgacatcaat | actcgccgcg | ttaaatccgt cactttctgc | 780 |
| gcacgcagca | ttccgcacat | gctggagcac | ttccgtgccg | ttctctgct ggtgacttcc | 840 |
| gcagaccgtc | ctgacgtgct | ggtggccgct | tgcctggcag | ccatgaacgg cgtagaaatc | 900 |
| ggtgccctgc | tgctgactgg | cggttacgaa | atggacgcgc | gcatttctaa actgtgcgaa | 960 |
| cgtgctttcg | ctaccggcct | gccggtattt | atggtgaaca | ccaacacctg gcagacctct | 1020 |
| ctgagcctgc | agagcttcaa | cctggaagtt | ccggttgacg | atcacgaacg tatcgagaaa | 1080 |
| gttcaggaat | acgttgctaa | ctacatcaac | gctgactgga | tcgaatctct gactgccact | 1140 |
| tctgagcgca | gccgtcgtct | ggaagtgctg | tttcagggtc | cgtctccgcc tgcgttccgt | 1200 |
| tatcagctga | ctgaacttgc | gcgcaaagcg | ggcaaacgta | tcgtactgcc ggaaggtgac | 1260 |
| gaaccgcgta | ccgttaaagc | agccgctatc | tgtgctgaac | gtggtatcgc aacttgcgta | 1320 |
| ctgctgggta | tccggcaga | gatcaaccgt | gttgcagcgt | ctcagggtgt gaactgggt | 1380 |
| gcagggattg | aaatcgttga | tccagaagtg | gttcgcgaaa | gctatgttgg tcgtctggtc | 1440 |
| gaactgcgta | agaacaaagg | catgaccgaa | accgttgccc | gcgaacagct ggaagacaac | 1500 |
| gtggtgctcg | gtacgctgat | gctggaacag | gatgaagttg | atggtctggt ttccggtgct | 1560 |
| gttcacacta | ccgcaaacac | catccgtccg | ccgctgcagc | tgatcaaaac tgcaccgggc | 1620 |
| agctccctgg | tatcttccgt | gttcttcatg | ctgctgccgg | aacaggttta cgtttacggt | 1680 |
| gactgtgcga | tcaacccgga | tccgaccgct | gaacagctgg | cagaaatcgc gattcagtcc | 1740 |
| gctgattccg | ctgcggcctt | cggtatcgaa | ccgcgcgttg | ctatgctctc ctactccacc | 1800 |
| ggtacttctg | gtgcaggtag | cgacgtgaaa | aagttcgcg | aagcaactcg tctggcgcag | 1860 |
| gaaaaacgtc | ctgacctgat | gatcgacggt | ccgctgcagt | acgacgctgc ggtaatggct | 1920 |

```
gacgttgcga aatccaaagc gccgaactct ccggttgcag gtcgcgctac cgtgttcatc    1980
ttcccggatc tgaacaccgg taacaccacc tacaaagcgg tacagcgttc tgccgacctg    2040
atctccatcg ggccgatgct gcagggtatg cgcaagccgg ttaacgacct gtcccgtggc    2100
gcactggttg acgatatcgt ctacaccatc gcgctgactg cgattcagtc tgcacagcag    2160
cagtaa                                                                2166
```

<210> SEQ ID NO 54
<211> LENGTH: 721
<212> TYPE: PRT
<213> ORGANISM: Artificial Sequence
<220> FEATURE:
<223> OTHER INFORMATION: Synthetic Polypeptide

<400> SEQUENCE: 54

```
Val Ser Arg Ile Ile Met Leu Ile Pro Thr Gly Thr Ser Val Gly Leu
1               5                   10                  15

Thr Ser Val Ser Leu Gly Val Ile Arg Ala Met Glu Arg Lys Gly Val
            20                  25                  30

Arg Leu Ser Val Phe Lys Pro Ile Ala Gln Pro Arg Thr Gly Gly Asp
        35                  40                  45

Ala Pro Asp Gln Thr Thr Thr Ile Val Arg Ala Asn Ser Ser Thr Thr
    50                  55                  60

Thr Ala Ala Glu Pro Leu Lys Met Ser Tyr Val Glu Gly Leu Leu Ser
65                  70                  75                  80

Ser Asn Gln Lys Asp Val Leu Met Glu Glu Ile Val Ala Asn Tyr His
                85                  90                  95

Ala Asn Thr Lys Asp Ala Glu Val Val Leu Val Glu Gly Leu Val Pro
            100                 105                 110

Thr Arg Lys His Gln Phe Ala Gln Ser Leu Asn Tyr Glu Ile Ala Lys
        115                 120                 125

Thr Leu Asn Ala Glu Ile Val Phe Val Met Ser Gln Gly Thr Asp Thr
    130                 135                 140

Pro Glu Gln Leu Lys Glu Arg Ile Glu Leu Thr Arg Asn Ser Phe Gly
145                 150                 155                 160

Gly Ala Lys Asn Thr Asn Ile Thr Gly Val Ile Val Asn Lys Leu Asn
                165                 170                 175

Ala Pro Val Asp Glu Gln Gly Arg Thr Arg Pro Asp Leu Ser Glu Ile
            180                 185                 190

Phe Asp Asp Ser Ser Lys Ala Lys Val Asn Asn Val Asp Pro Ala Lys
        195                 200                 205

Leu Gln Glu Ser Ser Pro Leu Pro Val Leu Gly Ala Val Pro Trp Ser
    210                 215                 220

Phe Asp Leu Ile Ala Thr Arg Ala Ile Asp Met Ala Arg His Leu Asn
225                 230                 235                 240

Ala Thr Ile Ile Asn Glu Gly Asp Ile Asn Thr Arg Arg Val Lys Ser
                245                 250                 255

Val Thr Phe Cys Ala Arg Ser Ile Pro His Met Leu Glu His Phe Arg
            260                 265                 270

Ala Gly Ser Leu Leu Val Thr Ser Ala Asp Arg Pro Asp Val Leu Val
        275                 280                 285

Ala Ala Cys Leu Ala Ala Met Asn Gly Val Glu Ile Gly Ala Leu Leu
    290                 295                 300

Leu Thr Gly Gly Tyr Glu Met Asp Ala Arg Ile Ser Lys Leu Cys Glu
305                 310                 315                 320
```

-continued

Arg Ala Phe Ala Thr Gly Leu Pro Val Phe Met Val Asn Thr Asn Thr
            325                 330                 335

Trp Gln Thr Ser Leu Ser Leu Gln Ser Phe Asn Leu Glu Val Pro Val
            340                 345                 350

Asp Asp His Glu Arg Ile Glu Lys Val Gln Glu Tyr Val Ala Asn Tyr
            355                 360                 365

Ile Asn Ala Asp Trp Ile Glu Ser Leu Thr Ala Thr Ser Glu Arg Ser
    370                 375                 380

Arg Arg Leu Glu Val Leu Phe Gln Gly Pro Ser Pro Ala Phe Arg
385                 390                 395                 400

Tyr Gln Leu Thr Glu Leu Ala Arg Lys Ala Gly Lys Arg Ile Val Leu
            405                 410                 415

Pro Glu Gly Asp Glu Pro Arg Thr Val Lys Ala Ala Ile Cys Ala
            420                 425                 430

Glu Arg Gly Ile Ala Thr Cys Val Leu Leu Gly Asn Pro Ala Glu Ile
            435                 440                 445

Asn Arg Val Ala Ala Ser Gln Gly Val Glu Leu Gly Ala Gly Ile Glu
    450                 455                 460

Ile Val Asp Pro Glu Val Val Arg Glu Ser Tyr Val Gly Arg Leu Val
465                 470                 475                 480

Glu Leu Arg Lys Asn Lys Gly Met Thr Glu Thr Val Ala Arg Glu Gln
            485                 490                 495

Leu Glu Asp Asn Val Val Leu Gly Thr Leu Met Leu Glu Gln Asp Glu
            500                 505                 510

Val Asp Gly Leu Val Ser Gly Ala Val His Thr Thr Ala Asn Thr Ile
            515                 520                 525

Arg Pro Pro Leu Gln Leu Ile Lys Thr Ala Pro Gly Ser Ser Leu Val
    530                 535                 540

Ser Ser Val Phe Phe Met Leu Leu Pro Glu Gln Val Tyr Val Tyr Gly
545                 550                 555                 560

Asp Cys Ala Ile Asn Pro Asp Pro Thr Ala Glu Gln Leu Ala Glu Ile
            565                 570                 575

Ala Ile Gln Ser Ala Asp Ser Ala Ala Ala Phe Gly Ile Glu Pro Arg
            580                 585                 590

Val Ala Met Leu Ser Tyr Ser Thr Gly Thr Ser Gly Ala Gly Ser Asp
            595                 600                 605

Val Glu Lys Val Arg Glu Ala Thr Arg Leu Ala Gln Glu Lys Arg Pro
    610                 615                 620

Asp Leu Met Ile Asp Gly Pro Leu Gln Tyr Asp Ala Ala Val Met Ala
625                 630                 635                 640

Asp Val Ala Lys Ser Lys Ala Pro Asn Ser Pro Val Ala Gly Arg Ala
            645                 650                 655

Thr Val Phe Ile Phe Pro Asp Leu Asn Thr Gly Asn Thr Thr Tyr Lys
            660                 665                 670

Ala Val Gln Arg Ser Ala Asp Leu Ile Ser Ile Gly Pro Met Leu Gln
            675                 680                 685

Gly Met Arg Lys Pro Val Asn Asp Leu Ser Arg Gly Ala Leu Val Asp
    690                 695                 700

Asp Ile Val Tyr Thr Ile Ala Leu Thr Ala Ile Gln Ser Ala Gln Gln
705                 710                 715                 720

Gln

<210> SEQ ID NO 55
<211> LENGTH: 2163
<212> TYPE: DNA
<213> ORGANISM: Artificial Sequence
<220> FEATURE:
<223> OTHER INFORMATION: Synthetic Oligonucleotide

<400> SEQUENCE: 55

| | | | | | |
|---|---|---|---|---|---|
| gtgtcccgta | ttattatgct | gatccctacc | ggaaccagcg | tcggtctgac | cagcgtcagc | 60 |
| cttggcgtga | tccgtgcaat | ggaacgcaaa | ggcgttcgtc | tgagcgtttt | caaacctatc | 120 |
| gctcagccgc | gtaccggtgg | cgatgcgccc | gatcagacta | cgactatcgt | gcgtgcgaac | 180 |
| tcttccacca | cgacggccgc | tgaaccgctg | aaaatgagct | acgttgaagg | tctgctttcc | 240 |
| agcaatcaga | agatgtgct | gatggaagag | atcgtcgcaa | actaccacgc | taacaccaaa | 300 |
| gacgctgaag | tcgttctggt | tgaaggtctg | tccccgacac | gtaagcacca | gtttgcccag | 360 |
| tctctgaact | acgaaatcgc | taaaacgctg | aatgcggaaa | tcgtcttcgt | tatgtctcag | 420 |
| ggcactgaca | ccccggaaca | gctgaaagag | cgtatcgaac | tgacccgcaa | cagcttcggc | 480 |
| ggtgccaaaa | acaccaacat | caccggcgtt | atcgttaaca | aactgaacgc | accggttgat | 540 |
| gaacagggtc | gtactcgccc | ggatctgtcc | gagattttcg | acgactcttc | caaagctaaa | 600 |
| gtaaacaatg | ttgatccggc | gaagctgcaa | gaatccagcc | cgctgccggt | tctcggcgct | 660 |
| gtgccgtgga | gctttgacct | gatcgcgact | cgtgcgatcg | atatggctcg | ccacctgaat | 720 |
| gcgaccatca | tcaacgaagg | cgacatcaat | actcgccgcg | ttaaatccgt | cactttctgc | 780 |
| gcacgcagca | ttccgcacat | gctggagcac | ttccgtgccg | gttctctgct | ggtgacttcc | 840 |
| gcagaccgtc | ctgacgtgct | ggtggccgct | tgcctggcag | ccatgaacgg | cgtagaaatc | 900 |
| ggtgccctgc | tgctgactgg | cggttacgaa | atggacgcgc | gcatttctaa | actgtgcgaa | 960 |
| cgtgctttcg | ctaccggcct | gccggtattt | atggtgaaca | ccaacacctg | gcagacctct | 1020 |
| ctgagcctgc | agagcttcaa | cctggaagtt | ccggttgacg | atcacgaacg | tatcgagaaa | 1080 |
| gttcaggaat | acgttgctaa | ctacatcaac | gctgactgga | tcgaatctct | gactgccact | 1140 |
| tctgagcgca | gccgtcgtct | gtctccgcct | gcgttccgtt | atcagctgac | tgaacttgcg | 1200 |
| cgcaaagcgg | gcaaacgtat | cgtactggaa | gtgctgtttc | agggtccgga | aggtgacgaa | 1260 |
| ccgcgtaccg | ttaaagcagc | cgctatctgt | gctgaacgtg | gtatcgcaac | ttgcgtactg | 1320 |
| ctgggtaatc | cggcagagat | caaccgtgtt | gcagcgtctc | agggtgtaga | actgggtgca | 1380 |
| gggattgaaa | tcgttgatcc | agaagtggtt | cgcgaaagct | atgttggtcg | tctggtcgaa | 1440 |
| ctgcgtaaga | acaaaggcat | gaccgaaacc | gttgcccgcg | aacagctgga | agacaacgtg | 1500 |
| gtgctcggta | cgctgatgct | ggaacaggat | gaagttgatg | gtctggtttc | cggtgctgtt | 1560 |
| cacactaccg | caaacaccat | ccgtccgccg | ctgcagctga | tcaaaactgc | accgggcagc | 1620 |
| tccctggtat | cttccgtgtt | cttcatgctg | ctgccggaac | aggtttacgt | ttacggtgac | 1680 |
| tgtgcgatca | cccggatcc | gaccgctgaa | cagctgcag | aaatcgcgat | tcagtccgct | 1740 |
| gattccgctg | cggccttcgg | tatcgaaccg | cgcgttgcta | tgctctccta | ctccaccggt | 1800 |
| acttctggtg | caggtagcga | cgtagaaaaa | gttcgcgaag | caactcgtct | ggcgcaggaa | 1860 |
| aaacgtcctg | acctgatgat | cgacggtccg | ctgcagtacg | acgctgcggt | aatggctgac | 1920 |
| gttgcgaaat | ccaaagcgcc | gaactctccg | gttgcaggtc | gcgctaccgt | gttcatcttc | 1980 |
| ccggatctga | acaccggtaa | caccacctac | aaagcggtac | agcgttctgc | cgacctgatc | 2040 |
| tccatcgggc | cgatgctgca | gggtatgcgc | aagccggtta | acgacctgtc | ccgtggcgca | 2100 |

```
ctggttgacg atatcgtcta caccatcgcg ctgactgcga ttcagtctgc acagcagcag    2160
taa                                                                   2163
```

<210> SEQ ID NO 56
<211> LENGTH: 720
<212> TYPE: PRT
<213> ORGANISM: Artificial Sequence
<220> FEATURE:
<223> OTHER INFORMATION: Synthetic Polypeptide

<400> SEQUENCE: 56

```
Val Ser Arg Ile Ile Met Leu Ile Pro Thr Gly Thr Ser Val Gly Leu
1               5                   10                  15

Thr Ser Val Ser Leu Gly Val Ile Arg Ala Met Glu Arg Lys Gly Val
            20                  25                  30

Arg Leu Ser Val Phe Lys Pro Ile Ala Gln Pro Arg Thr Gly Gly Asp
        35                  40                  45

Ala Pro Asp Gln Thr Thr Thr Ile Val Arg Ala Asn Ser Ser Thr Thr
    50                  55                  60

Thr Ala Ala Glu Pro Leu Lys Met Ser Tyr Val Gly Leu Leu Ser
65                  70                  75                  80

Ser Asn Gln Lys Asp Val Leu Met Glu Glu Ile Val Ala Asn Tyr His
                85                  90                  95

Ala Asn Thr Lys Asp Ala Glu Val Val Leu Val Glu Gly Leu Val Pro
            100                 105                 110

Thr Arg Lys His Gln Phe Ala Gln Ser Leu Asn Tyr Glu Ile Ala Lys
        115                 120                 125

Thr Leu Asn Ala Glu Ile Val Phe Val Met Ser Gln Gly Thr Asp Thr
    130                 135                 140

Pro Glu Gln Leu Lys Glu Arg Ile Glu Leu Thr Arg Asn Ser Phe Gly
145                 150                 155                 160

Gly Ala Lys Asn Thr Asn Ile Thr Gly Val Ile Val Asn Lys Leu Asn
                165                 170                 175

Ala Pro Val Asp Glu Gln Gly Arg Thr Arg Pro Asp Leu Ser Glu Ile
            180                 185                 190

Phe Asp Asp Ser Ser Lys Ala Lys Val Asn Asn Val Asp Pro Ala Lys
        195                 200                 205

Leu Gln Glu Ser Ser Pro Leu Pro Val Leu Gly Ala Val Pro Trp Ser
    210                 215                 220

Phe Asp Leu Ile Ala Thr Arg Ala Ile Asp Met Ala Arg His Leu Asn
225                 230                 235                 240

Ala Thr Ile Ile Asn Glu Gly Asp Ile Asn Thr Arg Arg Val Lys Ser
                245                 250                 255

Val Thr Phe Cys Ala Arg Ser Ile Pro His Met Leu Glu His Phe Arg
            260                 265                 270

Ala Gly Ser Leu Leu Val Thr Ser Ala Asp Arg Pro Asp Val Leu Val
        275                 280                 285

Ala Ala Cys Leu Ala Ala Met Asn Gly Val Glu Ile Gly Ala Leu Leu
    290                 295                 300

Leu Thr Gly Gly Tyr Glu Met Asp Ala Arg Ile Ser Lys Leu Cys Glu
305                 310                 315                 320

Arg Ala Phe Ala Thr Gly Leu Pro Val Phe Met Val Asn Thr Asn Thr
                325                 330                 335

Trp Gln Thr Ser Leu Ser Leu Gln Ser Phe Asn Leu Glu Val Pro Val
            340                 345                 350
```

Asp Asp His Glu Arg Ile Glu Lys Val Gln Glu Tyr Val Ala Asn Tyr
         355                 360                 365

Ile Asn Ala Asp Trp Ile Glu Ser Leu Thr Ala Thr Ser Glu Arg Ser
    370                 375                 380

Arg Arg Leu Ser Pro Pro Ala Phe Arg Tyr Gln Leu Thr Glu Leu Ala
385                 390                 395                 400

Arg Lys Ala Gly Lys Arg Ile Val Leu Glu Val Leu Phe Gln Gly Pro
                405                 410                 415

Glu Gly Asp Glu Pro Arg Thr Val Lys Ala Ala Ile Cys Ala Glu
                420                 425                 430

Arg Gly Ile Ala Thr Cys Val Leu Leu Gly Asn Pro Ala Glu Ile Asn
                435                 440                 445

Arg Val Ala Ala Ser Gln Gly Val Glu Leu Gly Ala Gly Ile Glu Ile
                450                 455                 460

Val Asp Pro Glu Val Val Arg Glu Ser Tyr Val Gly Arg Leu Val Glu
465                 470                 475                 480

Leu Arg Lys Asn Lys Gly Met Thr Glu Thr Val Ala Arg Glu Gln Leu
                485                 490                 495

Glu Asp Asn Val Val Leu Gly Thr Leu Met Leu Glu Gln Asp Glu Val
                500                 505                 510

Asp Gly Leu Val Ser Gly Ala Val His Thr Thr Ala Asn Thr Ile Arg
                515                 520                 525

Pro Pro Leu Gln Leu Ile Lys Thr Ala Pro Gly Ser Ser Leu Val Ser
                530                 535                 540

Ser Val Phe Phe Met Leu Leu Pro Glu Gln Val Tyr Val Tyr Gly Asp
545                 550                 555                 560

Cys Ala Ile Asn Pro Asp Pro Thr Ala Glu Gln Leu Ala Glu Ile Ala
                565                 570                 575

Ile Gln Ser Ala Asp Ser Ala Ala Phe Gly Ile Glu Pro Arg Val
                580                 585                 590

Ala Met Leu Ser Tyr Ser Thr Gly Thr Ser Gly Ala Gly Ser Asp Val
                595                 600                 605

Glu Lys Val Arg Glu Ala Thr Arg Leu Ala Gln Glu Lys Arg Pro Asp
                610                 615                 620

Leu Met Ile Asp Gly Pro Leu Gln Tyr Asp Ala Ala Val Met Ala Asp
625                 630                 635                 640

Val Ala Lys Ser Lys Ala Pro Asn Ser Pro Val Ala Gly Arg Ala Thr
                645                 650                 655

Val Phe Ile Phe Pro Asp Leu Asn Thr Gly Asn Thr Thr Tyr Lys Ala
                660                 665                 670

Val Gln Arg Ser Ala Asp Leu Ile Ser Ile Gly Pro Met Leu Gln Gly
                675                 680                 685

Met Arg Lys Pro Val Asn Asp Leu Ser Arg Gly Ala Leu Val Asp Asp
                690                 695                 700

Ile Val Tyr Thr Ile Ala Leu Thr Ala Ile Gln Ser Ala Gln Gln Gln
705                 710                 715                 720

<210> SEQ ID NO 57
<211> LENGTH: 1992
<212> TYPE: DNA
<213> ORGANISM: Artificial Sequence
<220> FEATURE:
<223> OTHER INFORMATION: Synthetic Oligonucleotide

<400> SEQUENCE: 57

```
atgtcctcac gtaaagagct tgccaatgct attcgtgcgc tgagcatgga cgcagtacag      60
aaagccaaat ccggtcaccc gggtgcccct atgggtatgg ctgacattgc cgaagtcctg     120
tggcgtgatt tcctgaaaca caacccgcag aatccgtcct gggctgaccg tgaccgcttc     180
gtgctgtcca acggccacgg ctccatgctg atctacagcc tgctgcacct caccggttac     240
gatctgccga tggaagaact gaaaaacttc cgtcagctgc actctaaaac tccgggtcac     300
ccggaagtgg gttacaccgc tggtgtggaa accaccaccg tccgctgggt cagggtatt      360
gccaacgcag tcggtatggc gattgcagaa aaaacgctgg cggcgcagtt taaccgtccg     420
ggccacgaca ttgtcgacca ctacacctac gccttcatgg cgacggctg catgatggaa      480
ggcatctccc acgaagtttg ctctctggcg gtacgctga agctgggtaa actgattgca      540
ttctacgatg acaacggtat ttctatcgat ggtcacgttg aaggctggtt caccgacgac     600
accgcaatgc gtttcgaagc ttacggctgg cacgttattc gcgacatcga cggtcatgac     660
gcggcatcta tcaaacgcgc agtagaagaa gcgcgcgcag tgactgacaa accttccctg     720
ctgatgtgca aaccatcat cggtttcggt tccccgaaca aagccggtac ccacgactcc      780
cacggtgcgc cgctgggcga cgctgaaatt gccctgaccc gcaacaact gggctggaaa      840
tatgcgccgt tcgaaatccc gtctgaaatc tatgctcagt gggatgcgaa agaagcaggc     900
caggcgaaag aatccgcatg gaacgagaaa ttcgctgctt acgcgaaagc ttatccgcag     960
gaagccgctg aatttacccg ccgtatgaaa ggcgaaatgc cgtctgactt cgacgctaaa    1020
gcgaaagagt tcatcgctaa actgcaggct aatccggcga aaatcgccag ccgtaaagcg    1080
tctcagaatg ctatcgaagc gttcggtccg ctgttgccgg aattcctcgg cggttctgct    1140
gacctggcgc cgtctaacct gaccctgtgg tctggttcta agcaatcaa cgaagatgct    1200
gcgggtaact acatccacta cggtgttcgc gagttcggta tgaccgcgat tgctaacggt    1260
atctccctgc acggtggctt cctgccgtac acctccacct tcctgatgtt cgtggaatac    1320
gcacgtaacg ccgtacgtat ggctgcgctg atgaaacagc gtcaggtgat ggtttacacc    1380
cacgactcca tcggtctggg cgaagacggc ccgactcacc agccggttga gcaggtcgct    1440
tctctgcgcg taaccccgaa catgtctaca tggcgtccgt gtgaccaggt tgaatccgcg    1500
gtcgcgtgga aatacggtgt tgagcgtcag gacggcccga ccgcactgat cctctcccgt    1560
cagaacctgg cgcagcagga acgaactgaa gagcaactgg caaacatcgc gcgcggtggt    1620
tatgtgctga agactgcgc cggtcagccg gaactgattt tcatcgctac cggttcagaa    1680
gttgaactgc tgttgctgc ctacgaaaaa ctgactgccg aaggcgtgaa agcgcgcgtg    1740
gtgtccatgc cgtctaccga cgcatttgac aagcaggatg ctgcttaccg tgaatccgta    1800
ctgccgaaag cggttactgc acgcgttgct gtagaagcgg gtattgctga ctactggtac    1860
aagtatgttg gcctgaacgg tgctatcgtc ggtatgacca ccttcggtga atctgctccg    1920
gcagagctgc tgtttgaaga gttcggcttc actgttgata cgttgttgc gaaagcaaaa    1980
gaactgctgt aa                                                        1992
```

<210> SEQ ID NO 58
<211> LENGTH: 2016
<212> TYPE: DNA
<213> ORGANISM: Artificial Sequence
<220> FEATURE:
<223> OTHER INFORMATION: Synthetic Oligonucleotide

<400> SEQUENCE: 58

| | |
|---|---|
| atgtcctcac gtaaagagct tgccaatgct attcgtgcgc tgagcatgga cgcagtacag | 60 |
| aaagccaaat ccggtcaccc gggtgccct atgggtatgg ctgacattgc cgaagtcctg | 120 |
| tggcgtgatt tcctgaaaca caacccgcag aatccgtcct gggctgaccg tgaccgcttc | 180 |
| gtgctgtcca acggccacgg ctccatgctg atctacagcc tgctgcacct caccggttac | 240 |
| gatctgccga tggaagaact gaaaaacttc cgtcagctgc actctaaaac tccgggtcac | 300 |
| ccggaagtgg gttacaccgc tggtgtggaa accaccaccg gtccgctggg tcagggtatt | 360 |
| gccaacgcag tcggtatggc gattgcagaa aaaacgctgg cggcgcagtt taaccgtccg | 420 |
| ggccacgaca ttgtcgacca ctacacctac gccttcatgg cgacggctg catgatggaa | 480 |
| ggcatctccc acgaagtttg ctctctggcg gtacgctga agctgggtaa actgattgca | 540 |
| ttctacgatg acaacggtat ttctatcgat ggtcacgttg aaggctggtt caccgacgac | 600 |
| accgcaatgc gtttcgaagc ttacggctgg cacgttattc gcgacatcga cggtcatgac | 660 |
| gcggcatcta tcaaacgcgc agtagaagaa gcgcgcgcag tgactgacaa accttccctg | 720 |
| ctgatgtgca aaccatcat cggtttcggt tccccgaaca aagccggtac ccacgactcc | 780 |
| cacggtgcgc cgctgggcga cgctgaaatt gccctgaccc gcgaacaact gggctggaaa | 840 |
| tatgcgccgt tcgaaatccc gtctgaaatc tatgctcagt gggatgcgaa agaagcaggc | 900 |
| caggcgaaag aatccgcatg aacgagaaa ttcgctgctt acgcgaaagc ttatccgcag | 960 |
| gaagccgctg aatttacccg ccgtatgaaa ggcgaaatgc cgtctgactt cgacgctaaa | 1020 |
| gcgaaagagt tcatcgctaa actgcaggct aatccggcga aaatcgccag ccgtaaagcg | 1080 |
| tctcagaatg ctatcgaagc gttcggtccg ctgttgccgg aattcctcgg cggttctgct | 1140 |
| gacctggcgc cgtctaacct gacctgtgg tctggttcta agcaatcaa cgaagatgct | 1200 |
| gcgggtaact acatccacta cggtgttcgc gagttcggta tgaccgcgat gctaacggt | 1260 |
| atctccctgc acggtggctt cctgccgtac acctccacct tcctgatgtt cgtggaatac | 1320 |
| gcacgtaacg ccgtacgtat ggctgcgctg atgaaacagc gtcaggtgat ggtttacacc | 1380 |
| cacgactcca tcggtctggg cgaagacggc ccgactcacc agccggttga gcaggtcgct | 1440 |
| tctctgcgcg taaccccgaa catgtctaca tggcgtccgt gtgaccaggt tgaatccgcg | 1500 |
| gtcgcgtgga atacggtgt tgagcgtcag gacggcccga ccgcactgat cctctcccgt | 1560 |
| cagaacctgg cgcagcagga acgaactgaa gagcaactgg caaacatcgc gcgcggtggt | 1620 |
| tatgtgctga agactgcgc cggtcagccg gaactgattt tcatcgctac cggttcagaa | 1680 |
| gttgaactgg ctgttgctgc ctacgaaaaa ctgactgccg aaggcgtgaa agcgcgcgtg | 1740 |
| gtgtccatgc cgtctaccga cgcatttgac aagcaggatg ctgcttaccg tgaatccgta | 1800 |
| ctgccgaaag cggttactgc acgcgttgct gtagaagcgg gtattgctga ctactggtac | 1860 |
| aagtatgttg gcctgaacgg tgctatcgtc ggtatgacca ccttcctgga agtgctgttt | 1920 |
| cagggtccgg gtgaatctgc tccggcagag ctgctgtttg aagagttcgg cttcactgtt | 1980 |
| gataacgttg ttgcgaaagc aaaagaactg ctgtaa | 2016 |

<210> SEQ ID NO 59
<211> LENGTH: 2016
<212> TYPE: DNA
<213> ORGANISM: Artificial Sequence
<220> FEATURE:
<223> OTHER INFORMATION: Synthetic Oligonucleotide

<400> SEQUENCE: 59

| | |
|---|---|
| atgtcctcac gtaaagagct tgccaatgct attcgtgcgc tgagcatgga cgcagtacag | 60 |

```
aaagccaaat ccggtcaccc gggtgcccct atgggtatgg ctgacattgc cgaagtcctg      120
tggcgtgatt tcctgaaaca caacccgcag aatccgtcct gggctgaccg tgaccgcttc      180
gtgctgtcca acggccacgg ctccatgctg atctacagcc tgctgcacct caccggttac      240
gatctgccga tggaagaact gaaaaacttc cgtcagctgc actctaaaac tccgggtcac      300
ccggaagtgg gttacaccgc tggtgtggaa accaccaccg gtccgctggg tcagggtatt      360
gccaacgcag tcgtatggc gattgcagaa aaaacgctgg cggcgcagtt taaccgtccg       420
ggccacgaca ttgtcgacca ctacacctac gccttcatgg gcgacggctg catgatggaa      480
ggcatctccc acgaagtttg ctctctggcg ggtacgctga agctgggtaa actgattgca      540
ttctacgatg acaacggtat ttctatcgat ggtcacgttg aaggctggtt caccgacgac      600
accgcaatgc gtttcgaagc ttacggctgg cacgttattc gcgacatcga cggtcatgac      660
gcggcatcta tcaaacgcgc agtagaagaa gcgcgcgcag tgactgacaa accttccctg      720
ctgatgtgca aaccatcat cggtttcggt tccccgaaca aagccggtac ccacgactcc       780
cacggtgcgc cgctgggcga cgctgaaatt gccctgaccc gcaacaact gggctggaaa       840 tatgcgccgt tcgaaatccc cgtctgaaatc tatgctcagt gggatgcgaa agaagcaggc    900
caggcgaaag aatccgcatg gaacgagaaa ttcgctgctt acgcgaaagc ttatccgcag      960
gaagccgctg aatttacccg ccgtatgaaa ggcgaaatgc cgtctgactt cgacgctaaa     1020
gcgaaagagt tcatcgctaa actgcaggct aatccggcga aaatcgccag ccgtaaagcg    1080
tctcagaatg ctatcgaagc gttcggtccg ctgttgccgg aattcctcgg cggttctgct     1140
gacctggcgc cgtctaacct gaccctgtgg tctggttcta aagcaatcaa cgaagatgct    1200
gcgggtaact acatccacta cggtgttcgc gagttcggta tgaccgcgat tgctaacggt    1260
atctccctgc acggtggctt cctgccgtac acctccacct tcctgatgtt cgtggaatac    1320
gcacgtaacg ccgtacgtat ggctgcgctg atgaaacagc gtcaggtgat ggtttacacc    1380
cacgactcca tcggtctggg cgaagacggc ccgactcacc agccggttga gcaggtcgct    1440
tctctgcgcg taaccccgaa catgtctaca tggcgtccgt gtgaccaggt tgaatccgcg    1500
gtcgcgtgga atacggtgt tgagcgtcag gacggcccga ccgcactgat cctctcccgt     1560
cagaacctgg cgcagcagga acgaactgaa gagcaactgg caaacatcgc gcgcggtggt    1620
tatgtgctga aagactgcgc cggtcagccg gaactgattt tcatcgctac cggttcagaa     1680
gttgaactgg ctgttgctgc ctacgaaaaa ctgactgccg aaggcgtgaa agcgcgcgtg    1740
gtgtccatgc cgtctaccga cgcatttgac aagcaggatg ctgcttaccg tgaatccgta    1800
ctgccgaaag cggttactgc acgcgttgct gtagaagcgg gtattgctga ctactggtac    1860
aagtatgttg cctgaacgg tgctatcgtc ggtatgacca ccttcggtct ggaagtgctg    1920
tttcagggtc cggaatctgc tccggcagag ctgctgtttg aagagttcgg cttcactgtt    1980
gataacgttg ttgcgaaagc aaaagaactg ctgtaa                               2016
```

<210> SEQ ID NO 60
<211> LENGTH: 2016
<212> TYPE: DNA
<213> ORGANISM: Artificial Sequence
<220> FEATURE:
<223> OTHER INFORMATION: Synthetic Oligonucleotide

<400> SEQUENCE: 60

```
atgtcctcac gtaaagagct tgccaatgct attcgtgcgc tgagcatgga cgcagtacag       60
```

```
aaagccaaat ccggtcaccc gggtgcccct atgggtatgg ctgacattgc cgaagtcctg    120
tggcgtgatt tcctgaaaca aacccgcag aatccgtcct gggctgaccg tgaccgcttc      180
gtgctgtcca acggccacgg ctccatgctg atctacagcc tgctgcacct caccggttac    240
gatctgccga tggaagaact gaaaaacttc cgtcagctgc actctaaaac tccgggtcac    300
ccggaagtgg gttacaccgc tggtgtggaa accaccaccg gtccgctggg tcagggtatt     360
gccaacgcag tcggtatggc gattgcagaa aaaacgctgg cggcgcagtt taaccgtccg    420
ggccacgaca ttgtcgacca ctacacctac gccttcatgg gcgacggctg catgatggaa    480
ggcatctccc acgaagtttg ctctctggcg gtacgctga agctgggtaa actgattgca    540
ttctacgatg acaacggtat ttctatcgat ggtcacgttg aaggctggtt caccgacgac    600
accgcaatgc gtttcgaagc ttacggctgg cacgttattc gcgacatcga cggtcatgac    660
gcggcatcta tcaaacgcgc agtagaagaa gcgcgcgcag tgactgacaa accttccctg    720
ctgatgtgca aaaccatcat cggtttcggt tccccgaaca aagccggtac ccacgactcc    780
cacggtcgcg cgctgggcga cgctgaaatt gccctgaccc gcaacaact gggctggaaa    840 tatgcgccgt tcgaaatccc gtctgaaatc tatgctcagt gggatgcgaa agaagcaggc    900
caggcgaaag aatccgcatg gaacgagaaa ttcgctgctt acgcgaaagc ttatccgcag    960
gaagccgctg aatttacccg ccgtatgaaa ggcgaaatgc cgtctgactt cgacgctaaa    1020
gcgaaagagt tcatcgctaa actgcaggct aatccggcga aaatcgccag ccgtaaagcg    1080
tctcagaatg ctatcgaagc gttcggtccg ctgttgccgg aattcctcgg cggttctgct    1140
gacctggcgc gtctaaccct gaccctgtgg tctggttcta agcaatcaa cgaagatgct    1200 gcgggtaact acatccacta cggtgttcgc gagttcggta tgaccgcgat tgctaacggt    1260
atctccctgc acggtggctt cctgccgtac acctccacct tcctgatgtt cgtggaatac    1320
gcacgtaacg ccgtacgtat ggctgcgctg atgaaacagc gtcaggtgat ggtttacacc    1380
cacgactcca tcggtctggg cgaagacggc ccgactcacc agccggttga gcaggtcgct    1440
tctctgcgcg taaccccgaa catgtctaca tggcgtccgt gtgaccaggt tgaatccgcg    1500
gtcgcgtgga aatacggtgt tgagcgtcag gacggcccga ccgcactgat cctctcccgt    1560
cagaacctgg cgcagcagga acgaactgaa gagcaactgg caaacatcgc gcgcggtggt    1620
tatgtgctga agactgcgc cggtcagccg gaactgattt tcatcgctac cggttcagaa    1680
gttgaactgg ctgttgctgc ctacgaaaaa ctgactgccg aaggcgtgaa agcgcgcgtg    1740
gtgtccatgc cgtctaccga cgcatttgac aagcaggatg ctgcttaccg tgaatccgta    1800
ctgccgaaag cggttactgc acgcgttgct gtagaagcgg gtattgctga ctactggtac    1860
aagtatgttg gcctgaacgg tgctatcgtc ggtatgacca ccttcggtga actggaagtg    1920
ctgtttcagg gtccgtctgc tccggcagag ctgctgtttg aagagttcgg cttcactgtt    1980
gataacgttg ttgcgaaagc aaaagaactg ctgtaa                               2016
```

<210> SEQ ID NO 61
<211> LENGTH: 2016
<212> TYPE: DNA
<213> ORGANISM: Artificial Sequence
<220> FEATURE:
<223> OTHER INFORMATION: Synthetic Oligonucleotide

<400> SEQUENCE: 61

```
atgtcctcac gtaaagagct tgccaatgct attcgtgcgc tgagcatgga cgcagtacag     60
aaagccaaat ccggtcaccc gggtgcccct atgggtatgg ctgacattgc cgaagtcctg    120
```

-continued

```
tggcgtgatt tcctgaaaca caacccgcag aatccgtcct gggctgaccg tgaccgcttc      180
gtgctgtcca acggccacgg ctccatgctg atctacagcc tgctgcacct caccggttac      240
gatctgccga tggaagaact gaaaaacttc cgtcagctgc actctaaaac tccgggtcac      300
ccggaagtgg gttacaccgc tggtgtgaaa accaccaccg tccgctggg  tcagggtatt      360 gccaacgcag tcggtatggc gattgcagaa aaaacgctgg cggcgcagtt taaccgtccg      420
ggccacgaca ttgtcgacca ctacacctac gccttcatgg cgacggctg  catgatggaa      480 ggcatctccc acgaagtttg ctctctggcg gtacgctga  agctgggtaa actgattgca      540
ttctacgatg acaacggtat ttctatcgat ggtcacgttg aaggctggtt caccgacgac      600
accgcaatgc gtttcgaagc ttacggctgg cacgttattc gcgacatcga cggtcatgac      660
gcggcatcta tcaaacgcgc agtagaagaa gcgcgcgcag tgactgacaa accttccctg      720
ctgatgtgca aaccatcat  cggtttcggt tccccgaaca agccggtac  ccacgactcc      780 cacggtgcgc cgctgggcga cgctgaaatt gccctgaccc gcaacaact  gggctggaaa      840 tatgcgccgt cgaaatccc  gtctgaaatc tatgctcagt gggatgcgaa agaagcaggc      900
caggcgaaag aatccgcatg gaacgagaaa ttcgctgctt acgcgaaagc ttatccgcag      960
gaagccgctg aatttacccg ccgtatgaaa ggcgaaatgc cgtctgactt cgacgctaaa      1020
gcgaaagagt tcatcgctaa actgcaggct aatccggcga aaatcgccag ccgtaaagcg      1080
tctcagaatg ctatcgaagc gttcggtccg ctgttgccgg aattcctcgg cggttctgct      1140
gacctggcgc cgtctaacct gaccctgtgg tctggttcta aagcaatcaa cgaagatgct      1200
gcgggtaact acatccacta cggtgttcgc gagttcggta tgaccgcgat tgctaacggt      1260
atctccctgc acggtggctt cctgccgtac acctccacct tcctgatgtt cgtggaatac      1320
gcacgtaacg ccgtacgtat ggctgcgctg atgaaacagc gtcaggtgat ggtttacacc      1380
cacgactcca tcggtctggg cgaagacggc ccgactcacc agccggttga gcaggtcgct      1440
tctctgcgcg taaccccgaa catgtctaca tggcgtccgt gtgaccaggt tgaatccgcg      1500
gtcgcgtgga aatacggtgt tgagcgtcag gacggcccga ccgcactgat cctctcccgt      1560
cagaacctgg cgcagcagga acgaactgaa gagcaactgg caaacatcgc gcgcggtggt      1620
tatgtgctga agactgcgc  cggtcagccg gaactgattt tcatcgctac cggttcagaa      1680
gttgaactgg ctgttgctgc ctacgaaaaa ctgactgccg aaggcgtgaa agcgcgcgtg      1740
gtgtccatgc cgtctaccga cgcatttgac aagcaggatg ctgcttaccg tgaatccgta      1800
ctgccgaaag cggttactgc acgcgttgct gtagaagcgg gtattgctga ctactggtac      1860
aagtatgttg gcctgaacgg tgctatcgtc ggtatgacca cttcggtga  atctctggaa      1920 gtgctgtttc agggtccggc tccggcagag ctgctgtttg aagagttcgg cttcactgtt      1980
gataacgttg ttgcgaaagc aaaagaactg ctgtaa                                2016
```

<210> SEQ ID NO 62
<211> LENGTH: 2016
<212> TYPE: DNA
<213> ORGANISM: Artificial Sequence
<220> FEATURE:
<223> OTHER INFORMATION: Synthetic Oligonucleotide

<400> SEQUENCE: 62

```
atgtcctcac gtaaagagct tgccaatgct attcgtgcgc tgagcatgga cgcagtacag       60
aaagccaaat ccggtcaccc gggtgcccct atgggtatgg ctgacattgc cgaagtcctg      120
```

```
tggcgtgatt tcctgaaaca caacccgcag aatccgtcct gggctgaccg tgaccgcttc    180
gtgctgtcca acggccacgg ctccatgctg atctacagcc tgctgcacct caccggttac    240
gatctgccga tggaagaact gaaaaacttc cgtcagctgc actctaaaac tccgggtcac    300
ccggaagtgg gttacaccgc tggtgtggaa accaccaccg gtccgctggg tcagggtatt    360
gccaacgcag tcggtatggc gattgcagaa aaaacgctgg cggcgcagtt taaccgtccg    420
ggccacgaca ttgtcgacca ctacacctac gccttcatgg cgacggctg catgatggaa     480 ggcatctccc acgaagtttg ctctctggcg ggtacgctga agctgggtaa actgattgca    540
ttctacgatg acaacggtat ttctatcgat ggtcacgttg aaggctggtt caccgacgac    600
accgcaatgc gtttcgaagc ttacggctgg cacgttattc gcgacatcga cggtcatgac    660
gcggcatcta tcaaacgcgc agtagaagaa gcgcgcgcag tgactgacaa accttccctg    720
ctgatgtgca aaccatcat cggtttcggt tccccgaaca agccggtac ccacgactcc      780 cacggtgcgc cgctgggcga cgctgaaatt gccctgaccc gcaacaact gggctggaaa     840 tatgcgccgt cgaaatccc gtctgaaatc tatgctcagt gggatgcgaa agaagcaggc    900
caggcgaaag aatccgcatg gaacgagaaa ttcgctgctt acgcgaaagc ttatccgcag    960
gaagccgctg aatttacccg ccgtatgaaa ggcgaaatgc cgtctgactt cgacgctaaa   1020
gcgaaagagt tcatcgctaa actgcaggct aatccggcga aaatcgccag ccgtaaagcg   1080
tctcagaatg ctatcgaagc gttcggtccg ctgttgccgg aattcctcgg cggttctgct   1140
gacctggcgc cgtctaacct gaccctgtgg tctggttcta agcaatcaa cgaagatgct   1200 gcgggtaact acatccacta cggtgttcgc gagttcggta tgaccgcgat tgctaacggt   1260
atctccctgc acggtggctt cctgccgtac acctccacct tcctgatgtt cgtggaatac   1320
gcacgtaacg ccgtacgtat ggctgcgctg atgaaacagc gtcaggtgat ggtttacacc   1380
cacgactcca tcggtctggg cgaagacggc ccgactcacc agccggttga gcaggtcgct   1440
tctctgcgcg taaccccgaa catgtctaca tggcgtccgt gtgaccaggt tgaatccgcg   1500
gtcgcgtgga atacggtgt tgagcgtcag gacggcccga ccgcactgat cctctcccgt   1560
cagaacctgg cgcagcagga acgaactgaa gagcaactgg caaacatcgc gcgcggtggt   1620
tatgtgctga agactgcgc cggtcagccg gaactgattt tcatcgctac cggttcagaa   1680
gttgaactgg ctgttgctgc ctacgaaaaa ctgactgccg aaggcgtgaa agcgcgcgtg   1740
gtgtccatgc cgtctaccga cgcatttgac aagcaggatg ctgcttaccg tgaatccgta   1800
ctgccgaaag cggttactgc acgcgttgct gtagaagcgg gtattgctga ctactggtac   1860
aagtatgttg gcctgaacgg tgctatcgtc ggtatgacca ccttcggtga atctgctccg   1920
ctggaagtgc tgtttcaggg tccggcagag ctgctgtttg aagagttcgg cttcactgtt   1980
gataacgttg ttgcgaaagc aaaagaactg ctgtaa                              2016
```

<210> SEQ ID NO 63
<211> LENGTH: 663
<212> TYPE: PRT
<213> ORGANISM: Artificial Sequence
<220> FEATURE:
<223> OTHER INFORMATION: Synthetic Polypeptide

<400> SEQUENCE: 63

Met Ser Ser Arg Lys Glu Leu Ala Asn Ala Ile Arg Ala Leu Ser Met
1               5                   10                  15

Asp Ala Val Gln Lys Ala Lys Ser Gly His Pro Gly Ala Pro Met Gly
            20                  25                  30

```
Met Ala Asp Ile Ala Glu Val Leu Trp Arg Asp Phe Leu Lys His Asn
    35                  40                  45

Pro Gln Asn Pro Ser Trp Ala Asp Arg Asp Arg Phe Val Leu Ser Asn
    50                  55                  60

Gly His Gly Ser Met Leu Ile Tyr Ser Leu Leu His Leu Thr Gly Tyr
65                  70                  75                  80

Asp Leu Pro Met Glu Glu Leu Lys Asn Phe Arg Gln Leu His Ser Lys
                85                  90                  95

Thr Pro Gly His Pro Glu Val Gly Tyr Thr Ala Gly Val Glu Thr Thr
                100                 105                 110

Thr Gly Pro Leu Gly Gln Gly Ile Ala Asn Ala Val Gly Met Ala Ile
            115                 120                 125

Ala Glu Lys Thr Leu Ala Ala Gln Phe Asn Arg Pro Gly His Asp Ile
        130                 135                 140

Val Asp His Tyr Thr Tyr Ala Phe Met Gly Asp Gly Cys Met Met Glu
145                 150                 155                 160

Gly Ile Ser His Glu Val Cys Ser Leu Ala Gly Thr Leu Lys Leu Gly
                165                 170                 175

Lys Leu Ile Ala Phe Tyr Asp Asp Asn Gly Ile Ser Ile Asp Gly His
            180                 185                 190

Val Glu Gly Trp Phe Thr Asp Asp Thr Ala Met Arg Phe Glu Ala Tyr
        195                 200                 205

Gly Trp His Val Ile Arg Asp Ile Asp Gly His Asp Ala Ala Ser Ile
    210                 215                 220

Lys Arg Ala Val Glu Ala Arg Ala Val Thr Asp Lys Pro Ser Leu
225                 230                 235                 240

Leu Met Cys Lys Thr Ile Ile Gly Phe Gly Ser Pro Asn Lys Ala Gly
            245                 250                 255

Thr His Asp Ser His Gly Ala Pro Leu Gly Asp Ala Glu Ile Ala Leu
        260                 265                 270

Thr Arg Glu Gln Leu Gly Trp Lys Tyr Ala Pro Phe Glu Ile Pro Ser
    275                 280                 285

Glu Ile Tyr Ala Gln Trp Asp Ala Lys Glu Ala Gly Gln Ala Lys Glu
    290                 295                 300

Ser Ala Trp Asn Glu Lys Phe Ala Ala Tyr Ala Lys Ala Tyr Pro Gln
305                 310                 315                 320

Glu Ala Ala Glu Phe Thr Arg Arg Met Lys Gly Glu Met Pro Ser Asp
                325                 330                 335

Phe Asp Ala Lys Ala Lys Glu Phe Ile Ala Lys Leu Gln Ala Asn Pro
                340                 345                 350

Ala Lys Ile Ala Ser Arg Lys Ala Ser Gln Asn Ala Ile Glu Ala Phe
            355                 360                 365

Gly Pro Leu Leu Pro Glu Phe Leu Gly Gly Ser Ala Asp Leu Ala Pro
        370                 375                 380

Ser Asn Leu Thr Leu Trp Ser Gly Ser Lys Ala Ile Asn Glu Asp Ala
385                 390                 395                 400

Ala Gly Asn Tyr Ile His Tyr Gly Val Arg Glu Phe Gly Met Thr Ala
                405                 410                 415

Ile Ala Asn Gly Ile Ser Leu His Gly Gly Phe Leu Pro Tyr Thr Ser
            420                 425                 430

Thr Phe Leu Met Phe Val Glu Tyr Ala Arg Asn Ala Val Arg Met Ala
        435                 440                 445
```

```
Ala Leu Met Lys Gln Arg Gln Val Met Val Tyr Thr His Asp Ser Ile
    450                 455                 460

Gly Leu Gly Glu Asp Gly Pro Thr His Gln Pro Val Glu Gln Ile Ala
465                 470                 475                 480

Ser Leu Arg Val Thr Pro Asn Met Ser Thr Trp Arg Pro Cys Asp Gln
                485                 490                 495

Val Glu Ser Ala Val Ala Trp Lys Tyr Gly Val Glu Arg Gln Asp Gly
                500                 505                 510

Pro Thr Ala Leu Ile Leu Ser Arg Gln Asn Leu Ala Gln Gln Glu Arg
                515                 520                 525

Thr Glu Glu Gln Leu Ala Asn Ile Ala Arg Gly Gly Tyr Val Leu Lys
    530                 535                 540

Asp Cys Ala Gly Gln Pro Glu Leu Ile Phe Ile Ala Thr Gly Ser Glu
545                 550                 555                 560

Val Glu Leu Ala Val Ala Ala Tyr Glu Lys Leu Thr Ala Glu Gly Val
                565                 570                 575

Lys Ala Arg Val Val Ser Met Pro Ser Thr Asp Ala Phe Asp Lys Gln
                580                 585                 590

Asp Ala Ala Tyr Arg Glu Ser Val Leu Pro Lys Ala Val Thr Ala Arg
    595                 600                 605

Val Ala Val Glu Ala Gly Ile Ala Asp Tyr Trp Tyr Lys Tyr Val Gly
610                 615                 620

Leu Asn Gly Ala Ile Val Gly Met Thr Thr Phe Gly Glu Ser Ala Pro
625                 630                 635                 640

Ala Glu Gln Leu Phe Glu Glu Phe Gly Phe Thr Val Asp Asn Val Val
                645                 650                 655

Ala Lys Ala Lys Ala Leu Leu
                660

<210> SEQ ID NO 64
<211> LENGTH: 671
<212> TYPE: PRT
<213> ORGANISM: Artificial Sequence
<220> FEATURE:
<223> OTHER INFORMATION: Synthetic Polypeptide

<400> SEQUENCE: 64

Met Ser Ser Arg Lys Glu Leu Ala Asn Ala Ile Arg Ala Leu Ser Met
1               5                   10                  15

Asp Ala Val Gln Lys Ala Lys Ser Gly His Pro Gly Ala Pro Met Gly
                20                  25                  30

Met Ala Asp Ile Ala Glu Val Leu Trp Arg Asp Phe Leu Lys His Asn
            35                  40                  45

Pro Gln Asn Pro Ser Trp Ala Asp Arg Asp Arg Phe Val Leu Ser Asn
    50                  55                  60

Gly His Gly Ser Met Leu Ile Tyr Ser Leu Leu His Leu Thr Gly Tyr
65              70                  75                  80

Asp Leu Pro Met Glu Glu Leu Lys Asn Phe Arg Gln Leu His Ser Lys
                85                  90                  95

Thr Pro Gly His Pro Glu Val Gly Tyr Thr Ala Gly Val Glu Thr Thr
                100                 105                 110

Thr Gly Pro Leu Gly Gln Gly Ile Ala Asn Ala Val Gly Met Ala Ile
            115                 120                 125

Ala Glu Lys Thr Leu Ala Ala Gln Phe Asn Arg Pro Gly His Asp Ile
    130                 135                 140
```

Val Asp His Tyr Thr Tyr Ala Phe Met Gly Asp Gly Cys Met Met Glu
145                 150                 155                 160

Gly Ile Ser His Glu Val Cys Ser Leu Ala Gly Thr Leu Lys Leu Gly
            165                 170                 175

Lys Leu Ile Ala Phe Tyr Asp Asp Asn Gly Ile Ser Ile Asp Gly His
            180                 185                 190

Val Glu Gly Trp Phe Thr Asp Thr Ala Met Arg Phe Glu Ala Tyr
            195                 200                 205

Gly Trp His Val Ile Arg Asp Ile Asp Gly His Asp Ala Ala Ser Ile
            210                 215                 220

Lys Arg Ala Val Glu Glu Ala Arg Ala Val Thr Asp Lys Pro Ser Leu
225                 230                 235                 240

Leu Met Cys Lys Thr Ile Ile Gly Phe Gly Ser Pro Asn Lys Ala Gly
            245                 250                 255

Thr His Asp Ser His Gly Ala Pro Leu Gly Asp Ala Glu Ile Ala Leu
            260                 265                 270

Thr Arg Glu Gln Leu Gly Trp Lys Tyr Ala Pro Phe Glu Ile Pro Ser
            275                 280                 285

Glu Ile Tyr Ala Gln Trp Asp Ala Lys Glu Ala Gly Gln Ala Lys Glu
            290                 295                 300

Ser Ala Trp Asn Glu Lys Phe Ala Ala Tyr Ala Lys Ala Tyr Pro Gln
305                 310                 315                 320

Glu Ala Ala Glu Phe Thr Arg Arg Met Lys Gly Glu Met Pro Ser Asp
                325                 330                 335

Phe Asp Ala Lys Ala Lys Glu Phe Ile Ala Lys Leu Gln Ala Asn Pro
            340                 345                 350

Ala Lys Ile Ala Ser Arg Lys Ala Ser Gln Asn Ala Ile Glu Ala Phe
            355                 360                 365

Gly Pro Leu Leu Pro Glu Phe Leu Gly Gly Ser Ala Asp Leu Ala Pro
            370                 375                 380

Ser Asn Leu Thr Leu Trp Ser Gly Ser Lys Ala Ile Asn Glu Asp Ala
385                 390                 395                 400

Ala Gly Asn Tyr Ile His Tyr Gly Val Arg Glu Phe Gly Met Thr Ala
            405                 410                 415

Ile Ala Asn Gly Ile Ser Leu His Gly Gly Phe Leu Pro Tyr Thr Ser
            420                 425                 430

Thr Phe Leu Met Phe Val Glu Tyr Ala Arg Asn Ala Val Arg Met Ala
            435                 440                 445

Ala Leu Met Lys Gln Arg Gln Val Met Val Tyr Thr His Asp Ser Ile
450                 455                 460

Gly Leu Gly Glu Asp Gly Pro Thr His Gln Pro Val Glu Gln Val Ala
465                 470                 475                 480

Ser Leu Arg Val Thr Pro Asn Met Ser Thr Trp Arg Pro Cys Asp Gln
            485                 490                 495

Val Glu Ser Ala Val Ala Trp Lys Tyr Gly Val Glu Arg Gln Asp Gly
            500                 505                 510

Pro Thr Ala Leu Ile Leu Ser Arg Gln Asn Leu Ala Gln Gln Glu Arg
            515                 520                 525

Thr Glu Glu Gln Leu Ala Asn Ile Ala Arg Gly Gly Tyr Val Leu Lys
            530                 535                 540

Asp Cys Ala Gly Gln Pro Glu Leu Ile Phe Ile Ala Thr Gly Ser Glu
545                 550                 555                 560

Val Glu Leu Ala Val Ala Ala Tyr Glu Lys Leu Thr Ala Glu Gly Val

```
                          565                 570                 575
Lys Ala Arg Val Val Ser Met Pro Ser Thr Asp Ala Phe Asp Lys Gln
                580                 585                 590

Asp Ala Ala Tyr Arg Glu Ser Val Leu Pro Lys Ala Val Thr Ala Arg
            595                 600                 605

Val Ala Val Glu Ala Gly Ile Ala Asp Tyr Trp Tyr Lys Tyr Val Gly
        610                 615                 620

Leu Asn Gly Ala Ile Val Gly Met Thr Thr Phe Leu Glu Val Leu Phe
625                 630                 635                 640

Gln Gly Pro Gly Glu Ser Ala Pro Ala Glu Leu Leu Phe Glu Glu Phe
                645                 650                 655

Gly Phe Thr Val Asp Asn Val Val Ala Lys Ala Lys Glu Leu Leu
                660                 665                 670

<210> SEQ ID NO 65
<211> LENGTH: 671
<212> TYPE: PRT
<213> ORGANISM: Artificial Sequence
<220> FEATURE:
<223> OTHER INFORMATION: Synthetic Polypeptide

<400> SEQUENCE: 65

Met Ser Ser Arg Lys Glu Leu Ala Asn Ala Ile Arg Ala Leu Ser Met
1               5                   10                  15

Asp Ala Val Gln Lys Ala Lys Ser Gly His Pro Gly Ala Pro Met Gly
                20                  25                  30

Met Ala Asp Ile Ala Glu Val Leu Trp Arg Asp Phe Leu Lys His Asn
            35                  40                  45

Pro Gln Asn Pro Ser Trp Ala Asp Arg Asp Arg Phe Val Leu Ser Asn
        50                  55                  60

Gly His Gly Ser Met Leu Ile Tyr Ser Leu Leu His Leu Thr Gly Tyr
65                  70                  75                  80

Asp Leu Pro Met Glu Glu Leu Lys Asn Phe Arg Gln Leu His Ser Lys
                85                  90                  95

Thr Pro Gly His Pro Glu Val Gly Tyr Thr Ala Gly Val Glu Thr Thr
                100                 105                 110

Thr Gly Pro Leu Gly Gln Gly Ile Ala Asn Ala Val Gly Met Ala Ile
            115                 120                 125

Ala Glu Lys Thr Leu Ala Ala Gln Phe Asn Arg Pro Gly His Asp Ile
        130                 135                 140

Val Asp His Tyr Thr Tyr Ala Phe Met Gly Asp Gly Cys Met Met Glu
145                 150                 155                 160

Gly Ile Ser His Glu Val Cys Ser Leu Ala Gly Thr Leu Lys Leu Gly
                165                 170                 175

Lys Leu Ile Ala Phe Tyr Asp Asp Asn Gly Ile Ser Ile Asp Gly His
                180                 185                 190

Val Glu Gly Trp Phe Thr Asp Asp Thr Ala Met Arg Phe Glu Ala Tyr
            195                 200                 205

Gly Trp His Val Ile Arg Asp Ile Asp Gly His Asp Ala Ala Ser Ile
        210                 215                 220

Lys Arg Ala Val Glu Ala Arg Ala Val Thr Asp Lys Pro Ser Leu
225                 230                 235                 240

Leu Met Cys Lys Thr Ile Ile Gly Phe Gly Ser Pro Asn Lys Ala Gly
                245                 250                 255

Thr His Asp Ser His Gly Ala Pro Leu Gly Asp Ala Glu Ile Ala Leu
```

```
                260                 265                 270
Thr Arg Glu Gln Leu Gly Trp Lys Tyr Ala Pro Phe Glu Ile Pro Ser
            275                 280                 285
Glu Ile Tyr Ala Gln Trp Asp Ala Lys Glu Ala Gly Gln Ala Lys Glu
        290                 295                 300
Ser Ala Trp Asn Glu Lys Phe Ala Ala Tyr Ala Lys Ala Tyr Pro Gln
305                 310                 315                 320
Glu Ala Ala Glu Phe Thr Arg Arg Met Lys Gly Glu Met Pro Ser Asp
                325                 330                 335
Phe Asp Ala Lys Ala Lys Glu Phe Ile Ala Lys Leu Gln Ala Asn Pro
            340                 345                 350
Ala Lys Ile Ala Ser Arg Lys Ala Ser Gln Asn Ala Ile Glu Ala Phe
        355                 360                 365
Gly Pro Leu Leu Pro Glu Phe Leu Gly Gly Ser Ala Asp Leu Ala Pro
    370                 375                 380
Ser Asn Leu Thr Leu Trp Ser Gly Ser Lys Ala Ile Asn Glu Asp Ala
385                 390                 395                 400
Ala Gly Asn Tyr Ile His Tyr Gly Val Arg Glu Phe Gly Met Thr Ala
                405                 410                 415
Ile Ala Asn Gly Ile Ser Leu His Gly Gly Phe Leu Pro Tyr Thr Ser
            420                 425                 430
Thr Phe Leu Met Phe Val Glu Tyr Ala Arg Asn Ala Val Arg Met Ala
        435                 440                 445
Ala Leu Met Lys Gln Arg Gln Val Met Val Tyr Thr His Asp Ser Ile
    450                 455                 460
Gly Leu Gly Glu Asp Gly Pro Thr His Gln Pro Val Glu Gln Val Ala
465                 470                 475                 480
Ser Leu Arg Val Thr Pro Asn Met Ser Thr Trp Arg Pro Cys Asp Gln
                485                 490                 495
Val Glu Ser Ala Val Ala Trp Lys Tyr Gly Val Glu Arg Gln Asp Gly
            500                 505                 510
Pro Thr Ala Leu Ile Leu Ser Arg Gln Asn Leu Ala Gln Gln Glu Arg
        515                 520                 525
Thr Glu Glu Gln Leu Ala Asn Ile Ala Arg Gly Gly Tyr Val Leu Lys
    530                 535                 540
Asp Cys Ala Gly Gln Pro Glu Leu Ile Phe Ile Ala Thr Gly Ser Glu
545                 550                 555                 560
Val Glu Leu Ala Val Ala Ala Tyr Glu Lys Leu Thr Ala Glu Gly Val
                565                 570                 575
Lys Ala Arg Val Val Ser Met Pro Ser Thr Asp Ala Phe Asp Lys Gln
            580                 585                 590
Asp Ala Ala Tyr Arg Glu Ser Val Leu Pro Lys Ala Val Thr Ala Arg
        595                 600                 605
Val Ala Val Glu Ala Gly Ile Ala Asp Tyr Trp Tyr Lys Tyr Val Gly
    610                 615                 620
Leu Asn Gly Ala Ile Val Gly Met Thr Thr Phe Gly Leu Glu Val Leu
625                 630                 635                 640
Phe Gln Gly Pro Glu Ser Ala Pro Ala Glu Leu Leu Phe Glu Glu Phe
                645                 650                 655
Gly Phe Thr Val Asp Asn Val Val Ala Lys Ala Lys Glu Leu Leu
            660                 665                 670

<210> SEQ ID NO 66
```

```
<211> LENGTH: 671
<212> TYPE: PRT
<213> ORGANISM: Artificial Sequence
<220> FEATURE:
<223> OTHER INFORMATION: Synthetic Polypeptide

<400> SEQUENCE: 66

Met Ser Ser Arg Lys Glu Leu Ala Asn Ala Ile Arg Ala Leu Ser Met
1               5                   10                  15

Asp Ala Val Gln Lys Ala Lys Ser Gly His Pro Gly Ala Pro Met Gly
                20                  25                  30

Met Ala Asp Ile Ala Glu Val Leu Trp Arg Asp Phe Leu Lys His Asn
            35                  40                  45

Pro Gln Asn Pro Ser Trp Ala Asp Arg Asp Arg Phe Val Leu Ser Asn
        50                  55                  60

Gly His Gly Ser Met Leu Ile Tyr Ser Leu Leu His Leu Thr Gly Tyr
65                  70                  75                  80

Asp Leu Pro Met Glu Glu Leu Lys Asn Phe Arg Gln Leu His Ser Lys
                85                  90                  95

Thr Pro Gly His Pro Glu Val Gly Tyr Thr Ala Gly Val Glu Thr Thr
                100                 105                 110

Thr Gly Pro Leu Gly Gln Gly Ile Ala Asn Ala Val Gly Met Ala Ile
            115                 120                 125

Ala Glu Lys Thr Leu Ala Ala Gln Phe Asn Arg Pro Gly His Asp Ile
        130                 135                 140

Val Asp His Tyr Thr Tyr Ala Phe Met Gly Asp Gly Cys Met Met Glu
145                 150                 155                 160

Gly Ile Ser His Glu Val Cys Ser Leu Ala Gly Thr Leu Lys Leu Gly
                165                 170                 175

Lys Leu Ile Ala Phe Tyr Asp Asp Asn Gly Ile Ser Ile Asp Gly His
                180                 185                 190

Val Glu Gly Trp Phe Thr Asp Asp Thr Ala Met Arg Phe Glu Ala Tyr
            195                 200                 205

Gly Trp His Val Ile Arg Asp Ile Asp Gly His Asp Ala Ala Ser Ile
        210                 215                 220

Lys Arg Ala Val Glu Glu Ala Arg Ala Val Thr Asp Lys Pro Ser Leu
225                 230                 235                 240

Leu Met Cys Lys Thr Ile Ile Gly Phe Gly Ser Pro Asn Lys Ala Gly
                245                 250                 255

Thr His Asp Ser His Gly Ala Pro Leu Gly Asp Ala Glu Ile Ala Leu
                260                 265                 270

Thr Arg Glu Gln Leu Gly Trp Lys Tyr Ala Pro Phe Glu Ile Pro Ser
            275                 280                 285

Glu Ile Tyr Ala Gln Trp Asp Ala Lys Glu Ala Gly Gln Ala Lys Glu
        290                 295                 300

Ser Ala Trp Asn Glu Lys Phe Ala Ala Tyr Ala Lys Ala Tyr Pro Gln
305                 310                 315                 320

Glu Ala Ala Glu Phe Thr Arg Arg Met Lys Gly Glu Met Pro Ser Asp
                325                 330                 335

Phe Asp Ala Lys Ala Lys Glu Phe Ile Ala Lys Leu Gln Ala Asn Pro
                340                 345                 350

Ala Lys Ile Ala Ser Arg Lys Ala Ser Gln Asn Ala Ile Glu Ala Phe
            355                 360                 365

Gly Pro Leu Leu Pro Glu Phe Leu Gly Gly Ser Ala Asp Leu Ala Pro
        370                 375                 380
```

```
Ser Asn Leu Thr Leu Trp Ser Gly Ser Lys Ala Ile Asn Glu Asp Ala
385                 390                 395                 400

Ala Gly Asn Tyr Ile His Tyr Gly Val Arg Glu Phe Gly Met Thr Ala
            405                 410                 415

Ile Ala Asn Gly Ile Ser Leu His Gly Gly Phe Leu Pro Tyr Thr Ser
            420                 425                 430

Thr Phe Leu Met Phe Val Glu Tyr Ala Arg Asn Ala Val Arg Met Ala
            435                 440                 445

Ala Leu Met Lys Gln Arg Gln Val Met Val Tyr Thr His Asp Ser Ile
450                 455                 460

Gly Leu Gly Glu Asp Gly Pro Thr His Gln Pro Val Glu Gln Val Ala
465                 470                 475                 480

Ser Leu Arg Val Thr Pro Asn Met Ser Thr Trp Arg Pro Cys Asp Gln
            485                 490                 495

Val Glu Ser Ala Val Ala Trp Lys Tyr Gly Val Glu Arg Gln Asp Gly
            500                 505                 510

Pro Thr Ala Leu Ile Leu Ser Arg Gln Asn Leu Ala Gln Gln Glu Arg
            515                 520                 525

Thr Glu Glu Gln Leu Ala Asn Ile Ala Arg Gly Gly Tyr Val Leu Lys
            530                 535                 540

Asp Cys Ala Gly Gln Pro Glu Leu Ile Phe Ile Ala Thr Gly Ser Glu
545                 550                 555                 560

Val Glu Leu Ala Val Ala Ala Tyr Glu Lys Leu Thr Ala Glu Gly Val
            565                 570                 575

Lys Ala Arg Val Val Ser Met Pro Ser Thr Asp Ala Phe Asp Lys Gln
            580                 585                 590

Asp Ala Ala Tyr Arg Glu Ser Val Leu Pro Lys Ala Val Thr Ala Arg
            595                 600                 605

Val Ala Val Glu Ala Gly Ile Ala Asp Tyr Trp Tyr Lys Tyr Val Gly
610                 615                 620

Leu Asn Gly Ala Ile Val Gly Met Thr Thr Phe Gly Glu Leu Glu Val
625                 630                 635                 640

Leu Phe Gln Gly Pro Ser Ala Pro Ala Glu Leu Leu Phe Glu Glu Phe
            645                 650                 655

Gly Phe Thr Val Asp Asn Val Val Ala Lys Ala Lys Glu Leu Leu
            660                 665                 670

<210> SEQ ID NO 67
<211> LENGTH: 671
<212> TYPE: PRT
<213> ORGANISM: Artificial Sequence
<220> FEATURE:
<223> OTHER INFORMATION: Synthetic Polypeptide

<400> SEQUENCE: 67

Met Ser Ser Arg Lys Glu Leu Ala Asn Ala Ile Arg Ala Leu Ser Met
1               5                   10                  15

Asp Ala Val Gln Lys Ala Lys Ser Gly His Pro Gly Ala Pro Met Gly
            20                  25                  30

Met Ala Asp Ile Ala Glu Val Leu Trp Arg Asp Phe Leu Lys His Asn
            35                  40                  45

Pro Gln Asn Pro Ser Trp Ala Asp Arg Asp Arg Phe Val Leu Ser Asn
        50                  55                  60

Gly His Gly Ser Met Leu Ile Tyr Ser Leu Leu His Leu Thr Gly Tyr
65                  70                  75                  80
```

```
Asp Leu Pro Met Glu Leu Lys Asn Phe Arg Gln Leu His Ser Lys
                 85                  90                  95

Thr Pro Gly His Pro Glu Val Gly Tyr Thr Ala Gly Val Glu Thr Thr
            100                 105                 110

Thr Gly Pro Leu Gly Gln Gly Ile Ala Asn Ala Val Gly Met Ala Ile
            115                 120                 125

Ala Glu Lys Thr Leu Ala Ala Gln Phe Asn Arg Pro Gly His Asp Ile
130                 135                 140

Val Asp His Tyr Thr Tyr Ala Phe Met Gly Asp Gly Cys Met Met Glu
145                 150                 155                 160

Gly Ile Ser His Glu Val Cys Ser Leu Ala Gly Thr Leu Lys Leu Gly
                165                 170                 175

Lys Leu Ile Ala Phe Tyr Asp Asp Asn Gly Ile Ser Ile Asp Gly His
                180                 185                 190

Val Glu Gly Trp Phe Thr Asp Thr Ala Met Arg Phe Glu Ala Tyr
                195                 200                 205

Gly Trp His Val Ile Arg Asp Ile Asp Gly His Asp Ala Ala Ser Ile
            210                 215                 220

Lys Arg Ala Val Glu Glu Ala Arg Ala Val Thr Asp Lys Pro Ser Leu
225                 230                 235                 240

Leu Met Cys Lys Thr Ile Ile Gly Phe Gly Ser Pro Asn Lys Ala Gly
                245                 250                 255

Thr His Asp Ser His Gly Ala Pro Leu Gly Asp Ala Glu Ile Ala Leu
            260                 265                 270

Thr Arg Glu Gln Leu Gly Trp Lys Tyr Ala Pro Phe Glu Ile Pro Ser
            275                 280                 285

Glu Ile Tyr Ala Gln Trp Asp Ala Lys Glu Ala Gly Gln Ala Lys Glu
            290                 295                 300

Ser Ala Trp Asn Glu Lys Phe Ala Ala Tyr Ala Lys Ala Tyr Pro Gln
305                 310                 315                 320

Glu Ala Ala Glu Phe Thr Arg Arg Met Lys Gly Glu Met Pro Ser Asp
                325                 330                 335

Phe Asp Ala Lys Ala Lys Glu Phe Ile Ala Lys Leu Gln Ala Asn Pro
            340                 345                 350

Ala Lys Ile Ala Ser Arg Lys Ala Ser Gln Asn Ala Ile Glu Ala Phe
            355                 360                 365

Gly Pro Leu Leu Pro Glu Phe Leu Gly Gly Ser Ala Asp Leu Ala Pro
            370                 375                 380

Ser Asn Leu Thr Leu Trp Ser Gly Ser Lys Ala Ile Asn Glu Asp Ala
385                 390                 395                 400

Ala Gly Asn Tyr Ile His Tyr Gly Val Arg Glu Phe Gly Met Thr Ala
                405                 410                 415

Ile Ala Asn Gly Ile Ser Leu His Gly Gly Phe Leu Pro Tyr Thr Ser
            420                 425                 430

Thr Phe Leu Met Phe Val Glu Tyr Ala Arg Asn Ala Val Arg Met Ala
            435                 440                 445

Ala Leu Met Lys Gln Arg Gln Val Met Val Tyr Thr His Asp Ser Ile
450                 455                 460

Gly Leu Gly Glu Asp Gly Pro Thr His Gln Pro Val Glu Gln Val Ala
465                 470                 475                 480

Ser Leu Arg Val Thr Pro Asn Met Ser Thr Trp Arg Pro Cys Asp Gln
                485                 490                 495
```

Val Glu Ser Ala Val Ala Trp Lys Tyr Gly Val Glu Arg Gln Asp Gly
            500                 505                 510

Pro Thr Ala Leu Ile Leu Ser Arg Gln Asn Leu Ala Gln Gln Glu Arg
        515                 520                 525

Thr Glu Glu Gln Leu Ala Asn Ile Ala Arg Gly Gly Tyr Val Leu Lys
    530                 535                 540

Asp Cys Ala Gly Gln Pro Glu Leu Ile Phe Ile Ala Thr Gly Ser Glu
545                 550                 555                 560

Val Glu Leu Ala Val Ala Ala Tyr Glu Lys Leu Thr Ala Glu Gly Val
            565                 570                 575

Lys Ala Arg Val Val Ser Met Pro Ser Thr Asp Ala Phe Asp Lys Gln
        580                 585                 590

Asp Ala Ala Tyr Arg Glu Ser Val Leu Pro Lys Ala Val Thr Ala Arg
    595                 600                 605

Val Ala Val Glu Ala Gly Ile Ala Asp Tyr Trp Tyr Lys Tyr Val Gly
610                 615                 620

Leu Asn Gly Ala Ile Val Gly Met Thr Thr Phe Gly Glu Ser Leu Glu
625                 630                 635                 640

Val Leu Phe Gln Gly Pro Ala Pro Ala Glu Leu Leu Phe Glu Glu Phe
            645                 650                 655

Gly Phe Thr Val Asp Asn Val Val Ala Lys Ala Lys Glu Leu Leu
        660                 665                 670

<210> SEQ ID NO 68
<211> LENGTH: 671
<212> TYPE: PRT
<213> ORGANISM: Artificial Sequence
<220> FEATURE:
<223> OTHER INFORMATION: Synthetic Polypeptide

<400> SEQUENCE: 68

Met Ser Ser Arg Lys Glu Leu Ala Asn Ala Ile Arg Ala Leu Ser Met
1               5                   10                  15

Asp Ala Val Gln Lys Ala Lys Ser Gly His Pro Gly Ala Pro Met Gly
            20                  25                  30

Met Ala Asp Ile Ala Glu Val Leu Trp Arg Asp Phe Leu Lys His Asn
        35                  40                  45

Pro Gln Asn Pro Ser Trp Ala Asp Arg Asp Arg Phe Val Leu Ser Asn
    50                  55                  60

Gly His Gly Ser Met Leu Ile Tyr Ser Leu Leu His Leu Thr Gly Tyr
65                  70                  75                  80

Asp Leu Pro Met Glu Glu Leu Lys Asn Phe Arg Gln Leu His Ser Lys
            85                  90                  95

Thr Pro Gly His Pro Glu Val Gly Tyr Thr Ala Gly Val Glu Thr Thr
        100                 105                 110

Thr Gly Pro Leu Gly Gln Gly Ile Ala Asn Ala Val Gly Met Ala Ile
    115                 120                 125

Ala Glu Lys Thr Leu Ala Ala Gln Phe Asn Arg Pro Gly His Asp Ile
130                 135                 140

Val Asp His Tyr Thr Tyr Ala Phe Met Gly Asp Gly Cys Met Met Glu
145                 150                 155                 160

Gly Ile Ser His Glu Val Cys Ser Leu Ala Gly Thr Leu Lys Leu Gly
            165                 170                 175

Lys Leu Ile Ala Phe Tyr Asp Asp Asn Gly Ile Ser Ile Asp Gly His
        180                 185                 190

-continued

```
Val Glu Gly Trp Phe Thr Asp Asp Thr Ala Met Arg Phe Glu Ala Tyr
            195                 200                 205
Gly Trp His Val Ile Arg Asp Ile Asp Gly His Asp Ala Ala Ser Ile
        210                 215                 220
Lys Arg Ala Val Glu Glu Ala Arg Ala Val Thr Asp Lys Pro Ser Leu
225                 230                 235                 240
Leu Met Cys Lys Thr Ile Ile Gly Phe Gly Ser Pro Asn Lys Ala Gly
                245                 250                 255
Thr His Asp Ser His Gly Ala Pro Leu Gly Asp Ala Glu Ile Ala Leu
            260                 265                 270
Thr Arg Glu Gln Leu Gly Trp Lys Tyr Ala Pro Phe Glu Ile Pro Ser
        275                 280                 285
Glu Ile Tyr Ala Gln Trp Asp Ala Lys Glu Ala Gly Gln Ala Lys Glu
    290                 295                 300
Ser Ala Trp Asn Glu Lys Phe Ala Ala Tyr Ala Lys Ala Tyr Pro Gln
305                 310                 315                 320
Glu Ala Ala Glu Phe Thr Arg Arg Met Lys Gly Glu Met Pro Ser Asp
                325                 330                 335
Phe Asp Ala Lys Ala Lys Glu Phe Ile Ala Lys Leu Gln Ala Asn Pro
            340                 345                 350
Ala Lys Ile Ala Ser Arg Lys Ala Ser Gln Asn Ala Ile Glu Ala Phe
        355                 360                 365
Gly Pro Leu Leu Pro Glu Phe Leu Gly Gly Ser Ala Asp Leu Ala Pro
    370                 375                 380
Ser Asn Leu Thr Leu Trp Ser Gly Ser Lys Ala Ile Asn Glu Asp Ala
385                 390                 395                 400
Ala Gly Asn Tyr Ile His Tyr Gly Val Arg Glu Phe Gly Met Thr Ala
                405                 410                 415
Ile Ala Asn Gly Ile Ser Leu His Gly Gly Phe Leu Pro Tyr Thr Ser
            420                 425                 430
Thr Phe Leu Met Phe Val Glu Tyr Ala Arg Asn Ala Val Arg Met Ala
        435                 440                 445
Ala Leu Met Lys Gln Arg Gln Val Met Val Tyr Thr His Asp Ser Ile
    450                 455                 460
Gly Leu Gly Glu Asp Gly Pro Thr His Gln Pro Val Glu Gln Val Ala
465                 470                 475                 480
Ser Leu Arg Val Thr Pro Asn Met Ser Thr Trp Arg Pro Cys Asp Gln
                485                 490                 495
Val Glu Ser Ala Val Ala Trp Lys Tyr Gly Val Glu Arg Gln Asp Gly
            500                 505                 510
Pro Thr Ala Leu Ile Leu Ser Arg Gln Asn Leu Ala Gln Gln Glu Arg
        515                 520                 525
Thr Glu Glu Gln Leu Ala Asn Ile Ala Arg Gly Gly Tyr Val Leu Lys
    530                 535                 540
Asp Cys Ala Gly Gln Pro Glu Leu Ile Phe Ile Ala Thr Gly Ser Glu
545                 550                 555                 560
Val Glu Leu Ala Val Ala Ala Tyr Glu Lys Leu Thr Ala Glu Gly Val
                565                 570                 575
Lys Ala Arg Val Val Ser Met Pro Ser Thr Asp Ala Phe Asp Lys Gln
            580                 585                 590
Asp Ala Ala Tyr Arg Glu Ser Val Leu Pro Lys Ala Val Thr Ala Arg
        595                 600                 605
Val Ala Val Glu Ala Gly Ile Ala Asp Tyr Trp Tyr Lys Tyr Val Gly
```

```
                610                 615                 620
Leu Asn Gly Ala Ile Val Gly Met Thr Thr Phe Gly Glu Ser Ala Pro
625                 630                 635                 640

Leu Glu Val Leu Phe Gln Gly Pro Ala Glu Leu Leu Phe Glu Glu Phe
                645                 650                 655

Gly Phe Thr Val Asp Asn Val Val Ala Lys Ala Lys Glu Leu Leu
            660                 665                 670
```

```
<210> SEQ ID NO 69
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 69
ctggaagtgc tgtttcaggg tccg                                             24

<210> SEQ ID NO 70
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 70
```

```
Met Lys Asn Ile Asn Pro Thr Gln Thr Ala Ala
1               5                   10
```

```
<210> SEQ ID NO 71
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 71
atgaaaaaca tcaatccaac gcagaccgct gcc                                   33

<210> SEQ ID NO 72
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 72
```

```
Met Leu Glu Val Leu Phe Gln Gly Pro Lys Asn Ile Asn Pro Thr Gln
1               5                   10                  15

Thr Ala Ala
```

```
<210> SEQ ID NO 73
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 73
atgctggaag tgctgtttca gggtccgaaa aacatcaatc caacgcagac cgctgcc        57

<210> SEQ ID NO 74
<211> LENGTH: 19
<212> TYPE: PRT
```

<210> SEQ ID NO 74
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 74

Met Lys Leu Glu Val Leu Phe Gln Gly Pro Asn Ile Asn Pro Thr Gln
1               5                   10                  15

Thr Ala Ala

<210> SEQ ID NO 75
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 75
atgaaactgg aagtgctgtt tcagggtccg aacatcaatc caacgcagac cgctgcc       57

<210> SEQ ID NO 76
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 76

Met Lys Asn Leu Glu Val Leu Phe Gln Gly Pro Ile Asn Pro Thr Gln
1               5                   10                  15

Thr Ala Ala

<210> SEQ ID NO 77
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 77
atgaaaaacc tggaagtgct gtttcagggt ccgatcaatc caacgcagac cgctgcc       57

<210> SEQ ID NO 78
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 78

Met Leu Glu Val Leu Phe Gln Gly Pro Ala Ala
1               5                   10

<210> SEQ ID NO 79
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 79
atgctggaag tgctgtttca gggtccggct gcc                                  33

<210> SEQ ID NO 80
<211> LENGTH: 11
<212> TYPE: PRT

<213> ORGANISM: Artificial Sequence
<220> FEATURE:
<223> OTHER INFORMATION: Synthetic Polypeptide

<400> SEQUENCE: 80

Met Lys Leu Glu Val Leu Phe Gln Gly Pro Ala
1               5                   10

<210> SEQ ID NO 81
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 81
atgaaactgg aagtgctgtt tcagggtccg gcc        33

<210> SEQ ID NO 82
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 82

Met Lys Asn Leu Glu Val Leu Phe Gln Gly Pro
1               5                   10

<210> SEQ ID NO 83
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 83
atgaaaaacc tggaagtgct gtttcagggt ccg        33

<210> SEQ ID NO 84
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 84

Met Lys Asn Ile Asn Leu Glu Val Leu Phe Gln Gly Pro Thr Gln Thr
1               5                   10                  15

Ala Ala

<210> SEQ ID NO 85
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 85
atgaaaaaca tcaatctgga agtgctgttt cagggtccaa cgcagaccgc tgcc        54

<210> SEQ ID NO 86
<211> LENGTH: 17
<212> TYPE: PRT
<213> ORGANISM: Artificial Sequence
<220> FEATURE:

```
<223> OTHER INFORMATION: Synthetic Polypeptide

<400> SEQUENCE: 86

Thr Ala Ala Trp Gln Ala Leu Glu Val Leu Phe Gln Gly Pro Gln Lys
1               5                   10                  15
His

<210> SEQ ID NO 87
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 87
accgctgcct ggcaggcact agaagtgctg tttcagggtc cgcagaaaca c        51
```